US011412966B2

(12) United States Patent
Halac et al.

(10) Patent No.: US 11,412,966 B2
(45) Date of Patent: Aug. 16, 2022

(54) TRANSCUTANEOUS ANALYTE SENSOR SYSTEMS AND METHODS

(71) Applicant: DexCom, Inc., San Diego, CA (US)

(72) Inventors: Jason Halac, San Diego, CA (US); John Michael Gray, San Diego, CA (US); Neal Davis Johnston, Dallas, TX (US); Justen Deering England, San Francisco, CA (US); Peter C. Simpson, Cardiff by the Sea, CA (US); Paul V. Neale, San Diego, CA (US); Jennifer Blackwell, San Diego, CA (US); Maria Noel Brown Wells, San Diego, CA (US); Kenneth Pirondini, San Diego, CA (US); Andrew Michael Reinhardt, Santee, CA (US); Mark Douglas Kempkey, Vista, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 17/446,280

(22) Filed: Aug. 27, 2021

(65) Prior Publication Data

US 2021/0386342 A1    Dec. 16, 2021

Related U.S. Application Data

(63) Continuation of application No. 15/387,088, filed on Dec. 21, 2016.

(Continued)

(51) Int. Cl.
*A61B 5/145* (2006.01)
*A61B 5/1473* (2006.01)
(Continued)

(52) U.S. Cl.
CPC ...... *A61B 5/14865* (2013.01); *A61B 5/14532* (2013.01); *A61B 5/14546* (2013.01);
(Continued)

(58) Field of Classification Search
CPC ............ A61B 5/14865; A61B 5/14532; A61B 5/6849; A61B 5/68335; A61B 2560/063
(Continued)

(56) References Cited

U.S. PATENT DOCUMENTS 5,196,025 A   3/1993   Ranalletta et al.
5,314,441 A   5/1994   Cusack et al.
(Continued)

FOREIGN PATENT DOCUMENTS

CN   101711678 A   5/2010
CN   103781422 A   5/2014
(Continued)

OTHER PUBLICATIONS

Examination Report No. 2 from Australian Patent Application No. 2019261741, dated Jun. 2, 2021, 4 pages.
(Continued)

*Primary Examiner* — Navin Natnithithadha
(74) *Attorney, Agent, or Firm* — Snell & Wilmer LLP

(57) ABSTRACT

Systems for applying a transcutaneous monitor to a person can include a telescoping assembly, a sensor, and a base with adhesive to couple the sensor to skin. The sensor can be located within the telescoping assembly while the base protrudes from a distal end of the system. The system can be configured to couple the sensor to the base by compressing the telescoping assembly.

30 Claims, 66 Drawing Sheets

Related U.S. Application Data

(60) Provisional application No. 62/412,100, filed on Oct. 24, 2016, provisional application No. 62/272,983, filed on Dec. 30, 2015.

(51) Int. Cl.
*A61B 5/1486* (2006.01)
*A61B 5/1468* (2006.01)
*A61B 5/00* (2006.01)

(52) U.S. Cl.
CPC ............ *A61B 5/688* (2013.01); *A61B 5/6832* (2013.01); *A61B 5/6848* (2013.01); *A61B 5/6849* (2013.01); *A61B 5/68335* (2017.08); *A61B 2560/063* (2013.01)

(58) Field of Classification Search
USPC ........................................ 600/309, 345–366
See application file for complete search history.

(56) References Cited

U.S. PATENT DOCUMENTS

| | | |
|---|---|---|
| 5,318,583 A | 6/1994 | Rabenau et al. |
| 5,360,405 A | 11/1994 | Yoon |
| 5,527,334 A | 6/1996 | Kanner et al. |
| 5,586,553 A | 12/1996 | Halili et al. |
| 5,807,375 A | 9/1998 | Gross et al. |
| 5,984,940 A | 11/1999 | Davis et al. |
| 6,102,896 A | 8/2000 | Roser |
| 6,175,752 B1 | 1/2001 | Say et al. |
| 6,186,982 B1 | 2/2001 | Gross et al. |
| 6,248,067 B1 | 6/2001 | Causey, III et al. |
| 6,275,717 B1 | 8/2001 | Gross et al. |
| 6,368,141 B1 | 4/2002 | Vanantwerp et al. |
| 6,560,471 B1 | 5/2003 | Heller et al. |
| 6,607,509 B2 | 8/2003 | Bobroff et al. |
| 6,607,543 B2 | 8/2003 | Purcell et al. |
| 6,695,860 B1 | 2/2004 | Ward et al. |
| 6,809,653 B1 | 10/2004 | Mann et al. |
| 6,960,192 B1 | 11/2005 | Flaherty et al. |
| 7,003,341 B2 | 2/2006 | Say et al. |
| 7,120,483 B2 | 10/2006 | Russell et al. |
| 7,144,404 B2 | 12/2006 | Whitson et al. |
| 7,150,755 B2 | 12/2006 | Levaughn et al. |
| 7,207,974 B2 | 4/2007 | Safabash et al. |
| 7,223,276 B2 | 5/2007 | List et al. |
| 7,297,136 B2 | 11/2007 | Wyrick |
| 7,303,549 B2 | 12/2007 | Flaherty et al. |
| 7,381,184 B2 | 6/2008 | Funderburk et al. |
| 7,407,493 B2 | 8/2008 | Cane' |
| 7,481,819 B2 | 1/2009 | Koeppel et al. |
| 7,494,465 B2 | 2/2009 | Brister et al. |
| 7,530,964 B2 | 5/2009 | Lavi et al. |
| 7,697,967 B2 | 4/2010 | Stafford |
| 7,699,807 B2 | 4/2010 | Faust et al. |
| 7,846,132 B2 | 12/2010 | Gravesen et al. |
| 7,850,652 B2 | 12/2010 | Liniger et al. |
| 7,885,697 B2 | 2/2011 | Brister et al. |
| 7,896,844 B2 | 3/2011 | Thalmann et al. |
| 7,946,984 B2 | 5/2011 | Brister et al. |
| 7,949,381 B2 | 5/2011 | Brister et al. |
| 7,955,297 B2 | 6/2011 | Radmer et al. |
| 7,985,203 B2 | 7/2011 | Haueter et al. |
| 8,025,658 B2 | 9/2011 | Chong et al. |
| 8,079,961 B2 | 12/2011 | Saikley et al. |
| 8,172,805 B2 | 5/2012 | Mogensen et al. |
| 8,262,618 B2 | 9/2012 | Scheurer |
| 8,298,172 B2 | 10/2012 | Nielsen et al. |
| 8,313,434 B2 | 11/2012 | Brister et al. |
| 8,366,682 B2 | 2/2013 | Wyrick |
| 8,366,729 B2 | 2/2013 | Levaughn et al. |
| 8,409,140 B2 | 4/2013 | Ejlersen et al. |
| 8,409,145 B2 | 4/2013 | Raymond et al. |
| 8,439,838 B2 | 5/2013 | Mogensen et al. |
| 8,475,373 B2 | 7/2013 | Brister et al. |
| 8,483,792 B2 | 7/2013 | Slomski et al. |
| 8,500,654 B2 | 8/2013 | Goldenberg |
| 8,562,567 B2 | 10/2013 | Gundberg |
| 8,615,281 B2 | 12/2013 | Yodfat et al. |
| 8,668,645 B2 | 3/2014 | Drucker et al. |
| 8,721,545 B2 | 5/2014 | Brister et al. |
| 8,747,363 B2 | 6/2014 | Nielsen et al. |
| 8,870,822 B2 | 10/2014 | Thalmann et al. |
| 8,880,138 B2 | 11/2014 | Cho |
| 9,215,992 B2 | 12/2015 | Donnay et al. |
| 9,295,786 B2 | 3/2016 | Gottlieb et al. |
| 9,380,975 B2 | 7/2016 | Karbowniczek et al. |
| 9,399,094 B2 | 7/2016 | Krag et al. |
| 9,498,159 B2 | 11/2016 | Heller et al. |
| 9,533,092 B2 | 1/2017 | Gyrn |
| 9,675,285 B2 | 6/2017 | Christian |
| 9,687,183 B2 | 6/2017 | Donnay et al. |
| 9,788,771 B2 | 10/2017 | Stafford |
| 9,808,574 B2 | 11/2017 | Yodfat et al. |
| 9,980,670 B2 | 5/2018 | Funderburk et al. |
| 10,010,280 B2 | 7/2018 | Donnay et al. |
| 10,076,606 B2 | 9/2018 | Ambruzs et al. |
| 10,194,842 B2 | 2/2019 | Peterson et al. |
| 10,194,843 B2 | 2/2019 | Peterson et al. |
| 10,251,605 B2 | 4/2019 | Liu et al. |
| 10,327,679 B2 | 6/2019 | Peterson et al. |
| 10,335,066 B2 | 7/2019 | Peterson et al. |
| 10,376,187 B2 | 8/2019 | Peterson et al. |
| 10,376,637 B2 | 8/2019 | Gyrn et al. |
| 10,413,183 B2 | 9/2019 | Antonio et al. |
| 10,420,508 B2 | 9/2019 | Antonio et al. |
| 10,456,064 B2 | 10/2019 | Peterson et al. |
| 10,492,685 B2 | 12/2019 | Bernstein et al. |
| 10,610,103 B2 | 4/2020 | Brister et al. |
| 10,610,135 B2 | 4/2020 | Kamath et al. |
| 10,610,136 B2 | 4/2020 | Kamath et al. |
| 10,610,141 B2 | 4/2020 | Böhm et al. |
| 10,624,539 B2 | 4/2020 | Brister et al. |
| 10,624,568 B2 | 4/2020 | Böhm et al. |
| 10,631,787 B2 | 4/2020 | Antonio et al. |
| 10,667,729 B2 | 6/2020 | Simpson et al. |
| 10,687,740 B2 | 6/2020 | Bohm et al. |
| 10,702,193 B2 | 7/2020 | Simpson et al. |
| 10,709,362 B2 | 7/2020 | Simpson et al. |
| 10,709,363 B2 | 7/2020 | Brister et al. |
| 10,709,364 B2 | 7/2020 | Kamath et al. |
| 10,722,152 B2 | 7/2020 | Brister et al. |
| 10,722,162 B2 | 7/2020 | Böhm et al. |
| 10,799,158 B2 | 10/2020 | Brister et al. |
| 10,813,576 B2 | 10/2020 | Brister et al. |
| 10,813,577 B2 | 10/2020 | Brister et al. |
| 10,827,956 B2 | 11/2020 | Brister et al. |
| 10,856,787 B2 | 12/2020 | Pryor et al. |
| 10,863,931 B2 | 12/2020 | Hernandez-Rosas et al. |
| 10,898,115 B2 | 1/2021 | Halac et al. |
| 10,918,313 B2 | 2/2021 | Brister et al. |
| 10,918,314 B2 | 2/2021 | Brister et al. |
| 10,918,316 B2 | 2/2021 | Pryor et al. |
| 10,932,700 B2 | 3/2021 | Simpson et al. |
| 10,980,450 B2 | 4/2021 | Wedekind et al. |
| 10,980,452 B2 | 4/2021 | Simpson et al. |
| 10,980,453 B2 | 4/2021 | Wedekind et al. |
| 10,980,461 B2 | 4/2021 | Simpson et al. |
| 10,985,804 B2 | 4/2021 | Miller et al. |
| 10,993,642 B2 | 5/2021 | Simpson et al. |
| 2002/0029058 A1 | 3/2002 | Levaughn et al. |
| 2003/0028126 A1 | 2/2003 | List |
| 2003/0100040 A1 | 5/2003 | Bonnecaze et al. |
| 2003/0100821 A1 | 5/2003 | Heller et al. |
| 2003/0187470 A1 | 10/2003 | Chelak et al. |
| 2004/0133164 A1 | 7/2004 | Funderburk et al. |
| 2004/0138588 A1 | 7/2004 | Saikley et al. |
| 2005/0090850 A1 | 4/2005 | Thoes et al. |
| 2005/0149089 A1 | 7/2005 | Trissel et al. |
| 2005/0283114 A1 | 12/2005 | Bresina et al. |
| 2006/0007017 A1 | 1/2006 | Mann et al. |
| 2006/0229512 A1 | 10/2006 | Petisce et al. |
| 2006/0235285 A1 | 10/2006 | Brister et al. |

(56) References Cited

U.S. PATENT DOCUMENTS

| | | |
|---|---|---|
| 2006/0241517 A1 | 10/2006 | Fowler et al. |
| 2006/0241669 A1 | 10/2006 | Stout et al. |
| 2006/0247671 A1 | 11/2006 | LeVaughn |
| 2006/0258939 A1 | 11/2006 | Pesach et al. |
| 2006/0258990 A1 | 11/2006 | Weber |
| 2006/0287630 A1 | 12/2006 | Hommann |
| 2007/0027381 A1 | 2/2007 | Stafford |
| 2007/0060814 A1 | 3/2007 | Stafford |
| 2007/0073129 A1 | 3/2007 | Shah et al. |
| 2007/0078322 A1 | 4/2007 | Stafford |
| 2007/0156094 A1 | 7/2007 | Safabash et al. |
| 2007/0167907 A1 | 7/2007 | Deslierres et al. |
| 2007/0173706 A1 | 7/2007 | Neinast et al. |
| 2007/0191702 A1 | 8/2007 | Yodfat et al. |
| 2007/0208245 A1 | 9/2007 | Brauker et al. |
| 2007/0208246 A1 | 9/2007 | Brauker et al. |
| 2007/0233167 A1 | 10/2007 | Weiss et al. |
| 2007/0249922 A1 | 10/2007 | Peyser et al. |
| 2007/0255302 A1 | 11/2007 | Koeppel et al. |
| 2008/0007141 A1 | 1/2008 | Deck |
| 2008/0009805 A1 | 1/2008 | Ethelfeld |
| 2008/0027474 A1 | 1/2008 | Curry et al. |
| 2008/0031941 A1 | 2/2008 | Pettersson |
| 2008/0051714 A1 | 2/2008 | Moberg et al. |
| 2008/0086039 A1 | 4/2008 | Heller et al. |
| 2008/0086043 A1 | 4/2008 | Heller et al. |
| 2008/0097246 A1 | 4/2008 | Stafford |
| 2008/0114227 A1 | 5/2008 | Haar et al. |
| 2008/0114280 A1 | 5/2008 | Stafford |
| 2008/0139903 A1 | 6/2008 | Bruce et al. |
| 2008/0161656 A1 | 7/2008 | Bruce et al. |
| 2008/0167641 A1 | 7/2008 | Hansen et al. |
| 2008/0188798 A1 | 8/2008 | Weber |
| 2008/0249383 A1 | 10/2008 | Sass et al. |
| 2008/0249473 A1 | 10/2008 | Rutti et al. |
| 2008/0281270 A1 | 11/2008 | Cross et al. |
| 2009/0012472 A1 | 1/2009 | Ahm et al. |
| 2009/0054812 A1 | 2/2009 | Mace |
| 2009/0088689 A1 | 4/2009 | Carter |
| 2009/0124979 A1 | 5/2009 | Raymond et al. |
| 2010/0010529 A1 | 1/2010 | Shi |
| 2010/0025174 A1 | 2/2010 | Dayton |
| 2010/0137695 A1 | 6/2010 | Yodfat et al. |
| 2010/0145377 A1 | 6/2010 | Lai et al. |
| 2010/0185178 A1 | 7/2010 | Sharp et al. |
| 2010/0228226 A1 | 9/2010 | Nielsen |
| 2010/0324392 A1 | 12/2010 | Yee et al. |
| 2010/0331642 A1 | 12/2010 | Bruce et al. |
| 2011/0060287 A1 | 3/2011 | Ambruzs et al. |
| 2011/0082484 A1 | 4/2011 | Saravia et al. |
| 2011/0098656 A1 | 4/2011 | Burnell et al. |
| 2011/0106126 A1 | 5/2011 | Love et al. |
| 2011/0144463 A1 | 6/2011 | Pesach et al. |
| 2011/0144683 A1 | 6/2011 | Butz et al. |
| 2011/0230735 A1 | 9/2011 | Wolfe et al. |
| 2011/0319729 A1 | 12/2011 | Donnay et al. |
| 2012/0150123 A1 | 6/2012 | Lawrence et al. |
| 2012/0184909 A1 | 7/2012 | Gyrn |
| 2012/0190941 A1 | 7/2012 | Donnay et al. |
| 2012/0190942 A1 | 7/2012 | Donnay et al. |
| 2012/0190943 A1 | 7/2012 | Donnay et al. |
| 2012/0197098 A1 | 8/2012 | Donnay et al. |
| 2012/0197222 A1 | 8/2012 | Donnay et al. |
| 2012/0265042 A1 | 10/2012 | Neinast et al. |
| 2012/0303043 A1 | 11/2012 | Donnay |
| 2013/0172695 A1 | 7/2013 | Nielsen et al. |
| 2013/0267811 A1 | 10/2013 | Pryor et al. |
| 2014/0121989 A1 | 5/2014 | Kamath et al. |
| 2014/0187876 A1 | 7/2014 | Ohkoshi |
| 2015/0190076 A1 | 7/2015 | Ohkoshi et al. |
| 2016/0235346 A1 | 8/2016 | Liu et al. |
| 2016/0235365 A1 | 8/2016 | Liu et al. |
| 2017/0188910 A1 | 7/2017 | Halac et al. |
| 2017/0188911 A1 | 7/2017 | Halac et al. |
| 2017/0188912 A1 | 7/2017 | Halac et al. |
| 2017/0290512 A1 | 10/2017 | Antonio et al. |
| 2017/0290532 A1 | 10/2017 | Antonio et al. |
| 2017/0290533 A1 | 10/2017 | Antonio et al. |
| 2019/0117131 A1 | 4/2019 | Halac et al. |
| 2019/0117133 A1 | 4/2019 | Halac et al. |
| 2019/0120784 A1 | 4/2019 | Halac et al. |
| 2019/0120785 A1 | 4/2019 | Halac et al. |
| 2021/0196162 A1 | 7/2021 | Halac et al. |
| 2021/0196163 A1 | 7/2021 | Halac et al. |
| 2021/0282674 A1 | 9/2021 | Halac et al. |
| 2021/0290122 A1 | 9/2021 | Halac et al. |
| 2021/0307657 A1 | 10/2021 | Halac et al. |
| 2021/0307695 A1 | 10/2021 | Halac et al. |

FOREIGN PATENT DOCUMENTS

| | | |
|---|---|---|
| EP | 0729366 B1 | 7/2002 |
| EP | 1475113 A1 | 11/2004 |
| JP | 2006346160 A | 12/2006 |
| NZ | 573020 A | 9/2010 |
| WO | WO-2005046780 A1 | 5/2005 |
| WO | WO-2006038044 A2 | 4/2006 |
| WO | WO-2006067217 A2 | 6/2006 |
| WO | WO-2006075016 A1 | 7/2006 |
| WO | WO-2006077262 A1 | 7/2006 |
| WO | WO-2007031125 A1 | 3/2007 |
| WO | WO-2008065646 A1 | 6/2008 |
| WO | WO-2008078319 A1 | 7/2008 |
| WO | WO-2008083379 A1 | 7/2008 |
| WO | WO-2008115409 A1 | 9/2008 |
| WO | WO-2008124597 A1 | 10/2008 |
| WO | WO-2009010396 A1 | 1/2009 |
| WO | WO-2010091028 A1 | 8/2010 |
| WO | WO-2010091105 A2 | 8/2010 |
| WO | WO-2011077893 A1 | 6/2011 |
| WO | WO-2012103429 A2 | 8/2012 |
| WO | WO-2013035455 A1 | 3/2013 |
| WO | WO-2013136968 A1 | 9/2013 |
| WO | WO-2014045448 A1 | 3/2014 |
| WO | WO-2015131432 A1 | 9/2015 |

OTHER PUBLICATIONS

Extended European Search Report for Application No. 20197430.0, dated Mar. 1, 2021, 7 pages.
Extended European Search Report for Application No. 16882396.1 dated Jul. 19, 2019, 3 pages.
First Office Action for Chinese Application No. 201680051051.4 dated Sep. 25, 2020, 13 pages.
International Preliminary Report on Patentability for Application No. PCT/US2016/068102 dated Jul. 12, 2018, 8 pages.
International Search Report and Written Opinion for Application No. PCT/US2016/068102 dated May 18, 2017, 10 pages.
Office Action for Japanese Application No. 2018-506139, dated Nov. 30, 2020, 10 pages.
Office Action for Japanese Application No. 2018-506139, dated Oct. 11, 2021, 5 pages.
Extended European Search Report for Application No. 21188295.6, dated Nov. 16, 2021, 9 pages.

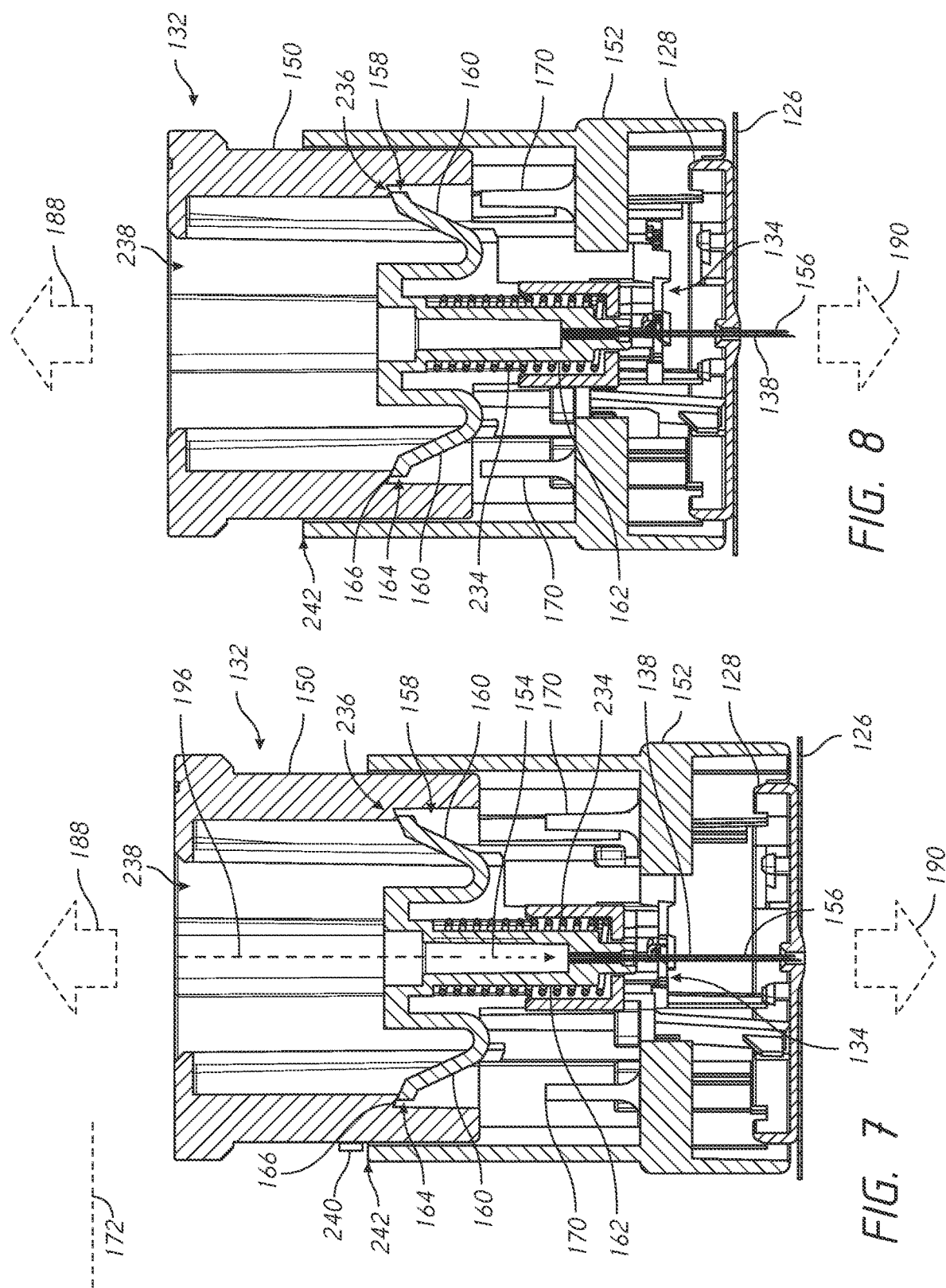

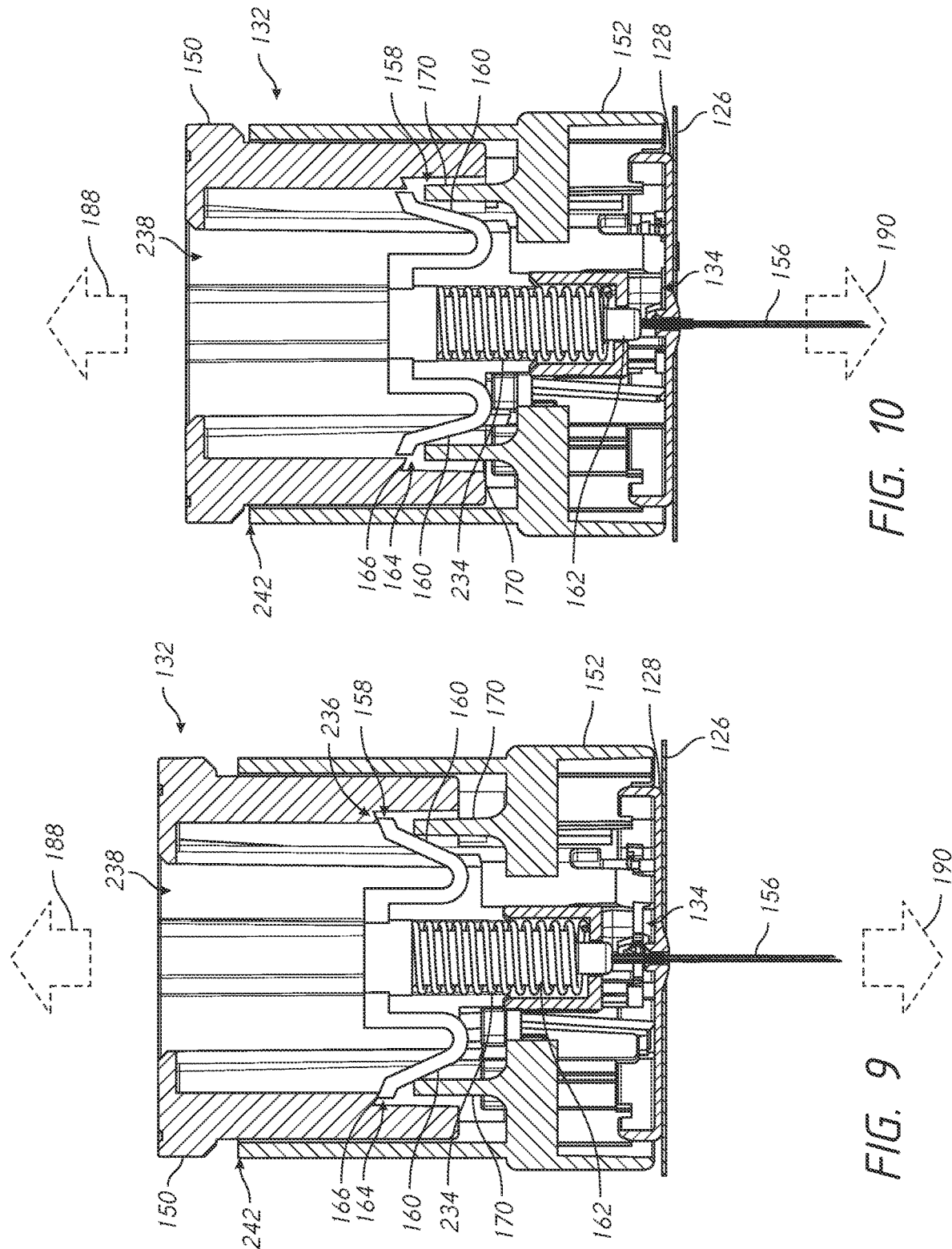

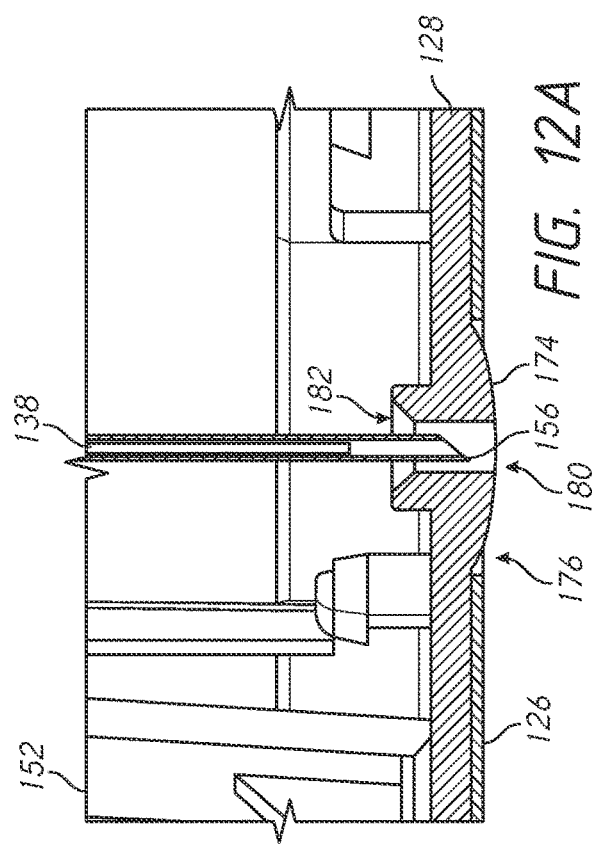
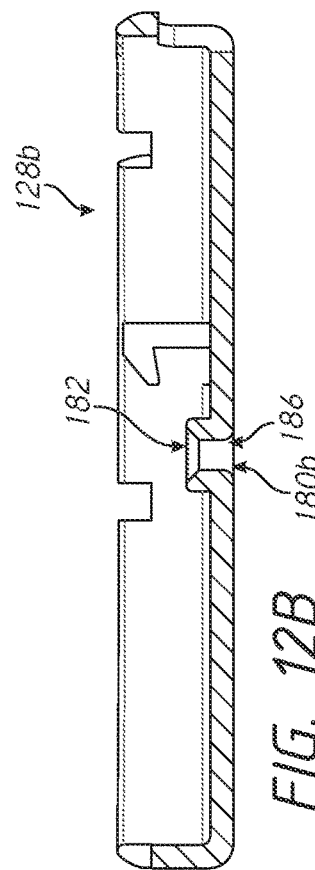
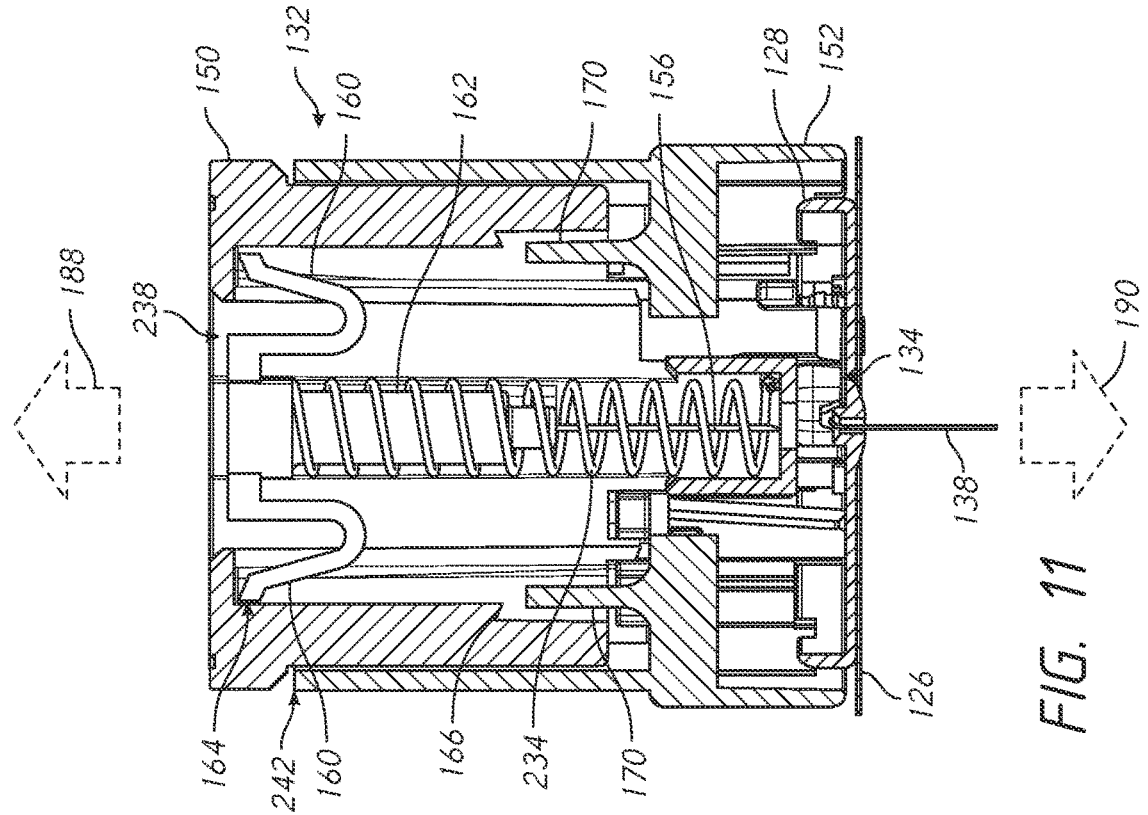
FIG. 12A
FIG. 12B
FIG. 11

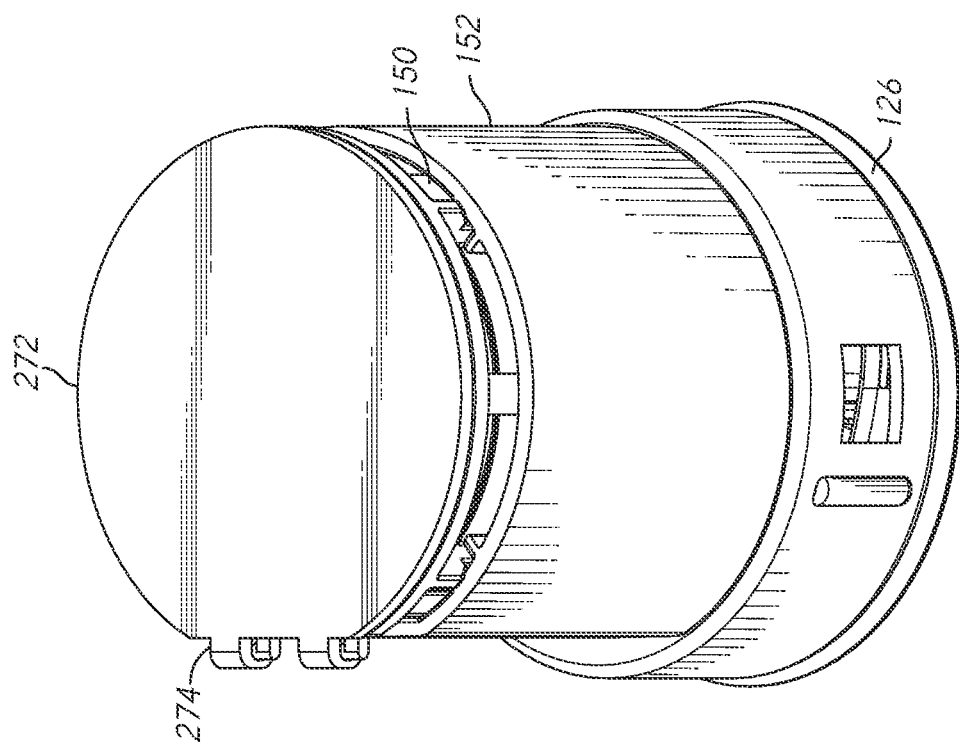
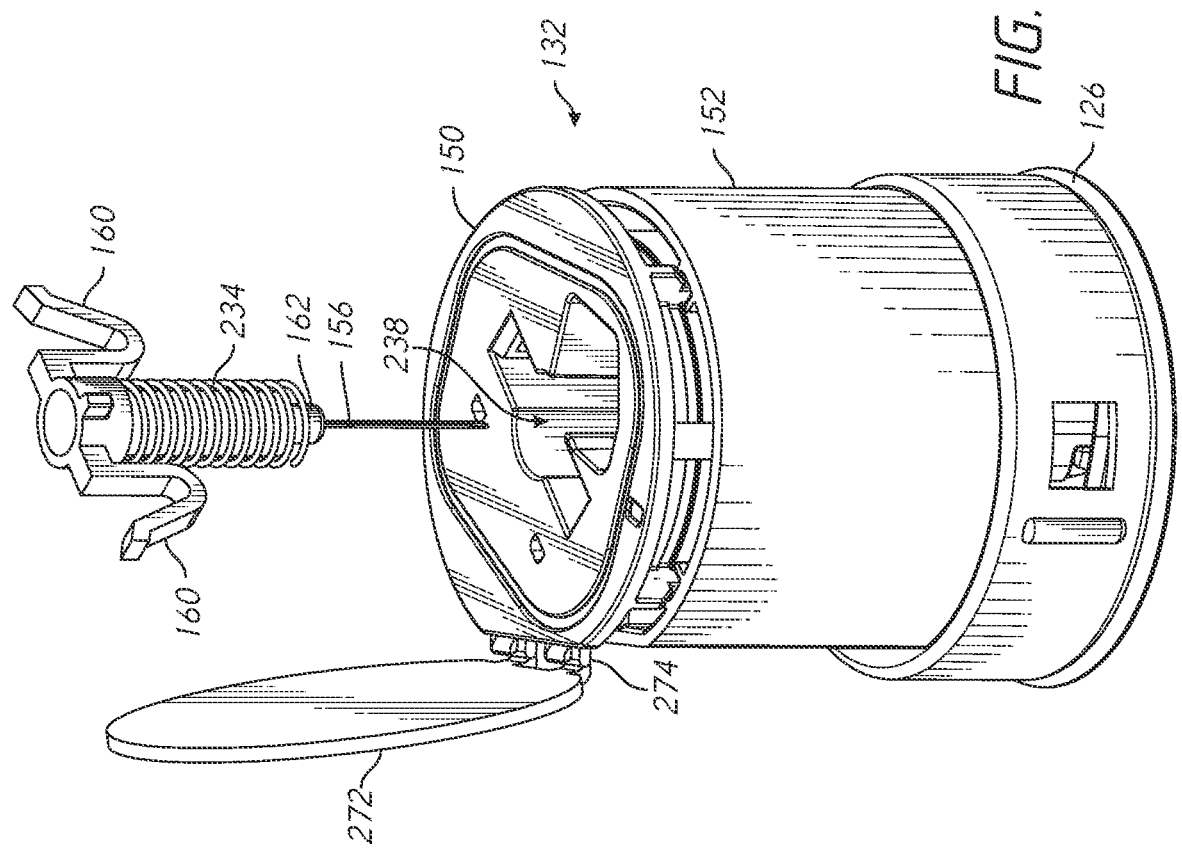

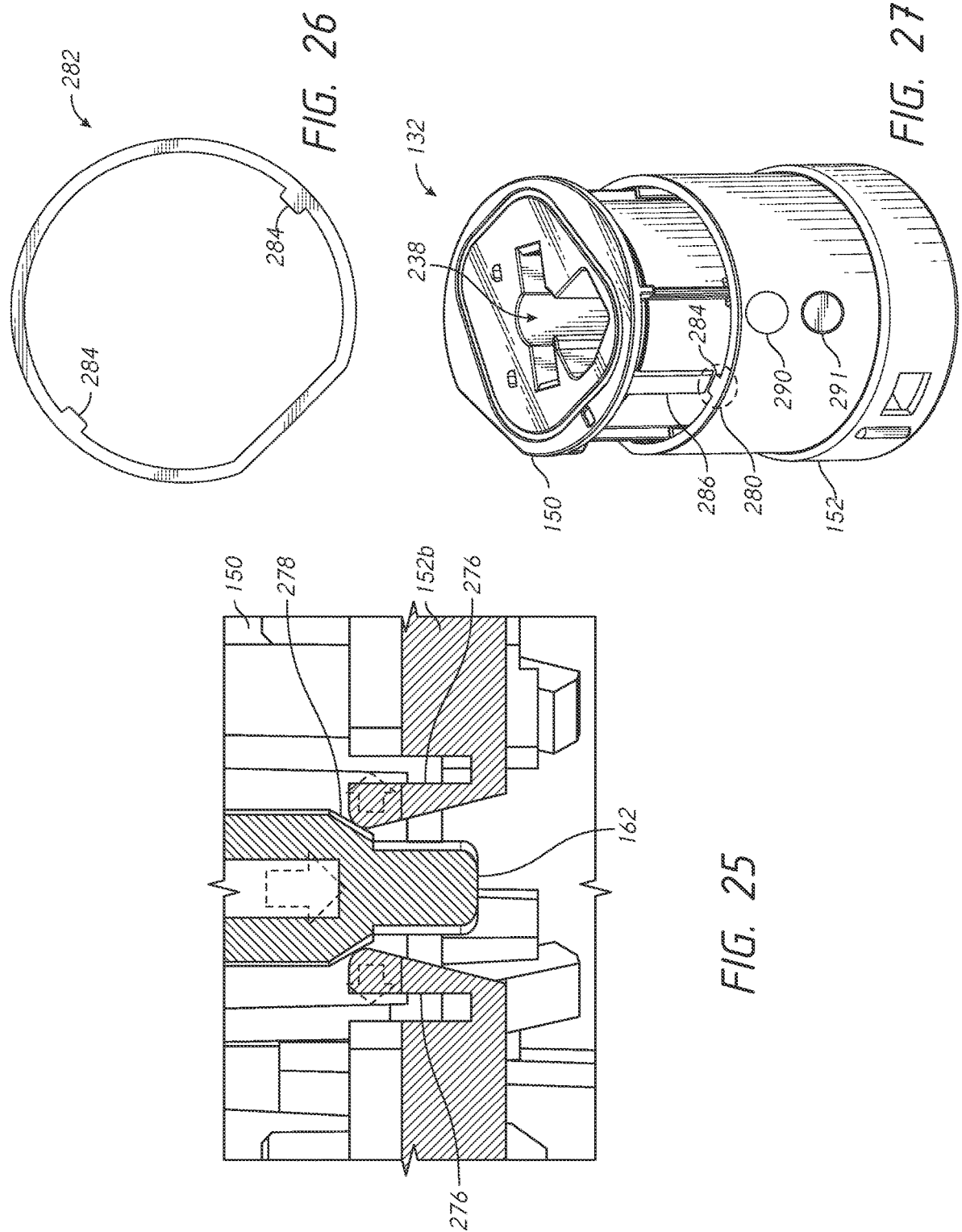

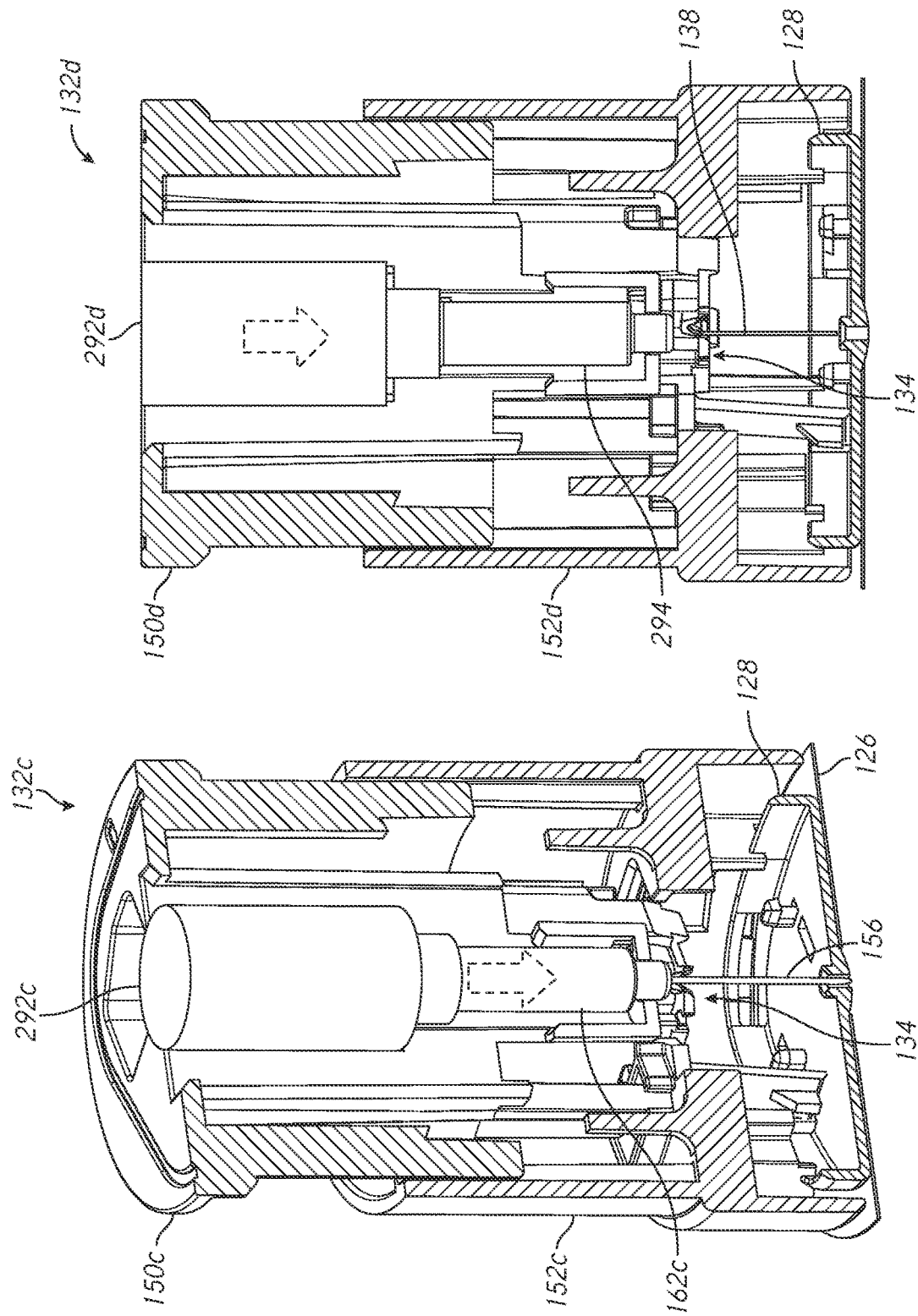

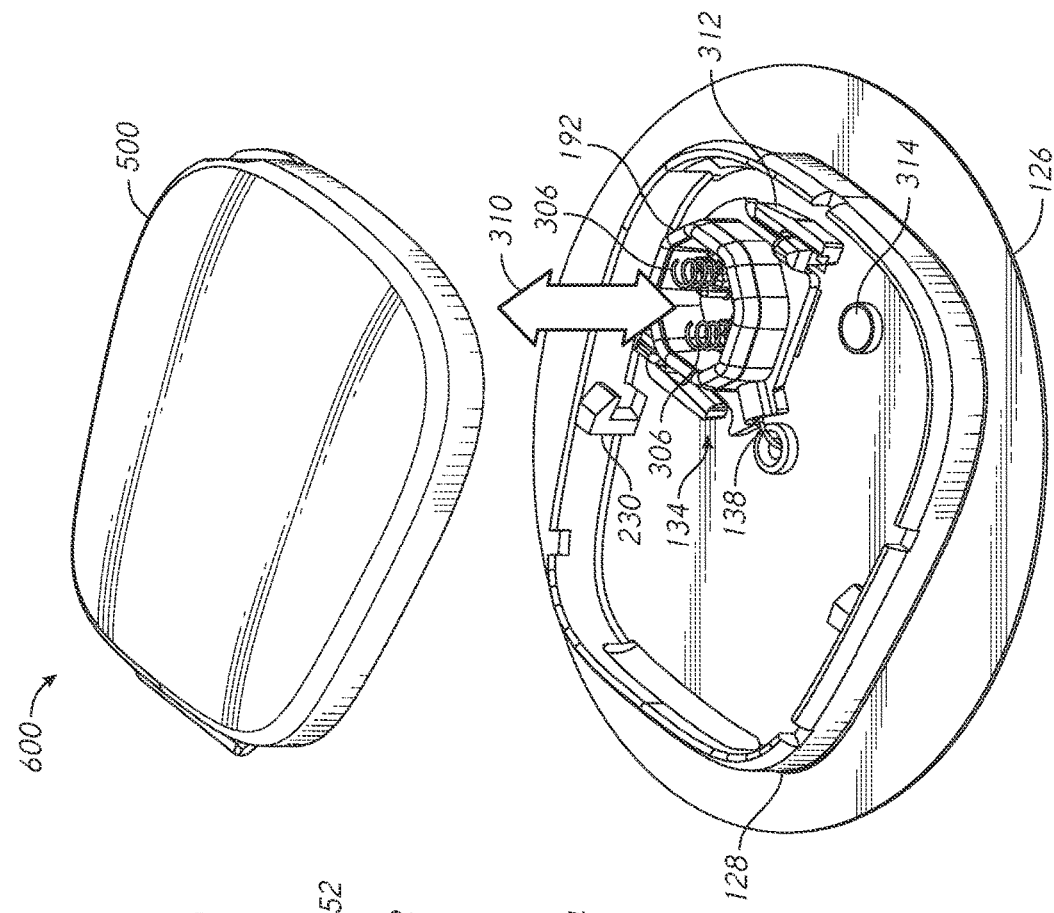
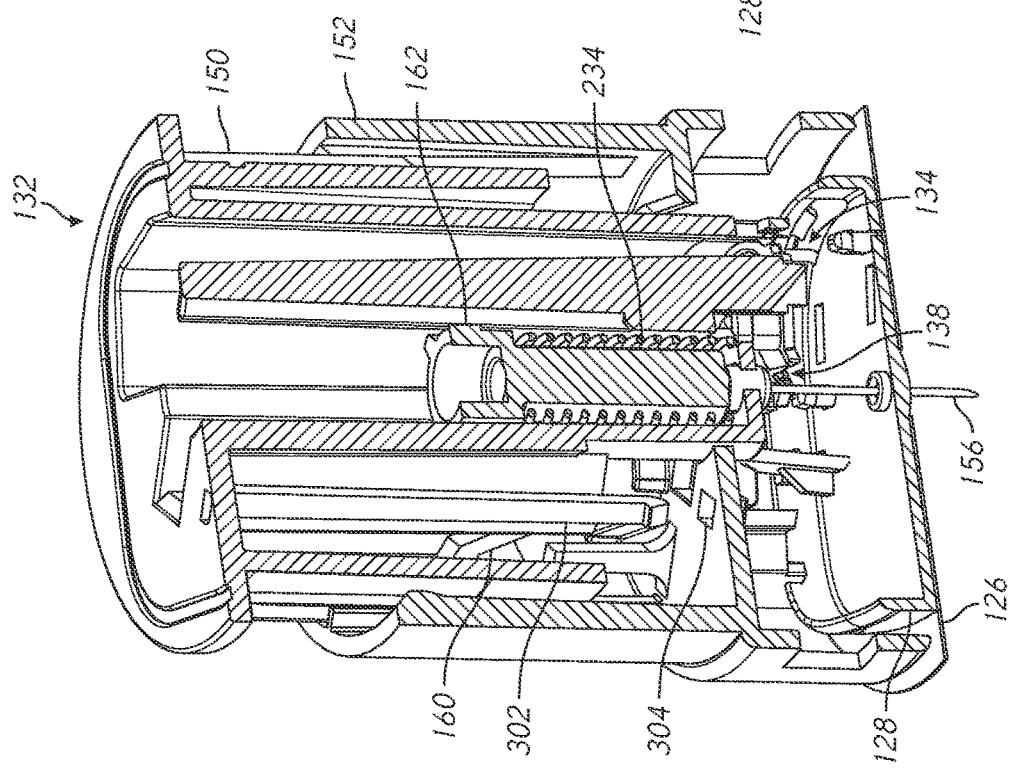
FIG. 33
FIG. 32

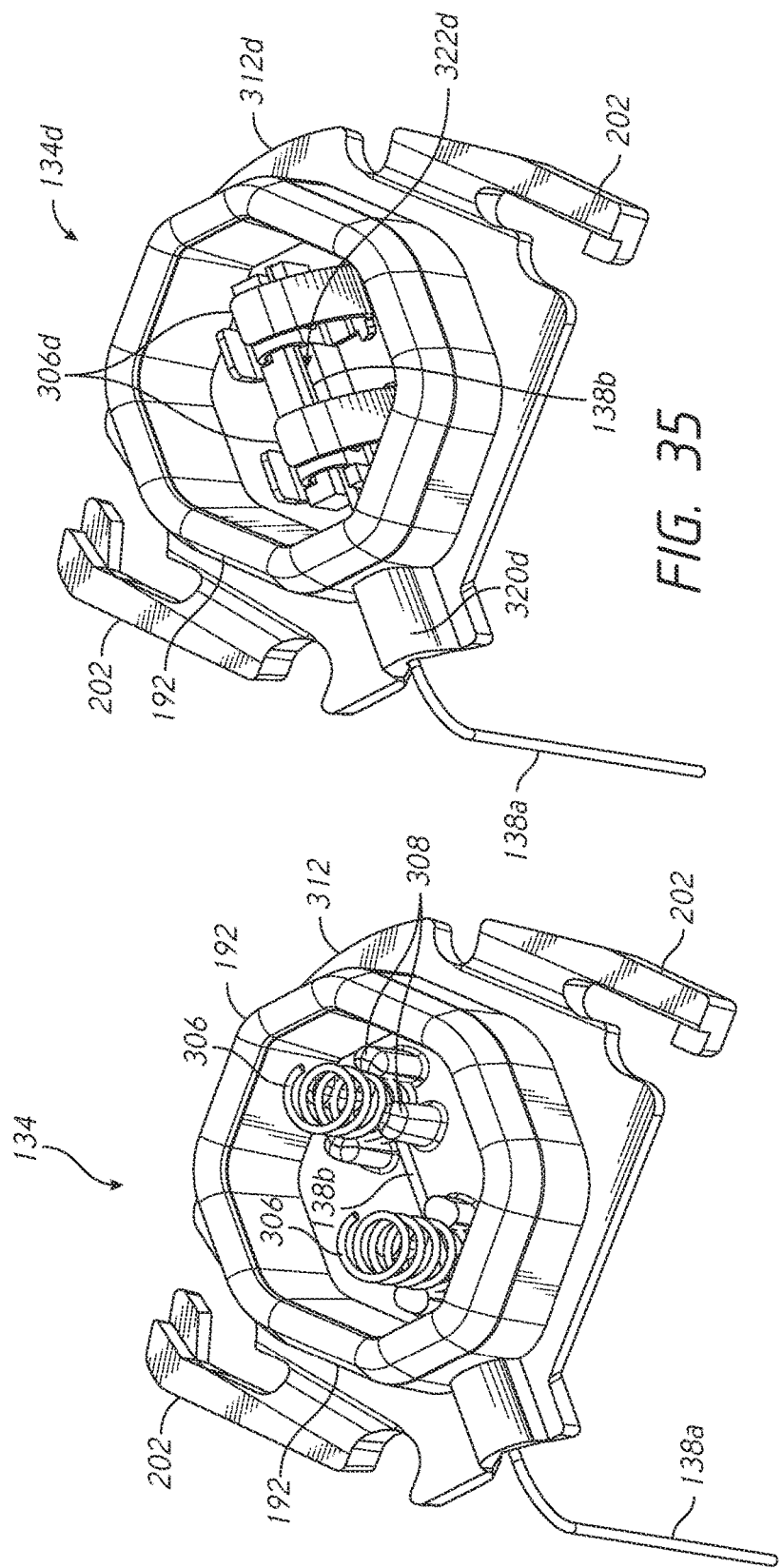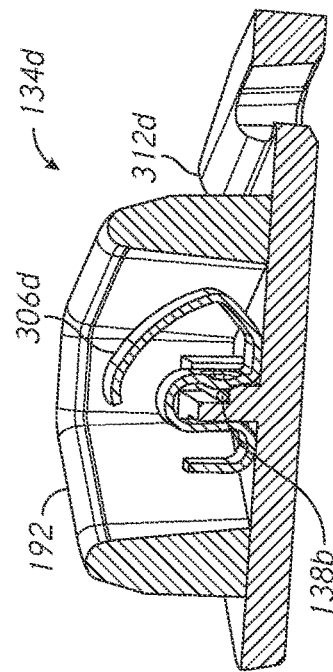
FIG. 34
FIG. 35
FIG. 36

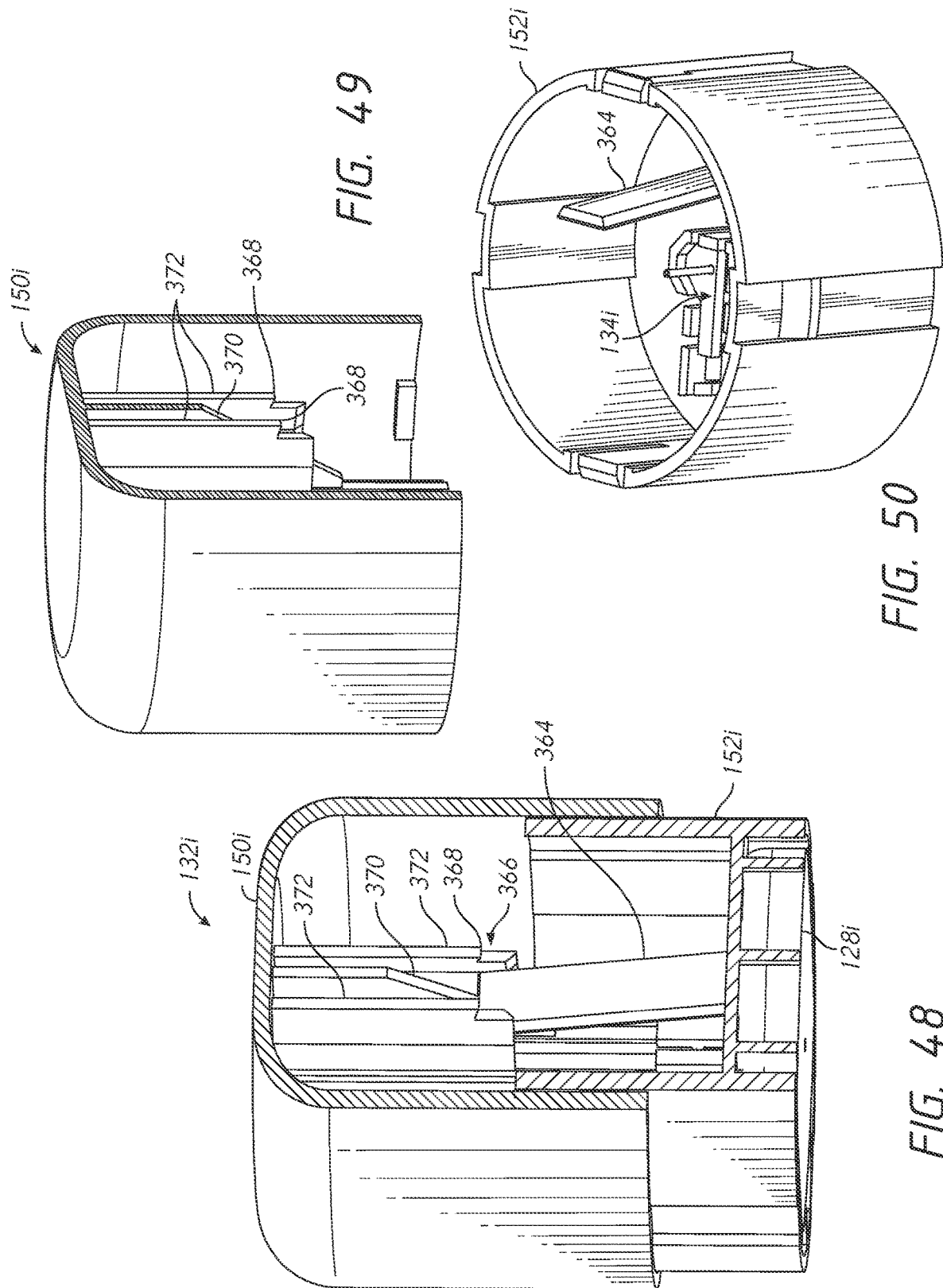

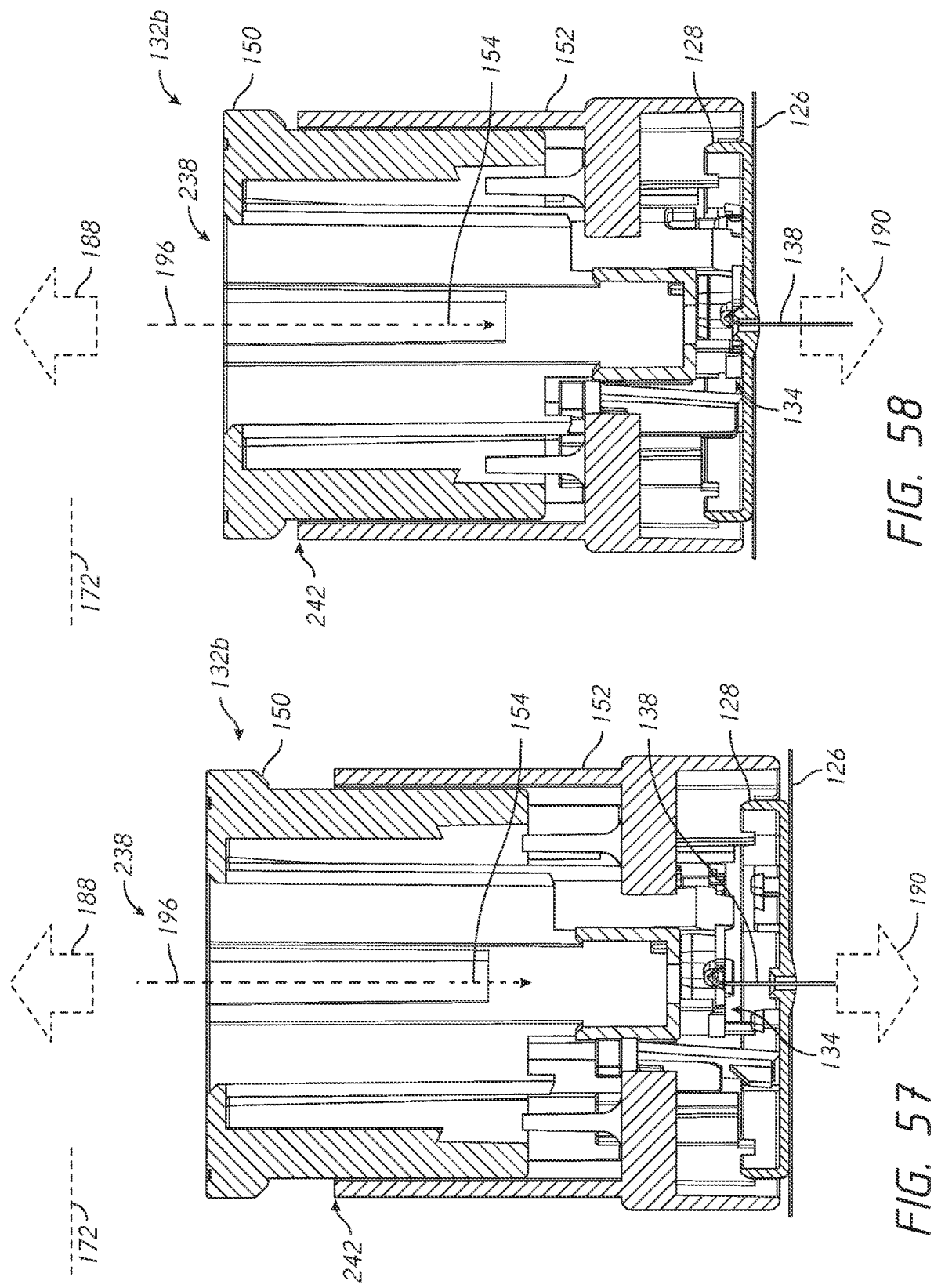

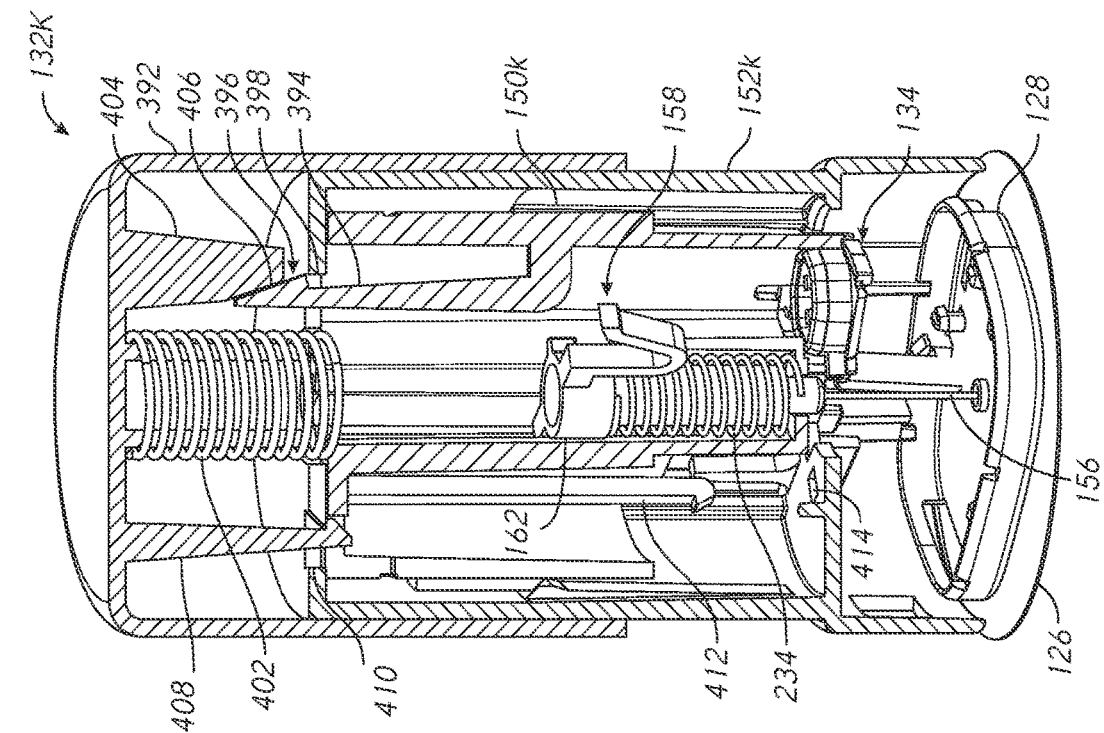
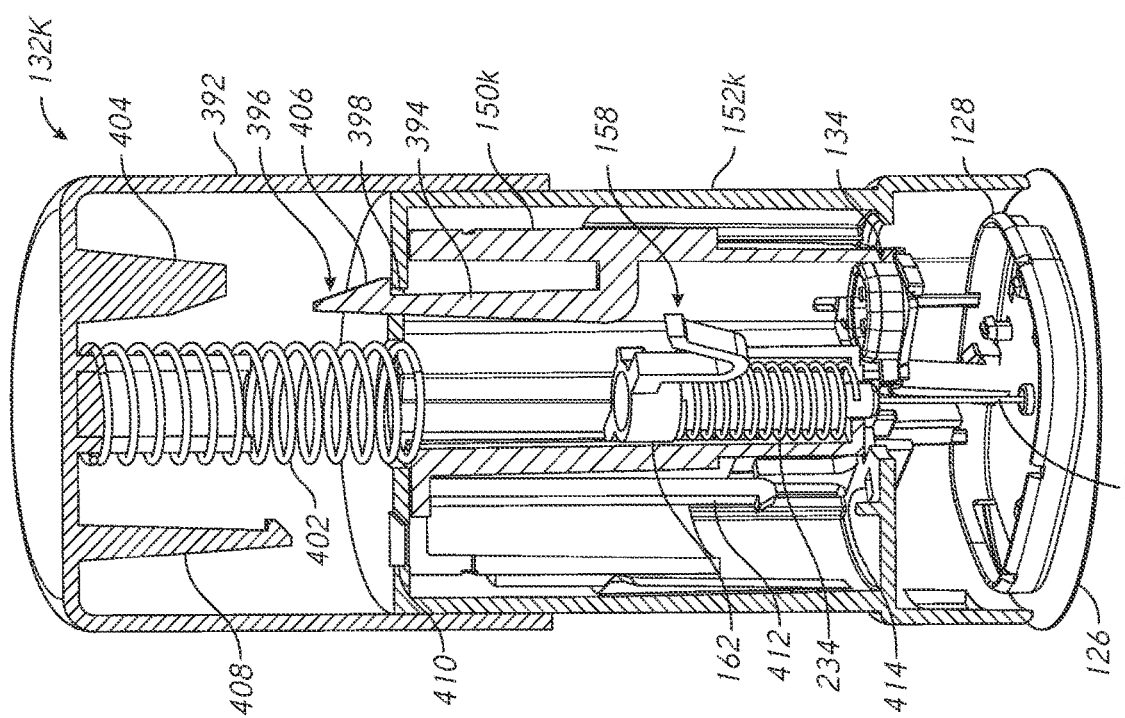

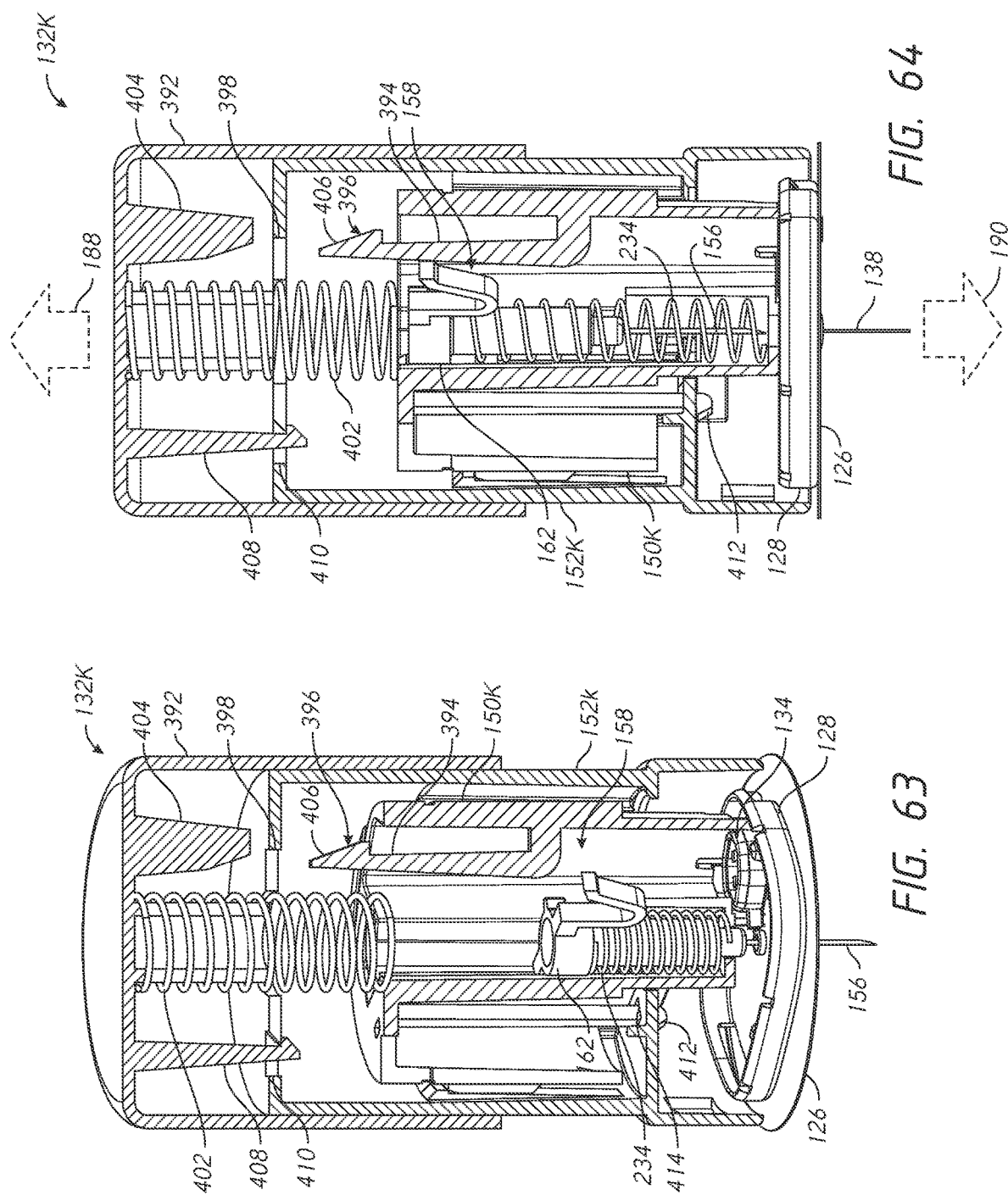

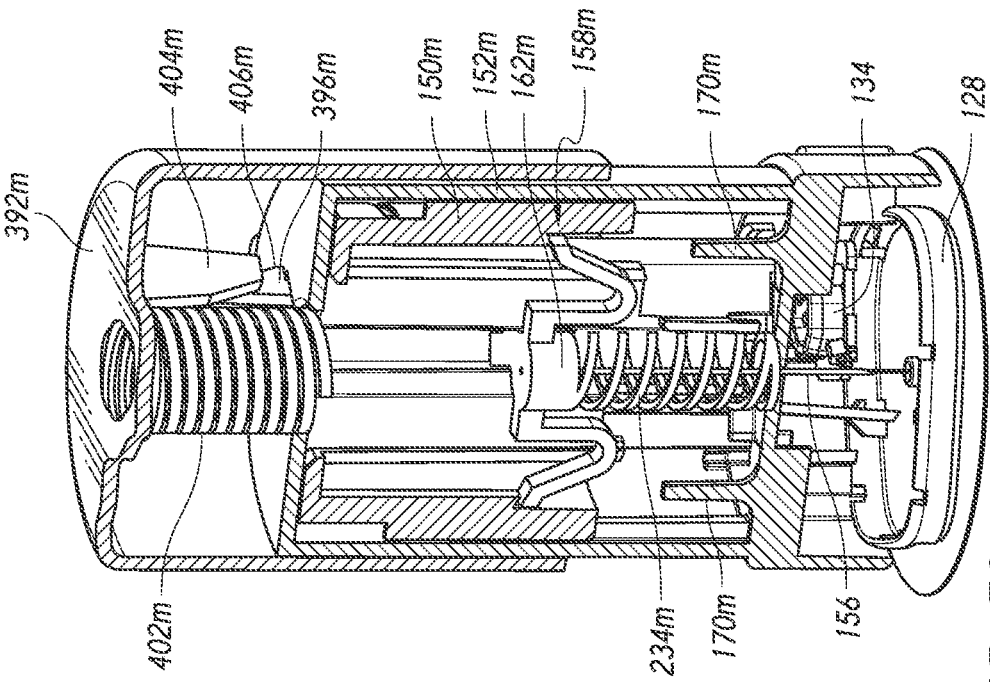
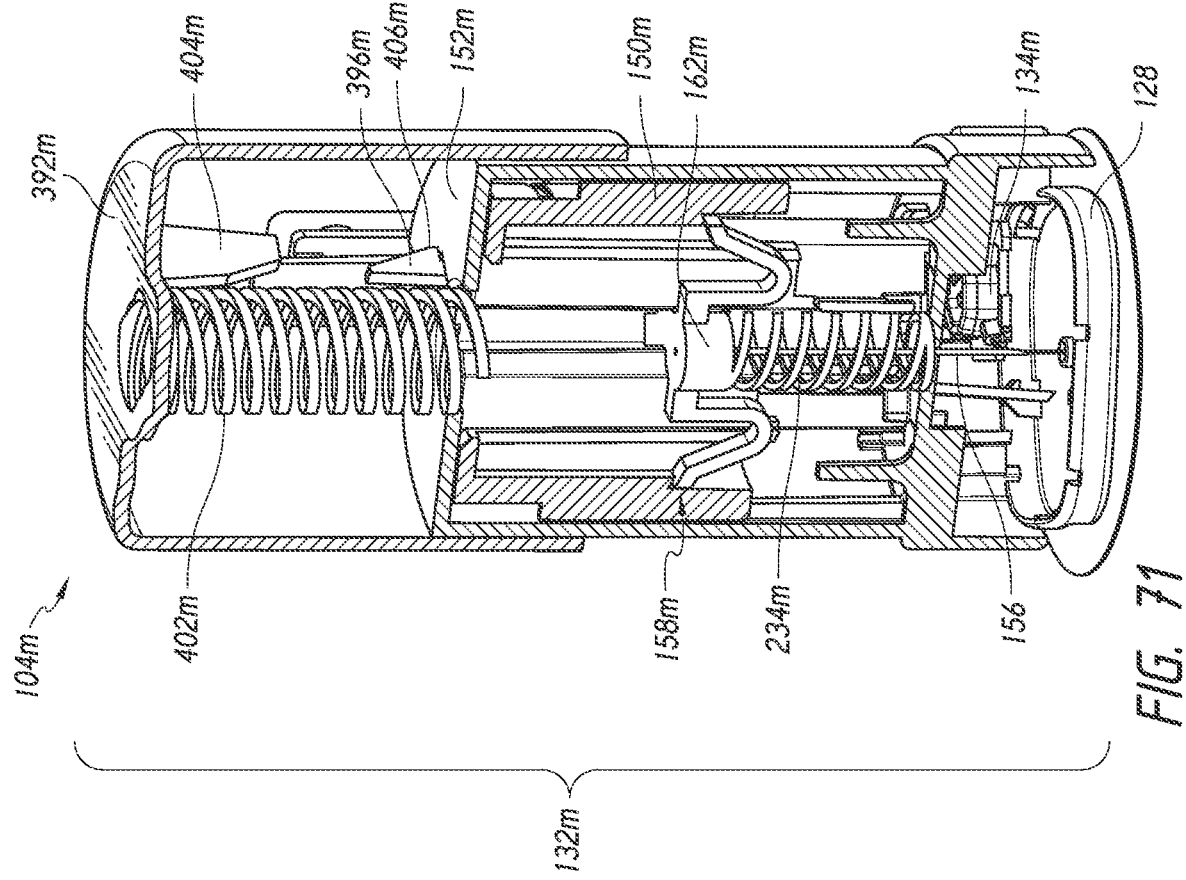
FIG. 71
FIG. 72

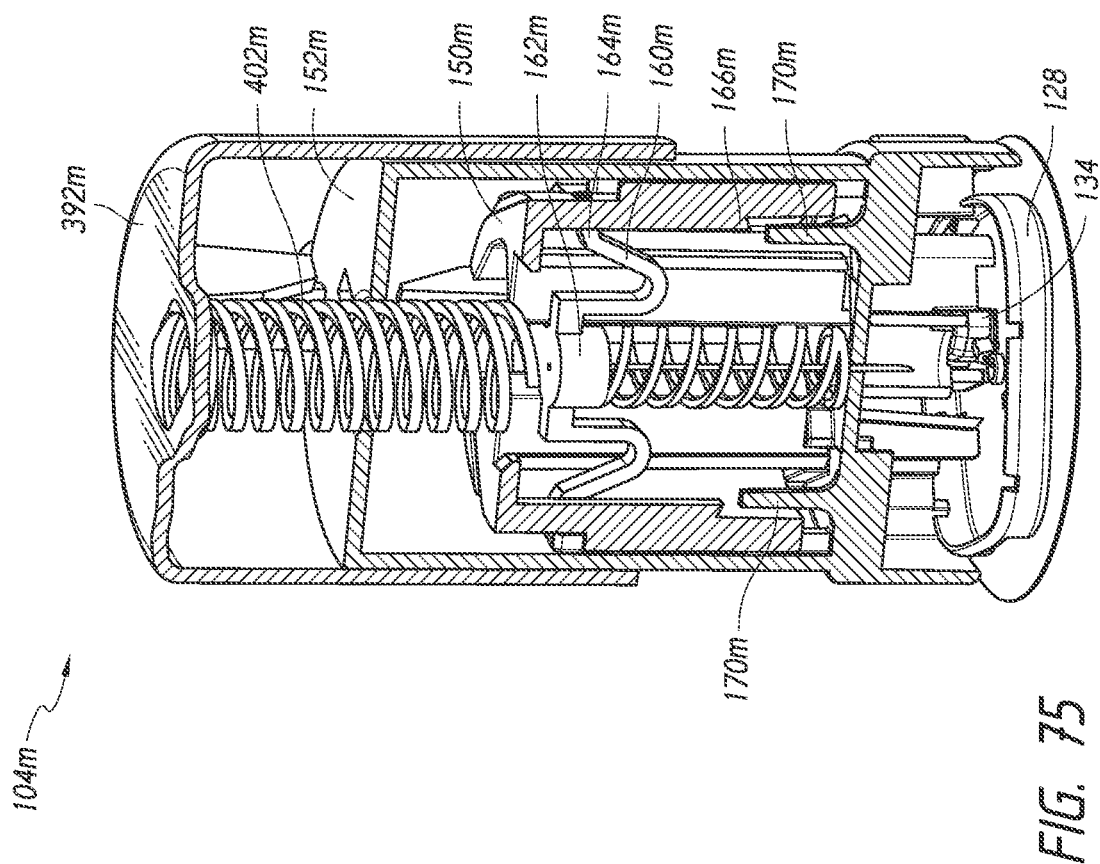

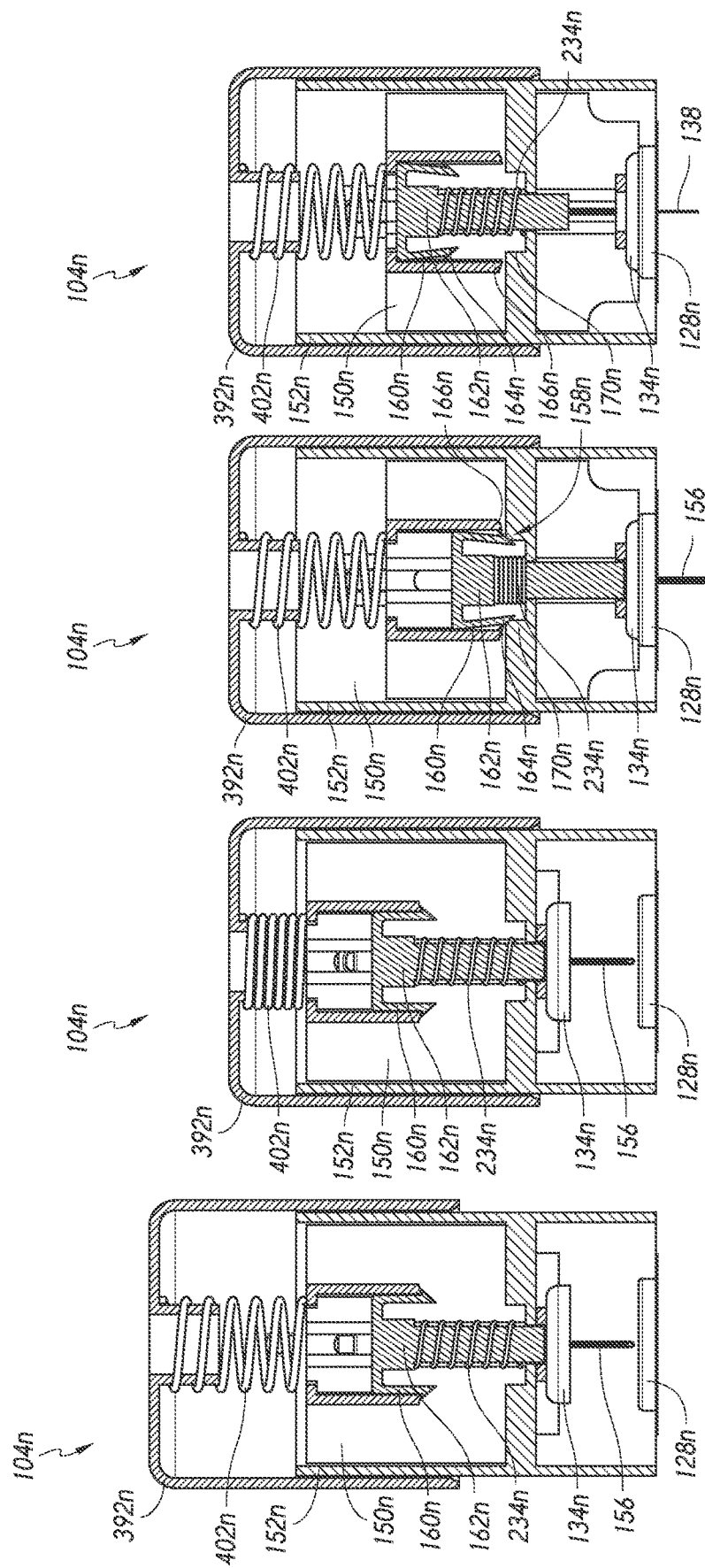

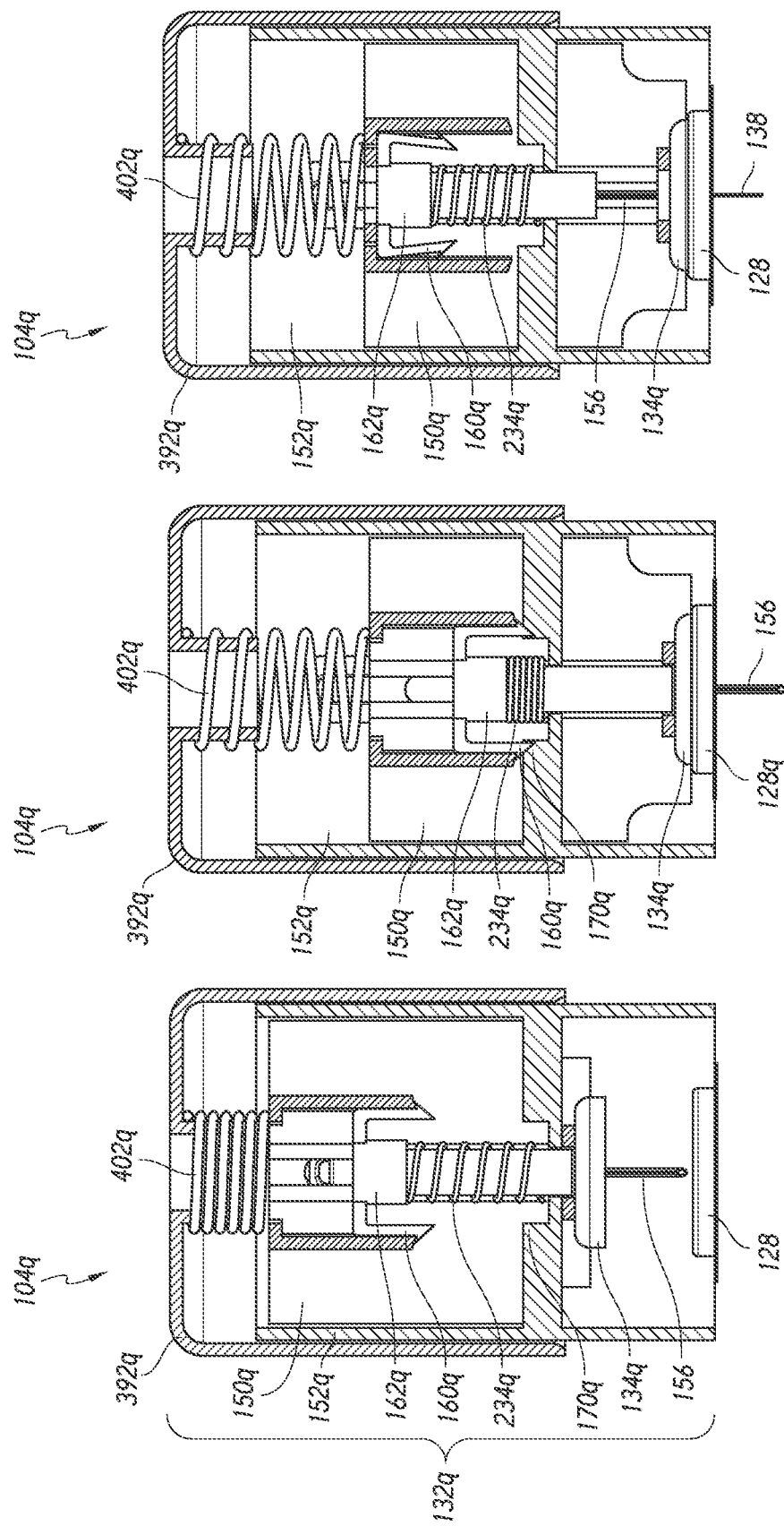

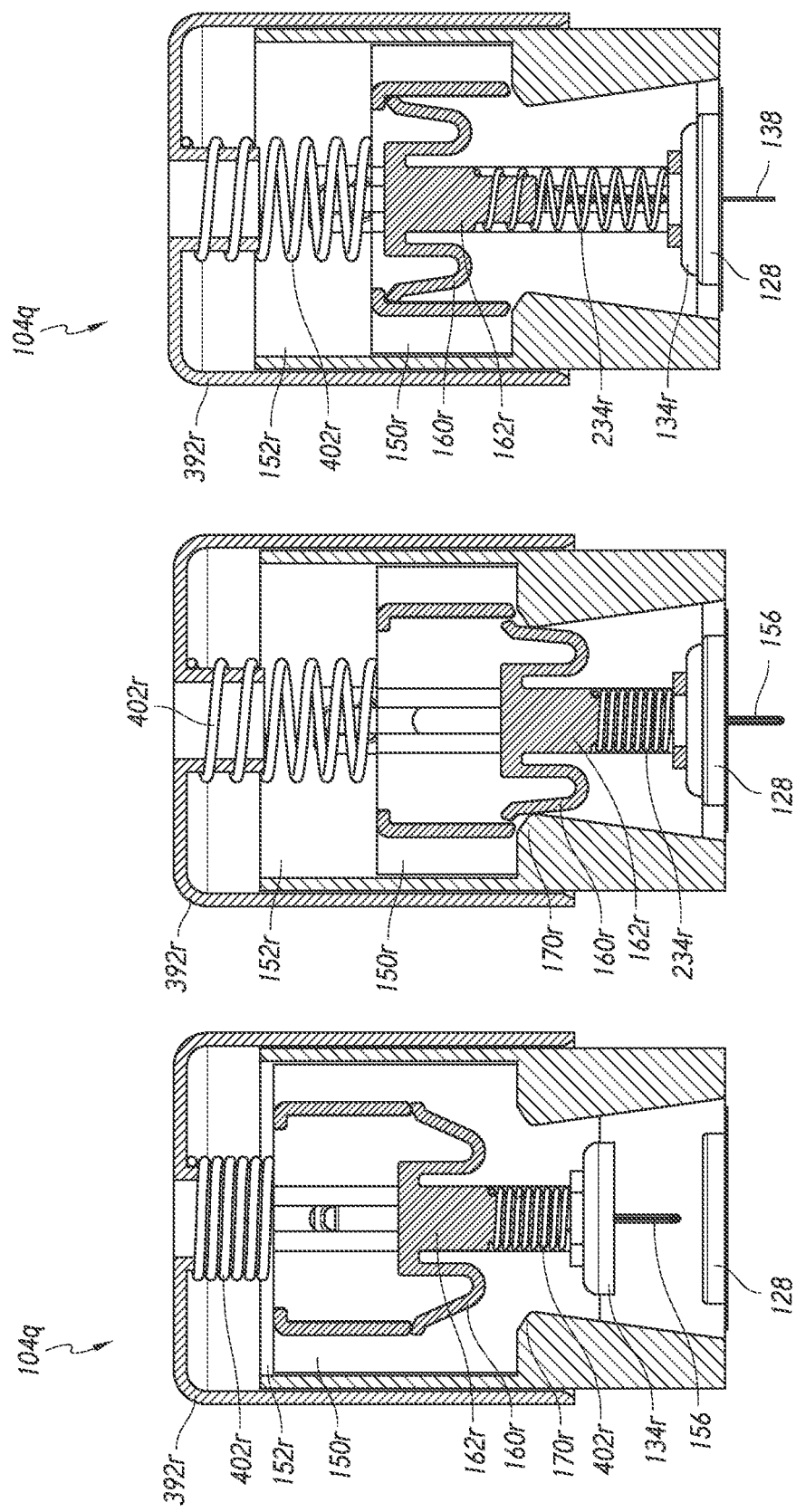

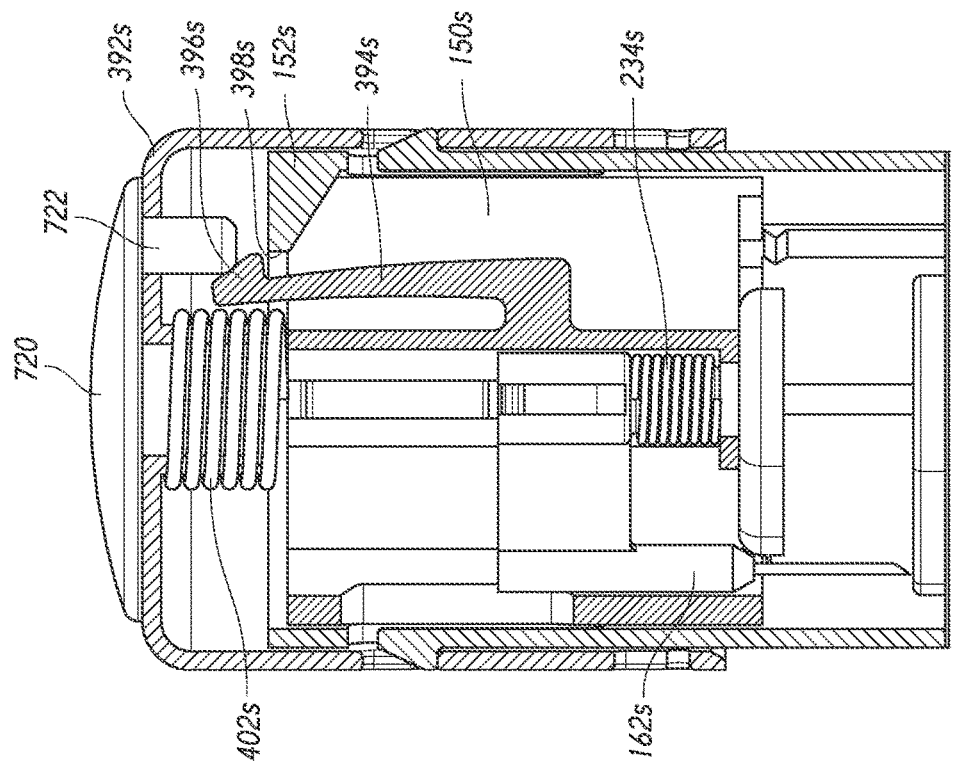
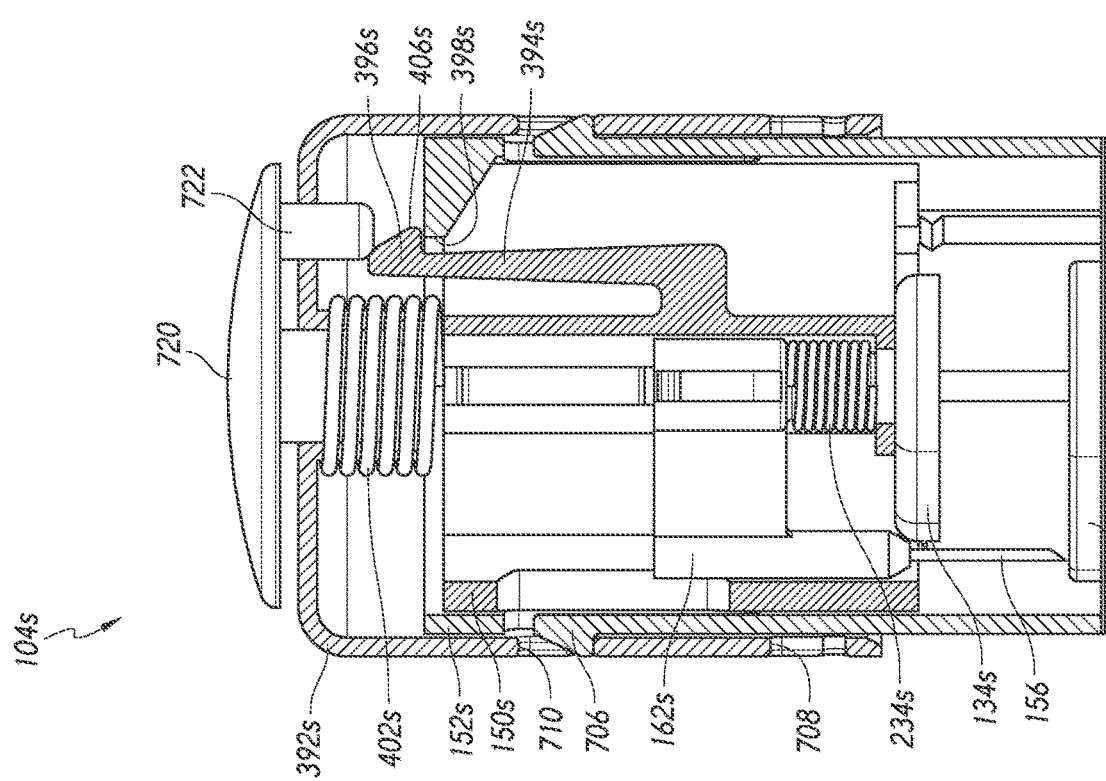

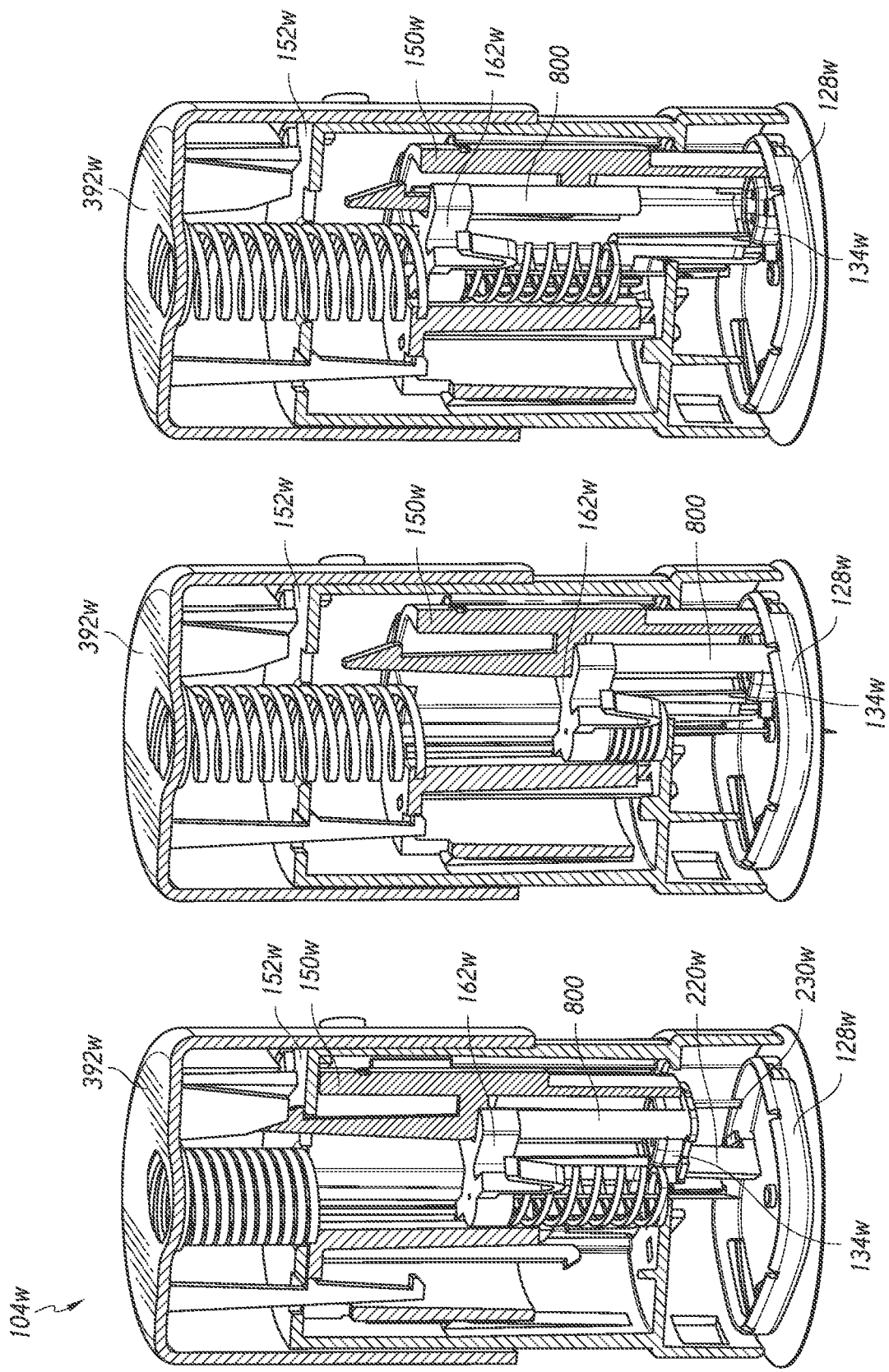

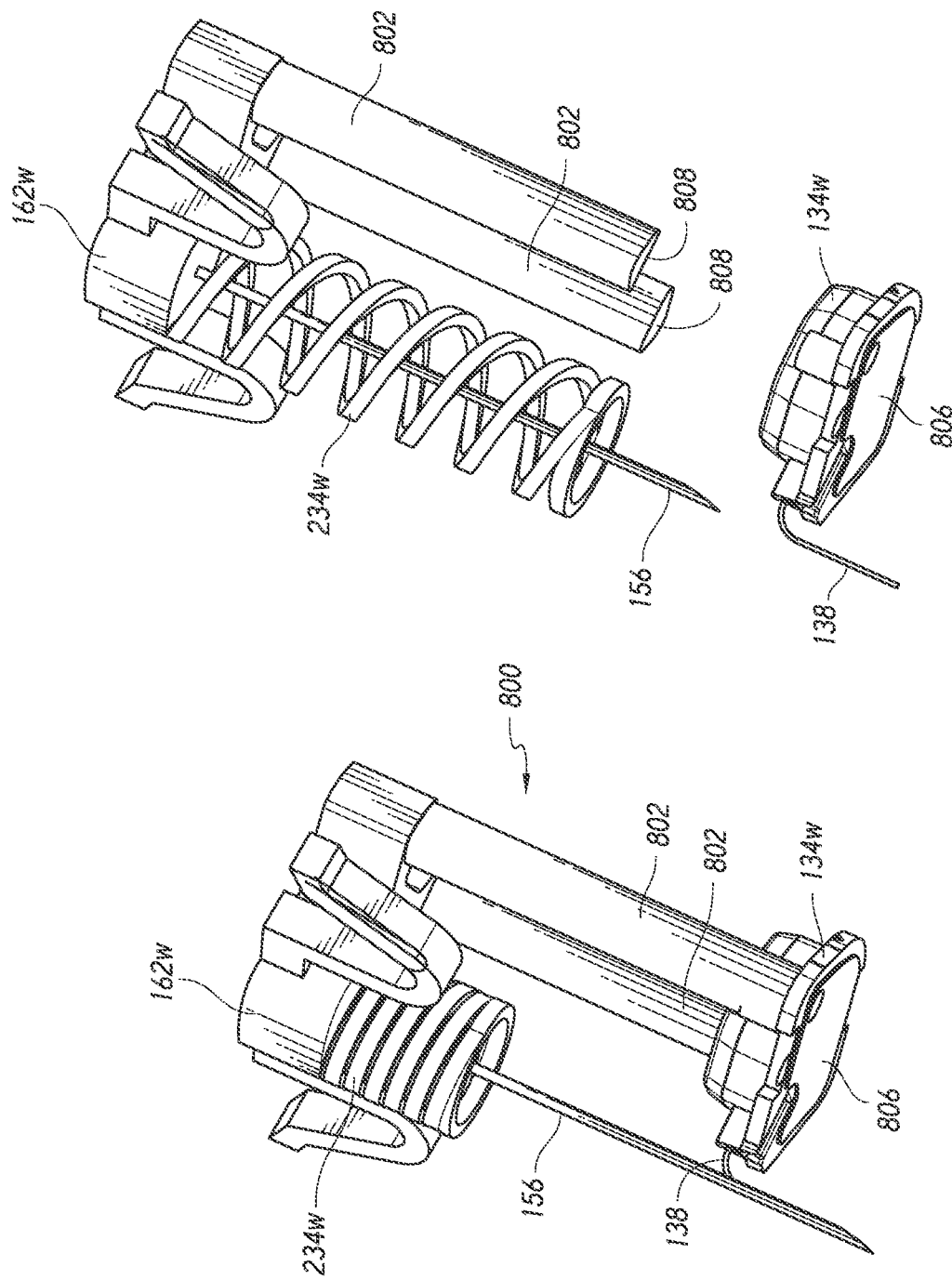

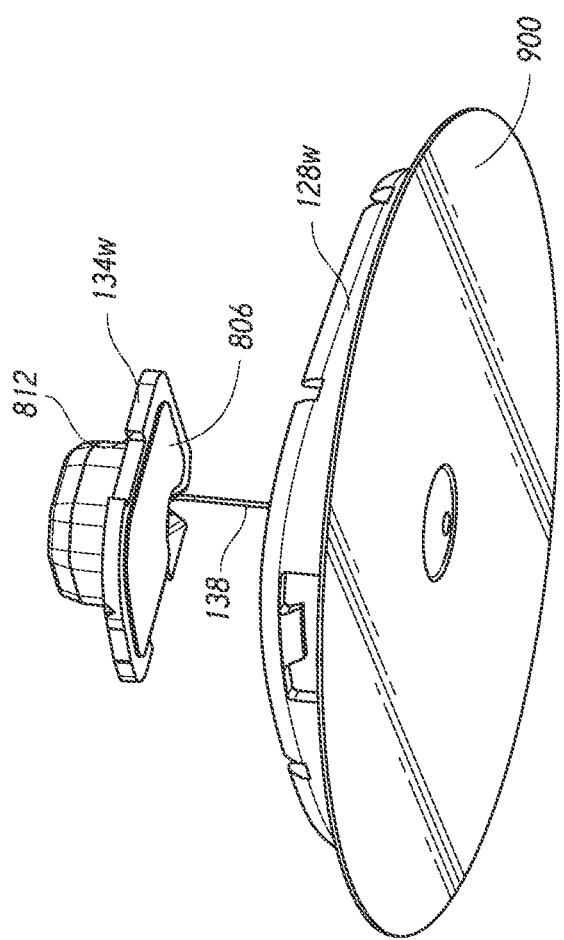
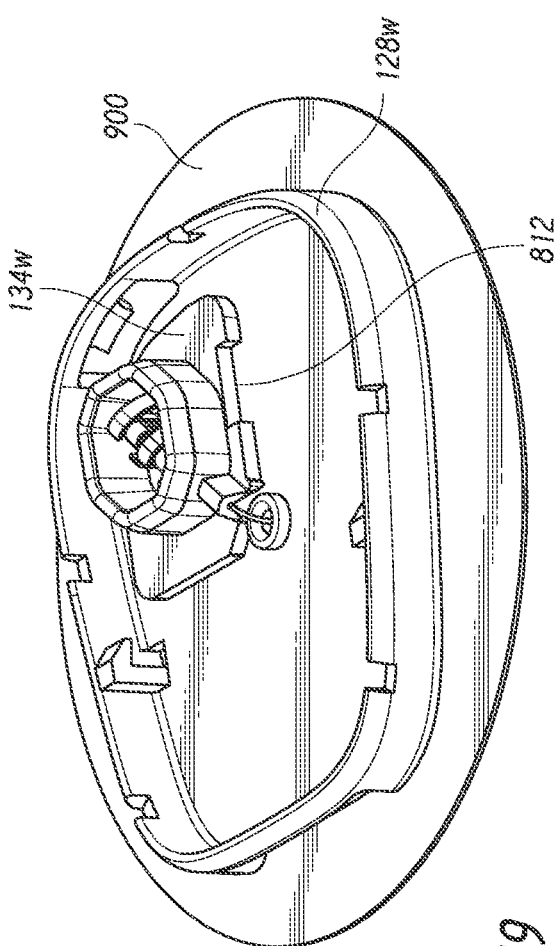

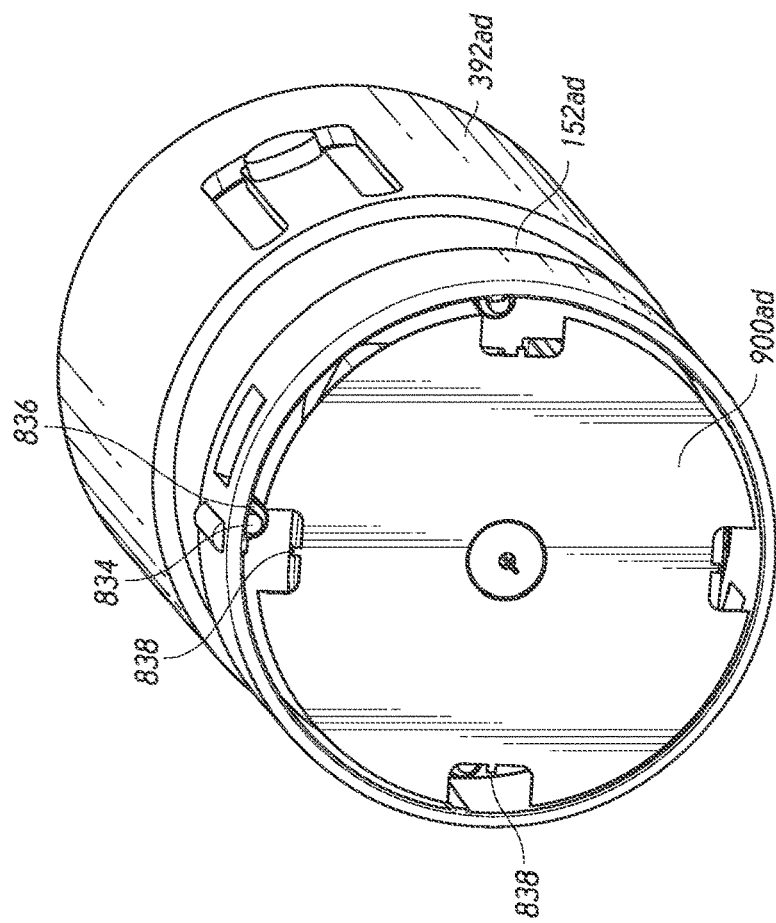
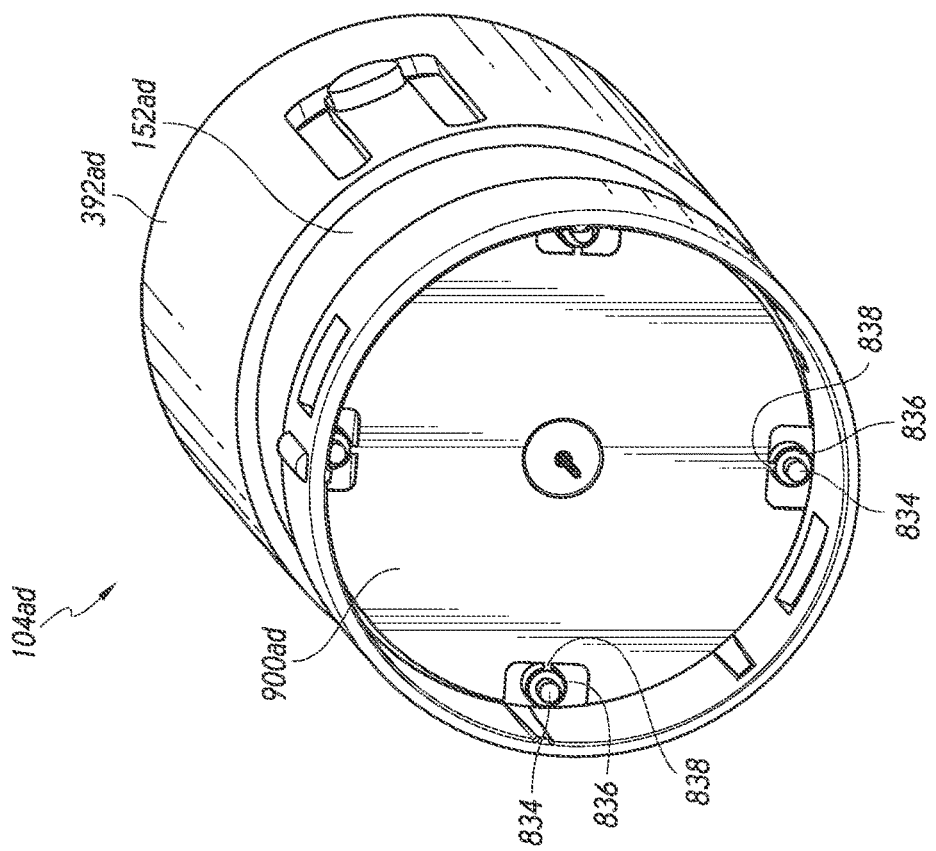

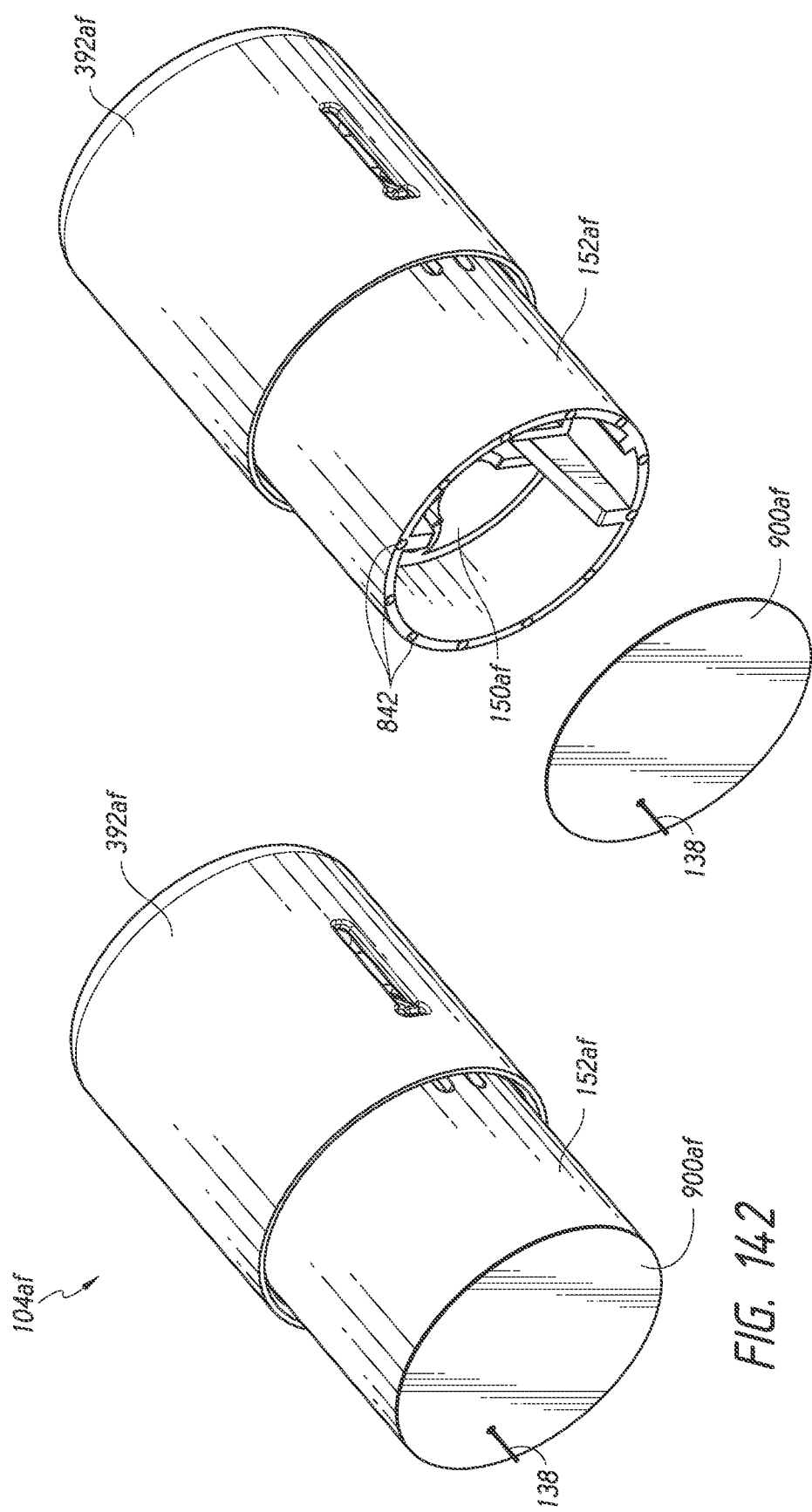

TRANSCUTANEOUS ANALYTE SENSOR SYSTEMS AND METHODS

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/387,088, filed Dec. 21, 2016, which, in turn, claims the benefit of U.S. Provisional Application No. 62/272,983, filed Dec. 30, 2015 and U.S. Provisional Application No. 62/412,100, filed Oct. 24, 2016. Each of the aforementioned applications is incorporated by reference herein in its entirety, and each is hereby expressly made a part of this specification.

FIELD

Various embodiments disclosed herein relate to measuring an analyte in a person. Certain embodiments relate to systems and methods for applying a transcutaneous analyte measurement system to a person.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter which transmits measurement data to a receiver which can process and display information based on the measurements.

The process of applying the sensor to the person is important for such a system to be effective and user friendly. The application process can result in the sensor assembly being attached to the person in a state where it is capable of sensing glucose level information, communicating the glucose level information to the transmitter, and transmitting the glucose level information to the receiver.

The analyte sensor can be placed into subcutaneous tissue. A user can actuate an applicator to insert the analyte sensor into its functional location. This transcutaneous insertion can lead to incomplete sensor insertion, improper sensor insertion, exposed needles, or unnecessary pain. Thus, there is a need for a system that more reliably enables transcutaneous sensor insertion while being easy to use and relatively pain-free.

SUMMARY

Various systems and methods described herein enable reliable, simple, and pain-minimizing transcutaneous insertion of analyte sensors. Some embodiments are a system for applying an on-skin sensor assembly to skin of a host. Systems can comprise a telescoping assembly having a first portion configured to move distally relative to a second portion from a proximal starting position to a distal position along a path; a sensor module coupled to the first portion, the sensor module including a sensor, electrical contacts, and a seal; and/or a base coupled to the second portion such that the base protrudes from a distal end of the system. The base can comprise an adhesive configured to couple the sensor module to the skin. The moving of the first portion to the distal position can couple the sensor module to the base. The sensor can be an analyte sensor; a glucose sensor; any sensor described herein or incorporated by reference; and/or any other suitable sensor.

In some embodiments (i.e., optional and independently combinable with any of the aspects and embodiments identified herein), the sensor module can include a sensor module housing. The sensor module housing can include a first flex arm.

In some embodiments (i.e., optional and independently combinable with any of the aspects and embodiments identified herein), the sensor can be located within the second portion while the base protrudes from the distal end of the system such that the system is configured to couple the sensor to the base via moving the first portion distally relative to the second portion.

In several embodiments (i.e., optional and independently combinable with any of the aspects and embodiments identified herein), the sensor can be coupled to the sensor module while the first portion is located in the proximal starting position.

In some embodiments, a needle is coupled to the first portion (of the telescoping assembly) such that the sensor and the needle move distally relative to the base and relative to the second portion. The system can comprise a needle release mechanism configured to retract the needle proximally.

In several embodiments, the base comprises a distal protrusion having a first hole. The distal protrusion can be configured to reduce a resistance of the skin to piercing. The sensor can pass through the first hole of the distal protrusion.

In some embodiments, a needle having a slot passes through the first hole of the distal protrusion. A portion of the sensor can be located in the slot such that the needle is configured to move distally relative to the base without dislodging the portion of the sensor from the slot.

In several embodiments, the distal protrusion is convex such that the distal protrusion is configured to tension the skin while the first portion moves distally relative to the second portion to prepare the skin for piercing. The distal protrusion can be shaped like a dome.

In some embodiments, the adhesive comprises a second hole. The distal protrusion can be located at least partially within the second hole such that the distal protrusion can tension at least a portion of the skin beneath the second hole.

In several embodiments, the adhesive covers at least a majority of the distal protrusion. The adhesive can cover at zero percent, at least 30 percent, at least 70 percent, and/or less than 80 percent of the distal protrusion. The distal protrusion can protrude at least 0.5 millimeters, less than 3 millimeters, and/or less than 5 millimeters.

In some embodiments, a sensor module is coupled to the first portion and is located at least 3 millimeters and/or at least 5 millimeters from the base while the first portion is in the proximal starting position. The system can be configured such that moving the first portion to the distal position couples the sensor module to the base.

In several embodiments, the sensor is already coupled to the sensor module while the first portion is located in the proximal starting position. For example, the sensor can be coupled to the sensor module at the factory (e.g., prior to the user opening a sterile barrier). The sensor can be located within the second portion while the base protrudes from the distal end of the system.

In some embodiments, the sensor is coupled to a sensor module. During a first portion of the path, the sensor module can be immobile relative to the first portion, and the base can be immobile relative to the second portion. During a second portion of the path, the system can be configured to move the first portion distally relative to the second portion to move the sensor module towards the base, couple the sensor module to the base, and/or enable the coupled sensor module and the base to detach from the telescoping assembly.

In several embodiments, a sensor module is coupled to the sensor. The system comprises a vertical central axis oriented from a proximal end to the distal end of the system. The sensor module can comprise a first flex arm that is oriented horizontally and is coupled to the base. The first flex arm can extend from an outer perimeter of the sensor module.

In some embodiments, the base comprises a first proximal protrusion coupled to the first flex arm to couple the sensor module to the base. A first horizontal locking protrusion can be coupled to an end portion of the first flexible arm. A second horizontal locking protrusion can be coupled to the first proximal protrusion of the base. The first horizontal locking protrusion can be located distally under the second horizontal locking protrusion to secure the sensor module to the base. The system can be configured such that moving the first portion of the telescoping assembly to the distal position causes the first flex arm to bend to enable the first horizontal locking protrusion to move distally relative to the second horizontal locking protrusion.

In several embodiments, the base comprises a second proximal protrusion coupled to a second flex arm of the sensor module. The first flex arm can be located on an opposite side of the sensor module relative to the second flex arm.

In some embodiments, a sensor module is coupled to the sensor. The system can comprise a vertical central axis oriented from a proximal end to the distal end of the system. The base can comprise a first flex arm that is oriented horizontally and is coupled to the sensor module. The sensor module can comprise a first distal protrusion coupled to the first flex arm to couple the sensor module to the base.

In several embodiments, a first horizontal locking protrusion is coupled to an end portion of the first flexible arm, a second horizontal locking protrusion is coupled to the first distal protrusion of the sensor module, and the second horizontal locking protrusion is located distally under the first horizontal locking protrusion to secure the sensor module to the base. The system can be configured such that moving the first portion of the telescoping assembly to the distal position causes the first flex arm to bend to enable the second horizontal locking protrusion to move distally relative to the first horizontal locking protrusion.

In some embodiments, the sensor module comprises a second distal protrusion coupled to a second flex arm of the base. The first distal protrusion can be located on an opposite side of the sensor module relative to the second distal protrusion.

In several embodiments, a sensor module is coupled to the sensor. The first portion can comprise a first flex arm and a second flex arm that protrude distally and latch onto the sensor module to releasably secure the sensor module to the first portion while the first portion is in the proximal starting position. The sensor module can be located remotely from the base while the first portion is in the proximal starting position (e.g., such that the sensor module does not touch the base).

In some embodiments, the sensor module is located within the second portion while the base protrudes from the distal end of the system such that the system is configured to couple the sensor module to the base via moving the first portion distally relative to the second portion.

In several embodiments, the system comprises a vertical central axis oriented from a proximal end to the distal end of the system. The first and second flex arms of the first portion can secure the sensor module to the first portion such that the sensor module is releasably coupled to the first portion with a first vertical holding strength. The sensor module can comprise a third flex arm coupled with a first proximal protrusion of the base such that the sensor module is coupled to the base with a second vertical holding strength.

In some embodiments, the second vertical holding strength is greater than the first vertical holding strength such that continuing to push the first portion distally once the sensor module is coupled to the base overcomes the first and second flex arms of the first portion to detach the sensor module from the first portion. The third flex arm can extend from an outer perimeter of the sensor module.

In several embodiments, the base protrudes from the distal end of the system while the first portion of the telescoping assembly is located in the proximal starting position and the sensor is located remotely relative to the base such that the system is configured to couple the sensor to the base via moving the first portion distally relative to the second portion. The base can comprise a first radial protrusion releasably coupled with a first vertical holding strength to a second radial protrusion of the second portion of the telescoping assembly.

In some embodiments, the first radial protrusion protrudes inward and the second radial protrusion protrudes outward. The system can be configured such that moving the first portion to the distal position moves the second radial protrusion relative to the first radial protrusion to detach the base from the telescoping assembly.

In several embodiments, the first portion of the telescoping assembly comprises a first arm that protrudes distally, the second portion of the telescoping assembly comprises a second flex arm that protrudes distally, and the system is configured such that moving the first portion from the proximal starting position to the distal position along the path causes the first arm to deflect the second flex arm and thereby detach the second flex arm from the base to enable the base to decouple from the telescoping assembly. When the first portion is in the proximal starting position, the first arm of the first portion can be at least partially vertically aligned with the second flex arm of the second portion to enable the first arm to deflect the second flex arm as the first portion is moved to the distal position.

In some embodiments, when the first portion is in the proximal starting position, at least a section of the first arm is located directly over the second flex arm to enable the first arm to deflect the second flex arm as the first portion is moved to the distal position.

In several embodiments, the second flex arm comprises a first horizontal protrusion, and the base comprises a second horizontal protrusion latched with the first horizontal protrusion to couple the base to the second portion of the telescoping assembly. The first arm of the first portion can deflect the second flex arm of the second portion to unlatch the base from the second portion of the telescoping assembly.

In some embodiments, the system is configured to couple the sensor to the base at a first position, and the system is configured to detach the base from the telescoping assembly at a second position that is distal relative to the first position.

In several embodiments, a third flex arm couples the sensor to the base at a first position, the second flex arm detaches from the base at a second position, and the second position is distal relative to the first position such that the system is configured to secure the base to the telescoping assembly until after the sensor is secured to the base.

In some embodiments, the base protrudes from the distal end of the system while the first portion of the telescoping assembly is located in the proximal starting position and the sensor is located remotely relative to the base. The system can further comprise a spring configured to retract a needle. The needle can be configured to facilitate inserting the sensor into the skin. When the first portion is in the proximal starting position, the spring can be in a first compressed state. The system can be configured such that moving the first portion distally from the proximal starting position further increases a compression of the spring. The first compressed state places the first and second portions in tension.

In several embodiments, a system is configured to apply an on-skin sensor assembly to the skin of a host (i.e., a person). The system can include a telescoping assembly having a first portion configured to move distally relative to a second portion from a proximal starting position to a distal position along a path; a sensor coupled to the first portion; and/or a latch configurable to impede a needle from moving proximally relative to the first portion. The sensor can be an analyte sensor; a glucose sensor; any sensor described herein or incorporated by reference; and/or any other suitable sensor.

In some embodiments, the first portion is releasably secured in the proximal starting position by a securing mechanism that impedes moving the first portion distally relative to the second portion. The system can be configured such that prior to reaching the distal position, moving the first portion distally relative to the second portion releases the latch thereby causing the needle to retract proximally into the system. The system can be configured such that moving the first portion distally relative to the second portion (e.g., moving the first portion to the distal position) releases the latch thereby causing the needle to retract proximally into the system. The securing mechanism can be an interference between the first portion and the second portion of the telescoping assembly.

In several embodiments, a first force profile is measured along the path. The first force profile can comprise a first magnitude coinciding with overcoming the securing mechanism; a third magnitude coinciding with releasing the latch; and a second magnitude coinciding with an intermediate portion of the path that is distal relative to overcoming the securing mechanism and proximal relative to releasing the latch.

In some embodiments, the second magnitude is less than the first and third magnitudes such that the system is configured to promote needle acceleration during the intermediate portion of the path to enable a suitable needle speed (e.g., a sufficiently high needle speed) at a time the needle first pierces the skin.

In several embodiments, the first magnitude is at least 100 percent greater than the second magnitude. The first magnitude can be greater than the third magnitude such that the system is configured to impede initiating a sensor insertion cycle unless a user is applying enough force to release the latch. The first magnitude can be at least 50 percent greater than the third magnitude.

In some embodiments, an intermediate portion of the path is distal relative to overcoming the securing mechanism and proximal relative to releasing the latch. The system can further comprise a second force profile coinciding with the intermediate portion of the path. A proximal millimeter of the second force profile can comprise a lower average force than a distal millimeter of the second force profile in response to compressing a spring configured to enable the system to retract the needle into the telescoping assembly.

In several embodiments, a first force profile is measured along the path. The first force profile can comprise a first average magnitude coinciding with moving distally past a proximal half of the securing mechanism and a second average magnitude coinciding with moving distally past a distal half of the securing mechanism. The first average magnitude can be greater than the second average magnitude such that the system is configured to impede initiating a sensor insertion cycle unless a user is applying enough force to complete the sensor insertion cycle (e.g., drive the needle and/or the sensor to the intended insertion depth).

In some embodiments, a first force peak (coinciding with moving distally past the proximal half of the securing mechanism) is at least 25 percent higher than the second average magnitude.

In several embodiments, a first force profile is measured along the path. The first force profile can comprise a first magnitude coinciding with overcoming the securing mechanism and a subsequent magnitude coinciding with terminating the securing mechanism. The first magnitude can comprise a proximal vector and the subsequent magnitude can comprise a distal vector.

In some embodiments, the securing mechanism can comprise a radially outward protrusion extending from the first portion. The radially outward protrusion can be located proximally relative to a proximal end of the second portion while the telescoping assembly is in the proximal starting position. The radially outward protrusion can be configured to cause the second portion to deform elliptically to enable the first portion to move distally relative to the second portion.

In several embodiments, the securing mechanism comprises a radially outward protrusion of the first portion that interferes with a radially inward protrusion of the second portion such that the securing mechanism is configured to cause the second portion to deform elliptically to enable the first portion to move distally relative to the second portion.

In some embodiments, the needle is retractably coupled to the first portion by a needle holder configured to resist distal movement of the first portion relative to the second portion. The securing mechanism can comprise a flexible arm of the second portion. The flexible arm can be releasably coupled to the needle holder to releasably secure the first portion to the second portion in the proximal starting position.

In several embodiments, the securing mechanism comprises a frangible coupling between the first portion and the second portion while the first portion is in the proximal starting position. The system can be configured such that moving the first portion to the distal position breaks the frangible coupling.

In some embodiments, the securing mechanism comprises a magnet that releasably couples the first portion to the second portion while the first portion is in the proximal starting position. The magnet can be attracted to a metal element coupled to the first portion or the second portion of the telescoping assembly.

In several embodiments, an electric motor drives the first portion distally relative to the second portion. The electric motor can be configured to move the needle in the skin.

In some embodiments, an on-skin sensor system is configured for transcutaneous glucose monitoring of a host. The system can comprise a sensor module housing, in which the sensor module housing can include a first flex arm; a sensor having a first section configured for subcutaneous sensing and a second section mechanically coupled to the sensor module housing; an electrical interconnect mechanically coupled to the sensor module housing and electrically coupled to the sensor; and/or a base coupled to the first flex arm of the sensor module housing. The base can have an adhesive configured to couple the base to the skin of the host. The sensor can be an analyte sensor; a glucose sensor; any sensor described herein or incorporated by reference; and/or any other suitable sensor.

In several embodiments, the electrical interconnect comprises a spring. The spring can comprise a conical portion and/or a helical portion.

In some embodiments, the sensor module housing comprises at least two proximal protrusions located around a perimeter of the spring. The proximal protrusions can be configured to help orient the spring. A segment of the sensor can be located between the proximal protrusions.

In several embodiments, the sensor module housing is mechanically coupled to a base having an adhesive configured to couple the base to skin of the host.

In some embodiments, the proximal protrusions orient the spring such that coupling an electronics unit to the base presses the spring against a first electrical contact of the electronics unit and a second electrical contact of the sensor to electrically couple the sensor to the electronics unit.

In several embodiments, the sensor module housing comprises a first flex arm that is oriented horizontally and is coupled to the base. The first flex arm can extend from an outer perimeter of the sensor module housing. The base can comprise a first proximal protrusion coupled to the first flex arm to couple the sensor module housing to the base.

In some embodiments, the electrical interconnect comprises a leaf spring, which can include one metal layer or multiple metal layers. The leaf spring can be a cantilever spring.

In some embodiments, the sensor module housing comprises a proximal protrusion having a channel in which at least a portion of the second section of the sensor is located. The channel can position a first area of the sensor such that the first area is electrically coupled to the leaf spring.

In some embodiments, the leaf spring arcs away from the first area and protrudes proximally to electrically couple with an electronics unit. At least a portion of the leaf spring can form a "W" shape. At least a portion of the leaf spring forms a "C" shape.

In several embodiments, the leaf spring bends around the proximal protrusion. The leaf spring can bend at least 120 degrees and/or at least 160 degrees around the proximal protrusion. The leaf spring can protrude proximally to electrically couple with an electronics unit.

In some embodiments, a seal is configured to impede fluid ingress to the leaf spring. The sensor module housing can be mechanically coupled to a base. The base can have an adhesive configured to couple the base to skin of the host.

In several embodiments, the leaf spring is oriented such that coupling an electronics unit to the base presses the leaf spring against a first electrical contact of the electronics unit and against a second electrical contact of the sensor to electrically couple the sensor to the electronics unit. A proximal height of the seal can be greater than a proximal height of the leaf spring such that the electronics unit contacts the seal prior to contacting the leaf spring.

In some embodiments, the sensor module housing comprises a first flex arm that is oriented horizontally and is coupled to the base. The first flex arm can extend from an outer perimeter of the sensor module housing. The base can comprise a first proximal protrusion coupled to the first flex arm to couple the sensor module housing to the base.

In several embodiments, the sensor module housing comprises a channel in which at least a portion of the second section of the sensor is located. A distal portion of the leaf spring can be located in the channel such that a proximal portion of the leaf spring protrudes proximally out the channel. The sensor module housing can comprise a groove that intersects the channel. The leaf spring can comprise a tab located in the groove to impede rotation of the leaf spring.

In some embodiments, the sensor module housing is mechanically coupled to a base that has an adhesive configured to couple the base to skin of the host. The sensor module housing can comprise a first flex arm that is oriented horizontally and is coupled to the base. The first flex arm can extend from an outer perimeter of the sensor module housing. The base can comprises a first proximal protrusion coupled to the first flex arm to couple the sensor module housing to the base.

In several embodiments, electrical interconnects (such as springs or other types of interconnects) comprises a resistance of less than 100 ohms and/or less than 5 ohms. Electrical interconnects can comprise a compression force of less than one pound over an active compression range.

In some embodiments, electrical interconnects may require a compression force of less than one pound to compress the spring 20 percent from a relaxed position, which is a substantially uncompressed position. In some embodiments, electrical interconnects may require a compression force of less than one pound to compress the spring 25 percent from a relaxed position, which is a substantially uncompressed position. In some embodiments, electrical interconnects may require a compression force of less than one pound to compress the spring 30 percent from a relaxed position, which is a substantially uncompressed position. In some embodiments, electrical interconnects may require a compression force of less than one pound to compress the spring 50 percent from a relaxed position, which is a substantially uncompressed position.

In several embodiments, the spring is configured such that compressing the spring 25 percent from a relaxed position requires a force of at least 0.05 pounds and less than 0.5 pounds, and requires moving an end of the spring at least 0.1 millimeter and less than 1.1 millimeter.

In some embodiments, a system for applying an on-skin sensor assembly to a skin of a host comprises a telescoping assembly having a first portion configured to move distally relative to a second portion from a proximal starting position to a distal position along a path; a sensor coupled to the first portion; and a base comprising adhesive configured to couple the sensor to the skin. The telescoping assembly can further comprise a third portion configured to move distally relative to the second portion.

In some embodiments, a first spring is positioned between the third portion and the second portion such that moving the third portion distally relative to the second portion compresses the first spring. In the proximal starting position of the telescoping assembly, the first portion can be locked to the second portion. The system can be configured such that moving the third portion distally relative to the second portion unlocks the first portion from the second portion.

In several embodiments, a first proximal protrusion having a first hook passes through a first hole in the second portion to lock the first portion to the second portion. The third portion can comprise a first distal protrusion. The system can be configured such that moving the third portion distally relative to the second portion engages a ramp to bend the first proximal protrusion to unlock the first portion from the second portion.

In some embodiments, the sensor is located within the second portion while the base protrudes from the distal end of the system such that the system is configured to couple the sensor to the base by moving the first portion distally relative to the second portion.

In several embodiments, a sensor module is coupled to a distal portion of the first portion such that moving the first portion to the distal position couples the sensor module to the base. The sensor can be coupled to the sensor module while the first portion is located in the proximal starting position.

In some embodiments, the system is configured such that moving the third portion distally relative to the second portion unlocks the first portion from the second portion and locks the third portion to the second portion.

In several embodiments, the system comprises a first protrusion that couples with a hole of at least one of the second portion and the third portion to lock the third portion to the second portion.

In some embodiments, the system comprises a second protrusion that couples with a hole of at least one of the first portion and the second portion to lock the first portion to the second portion in response to moving the first portion distally relative to the second portion.

In several embodiments, a first spring is positioned between the third portion and the second portion such that moving the third portion distally relative to the second portion compresses the first spring and unlocks the first portion from the second portion, which enables the compressed first spring to push the first portion distally relative to the second portion, which pushes at least a portion of the sensor out of the distal end of the system and triggers a needle retraction mechanism to enable a second spring to retract a needle.

In some embodiments, a system for applying an on-skin assembly to a skin of a host is provided. Advantageously, the system includes a sensor inserter assembly having a needle assembly, a sensor module, a base, an actuation member, and a retraction member, the sensor inserter assembly having an initial configuration in which at least the sensor module is disposed in a proximal starting position, the sensor inserter assembly further having a deployed configuration in which at least the sensor module and the base are disposed at a distal applied position. Preferably, the actuation member is configured to, once activated, cause the needle assembly to move a proximal starting position to a distal insertion position, and the retraction member is configured to, once activated, cause the needle assembly to move from the distal insertion position to a proximal retracted position.

The sensor module may comprise a sensor and a plurality of electrical contacts. In the initial configuration, the sensor can be electrically coupled to at least one of the electrical contacts. Optionally, in the initial configuration, the actuation member is in an unenergized state. In some embodiments, the actuation member can be configured to be energized by a user before being activated. In alternative embodiments, in the initial configuration, the actuation member is in an energized state.

In several embodiments the actuation member can include a spring. In an initial configuration, the spring can be in an unstressed state. In alternative embodiments, in the initial configuration, the spring is in a compressed state.

In some embodiments, the sensor inserter assembly may include a first portion and a second portion, the first portion being fixed, at least in an axial direction, with respect to the second portion at least when the sensor inserter assembly is in the initial configuration, the first portion being movable in at least a distal direction with respect to the second portion after activation of the actuation member. The first portion may be operatively coupled to the needle assembly so as to secure the needle assembly in the proximal starting position before activation of the actuation member and to urge the needle assembly toward the distal insertion position after activation of the actuation member.

In several embodiments, the retraction member is in an unenergized state when in the initial configuration. Advantageously, the retraction member is configured to be energized by the movement of the needle assembly from the proximal starting position to the distal insertion position. In the initial configuration, the retraction member may be in an energized state.

In still other embodiments, the retraction member comprises a spring. The spring may be integrally formed with the needle assembly. The spring may be operatively coupled to the needle assembly. In the initial configuration, the spring may be in an unstressed state. In other embodiments, in the initial configuration, the spring is in compression.

In some aspects, in the second configuration, the spring is in compression. In still other embodiments, in the second configuration, the spring is in tension.

In some embodiments, the sensor inserter assembly can further include a third portion, the third portion being operatively coupled to the first portion. The actuation member may be integrally formed with the third portion in certain embodiments. Optionally, the actuation member is operatively coupled to the third portion.

In some embodiments, the sensor inserter assembly includes interengaging structures configured to prevent movement of the first portion in the distal direction relative to the second portion until the interengaging structures are decoupled. Advantageously, the decoupling of the interengaging structures may activate the actuation member. In other embodiments, the interengaging structures may include a proximally extending tab of the first portion and a receptacle of the second portion configured to receive the proximally extending tab. Optionally, the sensor inserter assembly can include a decoupling member configured to decouple the interengaging structures. The decoupling member may have a distally extending tab of the third portion.

In yet other embodiments, the sensor inserter assembly can include interengaging structures configured to prevent proximal movement of the third portion with respect to the first portion. These interengaging structures may include a distally-extending latch of the third portion and a ledge of the first portion configured to engage the distally-extending latch.

In certain embodiments, the sensor inserter assembly can include interengaging structures configured to prevent proximal movement of the needle assembly at least when the needle assembly is in the distal insertion position. The interengaging structures can have radially-extending release features of the needle assembly and an inner surface of the first portion configured to compress the release features. Optionally, the sensor inserter assembly includes a decoupling member configured to disengage the interengaging structures of the first portion and the needle assembly. The decoupling member may include an inner surface of the second portion configured to further compress the release features. Advantageously, the system may further include a trigger member configured to activate the actuation member. The trigger member may be operatively coupled to the third portion. The trigger member may be integrally formed with the third portion. The trigger member may include a proximally-extending button. Alternatively, the trigger member may include a radially-extending button. The trigger member may be configured to decouple the interengaging structure of the first portion and the third portion.

In some embodiments, the system may further include a releasable locking member configured to prevent activation of the actuation member until the locking member is released. The releasable locking member may be configured to prevent proximal movement of the third portion with respect to the first portion until the locking member is released. The releasable locking member may include a proximally-extending tab of the first portion and a latch feature of the third portion configured to receive the proximally-extending tab. Advantageously, the releasable locking member is configured to prevent energizing of the sensor inserter assembly. In other aspects, the releasable locking member is configured to prevent energizing of the actuation member.

Embodiments may further include a system for applying an on-skin component to a skin of a host, the system may include a sensor inserter assembly having an on-skin component being movable in at least a distal direction from a proximal position to a distal position, a first securing feature configured to releasably secure the on-skin component in the proximal position, a second securing feature configured to secure the on-skin component in the distal position, and a first resistance configured to prevent movement of the on-skin component in a proximal direction at least when the on-skin component is in the distal position.

The first resistance feature can be configured to prevent movement of the on-skin component in a proximal direction when the on-skin component is secured in the distal position. In some embodiments, the first securing feature is configured to releasably secure the on-skin component to a needle assembly. The on-skin component may have a sensor module. The sensor module may include a sensor and a plurality of electrical contacts. Optionally, the sensor is electrically coupled to at least one of the electrical contacts, at least when the sensor inserter assembly is in the first configuration.

In some embodiments, the on-skin component comprises a base. The on-skin component may include a transmitter. The second securing feature can be configured to secure the on-skin component to a second on-skin component.

In other embodiments, the sensor inserter assembly includes at least one distally-extending leg, and wherein the first securing feature comprises an adhesive disposed on a distally-facing surface of the leg. The sensor inserter assembly may include at least one distally-extending member, and wherein the first securing feature comprises a surface of the distally-extending member configured to frictionally engage with a corresponding structure of the on-skin component. The corresponding structure of the on-skin component may include an elastomeric member. Optionally, the distally-extending member includes at least one leg of the sensor inserter assembly. The distally-extending member may include a needle.

In some embodiments of the system, the second securing feature includes an adhesive disposed on a distally-facing surface of the on-skin component. The second securing feature may have an elastomeric member configured to receive the on-skin component.

In other embodiments, the first resistance feature includes a distally-facing surface of the sensor inserter assembly. The first resistance feature may be distal to an adhesive disposed on a distally-facing surface of the on-skin component.

The system may further include a pusher configured to move the on-skin component from the proximal position to the distal position. Optionally, the system can further include a decoupling feature configured to decouple the pusher from the on-skin component at least after the on-skin component is in the distal position. The decoupling feature may have a frangible portion of the pusher. Optionally, the decoupling feature comprises a frangible portion of the on-skin component.

The system may further comprise a sensor assembly configured to couple with the on-skin component, wherein a third securing feature is configured to releasably secure the sensor assembly in a proximal position, and wherein a fourth securing feature is configured to secure the sensor assembly to the on-skin component.

Any of the features of each embodiment is applicable to all aspects and embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

FIGS. 7-11 illustrate cross-sectional side views of the applicator system from FIG. 3, according to some embodiments.

FIG. 12A illustrates a cross-sectional side view of a portion of the applicator system from FIG. 3, according to some embodiments.

FIG. 12B illustrates a cross-sectional side view of a base that can be used with the applicator system shown in FIG. 3, according to some embodiments.

FIGS. 20 and 21 illustrate perspective views of the needle after being removed from the telescoping assembly of FIG. 7, according to some embodiments.

FIG. 22 illustrates a perspective view of a cover of the telescoping assembly of FIG. 7, according to some embodiments.

FIG. 25 illustrates a cross-sectional side view of a portion of a securing mechanism, according to some embodiments.

FIG. 26 illustrates a top view of a ring, according to some embodiments.

FIG. 27 illustrates a perspective view of a securing mechanism, according to some embodiments.

FIG. 28 illustrates a cross-sectional perspective view of telescoping assembly with a motor, according to some embodiments.

FIGS. 29 and 30 illustrate cross-sectional side views of telescoping assemblies with a motor, according to some embodiments.

FIG. 32 illustrates a cross-sectional perspective view of a telescoping assembly with a downward locking feature, according to some embodiments.

FIG. 33 illustrates a perspective view of an on-skin senor assembly just before the electronics unit is coupled to the base, according to some embodiments.

FIGS. 34 and 35 illustrate perspective views of sensor modules that have springs, according to some embodiments.

FIG. 36 illustrates a cross-sectional perspective view of a portion of a sensor module, according to some embodiments.

FIG. 48 illustrates a cross-sectional perspective view of an applicator system, according to some embodiments.

FIG. 49 illustrates a cross-sectional perspective view of a proximal portion of a telescoping assembly, according to some embodiments.

FIG. 50 illustrates a perspective view of a distal portion of a telescoping assembly, according to some embodiments.

FIG. 55 illustrates a cross-sectional top view of four needles, according to some embodiments.

FIGS. 56-58 illustrate cross-sectional side views of a system that is similar to the embodiment shown in FIG. 7 except that the system does not include a needle, according to some embodiments.

FIGS. 61-63 illustrate cross-sectional perspectives views of a system that is similar to the embodiment shown in FIG. 7 except that the telescoping assembly includes an extra portion, according to some embodiments.

FIG. 64 illustrates a cross-sectional side view of the system shown in FIGS. 61-63, according to some embodiments.

FIG. 71 illustrates a cross-sectional perspective view of an applicator system, according to some embodiments, in a resting state.

FIG. 72 illustrates a cross-sectional perspective view of the applicator system of FIG. 71, with the actuation member energized.

FIG. 75 illustrates a cross-sectional perspective view of the applicator system of FIG. 71, with the on-skin component in a deployed position and the needle assembly retracted.

FIG. 76 illustrates a cross-sectional side view of another applicator system, according to some embodiments, in a resting state.

FIG. 77 illustrates a cross-sectional side view of the applicator system of FIG. 76, with the actuation member energized.

FIG. 78 illustrates a cross-sectional side view of the applicator system of FIG. 76, with the actuation member activated and with the needle assembly deployed in an insertion position.

FIG. 79 illustrates a cross-sectional side view of the applicator system of FIG. 76, with the on-skin component in a deployed position and the needle assembly retracted.

FIG. 86 illustrates a cross-sectional side view of another applicator system, according to some embodiments, in a resting state in which the actuation member is already energized.

FIG. 87 illustrates a cross-sectional side view of the applicator system of FIG. 86, with the actuation member activated and with the needle assembly deployed in an insertion position.

FIG. 88 illustrates a cross-sectional side view of the applicator system of FIG. 86, with the on-skin component in a deployed position and the needle assembly retracted.

FIG. 89 illustrates a cross-sectional side view of another applicator system, according to some embodiments, in a resting state in which the actuation member is already energized.

FIG. 90 illustrates a cross-sectional side view of the applicator system of FIG. 86, with the actuation member activated and with the needle assembly deployed in an insertion position.

FIG. 91 illustrates a cross-sectional side view of the applicator system of FIG. 86, with the on-skin component in a deployed position and the needle assembly retracted.

FIG. 97 illustrates a cross-sectional side view of the applicator system of FIG. 96.

FIG. 98 illustrates a cross-sectional side view of the applicator system of FIG. 92, during triggering.

FIG. 112 illustrates a cross-sectional perspective view of the applicator system of FIG. 110, with the actuation member energized.

FIG. 113 illustrates a cross-sectional perspective view of the applicator system of FIG. 110, with the actuation member activated and with the needle assembly and on-skin component deployed in a distal position.

FIG. 114 illustrates a cross-sectional perspective view of the applicator system of FIG. 110, with the on-skin component in a deployed position and separated from the retracted needle assembly.

FIG. 115 illustrates a perspective view of the needle assembly from the system of FIG. 110, shown securing the on-skin component during deployment, with the base removed for purposes of illustration.

FIG. 116 illustrates another perspective view of the needle assembly from the system of FIG. 110, shown separated from the on-skin component, with the base removed for purposes of illustration.

FIG. 118 illustrates a perspective view of the sensor module of FIG. 100, before being coupled to the base.

FIG. 119 illustrates a perspective view of the sensor module of FIG. 100, after being coupled to the base.

FIG. 133 illustrates a perspective view of the needle assembly and on-skin component of FIG. 132, after decoupling of the on-skin component from the needle assembly.

FIG. 134 illustrates an exploded perspective view of a portion of an applicator assembly, according to some embodiments, with a securing member configured to releasably couple an on-skin component to a needle assembly.

FIG. 135 illustrates a perspective view of a portion of the applicator assembly of FIG. 134, with the needle assembly coupled to the on-skin component.

FIG. 136 illustrates a perspective view of a portion of the applicator assembly of FIG. 134, with the needle assembly decoupled from the on-skin component.

FIG. 137 illustrates a perspective view of an applicator assembly, according to some embodiments, with an on-skin component releasably secured in a proximal position within the applicator assembly.

FIG. 138 illustrates a perspective view of the applicator assembly of FIG. 137, with the on-skin component released from securement.

FIG. 139 illustrates a perspective view of the on-skin component of FIG. 137, with the securing feature in a secured configuration.

FIG. 140 illustrates a perspective view of the on-skin component of FIG. 137, with the securing feature in a released configuration.

FIG. 141 illustrates a cross-sectional perspective view of a portion of an applicator assembly, according to some embodiments, with the second and third portions shown in cross section, and showing a base coupled to an applicator.

FIG. 142 illustrates a perspective view of another applicator assembly, according to some embodiments, showing a patch coupled to an applicator.

FIG. 143 illustrates a perspective view of the applicator assembly of FIG. 142, the patch decoupled from the applicator.

DETAILED DESCRIPTION OF CERTAIN INVENTIVE EMBODIMENTS

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

System Introduction

Figure 1:
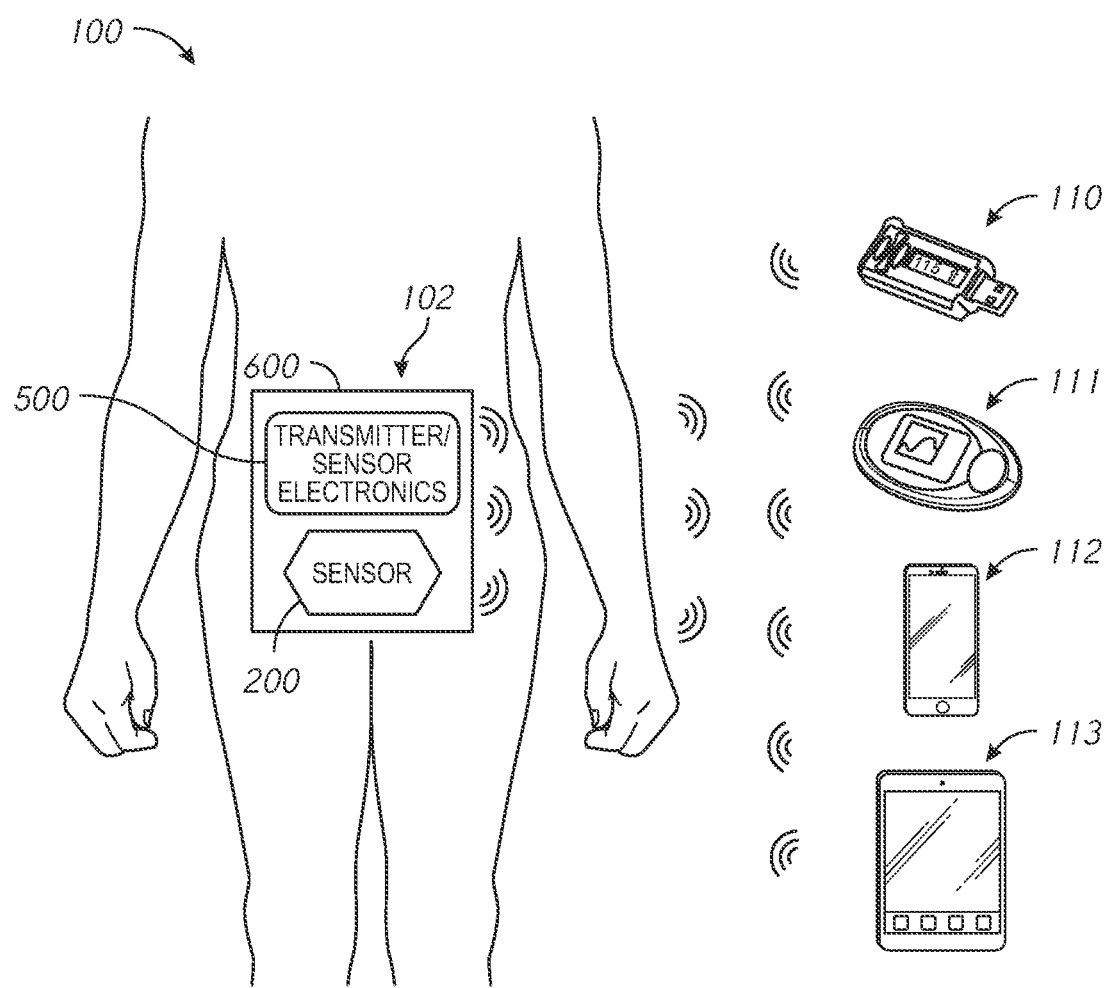
FIG. 1 illustrates a schematic view of a continuous analyte sensor system, according to some embodiments.

U.S. Patent Publication No. US-2013-0267811-A1, the entire contents of which are incorporated by reference herein, explains how FIG. 1 is a schematic of a continuous analyte sensor system 100 attached to a host (e.g., a person). The analyte sensor system 100 communicates with other devices 110-113 (which can be located remotely from the host). A transcutaneous analyte sensor system 102 comprising an on-skin sensor assembly 600 is fastened to the skin of a host via a base (not shown), which can be a disposable housing.

The system 102 includes a transcutaneous analyte sensor 200 and an electronics unit (referred to interchangeably as "sensor electronics" or "transmitter") 500 for wirelessly transmitting analyte information to a receiver. The receiver can be located remotely relative to the system 102. In some embodiments, the receiver includes a display screen, which can display information to a person such as the host. Example receivers include computers such as smartphones, smartwatches, tablet computers, laptop computers, and desktop computers. In some embodiments, receivers can be Apple Watches, iPhones, and iPads made by Apple Inc. In still further embodiments, the system 102 can be configured for use in applying a drug delivery device, such an infusion device, to the skin of a patient. In such embodiments, the system can include a catheter instead of, or in addition to, a sensor, the catheter being connected to an infusion pump configured to deliver liquid medicines or other fluids into the patient's body. In embodiments, the catheter can be deployed into the skin in much the same manner as a sensor would be, for example as described herein.

In some embodiments, the receiver is mechanically coupled to the electronics unit 500 to enable the receiver to receive data (e.g., analyte data) from the electronics unit 500. To increase the convenience to users, in several embodiments, the receiver does not need to be mechanically coupled to the electronics unit 500 and can even receive data from the electronics unit 500 over great distances (e.g., when the receiver is many feet or even many miles from the electronics unit 500).

During use, a sensing portion of the sensor 200 can be under the host's skin and a contact portion of the sensor 200 can be electrically connected to the electronics unit 500. The electronics unit 500 can be engaged with a housing (e.g., a base) which is attached to an adhesive patch fastened to the skin of the host.

The on-skin sensor assembly 600 may be attached to the host with use of an applicator adapted to provide convenient and secure application. Such an applicator may also be used for attaching the electronics unit 500 to a base, inserting the sensor 200 through the host's skin, and/or connecting the sensor 200 to the electronics unit 500. Once the electronics unit 500 is engaged with the base and the sensor 200 has been inserted into the skin (and is connected to the electronics unit 500), the sensor assembly can detach from the applicator.

The continuous analyte sensor system 100 can include a sensor configuration that provides an output signal indicative of a concentration of an analyte. The output signal including (e.g., sensor data, such as a raw data stream, filtered data, smoothed data, and/or otherwise transformed sensor data) is sent to the receiver.

In some embodiments, the analyte sensor system 100 includes a transcutaneous glucose sensor, such as is described in U.S. Patent Publication No. US-2011-0027127-A1, the entire contents of which are hereby incorporated by reference. In some embodiments, the sensor system 100 includes a continuous glucose sensor and comprises a transcutaneous sensor (e.g., as described in U.S. Pat. No. 6,565,509, as described in U.S. Pat. No. 6,579,690, as described in U.S. Pat. No. 6,484,046). The contents of U.S. Pat. Nos. 6,565,509, 6,579,690, and 6,484,046 are hereby incorporated by reference in their entirety.

In several embodiments, the sensor system 100 includes a continuous glucose sensor and comprises a refillable subcutaneous sensor (e.g., as described in U.S. Pat. No. 6,512,939). In some embodiments, the sensor system 100 includes a continuous glucose sensor and comprises an intravascular sensor (e.g., as described in U.S. Pat. No. 6,477,395, as described in U.S. Pat. No. 6,424,847). The contents of U.S. Pat. Nos. 6,512,939, 6,477,395, and 6,424,847 are hereby incorporated by reference in their entirety.

Various signal processing techniques and glucose monitoring system embodiments suitable for use with the embodiments described herein are described in U.S. Patent Publication No. US-2005-0203360-A1 and U.S. Patent Publication No. US-2009-0192745-A1, the contents of which are hereby incorporated by reference in their entirety. The sensor can extend through a housing, which can maintain the sensor on the skin and can provide for electrical connection of the sensor to sensor electronics, which can be provided in the electronics unit 500.

In several embodiments, the sensor is formed from a wire or is in a form of a wire. A distal end of the wire can be sharpened to form a conical shape (to facilitate inserting the wire into the tissue of the host). The sensor can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments, the smallest dimension of the elongated conductive body is less than 0.1 inches, less than 0.075 inches, less than 0.05 inches, less than 0.025 inches, less than 0.01 inches, less than 0.004 inches, and/or less than 0.002 inches.

The sensor may have a circular cross section. In some embodiments, the cross section of the elongated conductive body can be ovoid, rectangular, triangular, polyhedral, star-shaped, C-shaped, T-shaped, X-shaped, Y-shaped, irregular, or the like. In some embodiments, a conductive wire electrode is employed as a core. To such an electrode, one or two additional conducting layers may be added (e.g., with intervening insulating layers provided for electrical isolation). The conductive layers can be comprised of any suitable material. In certain embodiments, it may be desirable to employ a conductive layer comprising conductive particles (i.e., particles of a conductive material) in a polymer or other binder.

In some embodiments, the materials used to form the elongated conductive body (e.g., stainless steel, titanium, tantalum, platinum, platinum-iridium, iridium, certain polymers, and/or the like) can be strong and hard, and therefore can be resistant to breakage. For example, in several embodiments, the ultimate tensile strength of the elongated conductive body is greater than 80 kPsi and less than 500 kPsi, and/or the Young's modulus of the elongated conductive body is greater than 160 GPa and less than 220 GPa. The yield strength of the elongated conductive body can be greater than 60 kPsi and less than 2200 kPsi.

The electronics unit 500 can be releasably coupled to the sensor 200. The electronics unit 500 can include electronic circuitry associated with measuring and processing the continuous analyte sensor data. The electronics unit 500 can be configured to perform algorithms associated with processing and calibration of the sensor data. For example, the electronics unit 500 can provide various aspects of the functionality of a sensor electronics module as described in U.S. Patent Publication No. US-2009-0240120-A1 and U.S. Patent Publication No. US-2012-0078071-A1, the entire contents of which are incorporated by reference herein. The electronics unit 500 may include hardware, firmware, and/or software that enable measurement of levels of the analyte via a glucose sensor, such as an analyte sensor 200.

For example, the electronics unit 500 can include a potentiostat, a power source for providing power to the sensor 200, signal processing components, data storage components, and a communication module (e.g., a telemetry module) for one-way or two-way data communication between the electronics unit 500 and one or more receivers, repeaters, and/or display devices, such as devices 110-113. Electronics can be affixed to a printed circuit board (PCB), or the like, and can take a variety of forms. The electronics can take the form of an integrated circuit (IC), such as an Application-Specific Integrated Circuit (ASIC), a microcontroller, and/or a processor. The electronics unit 500 may include sensor electronics that are configured to process sensor information, such as storing data, analyzing data streams, calibrating analyte sensor data, estimating analyte values, comparing estimated analyte values with time-corresponding measured analyte values, analyzing a variation of estimated analyte values, and the like. Examples of systems and methods for processing sensor analyte data are described in more detail in U.S. Pat. Nos. 7,310,544, 6,931,327, U.S. Patent Publication No. 2005-0043598-A1, U.S. Patent Publication No. 2007-0032706-A1, U.S. Patent Publication No. 2007-0016381-A1, U.S. Patent Publication No. 2008-0033254-A1, U.S. Patent Publication No. 2005-0203360-A1, U.S. Patent Publication No. 2005-0154271-A1, U.S. Patent Publication No. 2005-0192557-A1, U.S. Patent Publication No. 2006-0222566-A1, U.S. Patent Publication No. 2007-0203966-A1 and U.S. Patent Publication No. 2007-0208245-A1, the contents of which are hereby incorporated by reference in their entirety.

One or more repeaters, receivers and/or display devices, such as a key fob repeater 110, a medical device receiver 111 (e.g., an insulin delivery device and/or a dedicated glucose sensor receiver), a smartphone 112, a portable computer 113, and the like can be communicatively coupled to the electronics unit 500 (e.g., to receive data from the electronics unit 500). The electronics unit 500 can also be referred to as a transmitter. In some embodiments, the devices 110-113 transmit data to the electronics unit 500. The sensor data can be transmitted from the sensor electronics unit 500 to one or more of the key fob repeater 110, the medical device receiver 111, the smartphone 112, the portable computer 113, and the like. In some embodiments, analyte values are displayed on a display device.

The electronics unit 500 may communicate with the devices 110-113, and/or any number of additional devices, via any suitable communication protocol. Example communication protocols include radio frequency; Bluetooth; universal serial bus; any of the wireless local area network (WLAN) communication standards, including the IEEE 802.11, 802.15, 802.20, 802.22 and other 802 communication protocols; ZigBee; wireless (e.g., cellular) telecommunication; paging network communication; magnetic induction; satellite data communication; and/or a proprietary communication protocol.

Additional sensor information is described in U.S. Pat. Nos. 7,497,827 and 8,828,201. The entire contents of 7,497,827 and 8,828,201 are incorporated by reference herein.

Any sensor shown or described herein can be an analyte sensor; a glucose sensor; and/or any other suitable sensor. A sensor described in the context of any embodiment can be any sensor described herein or incorporated by reference. Thus, for example, the sensor 138 shown in FIG. 7 can be an analyte sensor; a glucose sensor; any sensor described herein; and any sensor incorporated by reference. Sensors shown or described herein can be configured to sense, measure, detect, and/or interact with any analyte.

As used herein, the term "analyte" is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, or reaction products.

In some embodiments, the analyte for measurement by the sensing regions, devices, systems, and methods is glucose. However, other analytes are contemplated as well, including, but not limited to ketone bodies; Acetyl Co A; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; cortisol; testosterone; choline; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; triglycerides; glycerol; free ß-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Heli-* cobacter pylori, hepatitis B virus, herpes virus, HIV-1, IgE (atopic disease), influenza virus, *Leishmania donovani*, leptospira, measles/mumps/rubella, *Mycobacterium leprae*, *Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli*, vesicular *stomatis* virus, *Wuchereria bancrofti*, yellow fever virus); specific antigens (hepatitis B virus, HIV-1); acetone (e.g., succinylacetone); acetoacetic acid; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; glucagon; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), 5-hydroxyindoleacetic acid (FHIAA), and intermediaries in the Citric Acid Cycle.

Many embodiments described herein use an adhesive (e.g., the adhesive 126 in FIG. 7). One purpose of the adhesive can be to couple a base, a sensor module, and/or a sensor to a host (e.g., to skin of the host). The adhesive can be configured for adhering to skin. The adhesive can include a pad (e.g., that is located between the adhesive and the base). Additional adhesive information, including adhesive pad information, is described in U.S. patent application Ser. No. 14/835,603, which was filed on Aug. 25, 2015. The entire contents of U.S. patent application Ser. No. 14/835, 603 are incorporated by reference herein.

Distal Base Location

As noted above, systems can apply an on-skin sensor assembly to the skin of a host. The system can include a base that comprises an adhesive to couple a glucose sensor to the skin.

In some applicators, the base is hidden deep inside the applicator until the user moves the needle distally with the base. One challenge with this approach is that the insertion site (on the skin of the host) is not ideally prepared for sensor and/or needle insertion. For example, the distal end of the applicator may be a hoop that presses against the skin. The pressure of the applicator on the skin can cause the area of the skin within the hoop to form a convex shape. In addition, the skin within the hoop can be too easily compressed such that the skin lacks sufficient resilience and firmness. In this state, the sensor and/or needle may press the skin downward without immediately piercing the skin, which may result in improper sensor and/or needle insertion.

In several embodiments, the base is coupled to a telescoping assembly such that the base protrudes from the distal end of the system while the glucose sensor is located remotely from the base and is located within the telescoping assembly. This configuration enables the base to prepare the insertion site of the skin for sensor and/or needle insertion (e.g., by compressing the skin). Thus, these embodiments can dramatically improve the reliability of sensor and/or needle insertion while reducing pain associated with sensor and/or needle insertion.

The system can hold the base in a position that is distal relative to a glucose sensor module such that a glucose sensor is not attached to the base and such that the glucose sensor can move relative to the base. Moving the glucose sensor module distally towards the base can attach the glucose sensor to the base. This movement can occur as a result of compressing an applicator.

Figures 2, 3:
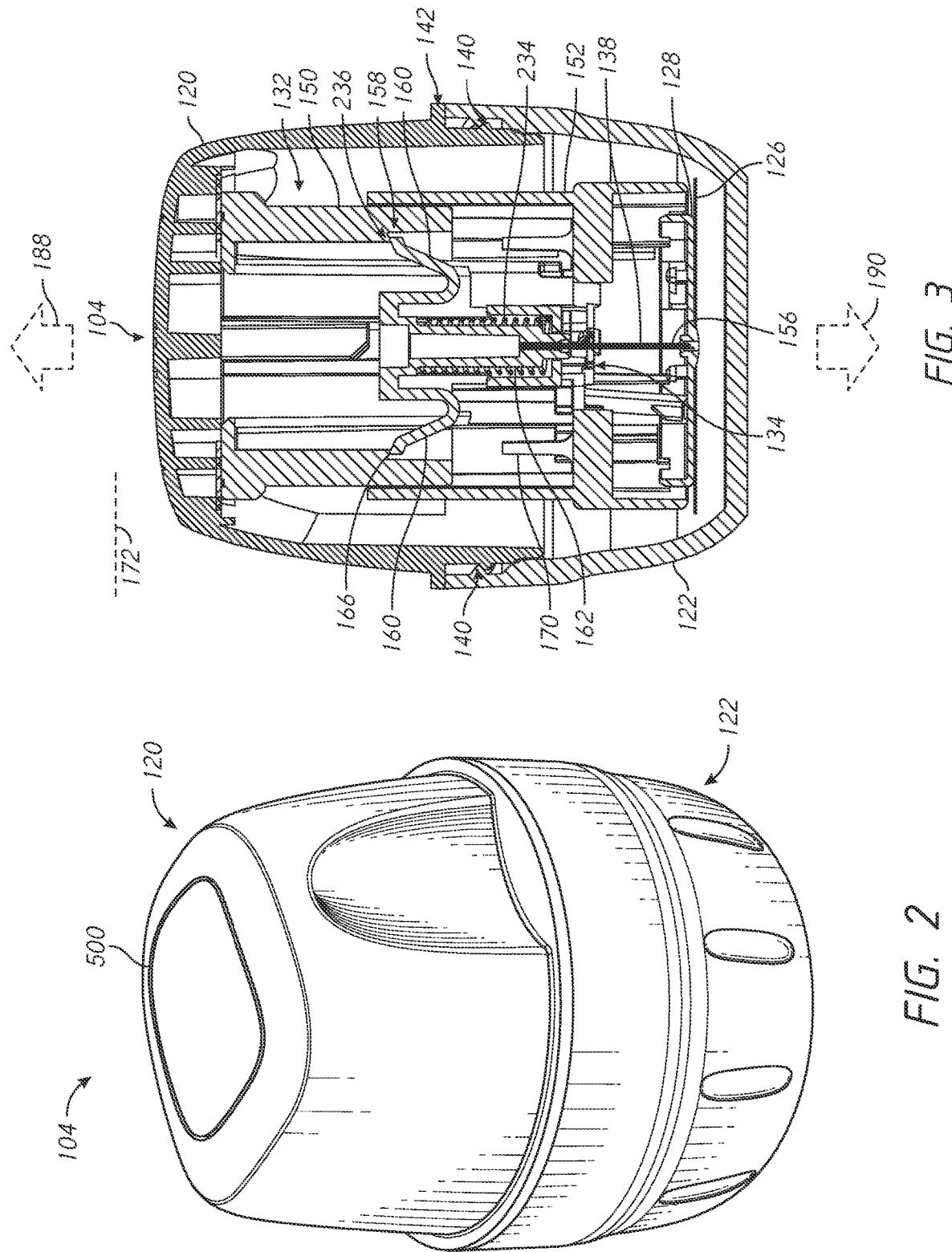
FIG. 2 illustrates a perspective view of an applicator system, according to some embodiments.
FIG. 3 illustrates a cross-sectional side view of the system from FIG. 2, according to some embodiments.

FIG. 2 illustrates a perspective view of an applicator system 104 for applying at least portions of an on-skin sensor assembly 600 (shown in FIG. 4) to skin of a host (e.g., a person). The system can include a sterile barrier having a shell 120 and a cap 122. The cap 122 can screw onto the shell 120 to shield portions of the system 104 from external contaminants.

The electronics unit 500 (e.g., a transmitter having a battery) can be detachably coupled to the sterile barrier shell 120. The rest of the applicator system 104 can be sterilized, and then the electronics unit 500 can be coupled to the sterile barrier shell 120 (such that the electronics unit 500 is not sterilized with the rest of the applicator system 104).

Figure 6:
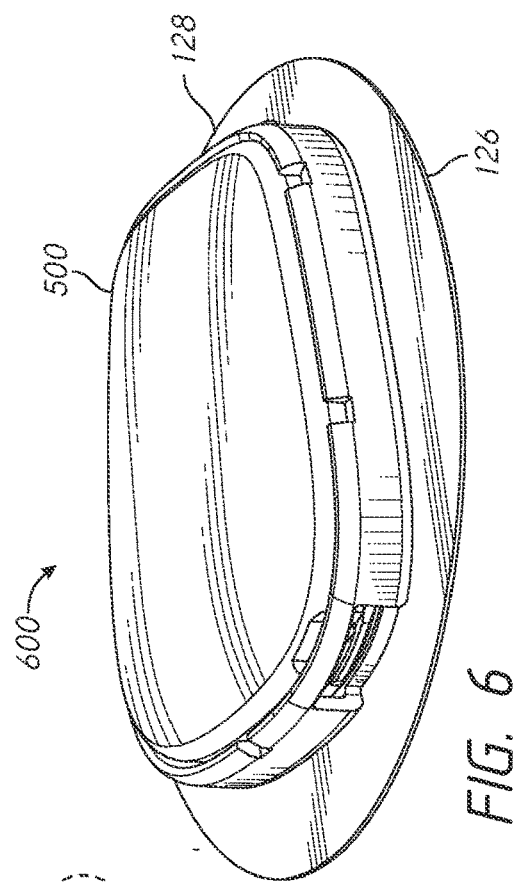

The user can detach the electronics unit 500 from the sterile barrier shell 120. The user can also couple the electronics unit 500 to the base 128 (as shown in FIG. 6) after the applicator system 104 places at least a portion of a sensor in a subcutaneous position (for analyte sensing).

Many different sterilization processes can be used with the embodiments described herein. The sterile barrier 120 and/or the cap 122 can block gas from passing through (e.g., can be hermetically sealed). The hermetic seal can be formed by threads 140 (shown in FIG. 3). The threads 140 can be compliant such that they deform to create a seal. The threads 140 can be located between the sterile barrier shell 120 and the cap 122.

The cap 122 can be made polypropylene and the shell 120 can be made from polycarbonate (or vice versa) such that one of the cap 122 and the shell 120 is harder than the other of the cap 122 and the 120. This hardness (or flexibility) difference enables one of the components to deform to create the thread 140 seal.

In some embodiments, at least one of the shell 120 and the cap 122 includes a gas-permeable material to enable sterilization gases to enter the applicator system 104. For example, as explained in the context of FIG. 60, the system can include a cover 272*h*.

Referring now to FIG. 3, the threads 140 can be configured such that a quarter rotation, at least 15 percent of a full rotation, and/or less than 50 percent of a full rotation uncouples the cap 122 from the shell 120. Some embodiments do not include threads 140. The cap 122 can be pushed onto the shell 120 (e.g., during assembly) even in some threaded embodiments.

A cap 122 can be secured to the shell 120 by a frangible member 142 configured such that removing the cap 122 from the shell 120 brakes the frangible member 142. The frangible member 142 can be configured like the safety ring (with a frangible portion) of a plastic soda bottle. Unscrewing the cap from the plastic soda bottle breaks the safety ring from the soda bottle's cap. This approach provides evidence of tampering. In the same way, the applicator system 104 can provide tamper evidence (due to the frangible member 142 being broken by removing the cap 122 from the shell 122).

U.S. Patent Publication No. US-2013-0267811-A1; U.S. Patent Application No. 62/165,837, which was filed on May 15, 2015; and U.S. Patent Application No. 62/244,520, which was filed on Oct. 21, 2015, include additional details regarding applicator system embodiments. The entire contents of U.S. Patent Publication No. US-2013-0267811-A1; U.S. Patent Application No. 62/165,837; and U.S. Patent Application No. 62/244,520 are incorporated by reference herein.

FIG. 3 illustrates a cross-sectional view of the system 104. A glucose sensor module 134 is configured to couple a glucose sensor 138 to the base 128 (e.g., a "housing"). The telescoping assembly 132 is located in a proximal starting position such that the glucose sensor module 134 is located proximally relative to the base 128 and remotely from the base 128. The telescoping assembly 132 is configured such that collapsing the telescoping assembly 132 connects the glucose sensor module 134 to the base 128 via one or more mechanical interlocks (e.g., snap fits, interference features).

The sterile barrier shell 120 is coupled to a telescoping assembly 132. After removing the cap 122, the system 104 is configured such that compressing the sterile barrier shell 120 distally (while a distal portion of the system 104 is pressed against the skin) can insert a sensor 138 (shown in FIG. 4) into the skin of a host to place the transcutaneous, glucose analyte sensor 138. In many figures shown herein, the sterile barrier shell 120 and cap 122 are hidden to increase the clarity of other features.

Collapsing the telescoping assembly 132 also pushes at least 2.5 millimeters of the glucose sensor 138 out through a hole in the base 128 such that at least 2.5 millimeters of the glucose sensor 138 that was previously located proximally relative to a distal end of the base protrudes distally out of the base 128. Thus, in some embodiments, the base 128 can remain stationary relative to a distal portion of the telescoping assembly 132 while the collapsing motion of the telescoping assembly 132 brings the glucose sensor module 134 towards the base 128 and then couples the sensor module 134 to the base 128.

This relative motion between the sensor module 134 and the base 128 has many benefits, such as enabling the base to prepare the insertion site of the skin for sensor and/or needle insertion (e.g., by compressing the skin). The starting position of the base 128 also enables the base 128 to shield people from a needle, which can be located inside the applicator system 104. For example, if the base 128 were directly coupled to the sensor module 134 in the proximal starting position of the telescoping assembly, the needle may protrude distally from the base 128. The exposed needle could be a potential hazard. In contrast, the distal starting position of the base 128 enables the base 128 to protect people from inadvertent needle insertion. Needle protection is especially important for caregivers (who are not the intended recipients of the on-skin sensor assembly 600 shown in FIG. 4).

Figure 4:
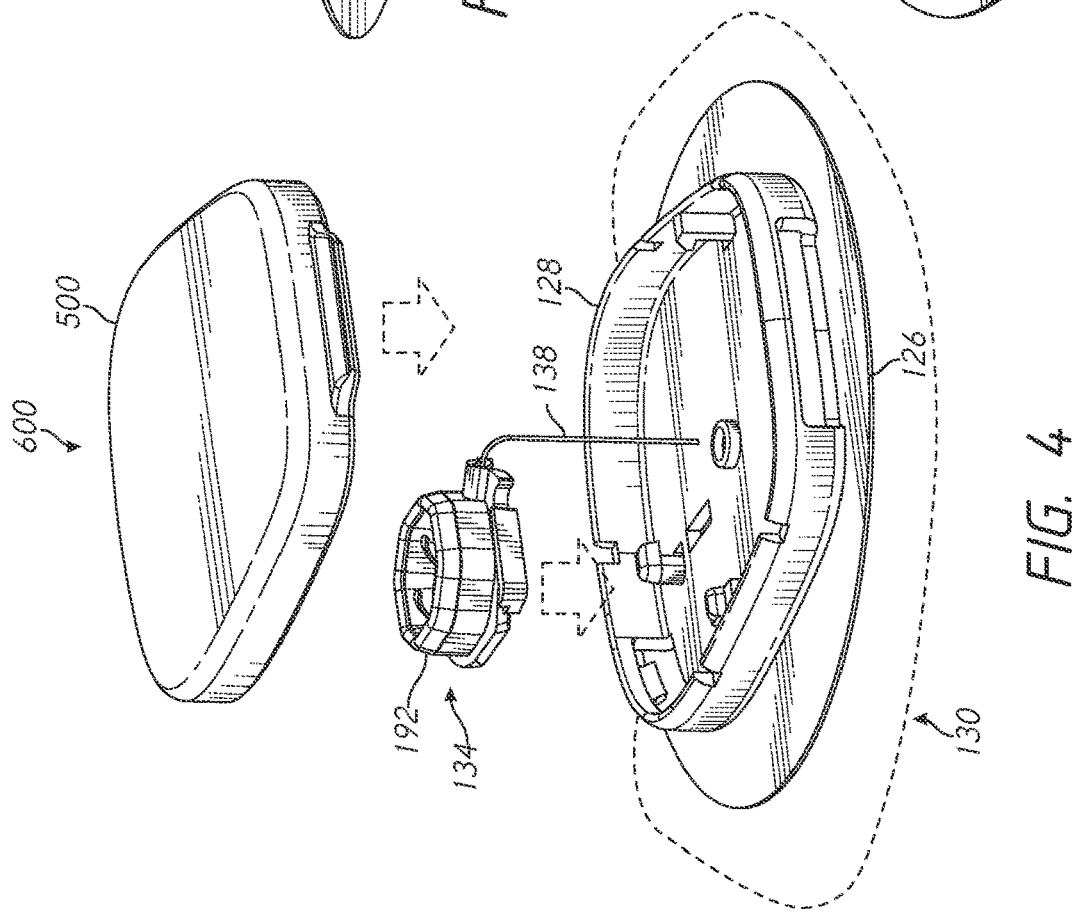
FIG. 4 illustrates a perspective view of an on-skin sensor assembly, according to some embodiments.

FIG. 4 illustrates a perspective view of the on-skin sensor assembly 600, which includes the base 128. An adhesive 126 can couple the base 128 to the skin 130 of the host. The adhesive 126 can be a foam adhesive suitable for skin adhesion. A glucose sensor module 134 is configured to couple a glucose sensor 138 to the base 128.

The applicator system 104 (shown in FIG. 2) can couple the adhesive 126 to the skin 130. The system 104 can also secure (e.g., couple via mechanical interlocks such as snap fits and/or interference features) the glucose sensor module 134 to the base 128 to ensure the glucose sensor 138 is coupled to the base 128. Thus, the adhesive 126 can couple the glucose sensor 138 to the skin 130 of the host.

After the glucose sensor module 134 is coupled to the base 128, a user (or an applicator) can couple the electronics unit 500 (e.g., a transmitter) to the base 128 via mechanical interlocks such as snap fits and/or interference features. The electronics unit 500 can measure and/or analyze glucose indicators sensed by the glucose sensor 138. The electronics unit 500 can transmit information (e.g., measurements, analyte data, glucose data) to a remotely located device (e.g., 110-113 shown in FIG. 1).

Figure 5:
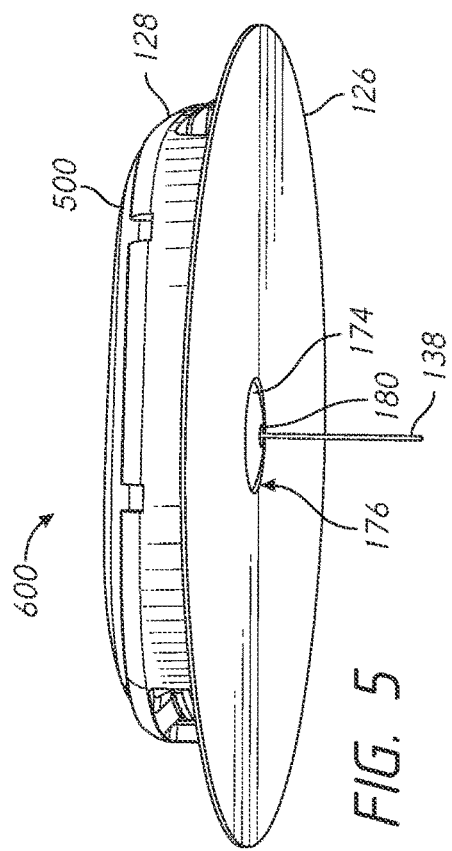
FIGS. 5 and 6 illustrate perspective views of a transmitter coupled to a base via mechanical interlocks, according to some embodiments.

FIG. 5 illustrates a perspective view of the electronics unit 500 coupled to the base 128 via mechanical interlocks such as snap fits and/or interference features. Adhesive 126 on a distal face of the base 128 is configured to couple the sensor assembly 600 to the skin. FIG. 6 illustrates another perspective view of the electronics unit 500 coupled to the base 128.

Any of the features described in the context of FIGS. 1-6 can be applicable to all aspects and embodiments identified herein. For example, many embodiments can use the on-skin sensor assembly 600 shown in FIG. 4 and can use the sterile barrier shell 120 shown in FIG. 2. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

FIGS. 7-11 illustrate cross-sectional views of the applicator system 104 from FIG. 3. The sterile barrier shell 120 and the cap 134 are hidden in FIGS. 7-11 to facilitate viewing the telescoping assembly 132.

The telescoping assembly 132 is part of a system for applying an on-skin sensor assembly 600 to skin of a host (shown in FIG. 4). The telescoping assembly 132 can apply portions of the system to the host. Additional portions of the system can be added to the on-skin sensor assembly 600 after the applicator system 104 couples initial portions of the sensor assembly 600 to the host. For example, as shown in FIG. 4, the electronics unit 500 (e.g., a transmitter) can be coupled to the on-skin sensor assembly 600 after the applicator system 104 (shown in FIG. 3) couples the base 128, the glucose sensor module 134, and/or the glucose sensor 138 to the skin 130 of the host.

In some embodiments, the applicator system 104 (shown in FIG. 3) couples at least one, at least two, at least three, at least four, and/or all of the following items to the skin of the host: the electronics unit 500, the glucose sensor module 134, the glucose sensor 138, the base 128, and the adhesive 126. The electronics unit 500 can be located inside the applicator system 104 such that the applicator system 104 is configured to couple the electronics unit 500 to the skin of the host.

FIG. 7 illustrates a telescoping assembly 132 having a first portion 150 (e.g., a "pusher") configured to move distally relative to a second portion 152 (e.g., a "needle guard") from a proximal starting position to a distal position along a path 154. FIG. 7 illustrates the telescoping assembly 132 in the proximal starting position. FIG. 8 illustrates the telescoping assembly 132 moving between the proximal starting position and the distal position. FIG. 11 illustrates the telescoping assembly 132 in the distal position. The path 154 (shown in FIG. 7) represents the travel between the proximal starting position and the distal position.

A first set of items can be immobile relative to the first portion 150, and a second set of items can be immobile relative to the second portion 152 while the first set of items move relative to the second set of items.

Referring now to FIG. 7, the glucose sensor 138 and the sensor module 134 are coupled to the first portion 150 (e.g., such that they are immobile relative to the first portion 150 during a proximal portion of the path 154). The base 128 is coupled to the second portion 152 such that the base 128 protrudes from a distal end of the system (e.g., the base protrudes from a distal end of the telescoping assembly 132). The base 128 comprises adhesive 126 configured to eventually couple the glucose sensor 138 to the skin (e.g., after at least a portion of the glucose sensor 138 is rigidly coupled to the base 128).

In FIG. 7, the glucose sensor 138 and the sensor module 134 are located within the second portion 152 while the base 128 protrudes from the distal end of the system (e.g., from the distal end of the telescoping assembly 132) such that the system is configured to couple the glucose sensor 138 to the base 128 via moving the first portion 150 distally relative to the second portion 152. The progression shown in FIGS. 7-11 illustrates moving the first portion 150 distally relative to the second portion 152.

The sensor module 138 is coupled to a distal portion of the first portion 150 such that moving the first portion 150 to the distal position (as described above) couples the sensor module 134 to the base 128. The glucose sensor 138 is coupled to the sensor module 134 (e.g., immobile relative to the sensor module 134) while the first portion 150 is located in the proximal starting position. The glucose sensor 138 can include a distally protruding portion and a proximal portion. The proximal portion can be rigidly coupled to the sensor module 134 such that the proximal portion cannot move relative to the sensor module 134 even though the distally protruding portion may bend relative to the sensor module 134.

A needle 156 (e.g., a "C-shaped" needle) is coupled to the first portion 150 such that the glucose sensor 138 and the needle 156 move distally relative to the base 128 and relative to the second portion 152. The system can further comprise a needle release mechanism 158 configured to retract the needle 156 proximally.

The needle 156 can have many different forms. Many different types of needles 156 can be used with the embodiments described herein. FIGS. 51-55 illustrate various needle embodiments that can be used with any of the embodiments described herein.

Figure 42:
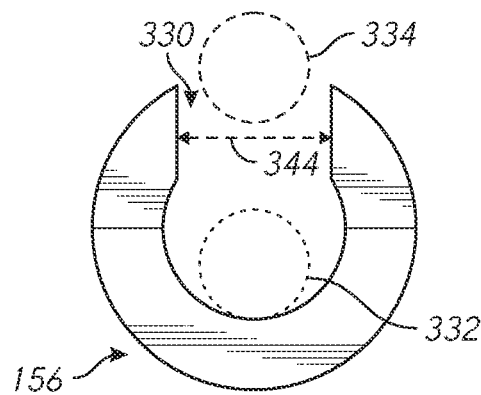
FIG. 42 illustrates a bottom view of a needle, according to some embodiments.

The needle 156 can guide the sensor 138 into the skin of the host. A distal portion of the sensor 138 can be located in a channel of the needle 156 (as shown in FIG. 42). Sometimes, a distal end of the sensor 138 sticks out of the needle 156 and gets caught on tissue of the host as the sensor 138 and needle 156 are inserted into the host. As a result, the sensor 138 may buckle and fail to be inserted deeply enough into the subcutaneous tissue. In other words, in some embodiments, the sensor wire must be placed within the channel of the C-shaped needle 156 to be guided into the tissue and must be retained in the channel 330 during deployment.

Figure 51:
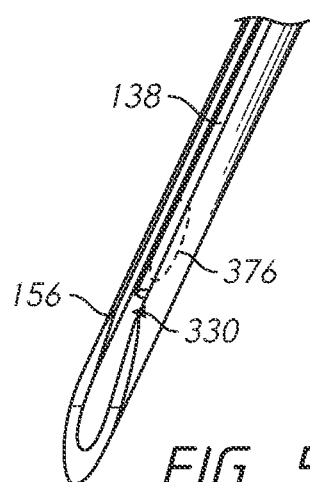
FIG. 51 illustrates a perspective view of a needle with adhesive, according to some embodiments.

The risk of the sensor 138 sticking out of the channel 330 (and thereby failing to be properly inserted into the host) can be greatly diminished by the embodiment illustrated in FIG. 51. In this embodiment, adhesive 376 bonds a distal portion of the glucose sensor 138 into the channel 330 of the needle 156. Retracting the needle 156 can break the bond of the adhesive 376 to enable a distal portion of the sensor 138 to stay in a subcutaneous location while the needle 156 is retracted (and even after the needle 156 is retracted).

Figure 52:
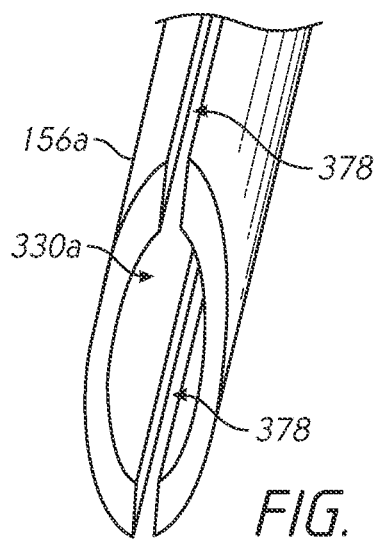
FIG. 52 illustrates a perspective view of a needle that has two separate sides, according to some embodiments.
Figure 53:
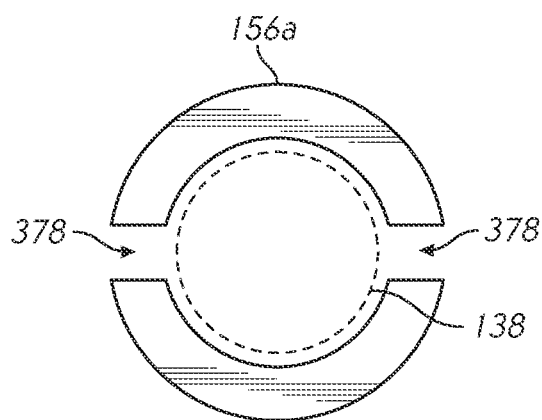
FIG. 53 illustrates a cross-sectional top view of the needle shown in FIG. 52, according to some embodiments.

The risk of the sensor 138 sticking out of the channel 330 (and thereby failing to be properly inserted into the host) can be greatly diminished by the embodiment illustrated in FIGS. 52 and 53. In this embodiment, the needle 156a comprises two sides, which can be separated by slots 378. The sensor 138 can have a width that is larger than the width of the slots 378 such that the sensor 138 cannot come out of the channel 330a until the two sides of the needle 156a are moved apart (to widen the slots 378).

Figure 54:
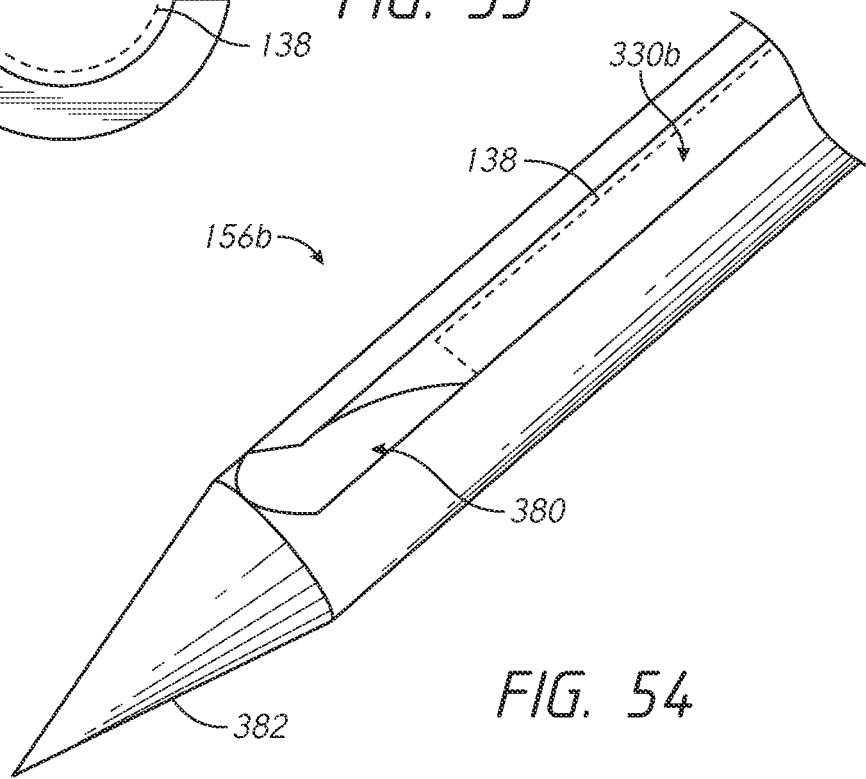
FIG. 54 illustrates a perspective view of a needle that has a ramp, according to some embodiments.

The embodiment illustrated in FIG. 54 can be used with any of the other embodiments described herein. The needle 156b includes a ramp 380 at the distal end of the channel 330b. The distal end of the needle 156b can include a conical tip 382. The ramp 380 can be configured to push the sensor 138 out of the channel 330b of the needle 156b as the needle 156b is retracted into the telescoping assembly 132 (shown in FIG. 7).

Figures 55, 56:
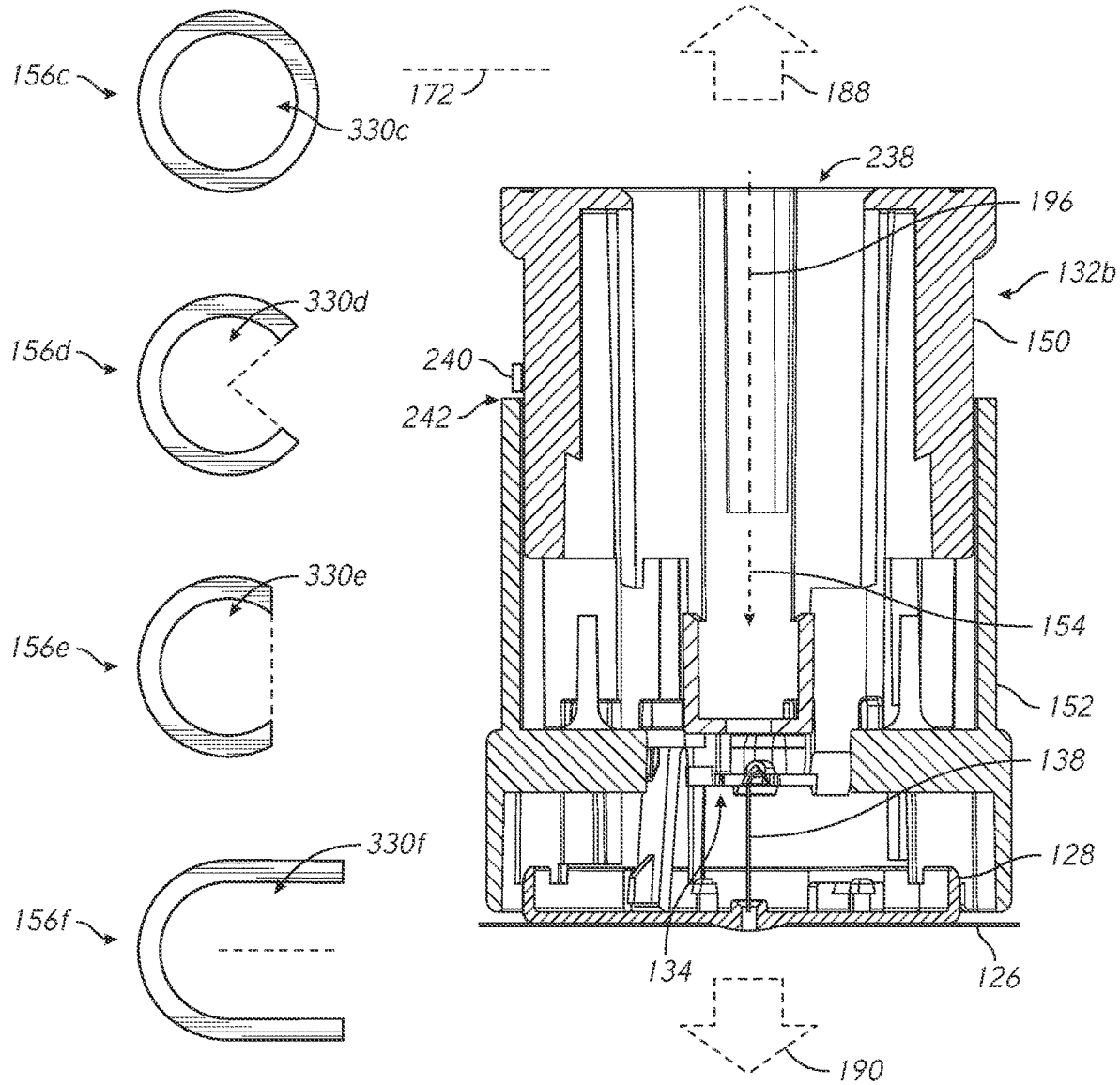

FIG. 55 illustrates cross sectional views of different needles 156c, 156d, 156e, 156f, which can be used as needle 156 in FIG. 7 or in any other embodiment described herein. Needle 156c includes an enclosed channel 330c. Needles 156d, 156e, 156f are C-needles, although many other C-needle shapes can be used in several embodiments. The ends of the needle 156d can be angled relative to each other. In some embodiments, the ends of the needle can be angled away from each other, in an opposite fashion as shown by 156d. In some embodiments, the ends of the needle can have flared edges, in which the flared edges are rounded to prevent the sensor from contacting sharp edges. The ends of the needle 156e can be parallel and/or flat relative to each other. The outside portion of the channel 330f can be formed by walls that are straight and/or parallel to each other (rather than by curved walls as is the case for other needles 156d, 156e). Some needles 156d can be manufactured via laser cutting, some needles 156e can be manufactured via wire electrical discharge machining ("EDM"), and some needles 156f can be manufactured via stamping.

As shown in FIG. 7, a needle hub 162 is coupled to the needle 156. The needle hub includes release features 160 that protrude outward. In some embodiments, the release features can comprise one, two, or more flexible arms. Outward ends 164 of the release features 160 catch on inwardly facing overhangs 166 (e.g., undercuts, detents) of the first portion 150 such that moving the first portion 150 distally relative to the second portion 152 causes the needle retraction mechanism 158 to move distally until a release point.

At the release point, proximal protrusions 170 of the second portion 152 engage the release features 160 (shown in FIG. 9), which forces the release features 160 to bend inward until the release features 160 no longer catch on the overhangs 166 of the first portion 150 (shown in FIG. 10). Once the release features 160 no longer catch on the overhangs 166 of the first portion 150, the spring 234 of the needle retraction mechanism 158 pushes the needle 156 and the needle hub 162 proximally relative to the first portion 150 and relative to the second portion 152 until the needle no longer protrudes distally from the base 128 and is completely hidden inside the telescoping assembly 132 (shown in FIG. 11).

The needle 156 can be removed from the embodiment illustrated in FIG. 7 to make a needle-free embodiment. Thus, a needle 156 is not used in some embodiments. For example, a distal end of the glucose sensor 138 can be formed in a conical shape to enable inserting the glucose sensor 138 into the skin without using a needle 156. Unless otherwise noted, the embodiments described herein can be formed with or without a needle 156.

In several embodiments, a needle can help guide the glucose sensor 138 (e.g., at least a distal portion of the glucose sensor) into the skin. In some embodiments, a needle is not part of the system and is not used to help guide the glucose sensor 138 into the skin. In needle embodiments and needle-free embodiments, skin piercing is an important consideration. Failing to properly pierce the skin can lead to improper placement of the glucose sensor 138.

Tensioning the skin prior to piercing the skin with the glucose sensor 138 and/or the needle 156 can dramatically improve the consistency of achieving proper placement of the glucose sensor 138. Tensioning the skin can be accomplished by compressing the skin with a distally protruding shape (e.g., a convex shape) prior to piercing the skin and at the moment of piercing the skin with the glucose sensor 138 and/or the needle 156.

FIG. 12A illustrates a portion of the cross section shown in FIG. 7. The base 128 includes an optional distally facing protrusion 174 located distally relative to the second portion 152 (and relative to the rest of the telescoping assembly 132). The distal protrusion 174 is convex and is shaped as a dome. In some embodiments, the distal protrusion 174 has block shapes, star shapes, and cylindrical shapes. Several base 128 embodiments do not include the protrusion 174.

The distal protrusion 174 can be located farther distally than any other portion of the base 128. The distal protrusion 174 can extend through a hole 176 in the adhesive 126 (as also shown in FIG. 5). A distal portion of the convex protrusion 174 can be located distally relative to the adhesive 126 while a proximal portion of the convex protrusion 174 is located proximally relative to the adhesive 126.

The distal protrusion 174 has a hole 180 through which the needle 156 and/or the glucose sensor 138 can pass. The distal protrusion 174 can compress the skin such that the distal protrusion 174 is configured to reduce a resistance of the skin to piercing.

FIG. 12B illustrates a cross sectional view of a base 128*b* that is identical to the base 128 illustrated in FIGS. 7 and 12B except for the following features: The base 128*b* does not include a protrusion 174. The base 128*b* includes a funnel 186 (e.g., a radius) on the distal side of the hole 180*b*.

Like the embodiment shown in FIG. 12A, the sensor 138 (e.g., an analyte sensor) and/or the needle 156 (shown in FIG. 12A) can pass through the hole 180*b* (shown in FIG. 12B). The funnels 182, 186 can be mirror images of each other or can be different shapes. The base 128*b* can be used with any of the embodiments described herein.

Figure 13:
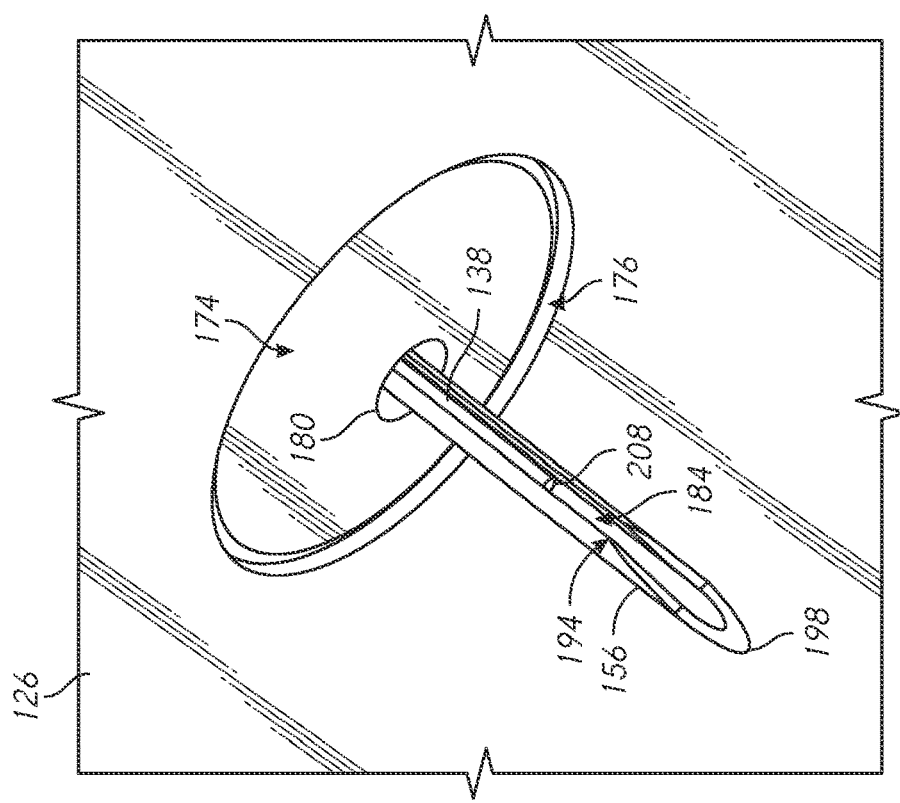
FIG. 13 illustrates a perspective view of a portion of the adhesive from FIG. 4, according to some embodiments.

FIG. 13 illustrates a perspective view of a portion of the adhesive 126. The needle 156 can have many different shapes and cross sections. In some embodiments, the needle 156 includes a slot 184 (e.g., the channel 330 shown in FIGS. 42 and 43) into which at least a portion of the glucose sensor 138 can be placed.

The needle 156 having a slot 184 passes through the hole 180 of the distal protrusion and through the hole 176 of the adhesive 126. A portion of the glucose sensor 138 is located in the slot 184 such that the needle 156 is configured to move distally relative to the base 128 (shown in FIG. 12A) without dislodging the portion of the glucose sensor 138 from the slot 184. The distal protrusion 174 is convex such that the distal protrusion 174 is configured to tension the skin while the first portion 150 moves distally relative to the second portion 152 of the telescoping assembly 132 (shown in FIG. 7) to prepare the skin for piercing.

As mentioned above, the adhesive 126 comprises a hole 176 through which at least a portion of the distal protrusion 174 of the base 128 can pass. The distal protrusion 174 is located within the hole 176 of the adhesive 126 such that the distal protrusion 174 can tension at least a portion of the skin within the second hole (e.g., located under the hole 176). The hole 176 can be circular or any other suitable shape. The hole 176 can be sized such that at least a majority of the distal protrusion 174 extends through the hole 176. A perimeter of the hole 176 can be located outside of the distal protrusion 174 such that the perimeter of the hole 176 is located radially outward relative to a perimeter of the protrusion 174 where the protrusion 174 connects with the rest of the base 128.

In some embodiments, the hole 176 of the adhesive 126 is large enough that the adhesive 126 does not cover any of the distal protrusion 174. In some embodiments, the adhesive 126 covers at least a portion of or even a majority of the distal protrusion 174. Thus, the adhesive 126 does not have to be planar and can bulge distally in an area over the distal protrusion 174.

In several embodiments, the adhesive 126 has a non-uniform thickness such that the thickness of the adhesive 126 is greater in an area surrounding a needle exit area than in other regions that are farther radially outward from the needle exit area. Thus, the distal protrusion 174 can be part of the adhesive 126 rather than part of the base 128. However, in several embodiments, the base 128 comprises the adhesive 126, and the distal protrusion 174 can be formed by the plastic of the base 128 or by the foam adhesive 126 of the base 128.

The needle 156 includes a distal end 198 and a heel 194. The heel 194 is the proximal end of the angled portion of the needle's tip. The purpose of the angled portion is to form a sharp end to facilitate penetrating tissue. The sensor 138 has a distal end 208.

During insertion of the needle 156 and the sensor 138 into the tissue; as the needle 156 and the sensor 138 first protrude distally from the system; and/or while the needle 156 and the sensor 138 are located within the telescoping assembly, the end 208 of the sensor 138 can be located at least 0.1 millimeter proximally from the heel 194, less than 1 millimeter proximally from the heel 194, less than 3 millimeters proximally from the heel 194, and/or within plus or minus 0.5 millimeters of the heel 194; and/or the end 208 of the sensor 138 can be located at least 0.3 millimeters proximally from the distal end 198 of the needle 156 and/or less than 2 millimeters proximally from the distal end 198.

Referring now to FIG. 12A, the distal protrusion 174 can protrude at least 0.5 millimeters and less than 5 millimeters from the distal surface of the adhesive 126. In embodiments where the adhesive 126 has a non-planar distal surface, the distal protrusion 174 can protrude at least 0.5 millimeters and less than 5 millimeters from the average distal location of the adhesive 126.

As described above, in some embodiments the base is coupled to a telescoping assembly such that the base protrudes from the distal end of the system while the glucose sensor is located remotely from the base and is located within the telescoping assembly. In other embodiments, however, the base is coupled to a telescoping assembly such that the base is located completely inside the telescoping assembly and the base moves distally with the sensor as the first portion is moved distally relative to the second portion of the telescoping assembly.

Figure 59:
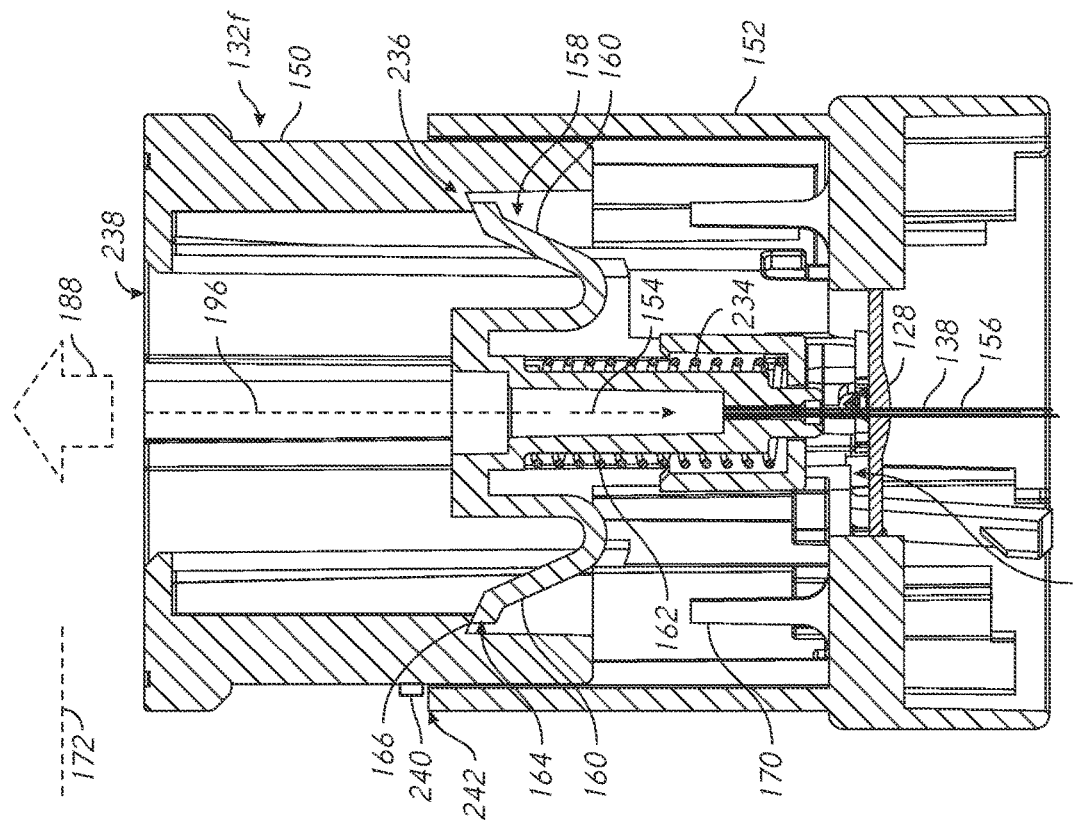
FIG. 59 illustrates a cross-sectional side view of a system that is similar to the embodiment shown in FIG. 7 except for the starting position and the movement of the base, according to some embodiments.

For example, FIG. 59 illustrates a base 128 coupled to the sensor module 134 and to the sensor 138 while the first portion 150 of the telescoping assembly 132f is located in the proximal starting position. The base 128 moves distally as the first portion 150 is moved distally relative to the second portion 152. The base 128 can be coupled to a distal end portion of the first portion 150 while the first portion 150 is located in the proximal starting position. All of the features and embodiments described herein can be configured and used with the base 128 positioning described in the context of FIG. 59.

All of the embodiments described herein can be used with the base coupled to a telescoping assembly such that the base is located completely inside the telescoping assembly and the base moves distally with the sensor as the first portion is moved distally relative to the second portion of the telescoping assembly. All of the embodiments described herein can be used with the base coupled to a telescoping assembly such that the base protrudes from the distal end of the system while the glucose sensor is located remotely from the base and is located within the telescoping assembly.

Sensor Module Docking and Base Detachment

As explained above, maintaining the base against the skin during insertion of the sensor and/or needle enables substantial medical benefits. Maintaining the base against the skin, however, can necessitate moving the sensor relative to the base during the insertion process. Once inserted, the sensor needs to be coupled to the base to prevent the sensor from inadvertently dislodging from the base. Thus, there is a need for a system that enables the sensor to move relative to the base and also enables locking the sensor to the base (without being overly burdensome on users).

Maintaining the base against the skin during the distal movement of the sensor and/or needle is enabled in many embodiments by unique coupling systems that secure the sensor (and the sensor module) to a first portion of a telescoping assembly and secure the base to a second portion of the telescoping assembly. Moving the first portion towards the second portion of the telescoping assembly can align the sensor with the base while temporarily holding the sensor. Then, the system can couple the sensor to the base. Finally, the system can detach the base and sensor from the telescoping assembly (which can be disposable or reusable with a different sensor).

As illustrated in FIG. 4, the sensor module 134 and the glucose sensor 138 are not initially coupled to the base 128. Coupling the sensor module 134 and the glucose sensor 138 to the base 128 via compressing the telescoping assembly 132 and prior to detaching the base 128 from the telescoping assembly 132 can be a substantial challenge, yet is enabled by many of the embodiments described herein.

Figure 14:
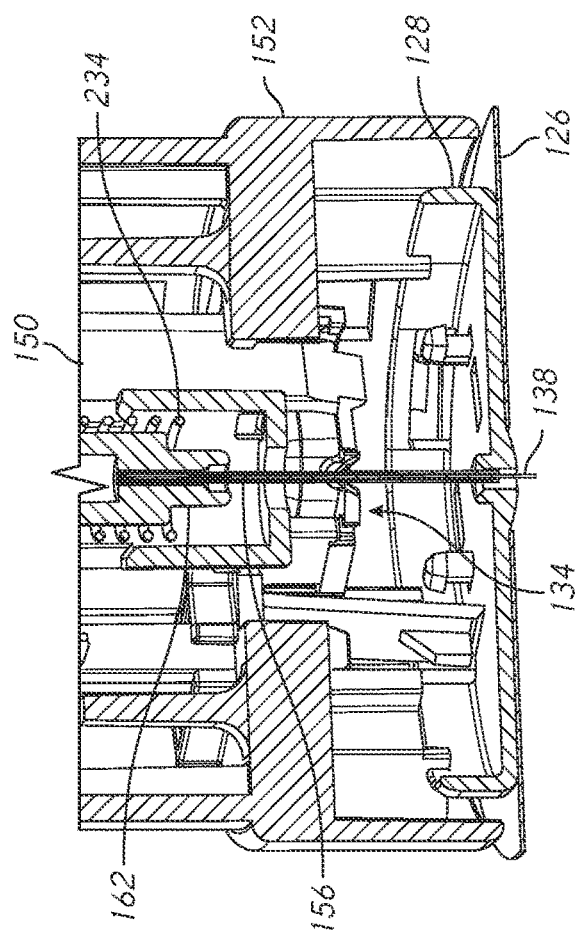
FIG. 14 illustrates a perspective view of a portion of the applicator system from FIG. 3, according to some embodiments.

As illustrated in FIGS. 7 and 14, the sensor module 134 (and the glucose sensor 138) can be located remotely from the base 128 even though they are indirectly coupled via the telescoping assembly 132. In other words, the sensor module 134 (and the glucose sensor 138) can be coupled to the first portion 150 of the telescoping assembly 132 while the base 128 is coupled to the second portion 152 of the telescoping assembly 132. In this state, the sensor module 134 and the glucose sensor 138 can move relative to the base 128 (e.g., as the sensor module 134 and the glucose sensor 138 move from the proximal starting position to the distal position along the path to "dock" the sensor module 134 and the glucose sensor 138 to the base 128).

After the sensor module 134 and the glucose sensor 138 are "docked" with the base 128, the system can detach the base 128 from the telescoping assembly 132 to enable the sensor module 134, the glucose sensor 138, and the base 128 to be coupled to the skin by the adhesive 126 while the telescoping assembly 132 and other portions of the system are discarded.

As shown in FIG. 7, the sensor module 134 is coupled to the first portion 150 and is located at least 5 millimeters from the base 128 while the first portion 150 is in the proximal starting position. The system is configured such that moving the first portion 150 to the distal position couples the sensor module 134 to the base 128 (as shown in FIG. 11). The glucose sensor 138 is coupled to the sensor module 134 while the first portion 150 is located in the proximal starting position. The glucose sensor 138 is located within the second portion 152 while the base 128 protrudes from the distal end of the system.

Arrow 188 illustrates the proximal direction in FIG. 7. Arrow 190 illustrates the distal direction in FIG. 7. Line 172 illustrates a horizontal orientation. As used herein, horizontal means within plus or minus 20 degrees of perpendicular to the central axis 196.

Figure 15:
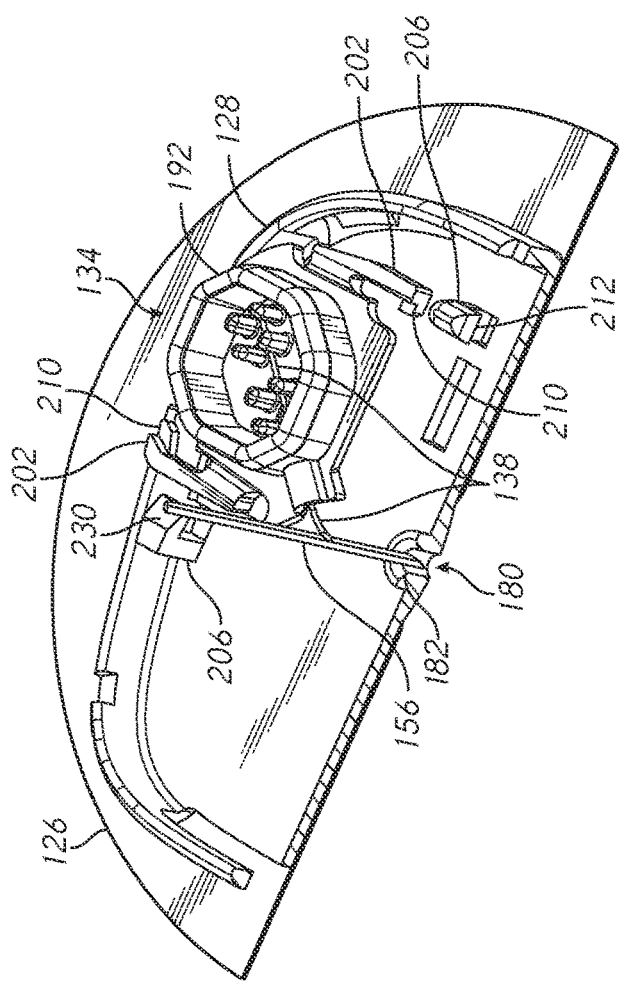

FIG. 15 illustrates a perspective view of a cross section of portions of the system shown in FIG. 7. The cross section cuts through the hole 180 of the base 128. Visible portions include the sensor module 134, the sensor 138, a seal 192, the needle 156, the base 128, and the adhesive 126. The sensor module 134 is in the proximal starting position. The seal 192 is configured to block fluid (e.g., bodily fluid) from entering the glucose sensor module 134.

The glucose sensor 138 is mechanically coupled to the sensor module 134. The glucose sensor 138 runs into an interior portion of the sensor module 134 and is electrically coupled to interconnects in the interior portion of the sensor module 134. The interconnects are hidden in FIG. 15 to facilitate seeing the proximal portion of the glucose sensor 138 inside the interior portion of the sensor module 134. Many other portions of the system are also hidden in FIG. 15 to enable clear viewing of the visible portions.

In many embodiments, the sensor module 134 moves from the position shown in FIG. 15 until the sensor module 134 snaps onto the base 128 via snap fits that are described in more detail below. FIG. 11 illustrates the sensor module 134 snapped to the base 128. This movement from the proximal starting position to the "docked" position can be accomplished by moving along the path 154 (shown in FIG. 7 and illustrated by the progression in FIGS. 7-11). (The arrow representing the path 154 is not necessarily drawn to scale.)

Referring now to FIGS. 7 and 15, during a first portion of the path 154, the sensor module 134 is immobile relative to the first portion 150, and the base 128 is immobile relative to the second portion 152 of the telescoping assembly 132. During a second portion of the path 154, the system is configured to move the first portion 150 distally relative to the second portion 152; to move the sensor module 134 towards the base 128; to move at least a portion of the sensor 138 through a hole 180 in the base 128; to couple the sensor module 134 to the base 128; and to enable the coupled sensor module 134 and the base 128 to detach from the telescoping assembly 132.

FIG. 7 illustrates a vertical central axis 196 oriented from a proximal end to the distal end of the system. (Part of the central axis 196 is hidden in FIG. 7 to avoid obscuring the arrow that represents the path 154 and to avoid obscuring the needle 156.)

FIG. 15 illustrates a flex arm 202 of the sensor module 134. The flex arm 202 is oriented horizontally and is configured to secure the sensor module 134 to a protrusion of the base 128. In some embodiments, the flex arm 202 is an alignment arm to prevent and/or impede rotation of the sensor module 134 relative to the base 128.

Figure 16:
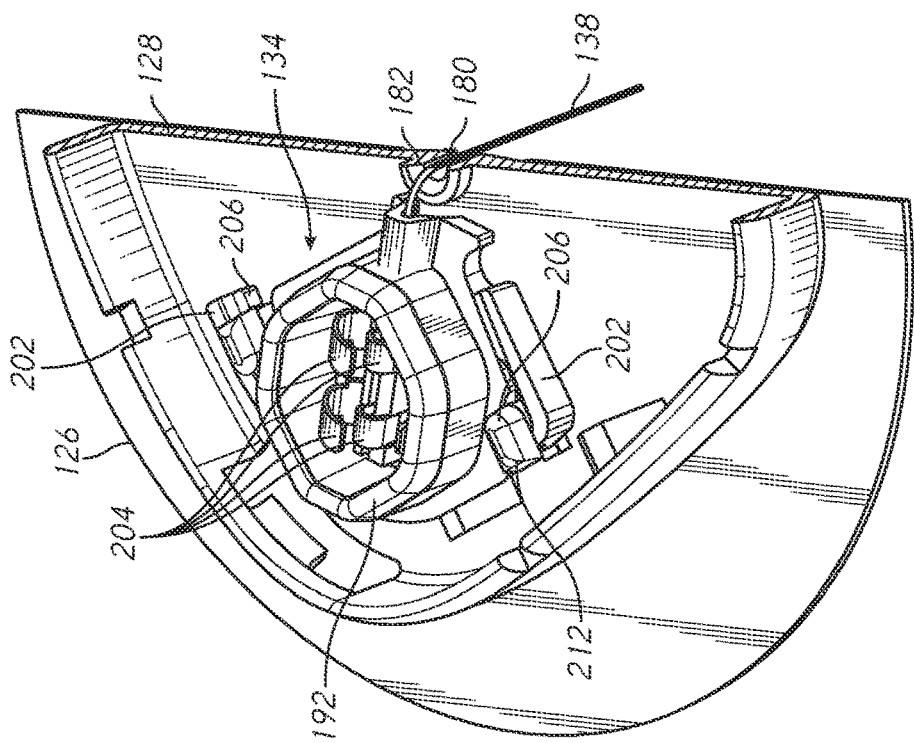
FIGS. 15 and 16 illustrate perspective views of cross sections of portions of the system shown in FIG. 7, according to some embodiments.

FIG. 16 illustrates a perspective view of a cross section in which the sensor module 134 is coupled to the base 128 via flex arms 202. Interconnects 204 protrude proximally to connect the sensor module 134 to the electronics unit 500 (e.g., a transmitter).

Referring now to FIGS. 15 and 16, the flex arms 202 extend from an outer perimeter of the sensor module 134. The base 128 comprises protrusions 206 that extend proximally from a planar, horizontal portion of the base 128.

Referring now to FIG. 16, each of the proximal protrusions 206 of the base 128 are coupled to a flex arm 202 of the sensor module 134. Thus, the coupling of the proximal protrusions 206 to the flex arms 202 couples the sensor module 134 to the base 128.

Each proximal protrusion 206 can include a locking protrusion 212 that extends at an angle of at least 45 degrees from a central axis of each proximal protrusion 206. In some embodiments, the locking protrusions 212 extend horizontally (e.g., as shown in FIG. 15). Each horizontal locking protrusion 212 is coupled to an end portion 210 of a flexible arm 202.

The end portion 210 of each flexible arm 202 can extend at an angle greater than 45 degrees and less than 135 degrees relative to a central axis of the majority of the flexible arm 202. The end portion 210 of each flexible arm 202 can include a horizontal locking protrusion (e.g., as shown in FIG. 15).

In FIGS. 15 and 16, a first horizontal locking protrusion is coupled to an end portion 210 of the first flexible arm 202. A second horizontal locking protrusion 212 is coupled to the first proximal protrusion 206 of the base 128. In FIG. 16, the first horizontal locking protrusion is located distally under the second horizontal locking protrusion 212 to secure the sensor module 134 to the base 128. The system is configured such that moving the first portion 150 of the telescoping assembly 132 to the distal position (shown in FIG. 11) causes the first flex arm 202 to bend to enable the first horizontal locking protrusion of the flex arm 202 to move distally relative to the second horizontal locking protrusion 212. Thus, the flex arm 202 is secured between the locking protrusion 212 and the distal face of the base 128.

At least a portion of the flex arm 202 (e.g., the end portion 210) is located distally under the horizontal locking protrusion 212 of the base 128 to secure the sensor module 134 to the base 128. The system is configured such that moving the first portion 150 of the telescoping assembly 132 to the distal position causes the flex arm 202 (e.g., the end portion 210) to bend away (e.g., outward) from the rest of the sensor module 134 to enable the horizontal locking protrusion of the flex arm 202 to go around the locking protrusion 212 of the proximal protrusion 206. Thus, at least a portion of the flex arm 202 can move distally relative to the horizontal locking protrusion 212 of the proximal protrusion 206 of the base 128.

The sensor module 134 can have multiple flex arms 202 and the base can have multiple proximal protrusions 206 configured to couple the sensor module 134 to the base 128. In some embodiments, a first flex arm 202 is located on an opposite side of the sensor module 134 relative to a second flex arm 202 (e.g., as shown in FIGS. 15 and 16).

In some embodiments, the base 128 comprises flex arms (e.g., like the flex arms 202 shown in FIGS. 15 and 16) and the sensor module 134 comprises protrusions that couple to the flex arms of the base 128. The protrusions of the sensor module 134 can be like the protrusions 206 shown in FIGS. 15 and 16 except that, in several embodiments, the protrusions extend distally towards the flex arms of the base 128. Thus, the base 128 can be coupled to the sensor module 134 with flex arms and mating protrusions regardless of whether the base 128 or the sensor module 134 includes the flex arms.

In several embodiments, a sensor module is coupled to the glucose sensor. The system comprises a vertical central axis oriented from a proximal end to the distal end of the system. The base comprises a first flex arm that is oriented horizontally and is coupled to the sensor module. The sensor module comprises a first distal protrusion coupled to the first flex arm to couple the sensor module to the base. A first horizontal locking protrusion is coupled to an end portion of the first flexible arm. A second horizontal locking protrusion is coupled to the first distal protrusion of the sensor module. The second horizontal locking protrusion is located distally under the first horizontal locking protrusion to secure the sensor module to the base. The system is configured such that moving the first portion of the telescoping assembly to the distal position causes the first flex arm to bend to enable the second horizontal locking protrusion to move distally relative to the first horizontal locking protrusion. The sensor module comprises a second distal protrusion coupled to a second flex arm of the base. The first distal protrusion is located on an opposite side of the sensor module relative to the second distal protrusion.

Docking the sensor module 134 to the base 128 can include securing the sensor module 134 to the first portion 150 of the telescoping assembly 132 while the first portion 150 moves the sensor module 134 towards the base 128. This securing of the sensor module 134 to the first portion 150 of the telescoping assembly 132 needs to be reliable, but temporary so the sensor module 134 can detach from the first portion 150 at an appropriate stage. The structure that secures the sensor module 134 to the first portion 150 of the telescoping assembly 132 generally needs to avoid getting in the way of the docking process.

Figure 17:
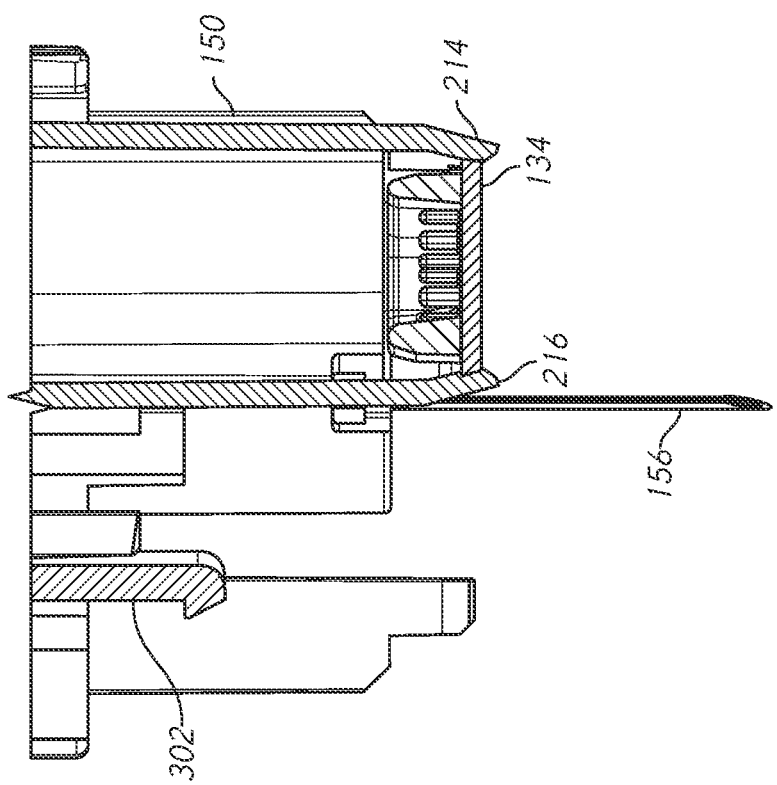
FIG. 17 illustrates a cross-sectional view of the first portion of the telescoping assembly from FIG. 7, according to some embodiments.

FIG. 17 illustrates a cross-sectional view of the first portion 150 of the telescoping assembly 132. FIG. 17 shows the glucose sensor module 134 and the needle 156. Some embodiments do not include the needle 156. Many items are hidden in FIG. 17 to provide a clear view of the flex arms 214, 216 of the first portion 150.

The first portion 150 comprises a first flex arm 214 and a second flex arm 216 that protrude distally and latch onto the sensor module 134 to releasably secure the sensor module 134 to the first portion 150 while the first portion 150 is in the proximal starting position (shown in FIG. 7). The flex arms 214, 216 can couple to an outer perimeter of the sensor module 134 such that distal ends of the flex arms 214, 216 wrap around a distal face of the sensor module 134. In some embodiments, the distal ends of the flex arms 214, 216 are located distally of the sensor module 134 while the first portion 150 is in the proximal starting position.

The base 128 is hidden in FIG. 17, but in the state illustrated in FIG. 17, the sensor module 134 is located remotely from the base 128 to provide a distance of at least 3 millimeters from the sensor module 134 to the base 128 while the first portion 150 is in the proximal starting position. This distance can be important to enable the base to rest on the skin as the needle 156 and/or the glucose sensor 138 pierce the skin and advance into the skin during the transcutaneous insertion.

Referring now to FIGS. 7 and 17, the sensor module 134 is located within the second portion 152 while the base 128 protrudes from the distal end of the system such that the system is configured to couple the sensor module 134 to the base 128 via moving the first portion 150 distally relative to the second portion 152. The sensor module 134 is located within the second portion 152 while the base 128 protrudes from the distal end of the system even though the sensor module 134 is moveable relative to the second portion 152 of the telescoping assembly 132. Thus, the first portion 150 moves the sensor module 134 through an interior region of the second portion 152 of the telescoping assembly 132 without moving the base 128 through the interior region of the second portion 152.

The system comprises a vertical central axis 196 oriented from a proximal end to the distal end of the system. The first flex arm 214 and the second flex arm 216 of the first portion 150 secure the sensor module 134 to the first portion 150 such that the sensor module 134 is releasably coupled to the first portion 150 with a first vertical holding strength (measured along the vertical central axis 196).

As shown in FIGS. 15 and 16, the sensor module 134 is coupled to the base 128 via at least one flex arm 202 such that the sensor module 134 is coupled to the base 128 with a second vertical holding strength. The flex arms 202 can extend from an outer perimeter of the sensor module 134. The flex arms 202 can be part of the base 128.

Referring now to FIG. 17, in some embodiments, the second vertical holding strength is greater than the first vertical holding strength such that continuing to push the first portion 150 distally once the sensor module 134 is coupled to the base 128 overcomes the first and second flex arms 214, 216 of the first portion 150 to detach the sensor module 134 from the first portion 150.

In some embodiments, the second vertical holding strength is at least 50 percent greater than the first vertical holding strength. In several embodiments, the second vertical holding strength is at least 100 percent greater than the first vertical holding strength. In some embodiments, the second vertical holding strength is less than 400 percent greater than the first vertical holding strength.

FIG. 6 illustrates the on-skin sensor assembly 600 in a state where it is attached to a host. The on-skin sensor assembly 600 can include the glucose sensor 138 and/or the sensor module 134 (shown in FIG. 7). In some embodiments, the on-skin sensor assembly 600 includes the needle 156. In several embodiments, however, the on-skin sensor assembly 600 does not include the needle 156.

As explained above, maintaining the base against the skin during insertion of the sensor and/or needle enables substantial medical benefits. Maintaining the base against the skin, however, can complicate detaching the base from the applicator. For example, in some prior-art systems, the base detaches after the base moves downward distally with a needle. This relatively long travel can enable several base detachment mechanisms. In contrast, when the base is maintained in a stationary position as the needle moves towards the base, releasing the base can be problematic.

Many embodiments described herein enable maintaining the base 128 against the skin during insertion of the sensor 138 and/or the needle 156. As mentioned above in the context of FIGS. 7-11, after the sensor module 134 is coupled to the base 128, the sensor module 134 and the base 128 need to detach from the telescoping assembly 132 to secure the glucose sensor 138 to the host and to enable the telescoping assembly to be thrown away, recycled, or reused.

Figure 18:
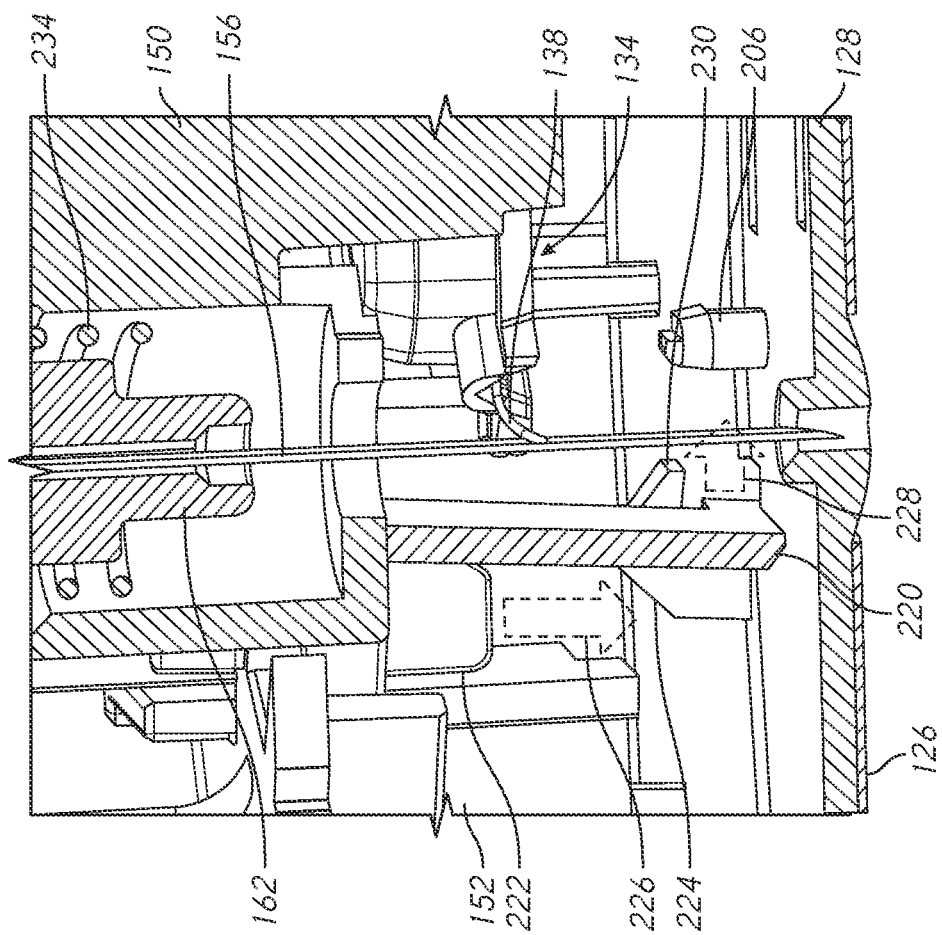
FIGS. 18 and 19 illustrate perspective views of portions of the applicator system from FIG. 7, according to some embodiments.

As shown in FIGS. 7-11, several embodiments hold the base 128 in a stationary position relative to the second portion 152 of the telescoping assembly 132 as the sensor module 134 moves towards the base 128. Referring now to FIG. 18, once the sensor module 134 is attached to the base 128, the system can release the base 128 by bending flex arms 220 that couple the base 128 to the second portion 152. FIG. 18 shows the system in a state prior to the sensor module 134 docking with the base 128 to illustrate distal protrusions 222 of the first portion 150 aligned with the flex arms 220 such that the distal protrusions 222 are configured to bend the flex arms 220 (via the distal protrusions 222 contacting the flex arms 220).

The distal protrusions 222 bend the flex arms 220 to detach the base 128 from the telescoping assembly 132 (shown in FIG. 7) after the sensor module 134 is coupled to the base 128 (as shown in FIGS. 11 and 16). The flex arms 220 can include a ramp 224. A distal end of the distal protrusions 222 can contact the ramp 224 and then can continue moving distally to bend the flex arm 220 as shown by arrow 228 in FIG. 18. This bending can uncouple the flex arm 220 from a locking feature 230 of the base 128. This unlocking is accomplished by the first portion 150 moving distally relative to the second portion 152, which causes the distal protrusions 222 to move as shown by arrow 226.

An advantage of the system shown in FIG. 18 is that the unlocking movement (of the arm 220 bending as shown by arrow 228) is perpendicular (within plus or minus 20 degrees) to the input force (e.g., as represented by arrow 226). Thus, the system is designed such that the maximum holding capability (e.g., of the locking feature 230) can be many times greater than the force necessary to unlock the arm 220 from the base 128. As a result, the system can be extremely reliable and insensitive to manufacturing variability and normal use variations.

In contrast, if the holding force and the unlocking force were oriented along the same axis (e.g., within plus or minus 20 degrees), the holding force would typically be equal to or less than the unlocking force. However, the unique structure shown in FIG. 18 allows the holding force to be at least two times larger (and in some cases at least four times larger) than the unlocking force. As a result, the system can prevent inadvertent unlocking of the base 128 while having an unlocking force that is low enough to be easily provided by a user or by another part of the system (e.g., a motor).

Another advantage of this system is that it controls the locking and unlocking order of operation. In other words, the structure precludes premature locking and unlocking. In a medical context, this control is extremely valuable because reliability is so critical. For example, in several embodiments, the process follows this order: The sensor module 134 couples to the base 128. Then, the first portion 150 releases the sensor module 134. Then, the second portion 152 releases the base 128. In several embodiments, the vertical locations of various locking and unlocking structures are optimized to ensure this order is the only order that is possible as the first portion 150 moves from the proximal starting position to the distal position along the path described previously. (Some embodiments use different locking and unlocking orders of operation.)

FIG. 7 illustrates the base 128 protruding from the distal end of the system while the first portion 150 of the telescoping assembly 132 is located in the proximal starting position. The sensor module 134 and at least a majority of the glucose sensor 138 are located remotely relative to the base 128. The system is configured to couple the sensor module 134 and the glucose sensor 138 to the base 128 via moving the first portion 150 distally relative to the second portion 152.

Figure 19:
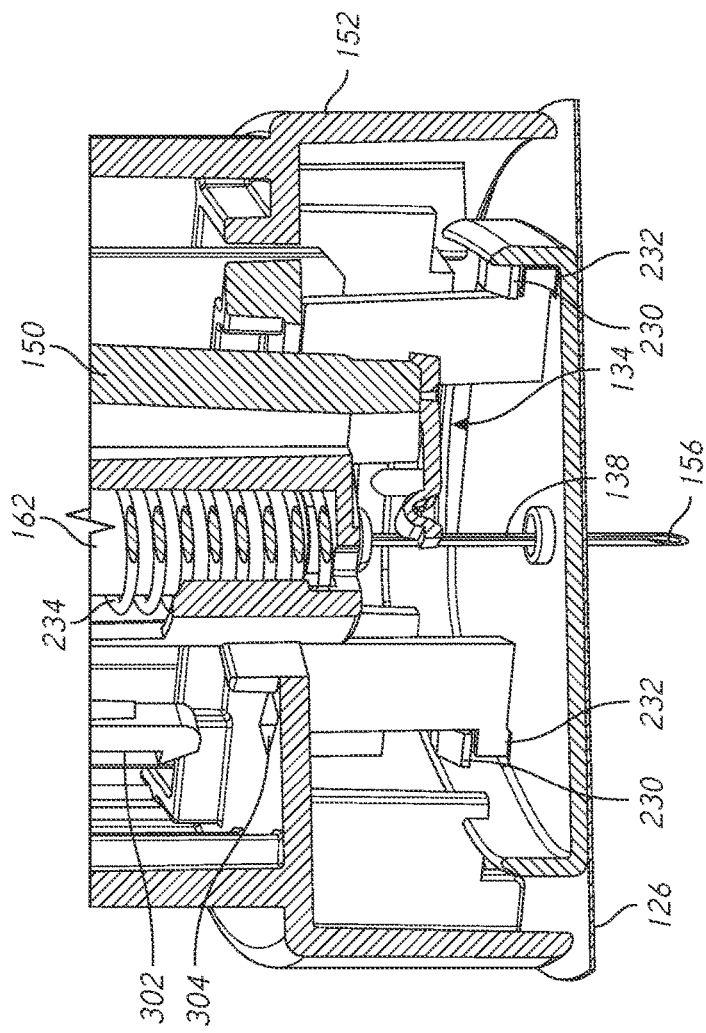

Referring now to FIGS. 18 and 19, the base 128 comprises a first radial protrusion 230 (e.g., a locking feature) releasably coupled with a first vertical holding strength to a second radial protrusion 232 (e.g., a locking feature) of the second portion 152 of the telescoping assembly 132 (shown in FIG. 7). The first radial protrusion 230 protrudes inward and the second radial protrusion protrudes outward 232. The system is configured such that moving the first portion 150 to the distal position moves the second radial protrusion 232 relative to the first radial protrusion 230 to detach the base 128 from the telescoping assembly 132.

The first portion 150 of the telescoping assembly 132 comprises a first arm 222 that protrudes distally. The second portion 152 of the telescoping assembly 132 comprises a second flex arm 220 that protrudes distally. The first arm 222 and the second flex arm 220 can be oriented within 25 degrees of each other (as measured between their central axes). The system is configured such that moving the first portion 150 from the proximal starting position to the distal position along the path 154 (shown in FIG. 7) causes the first arm 222 to deflect the second flex arm 220, and thereby detach the second flex arm 220 from the base 128 to enable the base 128 to decouple from the telescoping assembly 132 (shown in FIG. 7). Thus, the flex arm 220 is configured to releasably couple the second portion 152 to the base 128.

When the first portion 150 is in the proximal starting position, the first arm 222 of the first portion 150 is at least partially vertically aligned with the second flex arm 220 of the second portion 152 to enable the first arm 222 to deflect the second flex arm 220 as the first portion is moved to the distal position.

The first arm 222 and the second arm 220 can be oriented distally such that at least a portion of the first arm 222 is located proximally over a protrusion (e.g., the ramp 224) of the second arm 220. This protrusion can be configured to enable a collision between the first arm 222 and the protrusion to cause the second arm 220 to deflect (to detach the base 128 from the second portion 152).

In the embodiment illustrated in FIG. 18, when the first portion 150 is in the proximal starting position, at least a section of the first arm 222 is located directly over at least a portion of the second flex arm 220 to enable the first arm 222 to deflect the second flex arm 220 as the first portion 150 is moved to the distal position described above. The second flex arm 220 comprises a first horizontal protrusion (e.g., the locking feature 232). The base 128 comprises a second horizontal protrusion (e.g., the locking feature 230) latched with the first horizontal protrusion to couple the base 128 to the second portion 152 of the telescoping assembly 132. The first arm 222 of the first portion 150 deflects the second flex arm 220 of the second portion 152 to unlatch the base 128 from the second portion 152, which unlatches the base 128 from the telescoping assembly 132.

Referring now to FIG. 7, the system is configured to couple the glucose sensor 138 to the base 128 at a first position. The system is configured to detach the base 128 from the telescoping assembly 132 at a second position that is distal relative to the first position.

A third flex arm (e.g., flex arm 202 in FIG. 15) couples the glucose sensor 138 to the base 128 at a first position. The second flex arm (e.g., flex arm 220 in FIG. 18) detaches from the base at a second position. The second position is distal relative to the first position such that the system is configured to secure the base 128 to the telescoping assembly 132 until after the glucose sensor 138 is secured to the base 128.

Spring Compression

Needles used in glucose sensor insertion applicators can be hazardous. For example, inadvertent needle-sticks can transfer diseases. Using a spring to retract the needle can reduce the risk of needle injuries.

Referring now to FIG. 7, a spring 234 (e.g., a coil spring) can be used to retract the needle hub 162 that supports the c-shaped needle 156. The needle hub 162 can be released at the bottom of insertion depth (to enable the needle 156 to retract). For example, when the needle 156 reaches a maximum distal position, a latch 236 can release to enable the spring 234 to push the needle 156 proximally into a protective housing (e.g., into the first portion 150, which can be the protective housing).

Many applicators use pre-compressed springs. Many applicators use substantially uncompressed springs that are compressed by a user as the user compresses the applicator. One disadvantage of a pre-compressed spring is that the spring force can cause the components to creep (e.g., change shape over time), which can compromise the reliability of the design. One disadvantage of an uncompressed spring is that the first and second portions of the telescoping assembly can be free to move slightly relative to each other (when the assembly is in the proximal starting position). This "chatter" of the first and second portions can make the assembly seem weak and flimsy.

Many of the components described herein can be molded from plastic (although springs are often metal). Preventing creep in plastic components can help ensure that an applicator functions the same when it is manufactured and after a long period of time. One way to reduce the creep risk is to not place the parts under a load (e.g., in storage) that is large enough to cause plastic deformation during a storage time.

Generating the retraction energy by storing energy in a spring during deployment limits the duration of load on the system. For example, the retraction force of the spring can be at least partially generated by collapsing the telescoping assembly (rather storing the system with a large retraction force of a fully pre-compressed spring).

Transcutaneous and implantable sensors are affected by the in vivo properties and physiological responses in surrounding tissues. For example, a reduction in sensor accuracy following implantation of the sensor is one common phenomenon commonly observed. This phenomenon is sometimes referred to as a "dip and recover" process. Dip and recover is believed to be triggered by trauma from insertion of the implantable sensor, and possibly from irritation of the nerve bundle near the implantation area, resulting in the nerve bundle reducing blood flow to the implantation area.

Alternatively, dip and recover may be related to damage to nearby blood vessels, resulting in a vasospastic event. Any local cessation of blood flow in the implantation area for a period of time leads to a reduced amount of glucose in the area of the sensor. During this time, the sensor has a reduced sensitivity and is unable to accurately track glucose. Thus, dip and recover manifests as a suppressed glucose signal. The suppressed signal from dip and recover often appears within the first day after implantation of the signal, most commonly within the first 12 hours after implantation. Dip and recover normally resolves within 6-8 hours.

Identification of dip and recover can provide information to a patient, physician, or other user that the sensor is only temporarily affected by a short-term physiological response, and that there is no need to remove the implant as normal function will likely return within hours.

Minimizing the time the needle is in the body limits the opportunity for tissue trauma that can lead to phenomena such as dip and recover. Quick needle retraction helps to limit the time the needle is in the body. A large spring retraction force can quickly retract the needle.

The embodiment illustrated in FIG. 7 solves the "chatter" problem, avoids substantial creep, and enables quick needle retraction. The embodiment places the spring 234 in a slight preload between the first portion 150 and the second portion 152 of the telescoping assembly 132. In other words, when the first portion 150 is in the proximal starting position, the spring 234 is in a slightly compressed state due to the relaxed length of the spring 234 being longer than the length of the chamber in which the spring 234 resides inside the telescoping assembly 132.

In some embodiments, the relaxed length of the spring 234 is at least 4 percent longer than the length of the chamber. In several embodiments, the relaxed length of the spring 234 is at least 9 percent longer than the length of the chamber. In some embodiments, the relaxed length of the spring 234 is less than 18 percent longer than the length of the chamber. In several embodiments, the relaxed length of the spring 234 is less than 30 percent longer than the length of the chamber.

The spring 234 is compressed farther when the first portion 150 is moved distally relative to the second portion 152. In some embodiments, this slight preload has a much shorter compression length than the compression length of typical fully pre-compressed springs. In several embodiments, the preload causes a compression length of the spring 234 that is less than 25 percent of the compression length of the fully compressed spring 234. In some embodiments, the preload causes a compression length of the spring 234 that is greater than 3 percent of the compression length of the fully compressed spring 234. The slight preload eliminates the "chatter" while having a force that is too small to cause substantial creep of non-spring components in the system.

The spring 234 can be inserted into the first portion 150 via a hole 238 in the proximal end of the first portion 150. Then, the needle hub 162 (and the attached C-shaped needle 156) can be loaded through the proximal side of the first portion 150 of the telescoping assembly (e.g., via the hole 238 in the proximal end of the first portion 150).

The needle hub 162 is slid through the first portion 150 until radial snaps (e.g., the release feature 160 of the needle hub 162) engage a section of the first portion 150 (see the latch 236). Thus, the spring 234 is placed with a slight preload between the needle hub 162 and a distal portion of the first portion 150 of the telescoping assembly 132.

During applicator activation and the telescoping (e.g., collapsing of the first portion 150 into the second portion 152), the spring 234 is compressed farther. At the bottom of travel (e.g., at the distal ending position), the radial snaps of the needle hub 162 are forced radially inward by features (e.g., the protrusions 170) in the telescoping assembly 132 (as shown by the progression of FIGS. 7-11). This releases the needle hub 162 and allows the spring 234 to expand to drive the needle 156 proximally out of the host (and into the first portion 150 and/or the second portion 152).

As shown in FIG. 7, the base 128 protrudes from the distal end of the system while the first portion 150 of the telescoping assembly 132 is located in the proximal starting position and the glucose sensor 138 is located remotely relative to the base 128. The glucose sensor 138 is moveably coupled to the base 128 via the telescoping assembly 132 because the glucose sensor 138 is coupled to the first portion 150 and the base 128 is coupled to the second portion 152 of the telescoping assembly 132.

The system includes a spring 234 configured to retract a needle 156. The needle 156 is configured to facilitate inserting the glucose sensor 138 into the skin. In some embodiments, the system does not include the needle 156.

When the first portion 150 is in the proximal starting position, the spring 234 is in a first compressed state. The system is configured such that moving the first portion 150 distally from the proximal starting position increases a compression of the spring 234. The first compressed state places the first portion 150 and second portion 152 in tension. Latching features hold the first portion 150 and second portion 152 in tension. In other words, in the proximal starting position, the latching features are configured to prevent the spring 234 from pushing the first portion 150 proximally relative to the second portion 152. The latching features resist the first compressed state.

In several embodiments, the potential energy of the first compressed state is less than the amount of potential energy necessary to retract the needle 156. This low potential energy of the partially pre-compressed spring 234 is typically insufficient to cause creep, yet is typically sufficient to eliminate the "chatter" described above.

Redundant systems can help ensure that the needle 156 (and in some cases the sensor 138) can always be removed from the host after they are inserted into the host. If in extreme cases the necessary needle removal force is greater than the spring retraction force, the user can pull the entire telescoping assembly 132 proximally to remove the needle 156 and/or the sensor 138 from the host.

Some embodiments include a secondary retraction spring. In other words, in some embodiments, the spring 234 in FIG. 7 is actually two concentric springs. (In several embodiments, the spring 234 is actually just one spring.) The secondary spring can be shorter than the primary retraction spring. The secondary retraction spring can provide additional needle retraction force and can enable additional tailoring of the force profile.

Many users desire to minimize the amount of material they throw away (as trash). Moving the needle 156 to the back of the applicator post deployment enables easy access to remove the needle 156 post deployment.

Figure 20:
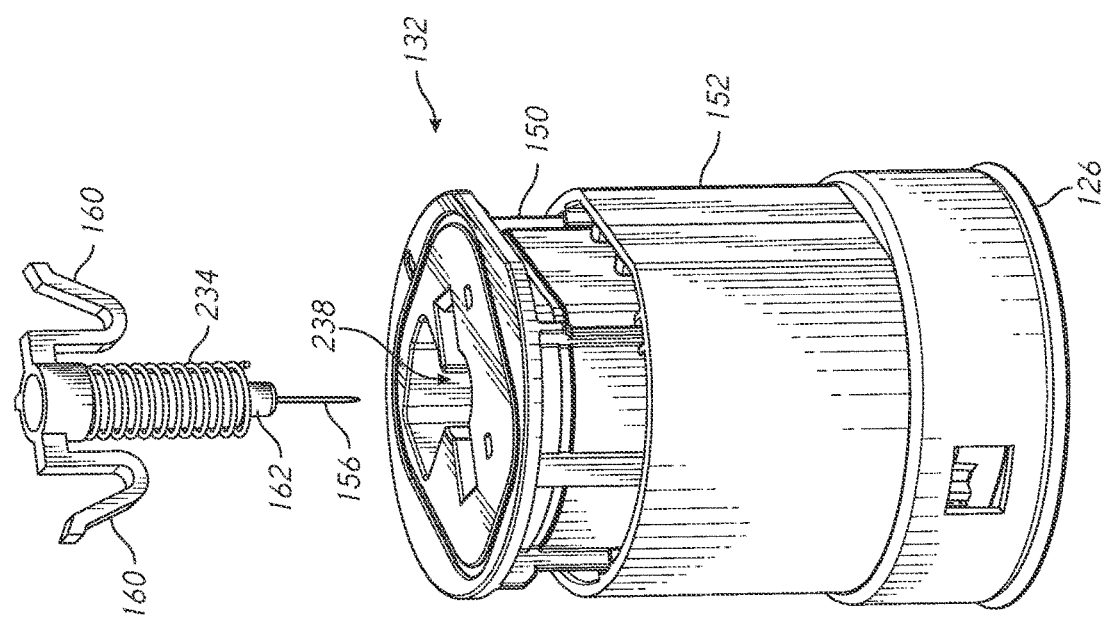

FIG. 20 illustrates a perspective view of the needle 156, the needle hub 162, and the spring 234 just after they were removed proximally from the hole 238 in a proximal end of the first portion 150 of the telescoping assembly 132.

The hole 238 is an opening at a proximal end of the applicator. The hole 238 is configured to enable removing the needle 156, the needle hub 162, and/or the spring 234. This opening can be covered by a removable cover (e.g., a sticker, a hinged lid).

FIGS. 21 and 22 illustrate perspective views where a removable cover 272 is coupled to the first portion 150 to cover the hole 238 through which the needle 156 can be removed from the telescoping assembly 132. A hinge 274 can couple the cover 272 to the first portion 150 such that the cover 272 can rotate to close the hole 238 (as shown in FIG. 22) and rotate to open the hole 238 (as shown in FIG. 21).

Removing the cover 272 can enable a user to remove the needle 156 from the applicator (e.g., the telescoping assembly 132) such that the user can throw the needle 156 in a sharps container and reuse the applicator with a new needle. Removing the needle 156 from the applicator can also enable throwing the rest of the applicator into a normal trash collector to reduce the amount of trash that needs to be held by the sharps container.

The features described in the context of FIGS. 20-22 and 60 can be combined with any of the embodiments described herein.

Figure 60:
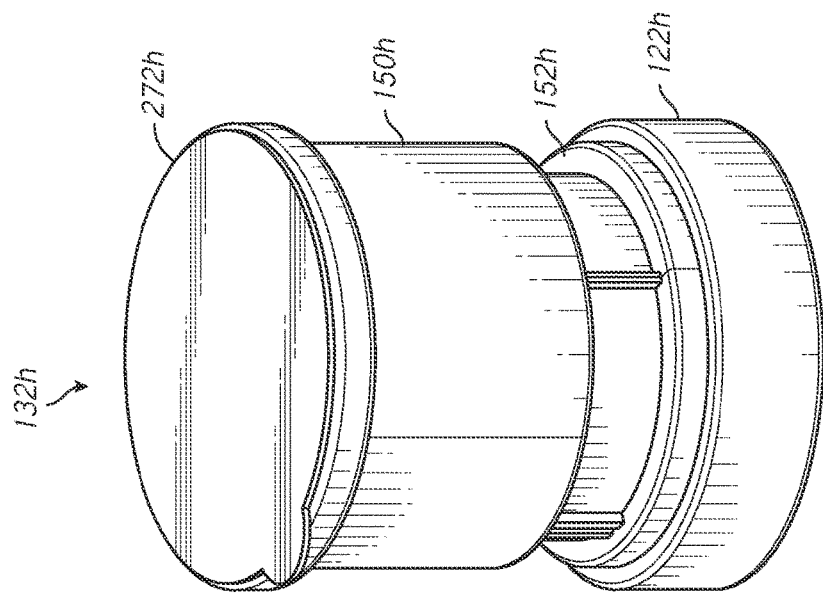
FIG. 60 illustrates a perspective view of a system having a cover, according to some embodiments.

FIG. 60 illustrates a perspective view of another telescoping assembly embodiment 132h. The cover 272h is adhered to a proximal end of the telescoping assembly 132h to cover a hole configured to retrieve a needle after the needle retracts (e.g., as described in the context of FIGS. 21 and 22). Peeling the cover 272h from the telescoping assembly 132h can enable a user to dump the needle 156 (shown in FIG. 7) into a sharps container.

In this embodiment, the cover 272h is a flexible membrane such as a Tyvek label made by E. I. du Pont de Nemours and Company ("DuPont"). The cover 272h can include an adhesive to bond the cover 272h to the proximal end of the telescoping assembly 132h.

In some embodiments, a second cover 272 is adhered to a distal end of the telescoping assembly 132h to cover the end of the telescoping assembly 132h through which the sensor 138 (shown in FIG. 7) passes. The distal end of the telescoping assembly 132h can also be covered by a plastic cap 122h.

The cover 272h can be configured to enable sterilization processes to pass through the material of the cover 272h to facilitate sterilization of the interior of the telescoping assembly 132h. For example, sterilization gases can pass through the cover 272h.

Any of the features described in the context of FIG. 60 can be applicable to all aspects and embodiments identified herein. For example, the embodiments described in the context of FIG. 60 can be combined with the embodiments described in the context of FIGS. 1-59 and 61-70.

The telescoping assembly 132h can use the same interior features and components as described in the context of FIG. 7. One important difference is that the first portion 150h slides on an outer surface of the second portion 152 (rather than sliding inside part of the second portion 152 as shown in FIG. 7). Also, the telescoping assembly 132h does not use a sterile barrier shell 120 (as shown in FIG. 2).

Any of the features described in the context of FIGS. 7-22 can be applicable to all aspects and embodiments identified herein. For example, the embodiments described in the context of FIGS. 7-22 can be combined with the embodiments described in the context of FIGS. 23-70. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Force Profiles

Referring now to FIG. 7, in some embodiments, moving the first portion 150 of the telescoping assembly 132 distally relative to the second portion 152 typically involves placing the distal end of the system against the skin of the host and then applying a distal force on the proximal end of the system. This distal force can cause the first portion 150 to move distally relative to the second portion 152 to deploy the needle 156 and/or the glucose sensor 138 into the skin.

The optimal user force generated axially in the direction of deployment is a balance between preventing accidental premature deployment and ease of insertion. A force that is ideal at a certain portion of distal actuation may be far less than ideal at another portion of distal actuation.

The user places the applicator (e.g., the telescoping assembly 132) against the skin surface and applies a force distally on the applicator (e.g., by pushing down on the proximal end of the applicator). When the user-generated force exceeds a threshold, the applicator collapses (e.g., telescopes distally) and the user drives the sensor into the body.

Several embodiments include unique force profiles that reduce accidental premature deployment; dramatically increase the likelihood of complete and proper deployment; and reduce patient discomfort. Specific structures enable these unique force profiles. For example, the following structures can enable the unique force profiles described herein: structures that hold the telescoping assembly 132 in the proximal starting position; structures that attach the sensor module 134 to the base 128; structures that release the sensor module 134 from the first portion 150; structures that prevent the needle 156 from retracting prematurely; structures that retract the needle 156; structures that release the base 128 from the second portion 152; structures that pad the collision at the distal position; and structures that hold the telescoping assembly 132 in a distal ending position. These structures are described in various sections herein.

Several embodiments include a system for applying an on-skin sensor assembly 600 to a skin 130 of a host (shown in FIG. 4). Referring now to FIG. 7, the system can comprise a telescoping assembly 132 having a first portion 150 configured to move distally relative to a second portion 152 from a proximal starting position to a distal position along a path 154; a glucose sensor 138 coupled to the first portion 150; and a latch 236 configurable to impede a needle 156 from moving proximally relative to the first portion.

The first portion 150 is releasably secured in the proximal starting position by a securing mechanism (e.g., the combination of 240 and 242 in FIG. 7) that impedes moving the first portion 150 distally relative to the second portion 152. The system is configured such that prior to reaching the distal position and/or by reaching the distal position, moving the first portion 150 distally relative to the second portion 152 releases the latch 236 thereby causing the needle 156 to retract proximally into the system.

In several embodiments, the securing mechanism is formed by an interference between the first portion 150 and the second portion 152. The interference can be configured to impede the first portion 150 from moving distally relative to the second portion 152. For example, a radially outward protrusion 240 of the first portion 150 can collide with a proximal end 242 of the second portion 152 such that moving the first portion 150 distally requires overcoming a force threshold to cause the first portion 150 and/or the second portion 152 to deform to enable the radially outward protrusion 240 to move distally relative to the proximal end 242 of the second portion 152.

Figure 23:
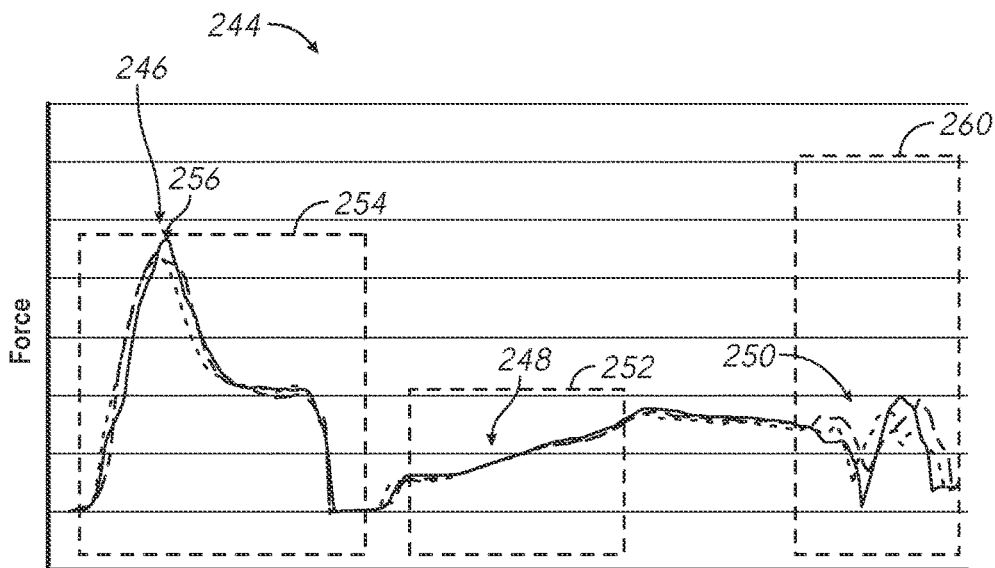
FIG. 23 illustrates a schematic view of force profiles, according to some embodiments.

The system can include a first force profile measured along the path 154. As shown in FIG. 23, the force profile 244 can include force on the Y axis and travel distance on the X axis. Referring now to FIGS. 7 and 23, the force profile 244 can be measured along the central axis 196.

One way in which the force profile 244 can be measured is to place the telescoping assembly 132 against the skin; place a force gauge such as a load cell on the proximal end of the telescoping assembly 132; calibrate the measurement system to account for the weight of the force gauge; and then press on the proximal side of the force gauge to drive the telescoping assembly 132 from the proximal starting position to the distal position along the path 154. FIG. 23 illustrates force versus distance from the proximal starting position based on this type of testing procedure.

The first force profile 244 can comprise a first magnitude 246 coinciding with overcoming the securing mechanism (e.g., 240 and 242), a third magnitude 250 coinciding with releasing the latch 236 (e.g., releasing the needle retraction mechanism), and a second magnitude 248 coinciding with an intermediate portion of the path 154 that is distal relative to overcoming the securing mechanism and proximal relative to releasing the latch 236.

In several embodiments, the second magnitude 248 is a peak force associated with compressing a needle retraction spring (e.g., the spring 234 in FIG. 7) prior to beginning to release the latch 236. This peak force can be at least 0.5 pounds, at least 1.5 pounds, less than 4 pounds, and/or less than 6 pounds.

In several embodiments, the third magnitude 250 is a peak force associated with releasing the needle retraction mechanism. This peak force can be at least 1 pound, at least 2 pounds, less than 4 pounds, and/or less than 6 pounds.

In some embodiments, the second magnitude 248 is less than the first magnitude 246 and the third magnitude 250 such that the system is configured to promote needle acceleration during the intermediate portion of the path 154 to enable a suitable needle speed at a time the needle 156 (or the glucose sensor 138) first pierces the skin.

The first magnitude 246 can be the peak force required to overcome the securing mechanism (e.g., 240 and 242). This peak force can be at least 5 pounds, at least 6 pounds, less than 10 pounds, and/or less than 12 pounds. The first magnitude 246 can be at least 100 percent greater than the second magnitude 248. The first magnitude 246 can be at least 200 percent greater than the second magnitude 248. The second magnitude 248 can be during a portion of the force profile 244 where the compression of the spring 234 is at least 50 percent of the maximum spring compression reached just before the needle 156 begins to retract proximally. The slope of the force profile 244 can be positive for at least 1 millimeter during the time at which the second magnitude 248 is measured (due to the increasing spring force as the spring compression increases).

The first magnitude 246 can be greater than the third magnitude 250 (and/or greater than the second magnitude 248) such that the system is configured to impede initiating a glucose sensor insertion cycle unless a user is applying enough force to release the latch 236. For example, the force necessary for the protrusion 240 to move distally relative to the proximal end 242 can deliberately be designed to be greater than the force necessary to retract the needle 156.

To provide a sufficient safety margin, the first magnitude 246 can be at least 50 percent greater than the third magnitude 250. In some embodiments, the first magnitude 246 is at least 75 percent greater than the third magnitude 250. To avoid a system where the first magnitude 246 is unnecessarily high in light of the forces required along the path 154 distally relative to the first magnitude 246, the first magnitude 246 can be less than 250 percent greater than the third magnitude 250.

A second force profile 252 can coincide with the intermediate portion of the path 154. For example, the second magnitude 248 can be part of the second force profile 252. This second force profile 252 can include a time period in which the slope is positive for at least 1 millimeter, at least 2.5 millimeters, less than 8 millimeters, and/or less than 15 millimeters (due to the increasing spring force as the spring compression increases).

A proximal millimeter of the second force profile 252 comprises a lower average force than a distal millimeter of the second force profile 252 in response to compressing a spring 234 configured to enable the system to retract the needle 156 into the telescoping assembly 132.

The system also includes a first force profile 254 (measured along the path 154). The first force profile 254 comprises a first average magnitude coinciding with moving distally past a proximal half of the securing mechanism and a second average magnitude coinciding with moving distally past a distal half of the securing mechanism. The first average magnitude is greater than the second average magnitude such that the system is configured to impede initiating a glucose sensor insertion cycle unless a user is applying enough force to complete the glucose sensor insertion cycle.

A first force peak 256 coincides with moving distally past the proximal half of the securing mechanism. The first force peak 256 is at least 25 percent higher than the second average magnitude.

The first force profile 254 comprises a first magnitude 246 coinciding with overcoming the securing mechanism and a subsequent magnitude coinciding with terminating the securing mechanism (e.g., moving past the distal portion of the securing mechanism). The first magnitude 246 comprises a proximal vector and the subsequent magnitude comprises a distal vector. FIG. 23 is truncated at zero force, so the distal vector appears to be have a magnitude of zero in FIG. 23, although the actual value is negative (e.g., negative 2 pounds).

The proximal vector means the system is resisting the distal movement of the first portion 150 relative to the second portion 152. The distal vector means that the second half of the securing mechanism can help propel the needle 156 and the sensor 138 towards the skin and/or into the skin. In other words, the distal vector assists the distal movement of the first portion 150 relative to the second portion 152.

The third force profile 260 can include many peaks and values due to the following events: the sensor module 134 docking to the base 128; the base detaching from the second portion 152 (and thus detaching from the telescoping assembly 132); the release feature 160 of the needle hub 162 defecting inward due to the proximal protrusions 170 of the second portion 152; the latch 236 releasing; the needle 156 retracting into an inner chamber of the first portion 150; and/or the first portion 150 hits the distal position (e.g., the end of travel).

As shown in FIG. 7, the securing mechanism can be a radially outward protrusion 240 (of the first portion 150) configured to collide with a proximal end 242 of the second portion 152 such that moving the first portion 150 distally requires overcoming a force threshold to cause the first portion 150 and/or the second portion 152 to deform to enable the radially outward protrusion 240 to move distally relative to the proximal end 242 of the second portion 152. The radially outward protrusion 240 is configured to cause the second portion 152 to deform elliptically to enable the first portion 150 to move distally relative to the second portion 152.

Figure 24:
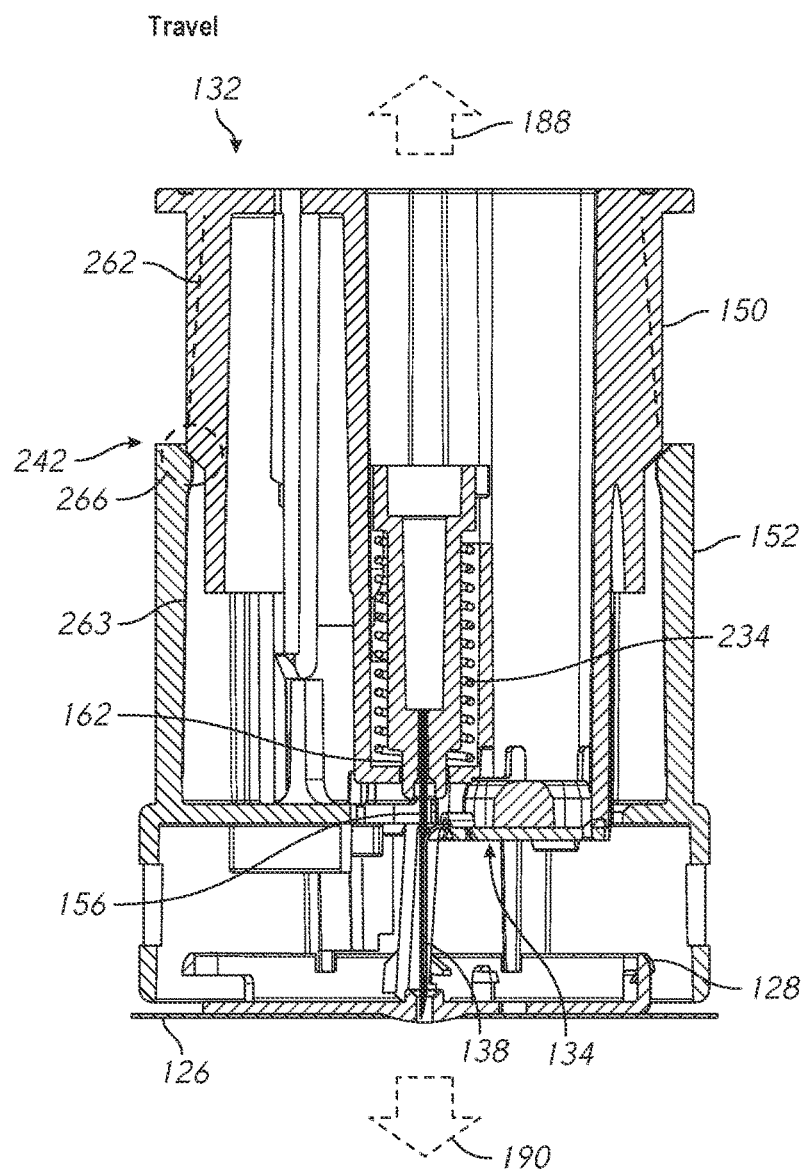
FIG. 24 illustrates a cross-sectional side view of a portion of an applicator system, according to some embodiments.

FIG. 24 illustrates another securing mechanism. At least a section of the first portion 150 interferes with a proximal end 242 of the second portion 152 such that pushing the first portion 150 distally relative to the second portion 152 requires a force greater than a force threshold. The force threshold is the minimum force necessary to deform at least one of the first portion 150 and the second portion 152 to overcome the interference 266, which is shown inside a dashed circle in FIG. 24.

Many different interference geometries and types are used in various embodiments. The interference can be between the first portion 150 and the second portion 152. The interference can be between the needle hub 162 and the second portion 152. For example, the interference can resist the distal movement of the needle hub 162.

In some embodiments, the first portion 150 includes a taper 262. Once an interfering section of the first portion 150 moves distally past the interference area 266, the taper 262 makes the system such that the interference 266 no longer impedes distal movement of the first portion 150.

The second portion 152 can also have a taper 263. The taper 263 can be on an interior surface of the second portion 152 such that the interior size gets larger as measured proximally to distally along the taper 263.

The interfering portion 242 of the second portion 152 can include a ramp (as shown in FIG. 24) to aid the deformation described above. The interfering section of the first portion 150 is located proximally relative to the interfering section of the second portion 152.

The securing mechanism can comprise a radially outward protrusion (e.g., 240 in FIG. 7) of the first portion 150 that interferes with a radially inward protrusion of the second portion 152 (e.g., as shown by the interference 266 in FIG. 24) such that the securing mechanism is configured to cause the second portion 152 to deform elliptically to enable the first portion 150 to move distally relative to the second portion 152.

Any of the features described in the context of FIGS. 24-32 can be applicable to all aspects and embodiments identified herein. For example, the embodiments described in the context of FIGS. 24-32 can be combined with the embodiments described in the context of FIGS. 1-23 and 33-70. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

FIG. 25 illustrates a cross sectional view of a portion of an embodiment in which the needle holder (e.g., the needle hub 162) is configured to resist distal movement of the first portion 150 relative to the second portion 152b. The second portion 152b is like other second portions 150 described herein (e.g., as shown in FIG. 7) except that the second portion 152b includes flex arms 276 that are at least part of the securing mechanism. The flex arms 276 are releasably coupled to the needle holder to releasably secure the first portion 150 to the second portion 152b in the proximal starting position (as shown in FIG. 7).

The needle 156 (shown in FIG. 7) is retractably coupled to the first portion 150 by the needle holder 162. The needle holder 162 is configured to resist distal movement of the first portion 150 relative to the second portion 152b due to a chamfer and/or a ramp 278 interfering with flex arms 276. Pushing the first portion 150 distally requires overcoming the force necessary to deflect the flex arms 276 outward such that the flex arms 276 move out of the way of the ramp 278.

FIG. 27 illustrates a perspective view of another securing mechanism, a frangible release 280. FIG. 26 illustrates a top view of a frangible ring 282. The ring 282 includes two frangible tabs 284 that protrude radially inward. In some embodiments, the tabs 284 are radially inward protrusions on opposite sides of the ring 282 relative to each other. The frangible member (e.g., the ring 282) can be part of the first portion 150, the second portion 152, or any other portion of the system. For example, the frangible member can be a feature of a molded second portion 152.

The ring 282 can be made of a brittle material configured to enable the tabs 284 to break when the first portion 150 is pushed distally relative to the second portion 152. For example, a section of the first portion 150 can be located proximally over the tab 284 when the first portion 150 is in the proximal starting position (as shown in FIG. 27 by the frangible release 280). Moving the first portion 150 distally can cause the section of the first portion 150 to bend and/or break the tab 284.

In some embodiments, a radially outward protrusion 286 of the first portion 150 is configured to bend and/or break the tab 284. The ring 282, the tab 284, and the other components described herein can be molded from a plastic such as acrylonitrile butadiene styrene, polyethylene, and polyether ether ketone. (Springs, interconnects, and needles can be made of steel.) In some embodiments, the ring 282 is at least 0.2 millimeters thick, at least 0.3 millimeters thick, less than 0.9 millimeters thick, and/or less than 1.5 millimeters thick.

The ring 282 can be secured between the first portion 150 and the second portion 152 of the telescoping assembly 132. The ring 282 can wrap around a perimeter of the first portion 150 and can be located proximally relative to the second portion 152 such that the ring 282 rests against a proximal end of the second portion 152.

The ring 282 enables a frangible coupling between the first portion 150 and the second portion 152 while the first portion 150 is in the proximal starting position. In FIG. 27, the system is configured such that moving the first portion 150 to the distal position breaks the frangible coupling (e.g., the frangible release 280).

In some embodiments, the tabs 284 are not part of a ring 282. The tabs 284 can be part of the second portion 152 or part of the first portion 150.

FIG. 27 also includes a magnet system 290. The magnet system 290 includes a magnet and a metal element in close enough proximity that the magnet is attracted to the metal element (e.g., a metal disk). For example, the second portion 152 can include a magnet, and the first portion 150 can include the metal element. In several embodiments, the second portion 152 can include a metal element, and the first portion 150 can include the magnet.

The magnet and metal element can be located such that they are located along a straight line oriented radially outward from the central axis 196 (shown in FIG. 7). This configuration can position the magnet for sufficient attraction to the metal element to resist movement of the first portion 150. For example, when the first portion 150 is in the proximal starting position, the magnetic force of the magnet system 290 can resist distal movement of the first portion.

Thus, the magnet releasably couples the first portion 150 to the second portion 152 while the first portion 150 is in the proximal starting position.

In several embodiments, a user can compress an internal spring or the spring can be pre-compressed (e.g., compressed fully at the factory). The telescoping assembly can include a button 291 configured to release the spring force to cause the needle and/or the sensor to move into the skin.

The cover 272*h* described in the context of FIG. 60 can be adhered to the proximal end of the first portion 150 shown in FIG. 27. The cover 272*h* can be used with any of the embodiments described herein.

Figure 31:
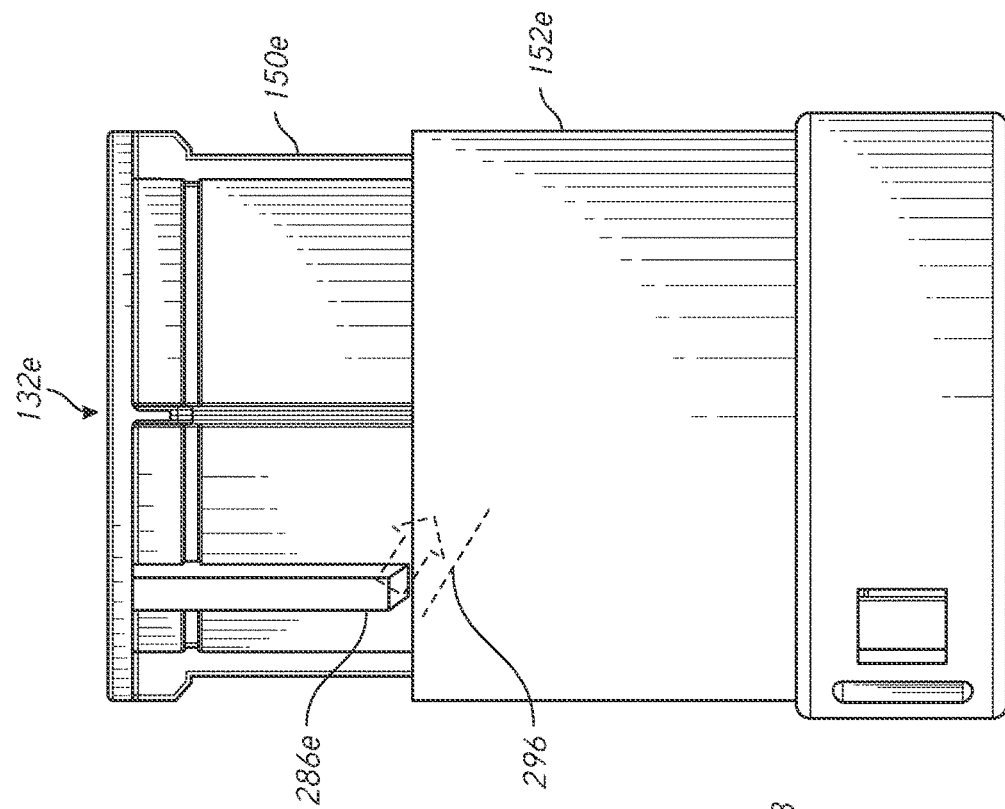
FIG. 31 illustrates a side view of a telescoping assembly that causes rotational movement, according to some embodiments.

FIG. 31 illustrates a side view of a telescoping assembly 132*e* having a first portion 150*e* and a second portion 152*e*. The first portion 150*e* includes a radially outward protrusion 286*e* configured to engage a radially inward ramp 296 located on an interior wall of the second portion 152*e*. When a user applies a distal, axial force on the first portion 150*e*, the protrusion 286*e* collides with the ramp 296. The angle of the ramp causes the first portion 150*e* to rotate relative to the second portion 152*e*. This rotation resists the distal force and acts as a securing mechanism. Once the protrusion 286*e* moves beyond the distal end of the ramp 296, the ramp 296 no longer causes rotation, and thus, no longer acts as a securing mechanism.

Many of the embodiments described herein rely on a compressive force of a person. Many unique structures enable the force profiles described herein. The structures help ensure the compressive force caused by a person pushing distally on a portion of the system results in reliable performance. One challenge of relying on people to push downward on the system to generation appropriate forces is that the input force can vary substantially by user. Even a single user can apply different input forces on different occasions.

One solution to this variability is to replace the need for a user-generated input force with a motor-generated force. The motor can provide reliable input forces. Motors also enable varying the force at different sections of the path from the proximal starting position to the distal position.

Figure 30:
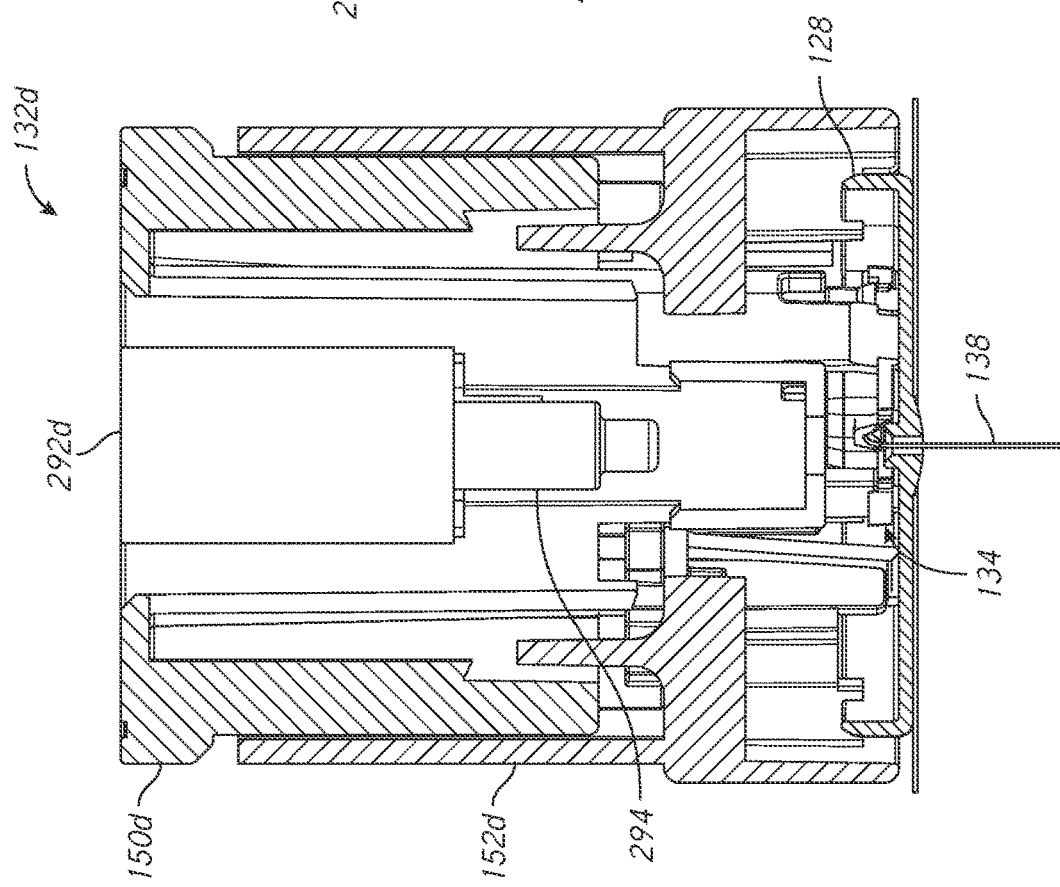

FIGS. 28-30 illustrates embodiments of telescoping assemblies 132*c*, 132*d* that include motors 290*c*, 290*d* to drive a needle 156 and/or a glucose sensor 138 into the skin. The motors 290*c*, 290*d* can be linear actuators that use an internal magnetic system to push a rod distally and proximally. The linear actuators can also convert a rotary input into linear motion to push a rod distally and proximally. The movement of the rod can move various portions of the system including the needle 156, the needle hub 162*c*, the first portion 150*c*, 150*d* of the telescoping assembly 132*c*, 132*d*, the sensor module 134, and/or the sensor 138. The motors 290*c*, 290*d* can include internal batteries to supply electricity for the motors 290*c*, 290*d*.

FIG. 28 illustrates a perspective, cross-sectional view of an embodiment in which the motor 290*c* pushes the needle hub 162*c* distally relative to the motor 290*c* and relative to the second portion 152*c*. The needle hub 162*c* can include a rod that slides in and out of the housing of the motor 292*c*. The distal movement of the needle hub 162*c* can push at least a portion of the needle 156 and/or the sensor 138 (shown in FIG. 7) into the skin. The distal movement of the needle hub 162*c* can move the sensor module 134 distally such that the sensor module 134 docks with the base 128. This coupling can precede the detachment of the base 128 from the telescoping assembly 132*c*.

FIGS. 29 and 30 illustrate side, cross-sectional views of another motor embodiment. In this embodiment, the rod 294 of the motor 292*d* is coupled to and immobile relative to the second portion 152*d* of the telescoping assembly 132*d*. The motor 292*d* is coupled to and immobile relative to the first portion 150*d* of the telescoping assembly 132*d*. As a result, pulling the rod 294 into the housing of the motor 292*d* causes the first portion 150*d* to move distally relative to the second portion 152*d*. The glucose module 134 is coupled to a distal portion of the first portion 150*d* (as described herein). Thus, the glucose sensor 138 is moved distally into the skin of the host and the glucose module 134 is coupled to the base 128. As illustrated in FIGS. 29 and 30, the embodiment does not include a needle. Similar embodiments can include a needle.

FIG. 32 illustrates a perspective, cross-section view of the telescoping assembly 132. In some embodiments, a protrusion 302 of the first portion 150 couples with a hole 304 of the second portion 152. The protrusion 302 can be oriented distally to latch with the hole 304 in response to the first portion 150 reaching the distal position.

In several embodiments, a protrusion 302 of the second portion 152 couples with a hole 304 of the first portion 150. The protrusion 302 can be oriented proximally to latch with the hole 304 in response to the first portion 150 reaching the distal position.

The protrusion 302 can be a flex arm that is at least 10 millimeters long, at least 15 millimeters long, and/or less than 50 millimeters long. The protrusion 302 can include an end portion that protrudes at an angle relative to the central axis of the majority of the protrusion 302. This angle can be at least 45 degrees, at least 75 degrees, less than 110 degrees, and/or less than 135 degrees.

Coupling the protrusion 302 to the hole 304 can permanently lock the first portion 150 in a downward position (that is distal to the proximal starting position and is within 3 millimeter of the distal position) while the needle 156 is in a retracted state. This locking can prevent the system from being reused and can prevent needle-stick injuries.

Any of the features described in the context of FIG. 23 can be applicable to all aspects and embodiments identified herein. For example, the embodiments described in the context of FIG. 23 can be combined with the embodiments described in the context of FIGS. 1-22 and 24-70. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Interconnects

Referring now to FIG. 4, in many embodiments, the electronic unit 500 drives a voltage bias through the sensor 138 so that current can be measured. Thus, the system is able to analyze glucose levels in the host. The reliability of the electrical connection between the sensor 138 and the electronics unit 500 is critical for accurate sensor data measurement.

In many embodiments, the host or a caregiver create the electrical connection between the sensor 138 and the electronics unit 500. A seal 192 can prevent fluid ingress as the electronics unit 500 is pressed onto the glucose sensor module 134. Oxidation and corrosion can change electrical resistance of the system and are sources of error and noise in the signal.

The electrical connections should be mechanically stable. Relative movement between the parts of the electrical system can cause signal noise, which can hinder obtaining accurate glucose data.

A low-resistance electrical connection is more power efficient. Power efficiency can help maximize the battery life of the electronics unit 500.

In embodiments where the host or caregiver must compress the electrical interconnect and/or seal 192, minimizing the necessary force increase user satisfaction. Lowering the user-applied force makes the transmitter easier to install. If the necessary force is too great, users and caregivers may inadvertently fail to apply adequate force, which can jeopardize the reliability and performance of the system. The force that the user needs to apply to couple the electronics unit 500 to the base 128 and sensor module 134 is strongly influenced by the force necessary to compress the interconnect. Thus, there is a need for an electrical interconnect with a lower compression force.

Manufacturing variability, host movement, and temperature variations while the host is using the on-skin sensor assembly 600 necessitate providing a robust electrical connection throughout an active compression range (which encompasses the minimum and maximum compression states reasonably possible). Thus, there is a need for electrical connections that are tolerant of compression variation within the active compression range.

Metallic springs (e.g., coil or leaf springs) can be compressed between the sensor 138 and the electronics unit 500 to provide a robust, reliable electrical connection that requires a low compression force to couple the electronics unit 500 to the base 128.

FIG. 33 illustrates a perspective view of an on-skin sensor assembly just before the electronics unit 500 (e.g., a transmitter) is snapped onto the base 128. Coupling the electronics unit 500 to the base 128 can compress the seal 192 to prevent fluid ingress and can compress an interconnect (e.g., springs 306) to create an electrical connection 310 between the glucose sensor 138 and the electronics unit 500.

Creating the electrical connection 310 and/or coupling the electronics unit 500 to the base 128 can cause the electronics unit 500 (e.g., a transmitter) to exit a sleep mode. For example, conductive members (e.g., of the sensor module 134 and/or of the base 128) can touch electrical contacts of the electronics unit 500 (e.g., electrical contacts of a battery of the electronics unit 500), which can cause the electronics unit 500 to exit a sleep mode. The conductive member of the sensor module 134 and/or of the base 128 can be a battery jumper that closes a circuit to enable electricity from the battery to flow into other portions of the electronics unit 500.

Thus, creating the electrical connection 310 and/or coupling the electronics unit 500 to the base 128 can "activate" the electronics unit 500 to enable and/or to prepare the electronics unit 500 to wirelessly transmit information to other devices 110-113 (shown in FIG. 1). U.S. Patent Publication No. US-2012-0078071-A1 includes additional information regarding transmitter activation. The entire contents of U.S. Patent Publication No. US-2012-0078071-A1 are incorporated by reference herein.

The distal face of the electronics unit 500 can include planar electrical contacts that touch the proximal end portions of the springs 306. The distal end portions of the springs 306 can contact various conductive elements of the glucose sensor 138. Thus, the springs 306 can electrically couple the electronics unit 500 to the various conductive elements of the glucose sensor 138. In the illustrated embodiment, two metallic springs 306 electrically connect the glucose sensor 138 and the electronics unit 500. Some embodiments use one spring 306. Other embodiments use three, four, five, ten, or more springs 306.

Metallic springs 306 (e.g., gold-plated springs) are placed above the sensor wire 138 in the sensor module 134. The sensor 138 is located between a rigid polymer base 128 and the bottom surface of the spring 306. The top surface of the spring 306 contacts a palladium electrode located in the bottom of the electronics module 500. The rigid electronics module 500 and the rigid polymer base 128 are brought together creating a compressed sandwich with the sensor 138 and the spring 306.

The springs 306 can be oriented such that their central axes are within 25 degrees of the central axis 196 of the telescoping assembly 132 (shown in FIG. 7). The springs 306 can have a helical shape. The springs 306 can be coil springs or leaf springs.

Springs 306 can have ends that are plain, ground, squared, squared and ground, or any other suitable configuration. Gold, copper, titanium, and bronze can be used to make the springs 306. Springs 306 can be made from spring steel. In several embodiments, the steels used to make the springs 306 can be low-alloy, medium-carbon steel or high-carbon steel with a very high yield strength. The springs 306 can be compression springs, torsion springs, constant springs, variable springs, helical springs, flat springs, machined springs, cantilever springs, volute springs, balance springs, leaf springs, V-springs, and/or washer springs.

Some embodiments use a spring-loaded pin system. The spring system can include a receptacle. A pin can be located partially inside the receptacle such that the pin can slide partially in and out of the receptacle. A spring can be located inside the receptacle such that the spring biases the pin outward towards the electronics unit 500. The receptacle can be electrically coupled to the sensor 138 such that pressing the electronics unit 500 onto the spring-loaded pin system electrically couples the electronics unit 500 and the sensor 138.

Mill-Max Mfg. Corp. of Oyster Bay, N.Y., U.S.A. ("Mill-Max") makes a spring-loaded pin system with a brass-alloy shell that is plated with gold over nickel. One Mill-Max spring-loaded pin system has a stainless steel spring and an ordering code of 0926-1-15-20-75-14-11-0.

In several embodiments, the electronics unit 500 includes a battery to provide electrical power to various electrical components (e.g., a transmitter) of the electronics unit 500.

In some embodiments, the base 128 can include a battery 314 that is located outside of the electronics unit 500. The battery 314 can be electrically coupled to the electrical connection 310 such that coupling the electronics unit 500 to the base 128 couples the battery 314 to the electronics unit 500. FIGS. 22B and 22C of U.S. Patent Publication No. US-2009-0076360-A1 illustrate a battery 444, which in some embodiments, can be part of the base (which can have many forms including the form of base 128 shown in FIG. 33 herein). The entire contents of U.S. Patent Publication No. US-2009-0076360-A1 are incorporated by reference herein.

FIG. 34 illustrates a perspective view of the sensor module 134. Protrusions 308 can secure the springs 306 to the sensor module 134. (Not all the protrusions 308 are labeled in order to increase the clarity of FIG. 34.) The protrusions 308 can protrude distally.

At least three, at least four, and/or less than ten protrusions 308 can be configured to contact a perimeter of a spring 306. The protrusions 308 can be separated by gaps. The gaps enable the protrusions 308 to flex outward as the spring 306 is inserted between the protrusions 308. The downward force of coupling the electronics unit 500 to the base 128 can push the spring 306 against the sensor 138 to electrically couple the spring 306 to the sensor 138. The sensor 138 can run between at least two of the protrusions 308.

FIG. 33 illustrates an on-skin sensor system 600 configured for transcutaneous glucose monitoring of a host. The on-skin sensor system 600 can be used with the other components shown in FIG. 7. The sensor module 134 can be replaced with the sensor modules 134d, 134e shown in FIGS. 35 and 37. Thus, the sensor modules 134d, 134e shown in FIGS. 35 and 37 can be used with the other components shown in FIG. 7.

Referring now to FIGS. 33 and 34, the system 600 can include a sensor module housing 312; a glucose sensor 138a, 138b having a first section 138a configured for subcutaneous sensing and a second section 138b mechanically coupled to the sensor module housing 312; and an electrical interconnect (e.g., the springs 306) mechanically coupled to the sensor module housing 312 and electrically coupled to the glucose sensor 138a, 138b. The springs can be conical springs, helical springs, or any other type of spring mentioned herein or suitable for electrical connections.

The sensor module housing 312 comprises at least two proximal protrusions 308 located around a perimeter of the spring 306. The proximal protrusions 308 are configured to help orient the spring 306. A segment of the glucose sensor 138b is located between the proximal protrusions 308 (distally to the spring 306).

The sensor module housing 312 is mechanically coupled to the base 128. The base 128 includes an adhesive 126 configured to couple the base 128 to skin of the host.

The proximal protrusions 308 orient the spring 306 such that coupling an electronics unit 500 to the base 128 presses the spring 306 against a first electrical contact of the electronics 500 unit and a second electrical contact of the glucose sensor 138b to electrically couple the glucose sensor 138a, 138b to the electronics unit 500.

Referring now to FIGS. 33 and 35-38, the system 600 can include a sensor module housing 312d, 312e; a glucose sensor 138a, 138b having a first section 138a configured for subcutaneous sensing and a second section 138b mechanically coupled to the sensor module housing 312d, 312e; and an electrical interconnect (e.g., the leaf springs 306d, 306e) mechanically coupled to the sensor module housing 312d, 312e and electrically coupled to the glucose sensor 138a, 138b. The sensor modules 134d, 134e can be used in place of the sensor module 134 shown in FIG. 7. The leaf springs 306d, 306e can be configured to bend in response to the electronics unit 500 coupling with the base 128.

As used herein, cantilever springs are a type of leaf spring. As used herein, a leaf spring can be made of a number of strips of curved metal that are held together one above the other. As used herein in many embodiments, leaf springs only include one strip (e.g., one layer) of curved metal (rather than multiple layers of curved metal). For example, the leaf spring 306d in FIG. 35 can be made of one layer of metal or multiple layers of metal. In some embodiments, leaf springs include one layer of flat metal secured at one end (such that the leaf spring is a cantilever spring).

As shown in FIGS. 35 and 36, the sensor module housing 312d comprises a proximal protrusion 320d having a channel 322d in which at least a portion of the second section of the glucose sensor 138b is located. The channel 322d positions a first area of the glucose sensor 138b such that the area is electrically coupled to the leaf spring 306d.

As shown in the cross-sectional, perspective view of FIG. 36, the leaf spring 306d arcs away from the first area and protrudes proximally to electrically couple with an electronics unit 500 (shown in FIG. 33). At least a portion of the leaf spring 306d forms a "W" shape. At least a portion of the leaf spring 306d forms a "C" shape. The leaf spring 306d bends around the proximal protrusion 320d. The leaf spring 306d protrudes proximally to electrically couple with an electronics unit 500 (shown in FIG. 33). The seal 192 is configured to impede fluid ingress to the leaf spring 306d.

The leaf spring 306d is oriented such that coupling an electronics unit 500 to the base 128 (shown in FIG. 33) presses the leaf spring 306d against a first electrical contact of the electronics unit 500 and a second electrical contact of the glucose sensor 138b to electrically couple the glucose sensor 138a, 138b to the electronics unit 500. The proximal height of the seal 192 is greater than a proximal height of the leaf spring 306d such that the electronics unit 500 contacts the seal 192 prior to contacting the leaf spring 306d.

Figure 37:
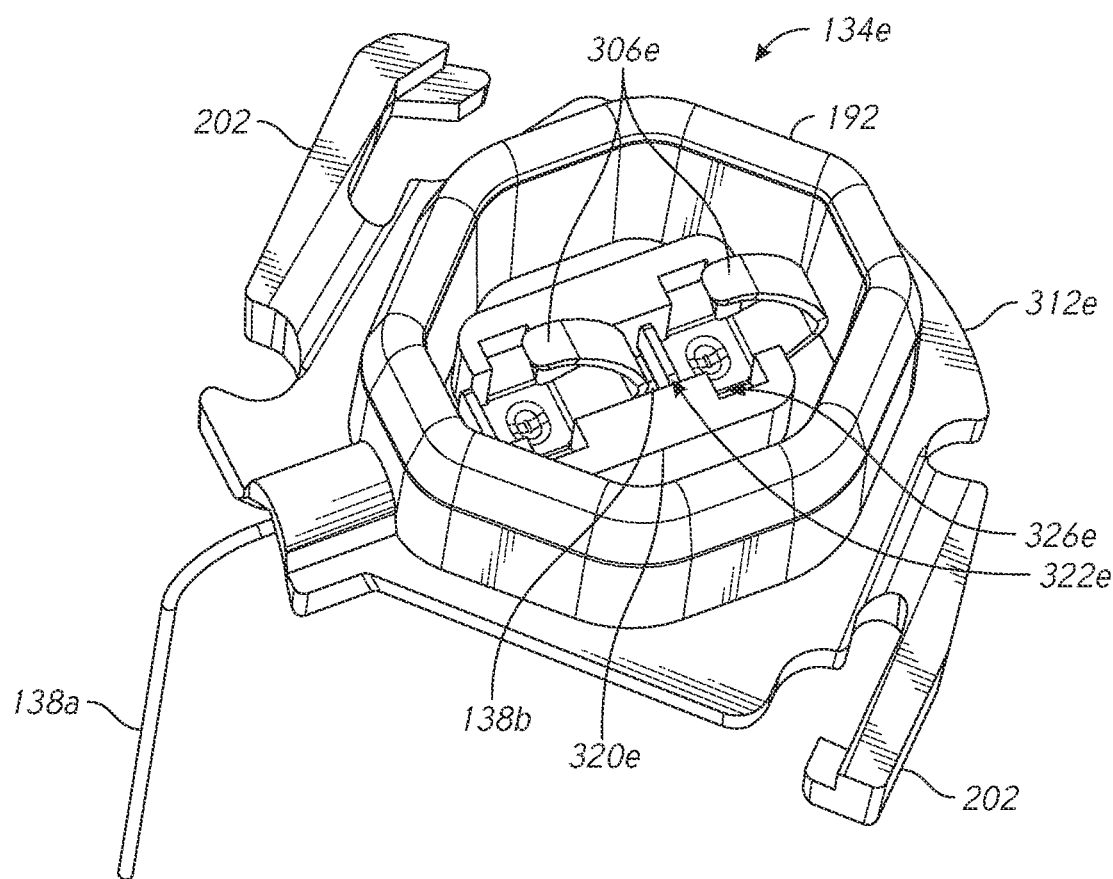
FIG. 37 illustrates a perspective view of a sensor module that has springs, according to some embodiments.
Figure 38:
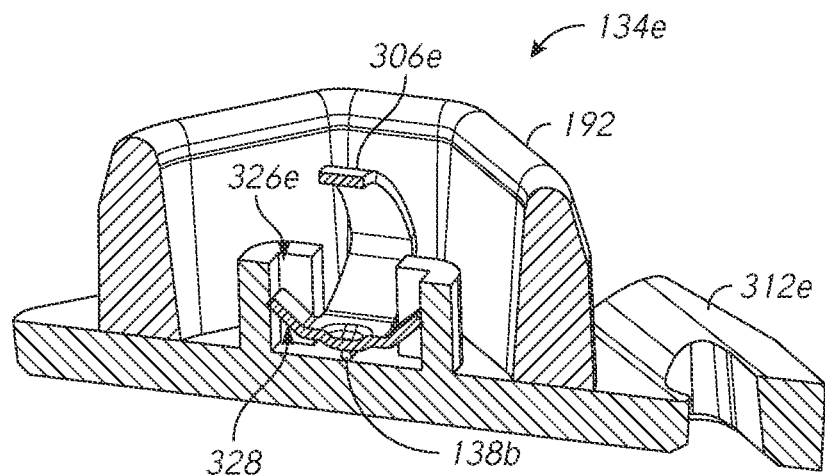
FIG. 38 illustrates a cross-sectional perspective view of a portion of a sensor module, according to some embodiments.

Referring now to FIGS. 33 and 37-38, the sensor module housing 312e comprises a channel 322e in which at least a portion of the second section of the glucose sensor 138b is located. A distal portion of the leaf spring 306e is located in the channel 322e such that a proximal portion of the leaf spring 306e protrudes proximally out the channel 322e.

The sensor module housing 312e comprises a groove 326e that cuts across the channel 322e (e.g., intersects with the channel 322e). The leaf spring 306e comprises a tab 328 located in the groove to impede rotation of the leaf spring. At least a portion of the leaf spring 306e forms a "C" shape.

FIGS. 36 and 38 illustrate two leaf spring shapes. Other embodiments use other types of leaf springs. Elements shown in FIGS. 33-38 can be combined.

Referring now to FIGS. 33-38, interconnects 306, 306d, 306e can comprise a palladium contact, an alloy, a clad material, an electrically conductive plated material, gold plated portions, silver material, and/or any suitable conductor. Interconnects 306, 306d, 306e described herein can have a resistance of less than 5 ohms, less than 20 ohms, and/or less than 100 ohms. Many interconnect embodiments enable a resistance of approximately 2.7 ohms or less, which can significantly increase battery life compared to higher resistance alternatives.

Reducing the force necessary to compress an interconnect 306, 306d, 306e (e.g., as an electronics unit 500 is coupled to the base 128) can reduce coupling errors and difficulties. For example, if the necessary force is high, odds are substantial that users will inadvertently fail to securely couple the electronics unit 500 to the base 128. In some cases, if the necessary force is too high, some users will be unable to couple the electronics unit 500 to the base 128. Thus, there is a need for systems that require less force to couple the electronics unit 500 to the base 128.

Many embodiments described herein (e.g., spring embodiments) dramatically reduce the force necessary to couple the electronics unit 500 to the base 128. The interconnects 306, 306d, 306e can have a compression force of at least 0.05 pounds; less than 0.5 pounds, less than 1 pound, less than 3 pounds; and/or less than 4.5 pounds over an active compression range.

In some embodiments, the interconnects 306, 306d, 306e may require a compression force of less than one pound to compress the spring 20 percent from a relaxed position, which is a substantially uncompressed position. In some embodiments, the interconnects 306, 306d, 306e may require a compression force of less than one pound to compress the spring 25 percent from a relaxed position, which is a substantially uncompressed position. In some embodiments, the interconnects 306, 306d, 306e may require a compression force of less than one pound to compress the spring 30 percent from a relaxed position, which is a substantially uncompressed position. In some embodiments, the interconnects 306, 306d, 306e change dependency to independent claim) may require a compression force of less than one pound to compress the spring 50 percent from a relaxed position, which is a substantially uncompressed position.

Springs 306, 306d, 306e can have a height of 2.6 millimeters, at least 0.5 millimeters, and/or less than 4 millimeters. The seal 192 can have a height of 2.0 millimeters, at least 1 millimeter, and/or less than 3 millimeters. In some embodiments, in their relaxed state (i.e., a substantially uncompressed state), springs 306, 306d, 306e protrude (e.g., distally) at least 0.2 millimeters and/or less than 1.2 millimeters from the top of the seal 192.

When the electronics unit 500 is coupled to the base 128, the compression of the springs 306, 306d, 306e can be 0.62 millimeters, at least 0.2 millimeters, less than 1 millimeter, and/or less than 2 millimeters with a percent compression of 24 percent, at least 10 percent, and/or less than 50 percent. Active compression range of the springs 306, 306d, 306e can be 16 to 40 percent, 8 to 32 percent, 40 to 57 percent, 29 to 47 percent, at least 5 percent, at least 10 percent, and/or less than 66 percent.

In some embodiments, the electrical connection between the sensor 138 and the electronics unit 500 is created at the factory. This electrical connection can be sealed at the factory to prevent fluid ingress, which can jeopardize the integrity of the electrical connection.

The electrical connection can be made via any of the following approaches: An electrode can pierce a conductive elastomer (such that vertical deformation is not necessary); the sensor can be "sandwiched" (e.g., compressed) between adjacent coils of a coil spring; conductive epoxy; brazing; laser welding; and resistance welding.

Referring now to FIGS. 4, 6, 7, and 33, one key electrical connection is between the electronics unit 500 (e.g., a transmitter) and the sensor module 134. Another key electrical connection is between the sensor module 134 and the glucose sensor 138. Both connections should be robust to enable connecting the sensor module 134 to the base 128, and then connecting the base 128 and sensor module 134 to the electronics unit 500 (e.g., a transmitter). A stable sensor module 134 allows the sensor module 134 to couple to the base 128 without causing signal noise in the future.

These two key electrical connections can be made at the factory (e.g., prior to the host or caregiver receiving the system). These electrical connections can also be made by the host or caregiver when the user attaches the electronics unit 500 to the base 128 and/or the sensor module 134.

In some embodiments, the connection between the glucose sensor 138 and the sensor module 134 can be made at the factory (e.g., prior to the user receiving the system), and then the user can couple the electronics unit 500 to the sensor module 134 and/or the base 128. In several embodiments, the electronics unit 500 can be coupled to the sensor module 134 and/or to the base 128 at the factory (e.g., prior to the user receiving the system), and then the user can couple this assembly to the glucose sensor 138.

Any of the features described in the context of FIGS. 33-38 can be applicable to all aspects and embodiments identified herein. For example, the embodiments described in the context of FIGS. 33-38 can be combined with the embodiments described in the context of FIGS. 1-32 and 39-70. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Referring now to FIG. 33, the battery 314 can be located inside the electronics unit 500 or can be part of the base 128. Maximizing the life of the battery 314 is important to many reasons. For example, the electronics unit 500 may be in storage for months or even years before it is used. If the battery 413 is substantially depleted during this storage, the number of days that a host can use the electronics unit (e.g., to measure an analyte) can be dramatically diminished.

In some embodiments, the electronics unit 500 is in a low-power-consumption state (e.g., a "sleep" mode) during storage (e.g., prior to being received by the host). This low-power-consumption state can drain the battery 314. Thus, there is a need for a system that reduces or even eliminates battery power consumption during storage and/or prior to the electronics unit 500 being coupled to the base 128.

As described in the context of FIG. 33, creating the electrical connection 310 and/or coupling the electronics unit 500 to the base 128 can cause the electronics unit 500 (e.g., a transmitter) to exit a sleep mode. For example, conductive members (e.g., of the sensor module 134 and/or of the base 128) can touch electrical contacts of the electronics unit 500 (e.g., electrical contacts of a battery of the electronics unit 500), which can cause the electronics unit 500 to exit a sleep mode and/or can begin the flow of electrical power from the battery. The conductive member of the sensor module 134 and/or of the base 128 can be a battery jumper that closes a circuit to enable electricity from the battery to flow into other portions of the electronics unit 500.

Thus, creating the electrical connection 310 and/or coupling the electronics unit 500 to the base 128 can "activate" the electronics unit 500 to enable and/or to prepare the electronics unit 500 to wirelessly transmit information to other devices 110-113 (shown in FIG. 1). U.S. Patent Publication No. US-2012-0078071-A1 includes additional information regarding electronics unit 500 activation (e.g., transmitter activation). The entire contents of U.S. Patent Publication No. US-2012-0078071-A1 are incorporated by reference herein.

Figure 65:
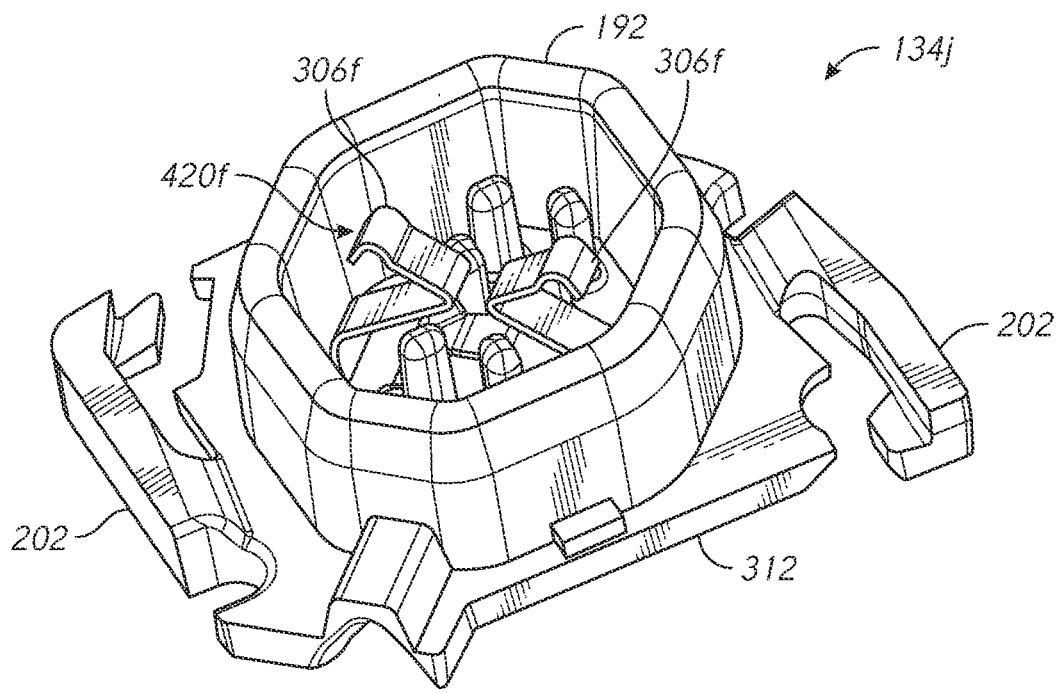
FIG. 65 illustrates a perspective view of portions of a sensor module, according to some embodiments.

FIG. 65 illustrates a perspective view of portions of a sensor module 134j. Some items, such as springs and sensors, are hidden in FIG. 65 to clarify that the sensor module 134j can use any spring or sensor described herein. The sensor module 134j can use any of the springs 306, 306d, 306e; sensors 138, 138a, 138b; protrusions 308; channels 322d, 322e; and grooves 326e described herein (e.g., as shown in FIGS. 34-40). The sensor module 134j can be used in the place of any other sensor module described herein. The sensor module 134j can be used in the embodiment described in the context of FIG. 7 and can be used with any of the telescoping assemblies described herein.

Figure 66:
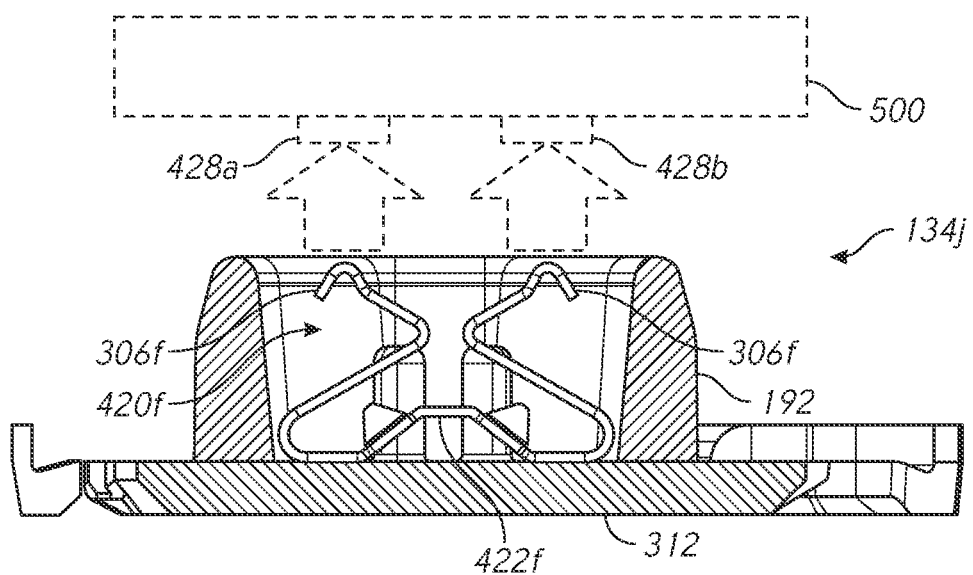
FIG. 66 illustrates a cross-sectional side view of the sensor module shown in FIG. 65, according to some embodiments.

FIG. 66 illustrates a cross-sectional side view of the sensor module shown in FIG. 65. Referring now to FIGS. 65-70, the sensor module 134j includes a conductive jumper 420f (e.g., a conductive connection that can comprise metal). The conductive jumper 420f is configured to electrically couple two electrical contacts 428a, 428b of the electronics unit 500 (e.g., a transmitter) in response to coupling the electronics unit 500 to the sensor module 134j and/or to the base 128.

The conductive jumper 420f can be located at least partially between two electrical connections 426 (e.g., springs 306, 306d, 306e shown in FIGS. 34-38). The conductive jumper 306f can include two springs 306f coupled by a conductive link 422f. A first spring 306f of the jumper 420f can be coupled to a first contact 428a, and a second spring 306f of the jumper 420f can be coupled to a second contact 428b, which can complete an electrical circuit to enable the battery to provide electricity to the electronics unit 500. The springs 306f can be leaf springs, coil springs, conical springs, and/or any other suitable type of spring. In some embodiments, the springs 306f are proximal protrusions that are coupled with the contacts 428a, 428b.

As shown in FIG. 66, the conductive link 422f can be arched such that a sensor 138b (shown in FIG. 34) passes under and/or through the arched portion of the conductive link 422f. In several embodiments, the conductive link 422f is oriented within plus or minus 35 degrees of perpendicular to the sensor 138b such that the conductive link 422f crosses over the portion of the sensor 138b that is located inside the seal area (e.g., within the interior of the seal 192).

Figure 67:
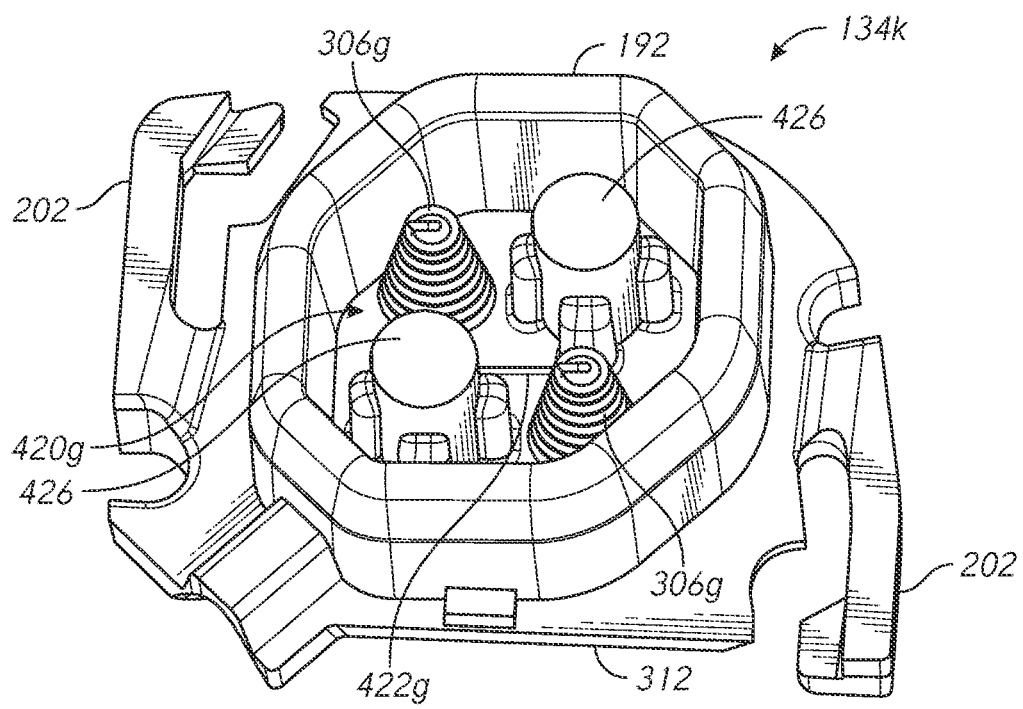
FIG. 67 illustrates a perspective view of portions of a sensor module, according to some embodiments.
Figure 68:
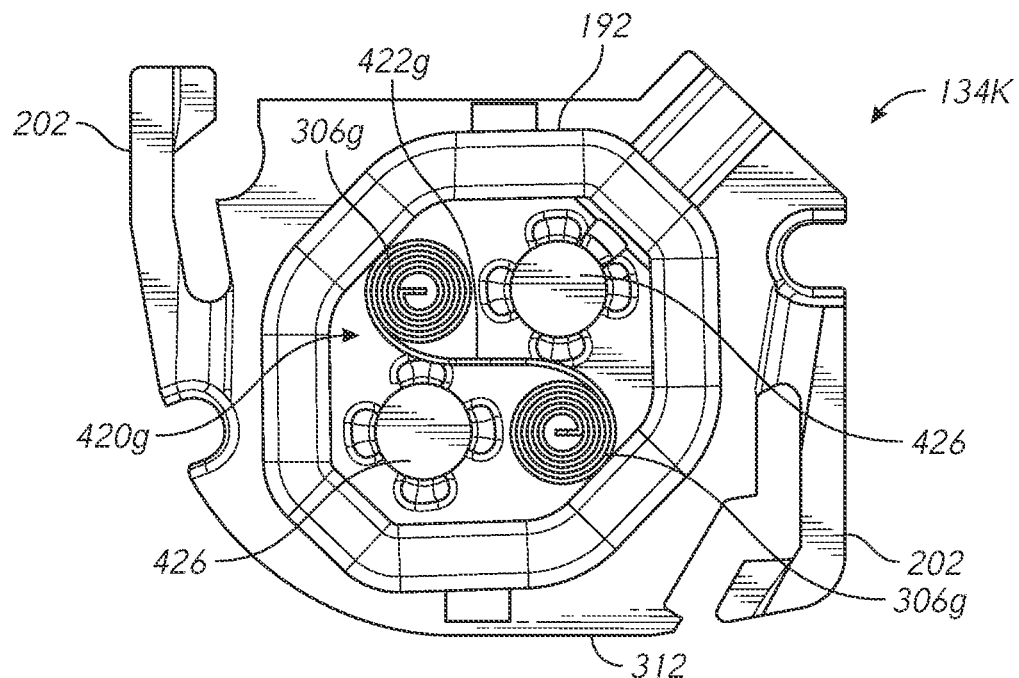
FIG. 68 illustrates a top view of the sensor module shown in FIG. 67, according to some embodiments.

FIG. 67 illustrates a perspective view of portions of a sensor module 134k that is similar to the sensor module 134j shown in FIGS. 65 and 66. FIG. 68 illustrates a top view of the sensor module 134k shown in FIG. 67.

Referring now to FIGS. 67 and 68, the sensor module 134k includes a different type of conductive jumper 420g, which includes two helical springs 306g conductively coupled by a conductive link 422g. The conductive link 422g is configured to cross over or under the sensor 138b (shown in FIG. 34). As shown in FIGS. 67 and 68, the springs 306g are conical springs, however, some embodiments do not use conical springs. The springs 306g are configured to electrically couple two electrical contacts 428a, 428b of the electronics unit 500 to start the flow the electricity within the electronics unit 500. Thus, the conductive jumper 420g can "activate" the electronics unit 500. The conductive jumper 420g can be used with any of the sensor modules described herein.

Figure 69:
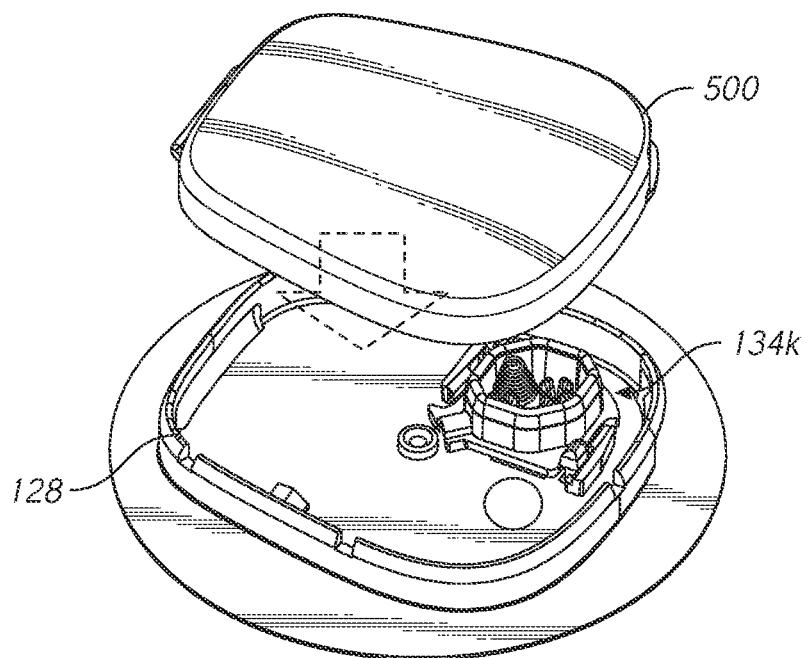
FIGS. 69 and 70 illustrate perspective views of an electronics unit just before the electronics unit is coupled to a base, according to some embodiments.
Figure 70:
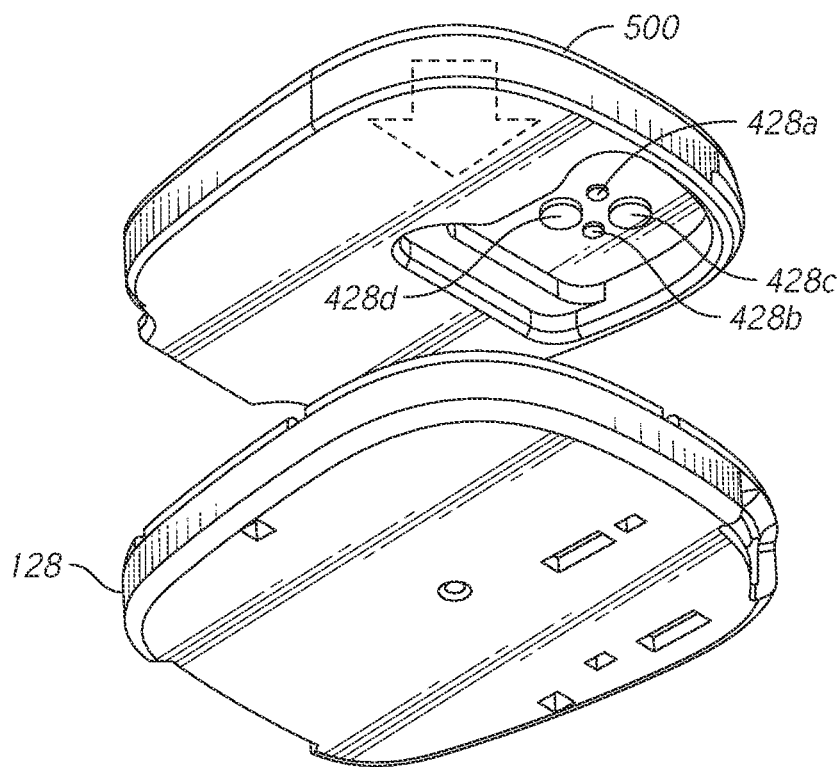

FIGS. 69 and 70 illustrate perspective views of an electronics unit 500 just before the electronics unit 500 is coupled to a base 128. As shown in FIG. 70, the electronics unit 500 can have two electrical contacts 428a, 428b configured to be electrically coupled to a conductive jumper 420f (shown in FIGS. 65 and 66), 420g (shown in FIGS. 67 and 68). The electronics unit 500 can also have two electrical contacts 428c, 428d configured to be electrically coupled to the springs 306, 306d, 306e (shown in FIGS. 34-38) and/or to any other type of electrical connection 426 between the sensor 138 (shown in FIG. 39) and the electronics unit 500.

Coupling the electronics unit 500 to the sensor module 134k and/or to the base 128 can electrically and/or mechanically couple the electrical contacts 428a, 428b to the conductive jumper 420f (shown in FIG. 65), 420g (shown in FIG. 67).

Coupling the electronics unit 500 to the sensor module 134k and/or to the base 128 can electrically and/or mechanically couple the electrical contacts 428c, 428d to the springs 306, 306d, 306e (shown in FIGS. 34-38) and/or to any other type of electrical connection 426 (e.g., as shown in FIG. 67) between the sensor 138 (shown in FIG. 39) and the electronics unit 500.

Any of the features described in the context of FIGS. 65-70 can be applicable to all aspects and embodiments identified herein. For example, the embodiments described in the context of FIGS. 65-70 can be combined with the embodiments described in the context of FIGS. 1-64. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Needle Angle and Off Set

Figure 43:
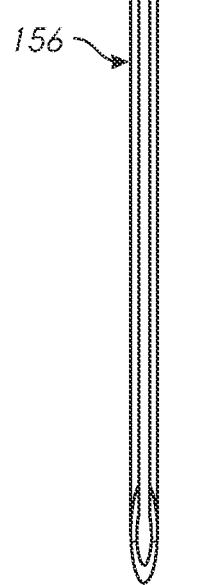
FIG. 43 illustrates a front view of a needle, according to some embodiments.

FIG. 43 shows a front view of a "C-shaped" needle 156. FIG. 42 illustrates a bottom view of the C-shaped needle 156. The needle 156 includes a channel 330. A section 138a (shown in FIG. 34) of the glucose sensor 138 (labeled in FIG. 7) that is configured for subcutaneous sensing can be placed in the channel 330 (as shown in FIG. 40).

The needle 156 can guide the sensor 138 into the skin of the host. A distal portion of the sensor 138 can be located in the channel 330 of the needle 156. Sometimes, a distal end of the sensor 138 sticks out of the needle 156 and gets caught on tissue of the host as the sensor 138 and needle 156 are inserted into the host. As a result, the sensor 138 may buckle and fail to be inserted deeply enough into the subcutaneous tissue. In other words, in some embodiments, the sensor wire must be placed within the channel 330 of the C-shaped needle 156 to be guided into the tissue and must be retained in the channel 330 during deployment.

Figure 40:
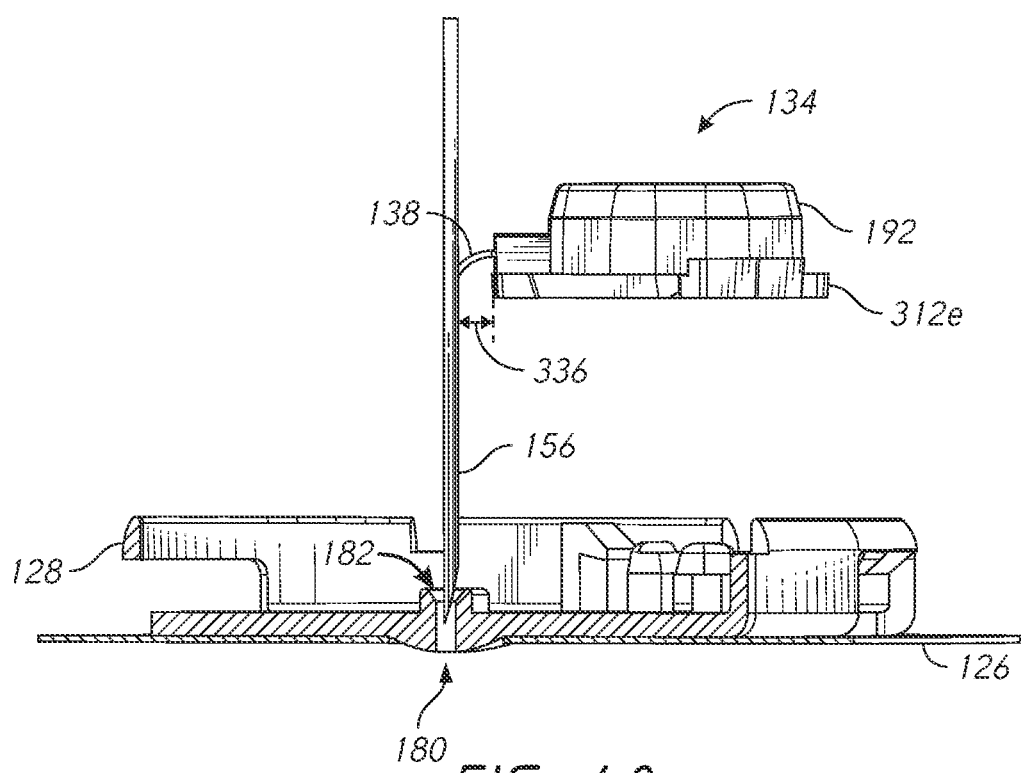
FIG. 40 illustrates a cross-sectional perspective view of assembly that has an offset, according to some embodiments.

The risk of the sensor 138 sticking out of the channel 330 (and thereby failing to be property inserted into the host) can be greatly diminished by placing the sensor 138 in the channel 330 of the needle 156 with a particular angle 338 (shown in FIG. 41) and offset 336 (shown in FIG. 40. Position B 334 in FIG. 42 illustrates a sensor sticking out of the channel 330.

The angle 338 and offset 336 cause elastic deformation of the sensor 138 to create a force that pushes the sensor 138 to the bottom of the channel 300 (as shown by position A 332 in FIG. 42) while avoiding potentially detrimental effects of improper angles 338 and offset 336. The angle 338 and offset 336 can also cause plastic deformation of the sensor 138 to help shape the sensor 138 in a way that minimizes the risk of the sensor 138 being dislodged from the channel 330 during insertion into the skin.

In several embodiments, the angle 338 and offset 336 shape portions of the sensor 138 for optimal insertion performance. For example, the angle 338 can bend the sensor 138 prior to placing portions of the sensor 138 in the channel 330 of the needle 156.

Figure 39:
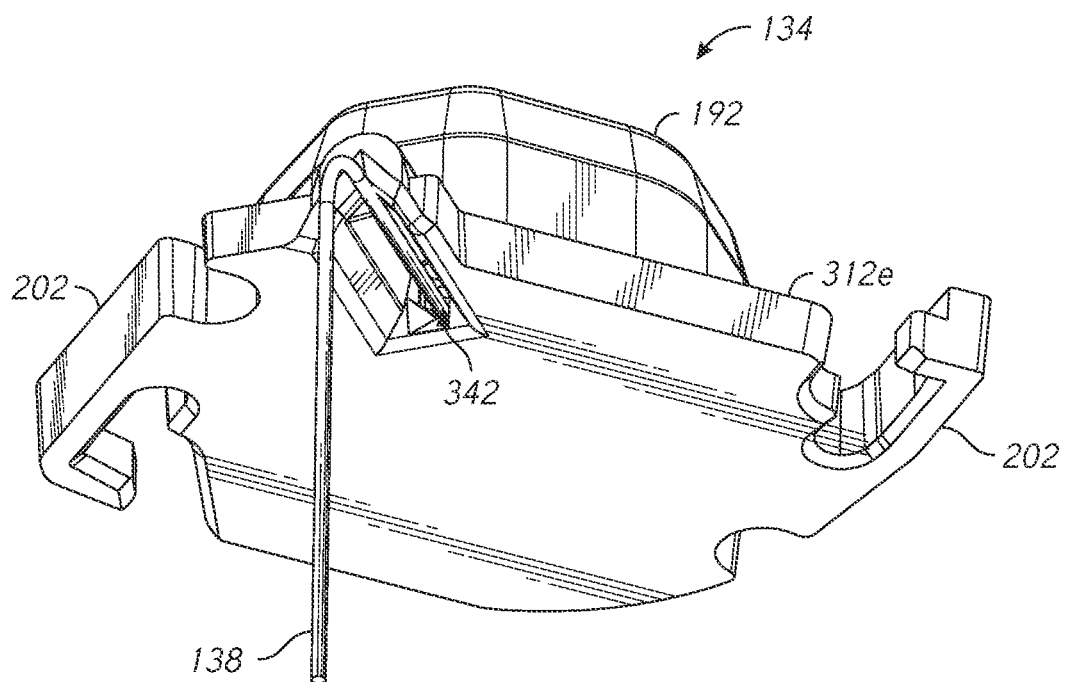
FIG. 39 illustrates a perspective view of a sensor module, according to some embodiments.

As illustrated in FIG. 39, a portion of the glucose sensor 138b (also labeled in FIG. 34) can be placed in a distally facing channel 342 (which, in some embodiments, is a tunnel). This channel 342 can help orient the glucose sensor 138b towards the channel 330 of the needle 156 (shown in FIG. 43).

Figure 41:
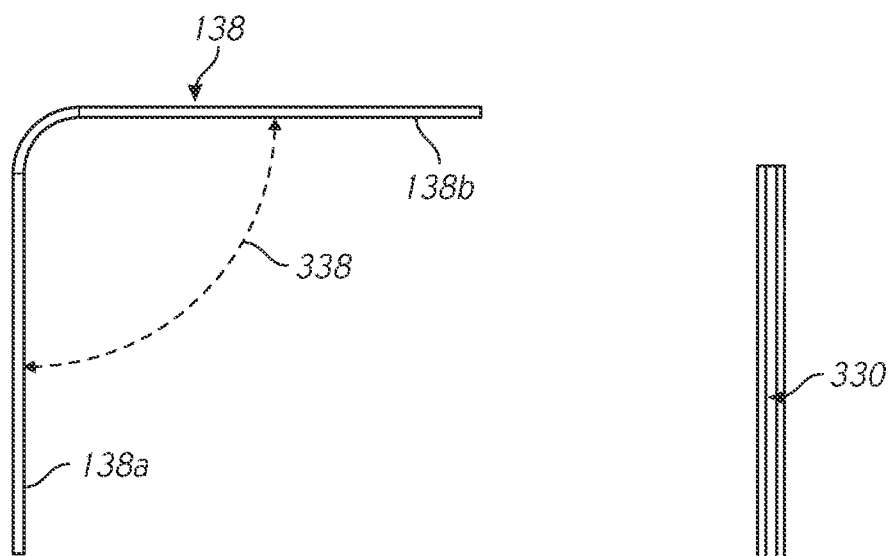
FIG. 41 illustrates a side view of a sensor, according to some embodiments.

As illustrated in FIG. 41, the glucose sensor 138 can include an angle 338 between a portion of the glucose sensor 138 that is coupled to the sensor module housing 312 (shown in FIG. 34) and a portion of the glucose sensor that is configured to be inserted into the host. In some embodiments, this angle 338 can be formed prior to coupling the sensor 138 to the sensor module house 312 (shown in FIG.

34) and/or prior to placing a portion of the sensor 138 in the channel 330 of the needle 156 (shown in FIG. 43).

Referring now to FIG. 41, an angle 338 that is less than 110 degrees can result in deployment failures (e.g., with an offset of 0.06 inches plus 0.06 inches and/or minus 0.03 inches). In some embodiments, an angle 338 that is less than 125 degrees can result in deployment failures (e.g., with an offset of 0.06 inches plus 0.06 inches and/or minus 0.03 inches). An angle 338 of 145 degrees (plus 5 degrees and/or minus 10 degrees) can reduce the probability of deployment failures. In some embodiments, the angle 338 is at least 120 degrees and/or less than 155 degrees.

In some embodiments, a manufacturing method includes bending the sensor 138 prior to placing portions of the sensor 138 in the channel 330 of the needle 156. In this manufacturing method, an angle is measured from a central axis of a portion of the glucose sensor 138 that is coupled to the sensor module housing 312 (shown in FIG. 34) and a portion of the glucose sensor that is configured to be inserted into the needle. According to this angle measurement, an angle that is greater than 70 degrees can result in deployment failures (e.g., with an offset of 0.06 inches plus 0.06 inches and/or minus 0.03 inches). In some embodiments, an angle that is greater than 55 degrees can result in deployment failures (e.g., with an offset of 0.06 inches plus 0.06 inches and/or minus 0.03 inches). An angle of 35 degrees (plus 10 degrees and/or minus 5 degrees) can reduce the probability of deployment failures. In some embodiments, the angle is at least 25 degrees and/or less than 60 degrees.

An offset 336 (shown in FIG. 40) that is too large can result in the sensor 138 not being reliably held in the channel 330 (shown in FIG. 42). In other words, a large offset 336 can result in the sensor 138 being located in position B 334 rather than securely in position A 332. An offset 336 that is too small can place too much stress on the sensor 138, which can break the sensor 138. In light of these factors, in several embodiments, the offset 336 is at least 0.02 inches, at least 0.04 inches, less than 0.08 inches, and/or less than 0.13 inches. In some embodiments, the offset 336 is equal to or greater than 0.06 inches and/or less than or equal to 0.10 inches. The offset 336 is measured as shown in FIG. 40 from the root of the needle 156.

In some embodiments, at least a portion of the bend of the sensor 138 can include a strain relief. For example, the bend of the sensor 138 can be encapsulated in a polymeric tube or an elastomeric tube to provide strain relief for the sensor 138. In some instances, the entire bend of the sensor 138 can be encapsulated in a polymeric tube or an elastomeric tube. In some embodiments, the tube is composed of a soft polymer. The polymeric tube or elastomeric tube can encapsulate the sensor 138 by a heat shrink process. In some embodiments, a silicone gel may be applied to the sensor at or near channel 342 (shown in FIG. 39), or along at least a portion of the underside of proximal protrusion 320d (shown in FIG. 35).

The needle channel width 344 (shown in FIG. 42) can be 0.012 inches. In some embodiments, the width 344 is equal to or greater than 0.010 inches and/or less than or equal to 0.015 inches. The width 344 of the channel 330 is measured at the narrowest span in which the glucose sensor 138 could be located.

Referring now to FIG. 40, a funnel 182 in the base 128 can help guide the needle 156 and/or the glucose sensor 138 into the hole 180. The funnel 182 and the hole 180 can help secure the sensor 138 in the C-shaped needle 156 during storage and deployment. For example, the hole 180 can be so small that there is not extra room (within the hole 180) for the sensor 138 to exit the channel 330 (shown in FIG. 42) of the needle 156.

Another role of the funnel 182 and hole 180 is to support the needle 156 and/or the sensor 138 against buckling forces during insertion of the needle 156 and/or the sensor 138 into the host.

The funnel 182 and the hole 180 also protect against inadvertent needle-stick injuries (because they are too small to enable, for example, a finger to reach the needle 156 prior to needle deployment).

The sensor module 134 is unable to pass through the funnel 182 and hole 180 (e.g., due to the geometries of the sensor module 134 and the funnel 182). Preventing the sensor module 134 from passing through the base 128 ensures the sensor module 134 is removed from the host's body when the base 128 is detached from the host. The angle 338 can prevent all of the sensor 138 from passing through the hole 180 to ensure the sensor 138 is removed from the host's body when the base 128 is detached from the host.

Any of the features described in the context of FIGS. 39-43 can be applicable to all aspects and embodiments identified herein. For example, the embodiments described in the context of FIGS. 39-43 can be combined with the embodiments described in the context of FIGS. 1-38 and 44-70. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Needle-Free

Some embodiments use a needle to help insert a glucose sensor into subcutaneous tissue. Some people, however, are fearful of needles. In addition, needle disposal can require using a sharps container, which may not be readily available.

Many embodiments do not use a needle to insert the sensor, which can help people feel more comfortable inserting the sensor and can eliminate the need to use a sharps container to dispose of the applicator or portions thereof.

U.S. Patent Publication No. US-2011-0077490-A1, U.S. Patent Publication No. US-2014-0107450-A1, and U.S. Patent Publication No. US-2014-0213866-A1 describe several needle-free embodiments. The entire contents of U.S. Patent Publication No. US-2011-0077490-A1, U.S. Patent Publication No. US-2014-0107450-A1, and U.S. Patent Publication No. US-2014-0213866-A1 are incorporated by reference herein.

Any of the embodiments described herein can be used with or without a needle. For example, the embodiments described in the context of FIGS. 1-50 can be used with or without a needle. For example, the embodiment shown in FIG. 7 can be used in a very similar way without the needle 156. In this needle-free embodiment, moving the first portion 150 distally drives a distal portion of the glucose sensor 138 into the skin (without the use of a needle 156). In needle-free embodiments, the sensor 138 can have sufficient buckling resistance such that (when supported by the hole 180) the sensor 138 does not buckle. Sharpening a distal tip of the sensor 138 can also facilitate needle-free insertion into the host.

FIG. 56 illustrates an embodiment very similar to the embodiment shown in FIG. 7 except that the embodiment of FIG. 56 does not include a needle. The telescoping assembly 132b pushes the sensor 138 (which can be any type of analyte sensor) into the body of the host. The embodiment shown in FIG. 56 does not include a needle hub 162, a spring 234, or a needle retraction mechanism 158 (as shown in FIG. 7) but can include any of the items and features described in the context of other embodiments herein.

FIG. 57 illustrates the first portion 150 moving distally relative to the second portion 152 of the telescoping assembly 132b to move the sensor module 134 and the sensor 138 towards the base 128 in preparation to couple the sensor module 134 and the sensor 138 to the base 128.

FIG. 58 illustrates the first portion 150 in a distal ending position relative to the second portion 152. The sensor module 134 and the sensor 138 are coupled to the base 128. The base 128 is no longer coupled to the telescoping assembly 132b such that the telescoping assembly 132b can be discarded while leaving the adhesive 126 coupled to the skin of the host (as described in the context of FIGS. 4-6).

The embodiment illustrated in FIGS. 56-58 can be integrated into the applicator system 104 shown in FIGS. 2 and 3.

The items and features described in the context of FIGS. 12A-50 can also be used with the embodiment illustrated in FIGS. 56-58. Items and features are described in the context of certain embodiments to reduce redundancy. The items and features shown in all the drawings, however, can be combined. The embodiments described herein have been designed to illustrate the interchangeability of the items and features described herein.

Figure 45:
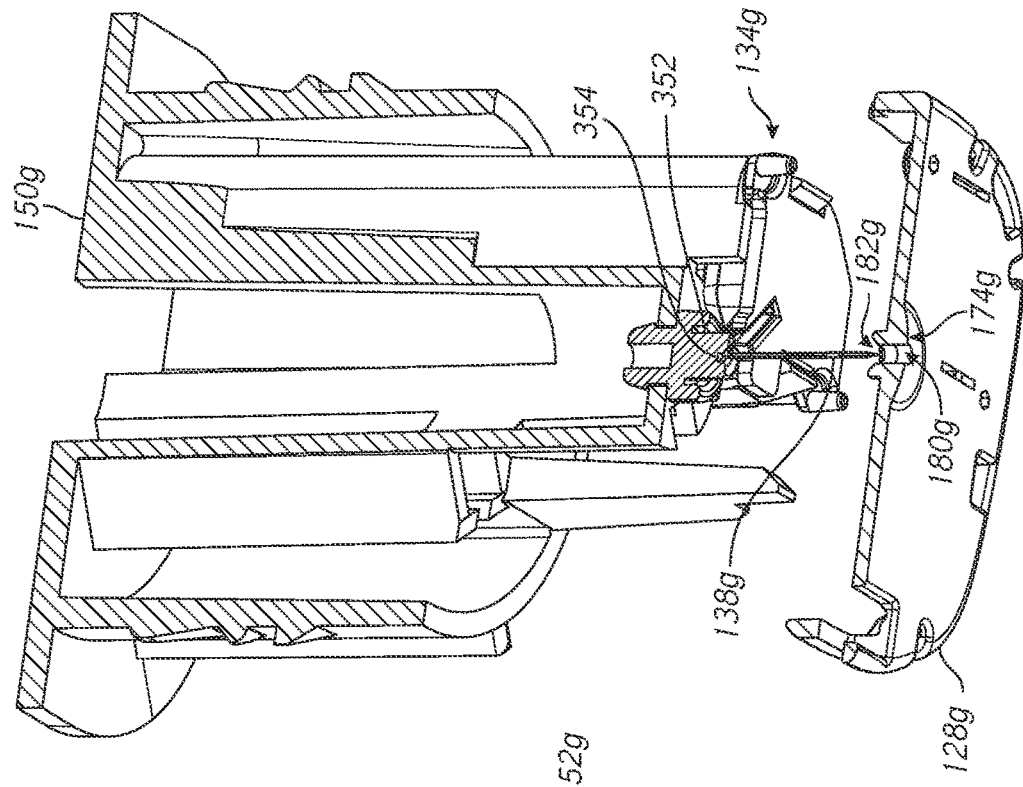
FIG. 45 illustrates a cross-sectional perspective view of a portion of an applicator system, according to some embodiments.
Figure 44:
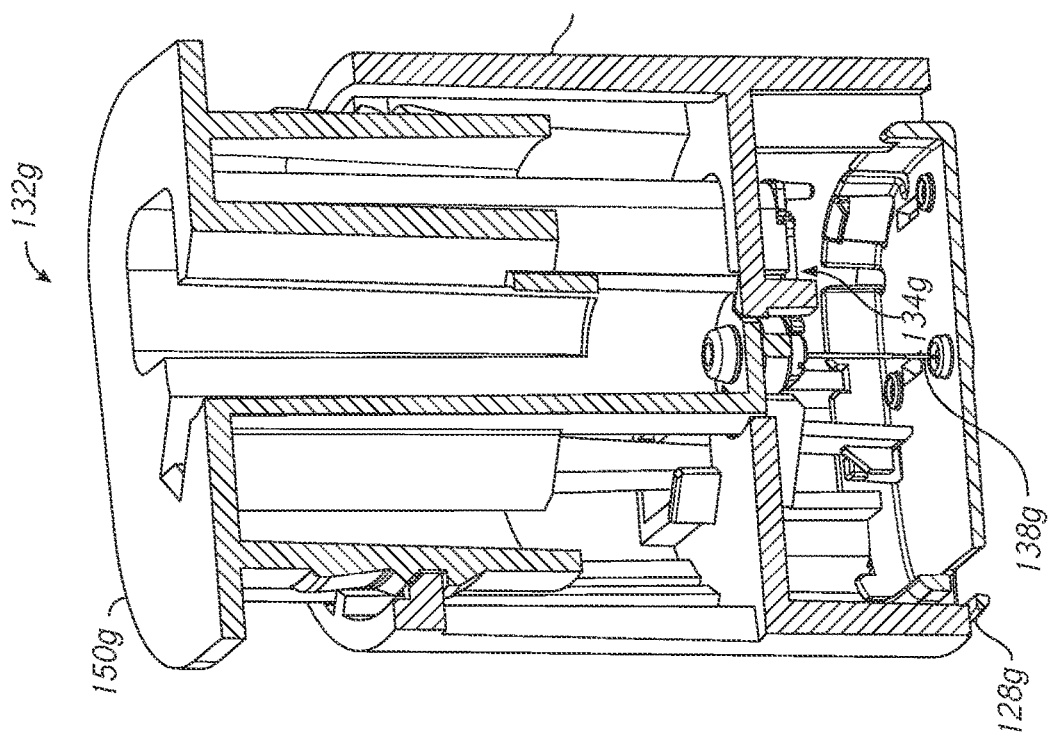
FIG. 44 illustrates a cross-sectional perspective view of an applicator system, according to some embodiments.

FIGS. 44 and 45 illustrate another embodiment of a telescoping assembly 132g. This embodiment includes a first portion 150g that moves distally relative to a second portion 152g to push a glucose sensor 138g through a hole in a base 128g and into a host.

The first portion 150g (e.g., a pusher) of the telescoping assembly 132g can include a distal protrusion 352 that supports a substantially horizontal section of the glucose sensor 138g (e.g., as the glucose sensor 138g protrudes out from the sensor module 134g). The end of the distal protrusion 352 can include a groove 354 in which at least a portion of the glucose sensor 138g is located. The groove 354 can help retain the glucose sensor 138g. The distal protrusion 352 can provide axial support to the glucose sensor 138g (e.g., to push the glucose sensor 138g distally into the tissue of the host).

The base 128g can include a funnel 182g that faces proximally to help guide a distal end of the glucose sensor 138g into a hole 180g in the base 128g. The hole 180g can radially support the sensor 138g as the sensor 138g is inserted into the tissue of the host.

When the first portion 150g of the telescoping assembly 132g is in the proximal starting position, the distal end of the glucose sensor 138g can be located in the hole 180g to help guide the glucose sensor 138g in the proper distal direction.

The hole 180g can exit a convex distal protrusion 174g in the base 128g. The convex distal protrusion 174g can help tension the skin prior to sensor insertion. As described more fully in other embodiments, the base 128g can rest against the skin of the host as the sensor module 134g moves distally towards the base 128g and then is coupled to the base 128g.

The telescoping assembly 132g (e.g., an applicator) does not include a needle. As a result, there is no sharp in the applicator, which eliminates any need for post-use sharp protection. This design trait precludes a need for a retraction spring or needle hub. The distal end of the sensor wire 138g can be sharpened to a point to mitigate a need for an insertion needle.

The telescoping assembly 132g (e.g., an applicator) can include the first portion 150g and the second portion 152g. The base 128g can be coupled to a distal end of the first portion 150g. The glucose sensor 138g and the sensor module 134g can be coupled to a distal end of the first portion 150g such that the applicator does not require a spring, needle, or needle hub; the first portion 150g is secured in a proximal starting position by an interference between the first portion 150g and the second portion 152g of the telescoping assembly 132g; and/or applying a distal force that is greater than a breakaway threshold of the interference causes the first portion 150g to move distally relative to the second portion 152g (e.g., until the sensor 138g is inserted into the tissue and the sensor module 134g is coupled to the base 128g).

Figure 47:
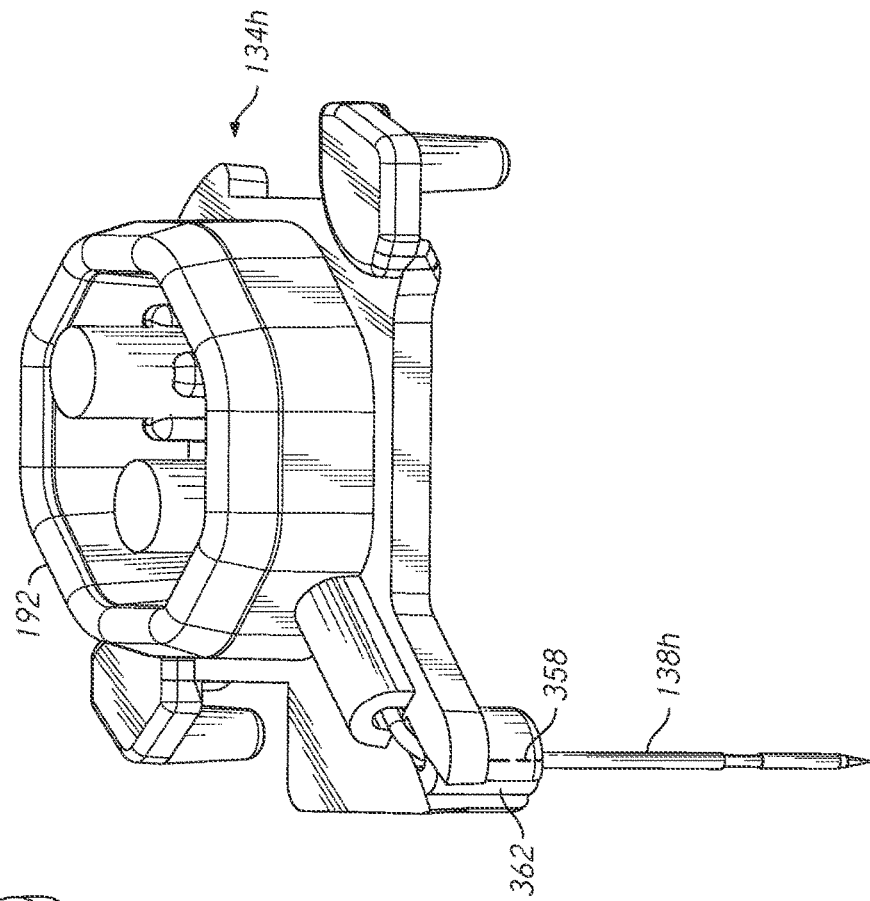
FIG. 47 illustrates a perspective view of a sensor module, according to some embodiments.
Figure 46:
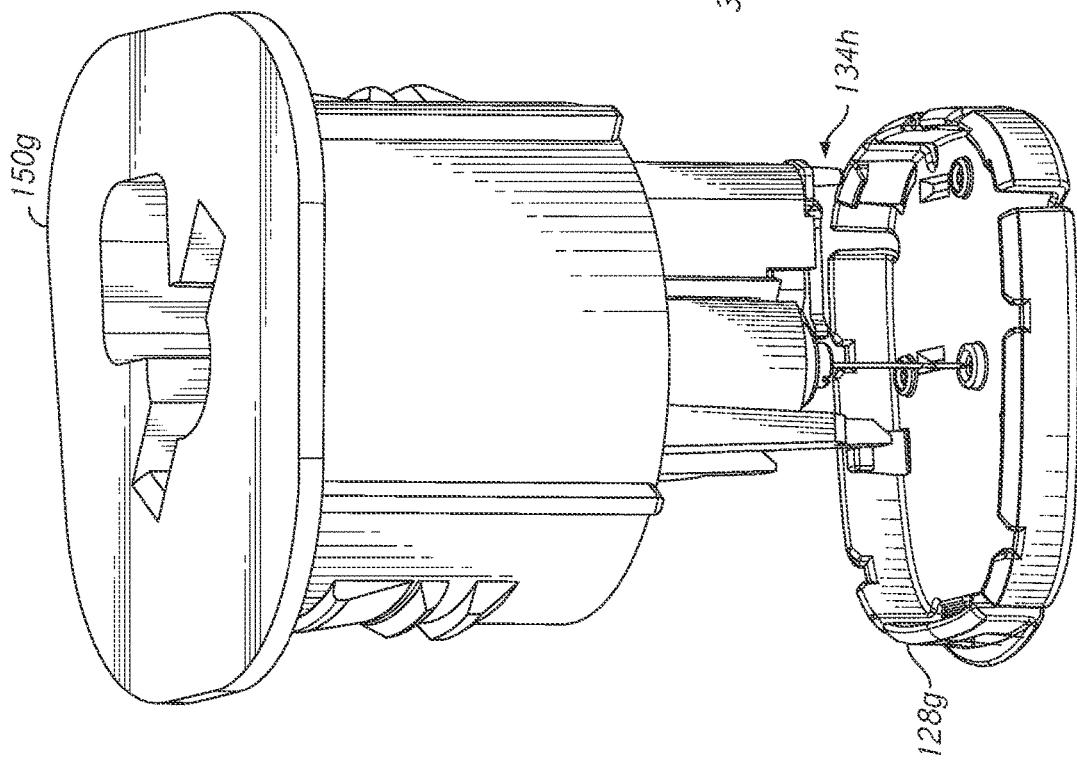
FIG. 46 illustrates a perspective view of a portion of an applicator system, according to some embodiments.

FIGS. 46 and 47 illustrate a similar needle-free embodiment. This embodiment does not use the distal protrusion 352 shown in FIG. 45. Instead, the sensor module 134h includes a distally oriented channel 358 that directs the sensor 138h distally such that the glucose sensor 138h includes a bend that is at least 45 degrees and/or less than 135 degrees. A channel cover 362 secures the glucose sensor 138h in the distally oriented channel 358.

The embodiments illustrated in FIGS. 44-47 can be integrated into the applicator system 104 shown in FIGS. 2 and 3. Referring now to FIG. 2, the electronics unit 500 (e.g., a transmitter having a battery) can be detachably coupled to the sterile barrier shell 120. The rest of the applicator system 104 can be sterilized, and then the electronics unit 500 can be coupled to the sterile barrier shell 120 (such that the electronics unit 500 is not sterilized with the rest of the applicator system 104).

The items and features described in the context of FIGS. 12A-43 and 48-70 can also be used with the embodiments illustrated in FIGS. 44-47. Items and features are described in the context of certain embodiments to reduce redundancy. The items and features shown in all the drawings, however, can be combined. The embodiments described herein have been designed to illustrate the interchangeability of the items and features described herein.

Any of the features described in the context of FIGS. 44-47 can be applicable to all aspects and embodiments identified herein. For example, the embodiments described in the context of FIGS. 44-47 can be combined with the embodiments described in the context of FIGS. 1-43 and 48-70. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

In some embodiments, the sensor 138 can be deployed (e.g., into the skin of the host) in response to coupling the electronics unit 500 (e.g., a transmitter) to the base 128. The sensor 138 can be any type of analyte sensor (e.g., a glucose sensor).

Premature deployment of the sensor 138 can cause insertion of the sensor 138 into the wrong person and/or insufficient sensor insertion depth. Premature deployment can also damage the sensor 138, which in some embodiments, can be fragile. Thus, there is a need to reduce the likelihood of premature sensor deployment.

One way to reduce the likelihood of premature sensor deployment is for the system to include an initial resistance (e.g., to coupling the electronics unit 500 to the base 128). The initial resistance can necessitate a force buildup prior to overcoming the initial resistance. When the initial resistance is overcome, the sensor 138 is typically deployed faster than would be the case without an initial resistance (e.g., due to the force buildup, which can be at least 0.5 pounds, 1 pound, and/or less than 5 pounds). This fast deployment can reduce pain associated with the sensor insertion process.

In some embodiments, the resistance to coupling the electronics unit 500 to the base 128 after overcoming the initial resistance is less than 10 percent of the initial resistance, less than 40 percent of the initial resistance, and/or at least 5 percent of the initial resistance. Having a low resistance to coupling the electronics unit 500 to the base 128 after overcoming the initial resistance can enable fast sensor insertion, which can reduce the pain associated with the sensor insertion process.

FIGS. 56-58 illustrate the first portion 150 deploying the sensor 138 into the skin of the host. In some embodiments, the first portion 150 is replaced with the electronics unit 500 shown in FIG. 4 such that coupling the electronics unit 500 to the base 128 pushes the sensor 138 into the skin of the host. Referring now to FIGS. 4 and 56-58, the protrusion 240 (as explained in other embodiments) can be a portion of the electronics unit 500 such that moving the electronics unit distally relative to the second portion 152 and/or coupling the electronics unit 500 to the base 128 requires overcoming the initial resistance of the protrusion 240.

In some embodiments configured such that the sensor 138 is deployed (e.g., into the skin of the host) in response to coupling the electronics unit 500 to the base 128, a telescoping assembly 132b is not used. Instead, features of the base 128 provide the initial resistance to coupling the electronics unit 500 to the base 128. Although the locking feature 230 in FIG. 33 is used for different purposes in some other embodiments, the locking feature 230 of the base 128 can couple with a corresponding feature of the electronics unit 500. This coupling can require overcoming an initial resistance.

Any of the features and embodiments described in the context of FIGS. 1-70 can be applicable to all aspects and embodiments in which the sensor 138 is deployed (e.g., into the skin of the host) in response to coupling the electronics unit 500 (e.g., a transmitter) to the base 128.

Vertical Locking

After a telescoping assembly (e.g., an applicator) has been used to insert a glucose sensor, the needle used to insert the glucose sensor could inadvertently penetrate another person. To guard against this risk, the telescoping assembly can protect people from subsequent needle-stick injuries by preventing the first portion of the telescoping assembly from moving distally relative to the second portion after the sensor has been inserted into the host.

FIG. 48 illustrates a perspective, cross-sectional view of a telescoping assembly 132i that includes a first portion 150i and a second portion 152i. Referring now to FIGS. 48-50, the first portion 150i is configured to telescope distally relative to the second portion 152i. The second portion 152i of the telescoping assembly 132i can include a proximal protrusion 364 that can slide past a lock-out feature 366 of the first portion 150i of the telescoping assembly 132i as the first portion 150i is moved distally.

The proximal protrusion 364 can be biased such that elastic deformation of the proximal protrusion 364 creates a force configured to press the proximal protrusion 364 into the bottom of the lock-out feature 366 once the proximal protrusion 364 engages the lock-out feature 366.

The proximal protrusion 364 does not catch on the lock-out feature 366 as the first portion 150i moves distally a first time. Once the first portion 150i is in a distal ending position, a spring can push the first portion 150i to a second proximal position. Rather than returning to the starting proximal position, the proximal protrusion 364 catches on the lock-out feature 366 (due to the bias of the proximal protrusion 364 and the distally facing notch 368 of the lock-out feature 366).

Once a proximal end of the proximal protrusion 364 is captured in the lock-out feature 366, the rigidity of the proximal protrusion 364 prevents the first portion 150i of the telescoping assembly 132i from moving distally a second time.

As the first portion 150i moves distally relative to the second portion 152i, a ramp 370 of the first portion 150i pushes the proximal protrusion 364 outward (towards the lock-out feature 366). The proximal protrusion 364 can be located between two distal protrusions 372 of the first portion 150i. The distal protrusions 372 can guide the proximal protrusion 364 along the ramp 370.

As a portion of the proximal protrusion 364 slides along the ramp 370 (as the first portion 150i moves distally), the ramp bends the proximal protrusion 364 until a portion of the proximal protrusion 364 that was previously between the two distal protrusions 372 is no longer between the distal protrusions 372. Once the portion of the proximal protrusion 364 is no longer between the two distal protrusions 372, the proximal protrusion 364 is in a state to catch on the notch 368. The notch 368 can be part of the distal protrusions 372.

The second portion 152i of the telescoping assembly 132i can include a proximal protrusion 364, which can be oriented at an angle between zero and 45 degrees relative to a central axis). The first portion 150i of the telescoping assembly 132i can include features that cause the proximal protrusion 364 to follow a first path as the first portion 150i moves distally and then to follow a second path as the first portion 150i moves proximally. The second path includes a locking feature 366 that prevents the first portion 150i from moving distally a second time.

The first portion 150i can include a ramp 370 that guides the proximal protrusion 364 along the first path. A distal protrusion (e.g., the ramp 370) of the first portion 150i can bias the proximal protrusion 364 to cause the proximal protrusion 364 to enter the second path as the first portion 150i moves proximally. The proximal protrusion 364 can be a flex arm. The lock 366 can comprise a distally facing notch 368 that catches on a proximal end of the proximal protrusion 364.

As shown in FIGS. 48 and 50, the telescoping assembly 132i can include a sensor module 134i. The sensor module 134i can be any of the sensor modules described herein.

Any of the features described in the context of FIGS. 48-50 can be applicable to all aspects and embodiments identified herein. For example, the embodiments described in the context of FIGS. 48-50 can be combined with the embodiments described in the context of FIGS. 1-47 and 51-70. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Dual-Spring Assembly

Partial sensor insertion can lead to suboptimal sensing. In some cases, partial sensor insertion can create a needle-stick hazard (due to the needle not retracting into a protective housing). Thus, there is a need for systems that ensure full sensor insertion.

The embodiment illustrated in FIGS. 61-64 dramatically reduces the odds of partial sensor insertion by precluding sensor insertion until sufficient potential energy is stored in the system. The potential energy is stored in a first spring 402.

The system includes many items from the embodiment illustrated in FIG. 7 (e.g., the base 128 and the sensor module 134). The system includes an optional needle 156 and needle hub 162. The embodiment illustrated in FIGS. 61-64 can also be configured to be needle-free by removing the needle 156, the second spring 234, the needle hub 162, and the needle retraction mechanism 158.

The telescoping assembly 132k has three portions 150k, 152k, 392. Moving the third portion 392 distally relative to the second portion 152k stores energy in the first spring 402 (by compressing the first spring 402). Once the first portion 150k is unlocked from the second portion 152k, the energy stored in the compressed first spring 402 is used to push the first portion 150k distally relative to the second portion 152k to drive the sensor 138 (shown in FIG. 7) into the skin of the host.

To ensure the first portion 150k does not move distally relative to the second portion 152k until the first spring 402 is sufficiently compressed (and thus has enough stored energy), the first portion 150k is locked to the second portion 152k. Once the first spring 402 is sufficiently compressed (and thus has enough stored energy), the system unlocks the first portion 150k from the second portion 152k to enable the stored energy to move the sensor 138 (and in some embodiments the needle 156) into the skin of the host.

The telescoping assembly 132k can lock the third portion 392 to the second portion 152k in response to the third portion 392 reaching a sufficiently distal position relative to the second portion 152k. A protrusion 408 can couple with a hole 410 to lock the third portion 392 to the second portion 152k.

Some embodiments do not include locking protrusion 408 and do not lock the third portion 392 to the second portion 152k in response to the third portion 392 reaching a sufficiently distal position relative to the second portion 152k.

In several embodiments, sufficiently distal positions are at least 3 millimeters, at least 5 millimeters, and/or less than 30 millimeters distal relative to the proximal starting position.

The telescoping assembly 132k can lock the first portion 150k to the second portion 152k in response to the first portion 150k reaching a sufficiently distal position relative to the second portion 152k. A protrusion 412 (e.g., a distal protrusion) can couple with a hole 414 (e.g., in a surface that is within plus or minus 30 degrees of perpendicular to the central axis of the telescoping assembly 132k) to lock the first portion 150k to the second portion 152k.

Some embodiments include a needle 156 to help insert a sensor into skin of a host. In embodiments that include a needle 156, the telescoping assembly 132k can include the needle retraction mechanism 158 described in the context of FIG. 7. Moving the first portion 150k to a sufficiently distal position relative to the second portion 152k can trigger the needle retraction mechanism 158 (e.g., can release a latch) to enable a second spring 234 to retract the needle 156.

FIG. 61 illustrates a system for applying an on-skin sensor assembly 600 (shown in FIGS. 4-6) to a skin of a host. The system comprises a telescoping assembly 132k having a first portion 150k configured to move distally relative to a second portion 152k from a proximal starting position (e.g., the position shown in FIG. 61) to a distal position (e.g., the position shown in FIG. 64) along a path; a sensor 138 (shown in FIG. 64) coupled to the first portion 150k; and a base 128 comprising adhesive 126 configured to couple the sensor 138 to the skin. The telescoping assembly 132k can further comprise a third portion 392 configured to move distally relative to the second portion 152k.

In some embodiments, the first portion 150k is located inside of the second portion 152k such that the second portion 152k wraps around the first portion 150k in a cross section taken perpendicularly to the central axis of the telescoping assembly 132k.

In some embodiments, a first spring 402 is positioned between the third portion 392 and the second portion 152k such that moving the third portion 392 distally relative to the second portion 152k compresses the first spring 402. The first spring 402 can be a metal helical spring and/or a metal conical spring. In several embodiments, the first spring 402 is a feature molded as part of the third portion 392, as part of the second portion 152k, or as part of the first portion 150k. The first spring 402 can be molded plastic.

The telescoping assembly 132k can be configured such that the first spring 402 is not compressed in the proximal starting position and/or not compressed during storage. In several embodiments, the telescoping assembly 132k can be configured such that the first spring 402 is not compressed more than 15 percent in the proximal starting position and/or during storage (e.g., to avoid detrimental spring relaxation and/or creep of other components such as at least one of the third portion 392, the second portion 152k, and the first portion 150k).

Some embodiments that include a needle 156 do not include a needle hub 162. In these embodiments, the second spring 234 can be located between the second portion 152k and the first portion 150k such that moving the first portion 150k distally relative to the second portion 152k compresses the second spring 234 to enable the second spring 234 to push the first portion 150k proximally relative to the second portion 152k to retract the needle 156 (e.g., after sensor insertion).

In several embodiments, the second spring 234 is compressed while the telescoping assembly 132k is in the proximal starting position. For example, the second spring 234 can be compressed at the factory while the telescoping assembly 132k is being assembled such that when the user receives the telescoping assembly 132k, the second spring 234 is already compressed (e.g., compressed enough to retract the needle 156).

The second spring 234 can have any of the attributes and features associated with the spring 234 described in the context of other embodiments herein (e.g., in the context of the embodiment of FIG. 7).

In some embodiments, the movement of the sensor module 134 (e.g., an analyte sensor module) and the sensor 138 (e.g., an analyte sensor) relative to the base 128 can be as described in the context of other embodiments (e.g., as shown by the progression illustrated by FIGS. 7-11).

In the proximal starting position of the telescoping assembly 132k, the first portion 150k can be locked to the second portion 152k. The system can be configured such that moving the third portion 392 distally relative to the second portion 152k unlocks the first portion 150k from the second portion 152k.

In several embodiments, a first proximal protrusion 394 having a first hook 396 passes through a first hole 398 in the second portion 152k to lock the first portion 150k to the second portion 152k. The third portion 392 can comprise a first distal protrusion 404. The system can be configured such that moving the third portion 392 distally relative to the second portion 152k engages a ramp 406 to bend the first proximal protrusion 394 to unlock the first portion 150k from the second portion 152k.

In some embodiments, the sensor 138 is located within the second portion 152k while the base 128 protrudes from the distal end of the system such that the system is configured to couple the sensor 138 to the base 128 by moving the first portion 150k distally relative to the second portion 152k.

In several embodiments, a sensor module 134 is coupled to a distal portion of the first portion 150k such that moving the first portion 150k to the distal position couples the sensor module 134 to the base 128. This coupling can be as described in the context of other embodiments herein. The sensor 138 can be coupled to the sensor module 134 while the first portion 150k is located in the proximal starting position.

The system can be configured such that the third portion 392 moves distally relative to the second portion 152k before the first spring 402 moves the first portion 150k distally relative to the second portion 152k. The system can be configured such that moving the third portion 392 distally relative to the second portion 152k unlocks the first portion 150k from the second portion 150k and locks the third portion 392 to the second portion 152k.

A first protrusion 408 couples with a hole 410 of at least one of the second portion 152k and the third portion 392 to lock the third portion 392 to the second portion 152k.

In some embodiments, the system comprises a second protrusion 412 that couples with a hole 414 of at least one of the first portion 150k and the second portion 152k to lock the first portion 150k to the second portion 152k in response to moving the first portion 150k distally relative to the second portion 152k.

In several embodiments, a first spring 402 is positioned between the third portion 392 and the second portion 152k such that moving the third portion 392 distally relative to the second portion 152k compresses the first spring 402 and unlocks the first portion 150k from the second portion 152k, which enables the compressed first spring 402 to push the first portion 150k distally relative to the second portion 152k, which pushes at least a portion of the sensor 138 out of the distal end of the system and triggers a needle retraction mechanism 158 to enable a second spring 234 to retract a needle 156.

In yet another aspect, disclosed herein is a dual spring-based sensor insertion device having a pre-connected sensor assembly (i.e. an analyte sensor electrically coupled to at least one electrical contact before sensor deployment). Such a sensor insertion device provides convenient and reliable insertion of a sensor into a user's skin by a needle as well as reliable retraction of a needle after the sensor is inserted, which are features that provide convenience to users as well as predictability and reliability of the insertion mechanism. The reliability and convenience of a dual spring based sensor insertion device having an automatic insertion and automatic retraction provide is a significant advancement in the field of sensor insertion devices. Furthermore, such a device can provide both safety and shelf stability.

In several embodiments, the insertion device can include a first spring and a second spring. In such embodiments, either or both of the first spring and the second spring can be integrally formed with portions of a telescoping assembly, such as the first portion and the second portion of a telescoping assembly. In several embodiments, either or both of the first spring and the second spring can be formed separately from and operatively coupled to portions of the telescoping assembly. For example, in some embodiments, the insertion spring can be integrally formed with a portion of the telescoping assembly while the retraction spring is a separate part which is operatively coupled to a portion of the telescoping assembly.

In some embodiments, rather than being configured to undergo compression during energization, either or both of the first spring and the second spring can be configured to undergo tensioning during energization. In these embodiments, the couplings between the springs and the portions of the telescoping assembly, as well as the couplings between the moving portions of the assembly (for example in the resting state, and during activation, deployment, and retraction) can be adjusted to drive and/or facilitate the desired actions and reactions within the system. For example, in an embodiment employing a tensioned retraction spring to drive the insertion process, the retraction spring can be coupled to or integrally formed with the second portion of the telescoping assembly. In such an embodiment, the retraction spring can be pre-tensioned in the resting state. In other such embodiments, the retraction spring can be untensioned in the resting state, and tensioned during the sensor insertion process.

In several embodiments, either or both of the first spring and the second spring can be substantially unenergized and/or unstressed when the system is in a resting state. In several embodiments, either or both of the first spring and the second spring can be energized and/or stressed when the system is in a resting state. As used herein, the term "energized" means that enough potential energy is stored in the spring to perform the desired actions and reactions within the system. In some embodiments, the first spring can be partly energized in the resting state, such that the user can supply a lesser amount of force to fully energize the first spring. In some embodiments, the second spring can be partly energized in the resting state, such that the energy stored in the first spring (either in the resting state or after energization by a user) can provide force to energize the second spring. In some embodiments, the energy stored in the first spring can provide sufficient force to energize the second spring to at least retract the needle from the skin. In some embodiments, either or both of the first spring and the second spring can be compressed or tensioned by 50% or more, 60% or more, 70% or more, 80% or more, 90% or more, or 100% in the resting state. In other embodiments, either or both of the first spring and the second spring can be compressed or tensioned by 50% or less, 40% or less, 30% or less, 20% or less, 15% or less, 10% or less, 5% or less, or 0% in the resting state.

In embodiments in which both the first spring and the second spring are substantially unenergized in the resting state, they can be stressed by the same amounts, similar amounts, or entirely different amounts. In embodiments in which both the first spring and the second spring are effectively energized in the resting state, they can be stressed by the same amounts, similar amounts, or entirely different amounts. In embodiments in which the second spring is substantially unenergized in the resting state, the first spring can be configured to store enough energy to drive both the desired movement in the system (e.g., the movement of the first portion in a distal direction), as well as the energization of the second spring.

With reference now to FIGS. 71-75, another embodiment of a system 104*m* for applying an on-skin sensor assembly to skin of a host is illustrated. The embodiment illustrated in FIGS. 71-75 may reduce the potential of incomplete sensor insertion by precluding sensor insertion until sufficient potential energy is stored in the system. The potential energy for inserting the sensor can be stored in an actuator, such as a first spring 402*m*. The embodiment may provide other advantages such as controlled speed, controlled force, and improved user experience.

The system 104*m* may include many features from the embodiment illustrated in FIG. 7 (e.g., the needle 156, the base 128 and the sensor module 134). The system 104*m* may include alternative elements, such as, but not limited to, a needle hub 162*m*, a second spring 234*m*, and a needle retraction mechanism 158*m*. The embodiment illustrated in FIGS. 71-75 can also be configured to be needle-free by removing the needle 156, the second spring 234*m*, the needle hub 162*m*, and the needle retraction mechanism 158*m*. In such embodiments, the sensor may be a self-insertable sensor.

The system 104*m* may include many features that are similar to those of the embodiment illustrated in FIGS. 61-64 (e.g., a telescoping assembly 132*m*) including a first portion 150*m*, a second portion 152*m*, and a third portion 392*m*; with locking features 396*m* and 398*m* configured to releasably lock the first portion 150*m* to the second portion 152*m* until the third portion 392*m* has reached a sufficiently distal position relative to the second portion 152*m* to compress the first spring 402*m* and store enough energy in the spring 402*m* to drive insertion of the sensor 138 (and in some embodiments the needle 156) into the skin of a host; locking features 408*m* and 410*m* configured to lock the third portion 392*m* to the second portion 152*m* (e.g., to prevent proximal movement of the third portion 392*m* relative to the second portion 152*m*) in response to the third portion 392*m* reaching a sufficiently distal position relative to the second portion 152*m*; unlocking features 404*m* and 406*m* configured to unlock the locking features 396*m* and 398*m* at least after the third portion 392*m* is locked to the second portion 152*m* and/or the first spring 402*m* is sufficiently compressed; locking features 412*m* and 414*m* configured to lock the first portion 150*m* to the second portion 152*m* in response to the first portion 150*m* reaching a sufficiently distal position relative to the second portion 152*m* to drive the sensor 138 (and in some embodiments the needle 156) into the skin of the host; and a needle retraction mechanism 158*m* configured to unlock the needle hub 162*m* from the first portion 150*m* (e.g., to allow proximal movement of the needle hub 162*m* with respect to the first portion 150*m*) at least once the needle hub 162*m* has reached a sufficiently distal position and thereby enable a second spring 234*m* to retract the needle 156).

FIG. 71 illustrates a cross-sectional perspective view of the applicator system 104*m* in a resting state (e.g., as provided to the consumer, before activation by the user and deployment of the applicator system). As illustrated in the figure, the first spring 402*m* can be neither in tension nor compression, such that the first spring is substantially unenergized. In some embodiments, the first spring 402*m* can be slightly in tension or slightly in compression (e.g., neither tensioned nor compressed by more than 15 percent) in a resting state, such that the first spring is substantially or mostly unenergized in the resting state. In some embodiments, the first spring can be effectively unenergized, e.g. can be minimally energized but not to an extent that would create any type of chain reaction in the system, in a resting state.

In the embodiment illustrated in FIGS. 71-75, the first spring 402*m* is integrally formed as part of the third portion 392*m*. In some embodiments, the first spring 402*m* can be integrally formed as part of other components of the system 104*m*, such as, but not limited to, the first portion 150*m*, second portion 152*m*, etc. An integrally formed spring such as the one illustrated in FIGS. 71-75 offers advantages including the reduction in the number of parts in a system as well as the reduction in the amount of assembly processes. The first spring 402*m* can be molded plastic. As illustrated in FIG. 71, in the resting state, the second spring 234*m* is also substantially unenergized (e.g., neither tensioned nor compressed by more than 15 percent). The second spring 234*m* is integrally formed as part of the needle hub 162*m*. In some embodiments, the second spring 234*m* can be integrally formed as part of other components of the system 104*m*, such as, but not limited to, the first portion 150*m*, second portion 152*m*, base 128, etc. The second spring 234*m* can be molded plastic. Such a configuration can simplify manufacture and assembly of the system 104*m*, while avoiding detrimental relaxation and/or creep of the first spring 402*m*, the second spring 234*m*, or other components of the system 104*m* during storage and/or before deployment. It is also contemplated that in other embodiments, the first spring 402*m* and/or the second spring 234*m* can comprise metal.

In some embodiments, first spring 402*m* and/or second spring 234*m* can comprise a molded plastic, such as, but not limited to: polycarbonate (PC), acrylonitrile butadiene styrene (ABS), PC/ABS blend, Nylon, polyethylene (PE), polypropylene (PP), and Acetal. In some embodiments, first spring 402*m* and/or second spring 234*m* have a spring constant less than 10 lb/inch.

Applicator system 104 may be energized by moving one component relative to another. For example, moving the third portion 392*m* distally relative to the second portion 152*m*, when the second portion 152*m* is placed against the skin of a host or another surface can store energy in the first spring 402*m* as it compresses against first portion 150*m*. The third portion 392*m* may be moved distally until the locking features 408*m* and 410*m* (see FIG. 73) engage together. In some embodiments, the third portion 392*m* may be moved further distally until unlocking features 404*m* engages locking feature 396*m*. Unlocking feature 404*m* may engage and release locking feature 396*m* and allow first portion 150*m* to move distally. In some embodiments, locking features 408*m* and 410*m* couple together before locking feature 396*m* is disengaged from locking feature 398*m*. In other embodiments, unlocking feature 404*m* engages locking feature 396*m* and causes locking feature 396*m* to disengage from locking feature 398*m*, locking features 408*m* and 410*m* may couple together. In some embodiments, locking feature 408*m* is a protrusion featuring a hook portion, locking feature 410*m* is a hole featuring an angled surface, unlocking feature 404*m* is a distal protrusion featuring an angled surface, locking feature 396*m* is a hook featuring a ramp 406*m*, and locking feature 398*m* is an aperture. The sensor module 134 remains in a proximal starting position while the first spring 402*m* is being energized.

Figure 73:
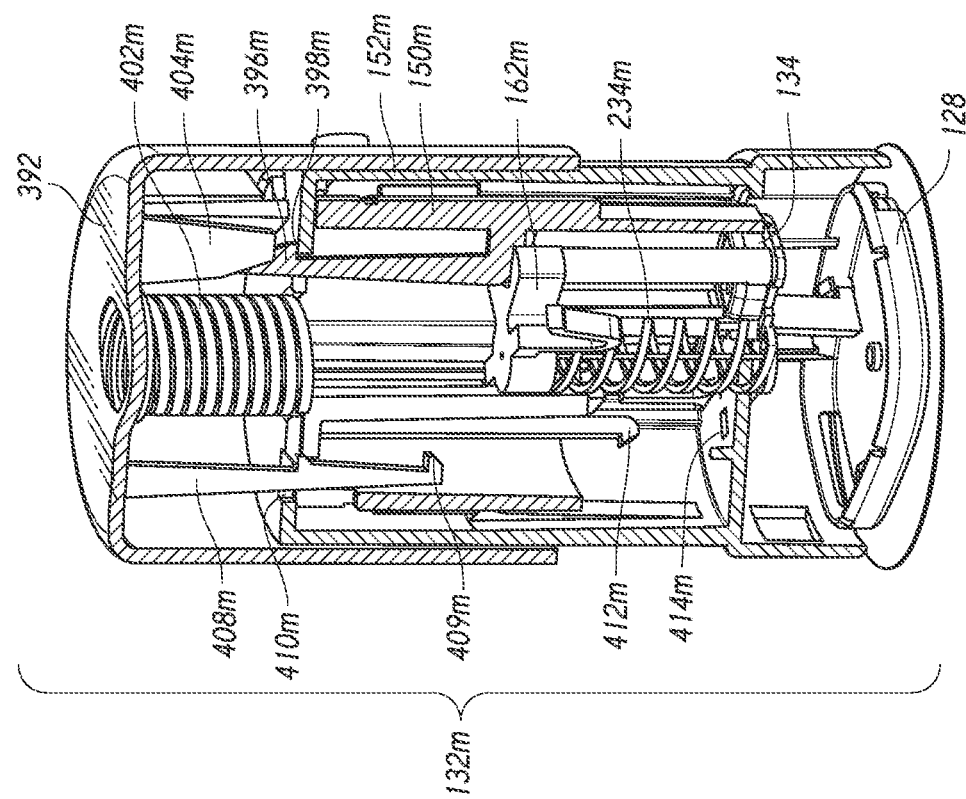
FIG. 73 illustrates a rotated cross-sectional perspective view of the applicator system of FIG. 72.

FIG. 72 illustrates a cross-sectional perspective view of the applicator system 104*m*, with the first spring 402*m* compressed and with the unlocking features 404*m* and 406*m* engaged so as to unlock the first portion 150m from the second portion 152m. Until the first portion 150m is unlocked from the second portion 152m, the sensor module 134 remains at its proximal starting position, and the second spring 234m remains substantially unenergized. FIG. 73 illustrates a rotated cross-sectional perspective view of the applicator system 104m, and shows the locking features 408m and 410m engaged to prevent proximal movement of the third portion 392m with respect to the second portion 152m. In some embodiments, as illustrated in FIG. 73, the system can include a secondary locking feature 409m which is configured to cooperate with the opening 410m to prevent the third portion 392 from falling off or otherwise separating from the remainder of the system 104m prior to deployment.

Figure 74:
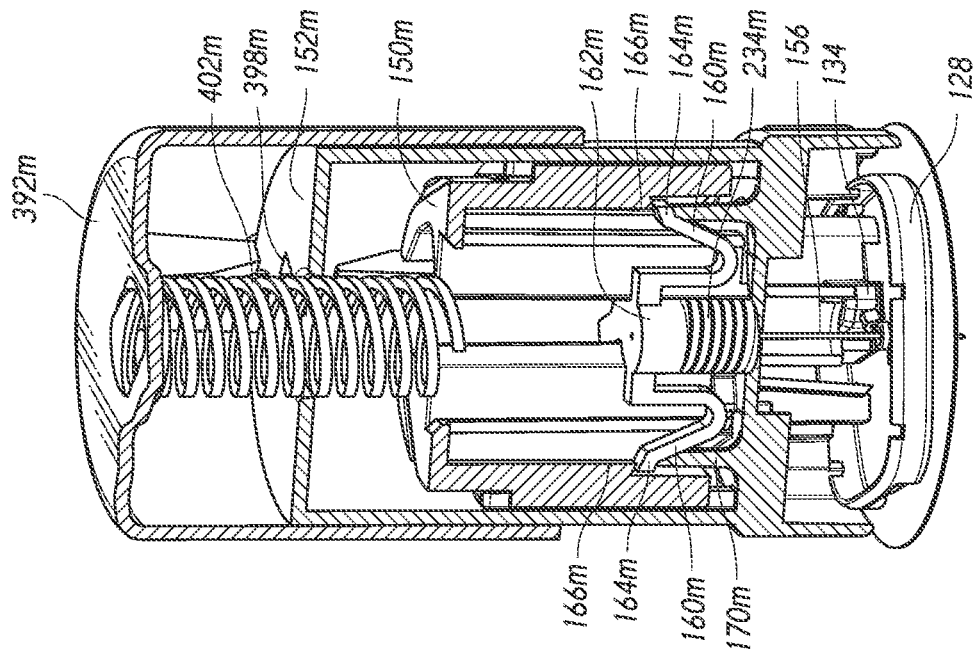
FIG. 74 illustrates a cross-sectional perspective view of the applicator system of FIG. 71, with the actuation member activated and with the needle assembly deployed in an insertion position.

FIG. 74 illustrates a cross-sectional perspective view of the applicator system 104m, with the system 104m having been activated by the disengagement of the first portion 150m with respect to the second portion 152m. As can be seen in FIG. 74, once the first portion 150m and the second portion 152m are disengaged or released, the potential energy stored in the first spring 402m drives the first portion 150m in a distal direction along with the needle hub 162m and the sensor module 134. This movement compresses the second spring 234m and deploys the needle 156 and the sensor module 134 distally to a distal insertion position in which the sensor module 134 is coupled to the base 128 and the needle 156 extends distally of the base 128. Once the needle 156 and the sensor module 134 reach the distal insertion position, the locking features 412m, 414m (see FIG. 73) engage to prevent proximal movement of the first portion 150m with respect to the second portion 152m, and the unlocking features of the needle retraction mechanism 158m (e.g., the proximal protrusions 170m, the release feature 160m, and the latch 236m comprising ends 164m of the release feature 160m and overhangs 166m of the first portion 150m) cooperate to release the latch 236m. Optionally, the user may hear a click after the second spring 243m is activated, which may indicate to the user that the cap is locked in place.

Once the latch 236m is released, the potential energy stored in the compressed second spring 234m drives the needle hub 162m back in a proximal direction, while the first portion 150m remains in a distal deployed position along with the sensor module 134. The potential energy stored can be between 0.25 pounds to 4 pounds. In preferred embodiments, the potential energy stored is between about 1 to 2 pounds. FIG. 75 illustrates a cross-sectional perspective view of the applicator system 104m with the sensor module 134 in a distal deployed position, coupled to the base 128, and with the needle hub 162m retracted to a proximal retracted position.

Systems configured in accordance with embodiments may provide an inherently safe and shelf stable system for insertion of a sensor. An unloaded (i.e. substantially uncompressed and substantially unactivated) spring may not fire prematurely. Indeed, such a system is largely incapable of unintentional firing without direct interaction from a user since the first spring and/or second spring are substantially un-energized on the shelf. Moreover, it is contemplated that a system having a substantially uncompressed spring prior to activation possesses shelf stability since elements of the system are not exposed to a force or phase change over time (such as creep, environment, defects from time dependent load conditions, etc.) as compared to pre-energized insertion devices. Substantially uncompressed first and second springs can provide a system where the substantially unenergized first spring 404m is configured to load energy sufficient to drive a sensor from a proximal position to a distal position and also to transfer energy to the second spring 234m to drive a needle to a fully retracted position.

Other embodiments can also be configured to achieve these benefits. For example, FIGS. 76-79 illustrate another embodiment of a system 104n for applying an on-skin sensor assembly to skin of a host. The system 104n includes many features that are similar to those of the embodiment illustrated in FIGS. 71-75 (e.g., a telescoping assembly 132n including a first portion 150n, a second portion 152n, and a third portion 392n; a needle hub 162n; a first spring 402n; and a second spring 234n). In the embodiment illustrated in FIGS. 76-79, the first spring 402n is formed separately from and operatively coupled to the third portion 392n. The second spring 234n is formed separately from and operatively coupled to the needle hub 162n. The first spring and/or the second spring can each comprise a helical spring having a circular cross section. In some embodiments, the first spring and/or the second spring can each comprise a helical spring having a square or non-circular cross section. The first spring and/or the second spring can comprise metal, such as, but not limited to, stainless steel, steel, or other types of metals. Alternatively, in some embodiments, one or both of the first spring and the second spring can be integrally formed with a portion of the applicator assembly. For example and without limitation, in some embodiments the first spring can be integrally formed with the first portion. In some embodiments, the second spring can be integrally formed with the needle hub. In several embodiments, the first spring and/or the second spring can be molded plastic, such as, but not limited to, PC or ABS.

FIG. 76 illustrates a cross-sectional side view of the system 104n in a resting state, in which both the first spring 402n and the second spring 234n are unstressed and unenergized. In the resting state, the first portion 150n can be fixed with respect to the second portion 152n, at least in an axial direction, whereas the third portion 392n is movable in at least a distal direction with respect to the first portion 150n. The first portion 150n and the second portion 152n can be fixed with respect to one another in any suitable fashion, for example by cooperating releasable locking features (e.g., the locking features as described in FIGS. 71-75, or similar features) coupled to or forming part of the first portion 150n and the second portion 152n. The system 104n includes an on-skin component 134n which is releasably coupled to the needle hub 162n. The on-skin component can comprise a sensor module, such as the sensor module 134 described in connection with FIG. 3, or a combined sensor module and base assembly, or an integrated sensor module/base/transmitter assembly, or any other component which is desirably applied to the skin of a host, whether directly or indirectly, for example via an adhesive patch.

In the resting state illustrated in FIG. 76, the on-skin component 134n is disposed at a proximal starting position, between the proximal and distal ends of the system 104n. The distal end of the needle 156 may also be disposed between the proximal and distal ends of the system 104n. In the resting state, the distal end of the first spring 402n abuts a proximally-facing surface of the first portion 150n. The application of force against the proximally-facing surface of the third portion 392n causes the third portion 392n to move distally with respect to the first portion 150n, compressing and thus energizing the first spring 402n. In some embodiments, this process may be similar to the spring energization process described in connection with FIG. 71.

FIG. 77 illustrates a cross-sectional side view of the applicator system of FIG. 76, with the first spring 402n energized. When the third portion 392n has been moved sufficiently distally to energize the first spring 402n, the third portion 392n becomes fixed, at least in an axial direction, with respect to the second portion 152n. At or about the same time (e.g. simultaneously or subsequently), the first portion 150n becomes movable in at least a distal direction with respect to the second portion 152n. The third portion 392n and the second portion 150n can be fixed with respect to one another in any suitable fashion, for example by cooperating locking features (e.g., the locking features described in FIGS. 71-75, or similar features) coupled to or forming part of the third portion 392n and the second portion 152n, which are configured to engage with one another once the third portion 392n has reached a sufficiently distal position. The first portion 150n and the second portion 152n can be rendered movable with respect to one another by structure(s) (not shown in FIGS. 76-79) configured to release the locking features which coupled them together in the resting configuration illustrated in FIG. 76. The first portion 150n includes overhangs (sometimes referred to as detents, undercuts, and/or needle hub engagement features) 166n which cooperate with release feature 160n of the needle hub 162n to fix the needle hub 162n with respect to the first portion 150n, both while the system is in a resting state and during energization of the spring 392n.

FIG. 78 illustrates a cross-sectional side view of the system 104n, with the first portion 150n and the second portion 152n unlocked, activating the first spring 402n and allowing the energy stored therein to drive the first portion 150n in a distal direction. The movement of the first portion 150n also urges the needle hub 162n (as well as the on-skin component 134n which is coupled to the needle hub 162n) in a distal direction, compressing the second spring 234n against a proximally-facing surface of the second portion 152n, coupling the on-skin component 134n to the base 128n, and driving the needle 156 into the distal insertion position illustrated in FIG. 78. When the needle hub 162n has reached a sufficiently distal position to achieve these functions, the ends of the release feature 160n contact ramps 170n of the second portion 152n which cause the release feature 160n to compress inward (towards the central axis of the system 104n), disengaging the ends of the release feature 160n from the overhangs 166n. In some embodiments, this process may be similar to the spring compression process described in connection with FIG. 74. In some embodiments, ramps 170n are proximally facing ramps. In other embodiments, ramps 170n are distally facing ramps (not shown). In some embodiments, the release feature or features can be configured to be compressed inward (or otherwise released) by relative rotational movement of certain components of the system, such as, for example, by twisting or other rotational movement of the first portion with respect to the second portion. In some embodiments, the release feature or features can extend in a direction normal to the axis of the system, and/or can extend circumferentially about the axis of the system, instead of (or in addition to) extending generally parallel to the axis of the system as illustrated in FIG. 78.

FIG. 79 illustrates a cross-sectional side view of the system 104n, with the needle hub 162n released from engagement with the overhangs 166, activating the second spring 234n and allowing the energy stored therein to drive the needle hub 162n in a proximal direction. As the needle hub 162n retracts to a proximal position, the on-skin component 134n decouples from the needle hub 162n to remain in a deployed position, coupled to the base 128n.

FIGS. 80-85 illustrate another embodiment of a system 104p for applying an on-skin sensor assembly to skin of a host. A sensor insertion system such as the one illustrated in FIGS. 80-85 may provide enhanced predictability in spring displacement of the second energized spring 234p because the second spring 234p is already compressed. Such a configuration can aid in properly ensuring the needle is retracted at a sufficient distance from the skin. In some embodiments, a system incorporating a pre-energized retraction spring can provide effective and reliable insertion and retraction while requiring a lesser amount of user-supplied force than, for example, a system in which both the insertion and retraction springs are substantially unenergized prior to deployment, making such a configuration more convenient for at least some users. Further, in some embodiments, a system incorporating one or more metal springs can provide effective and reliable insertion and retraction while requiring a lesser amount of force than a system in which both the insertion and retraction springs comprise plastic. The system 104p includes many features that are similar to those of the embodiment illustrated in FIGS. 76-79 (e.g., a telescoping assembly 132p including a first portion 150p, a second portion 152p, and a third portion 392p; a needle hub 162p; a first spring 402p; a second spring 234p; an on-skin component 134n, and a base 128p). In the embodiment illustrated in FIGS. 80-85, the first spring 402p is formed separately from and operatively coupled to the third portion 392p. The second spring 234p is formed separately from and operatively coupled to the needle hub 162p. The first spring and/or the second spring can comprise metal. Alternatively, in some embodiments, one or both of the first spring and the second spring can be integrally formed with a portion of the applicator assembly. For example and without limitation, in some embodiments the first spring can be integrally formed with the first portion. In some embodiments, the second spring can be integrally formed with the needle hub. In several embodiments, the first spring and/or the second spring can be molded plastic.

Figure 80:
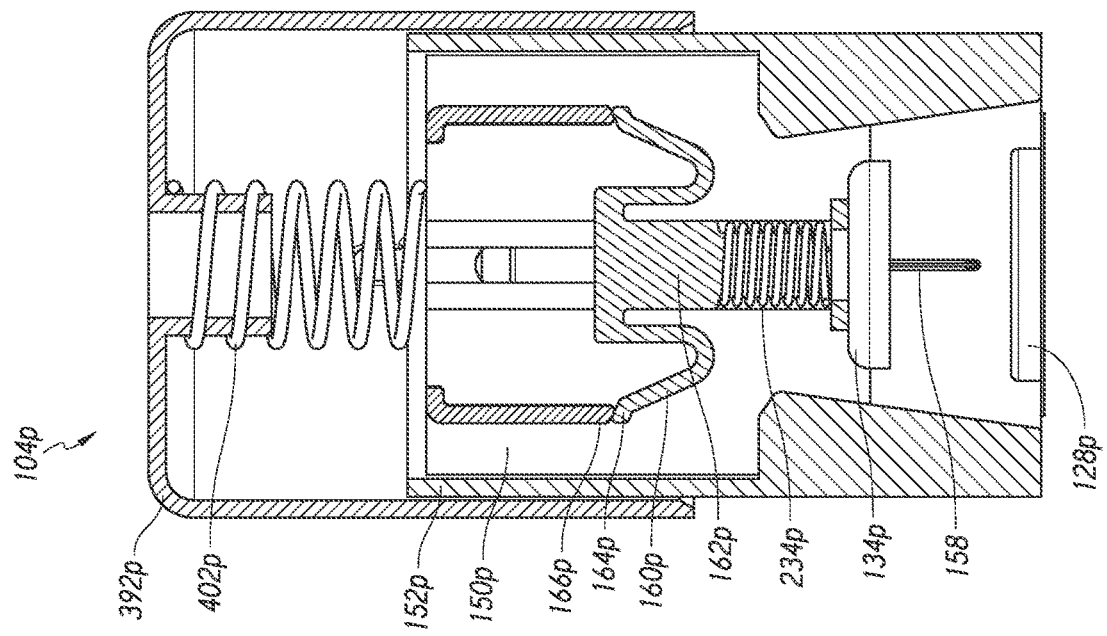
FIG. 80 illustrates a cross-sectional side view of another applicator system, according to some embodiments, in a resting state.

FIG. 80 illustrates a cross-sectional side view of the system 104p in a resting state, in which the first spring 402p is substantially unstressed and unenergized, but in which the second spring 234n is pre-energized (e.g., compressed). In the resting state illustrated in FIG. 80, the first portion 150p is locked to the second portion 152p so as to prevent proximal or distal movement of the first portion 150p with respect to the second portion 152p. The first portion 150p and the second portion 152n can be locked together in any suitable fashion, for example by cooperating releasable locking features 396p and 398p (see FIGS. 84 and 85) coupled to or forming part of the first portion 150p and the second portion 152p. The needle hub 162n is also releasably fixed to the first portion 150p. The needle hub 162n can be fixed to the first portion 150p in any suitable fashion, for example by features of the first portion 150p configured to engage or compress release feature (sometimes referred to as needle hub resistance features) 160p of the needle hub 162p.

In the resting state illustrated in FIG. 80, the on-skin component 134p is disposed at a proximal starting position, such that the distal end of the needle 156 is disposed between the proximal and distal ends of the system 104p. In the resting state, the distal end of the first spring 402p abuts a proximally-facing surface of the first portion 150p. The application of force against the proximally-facing surface of the third portion 392p causes the third portion 392p to move distally with respect to the first portion 150p, compressing and thus energizing the first spring 402p. In some embodiments, this process may be similar to the spring energization process described in connection with FIG. 76.

Figure 81:
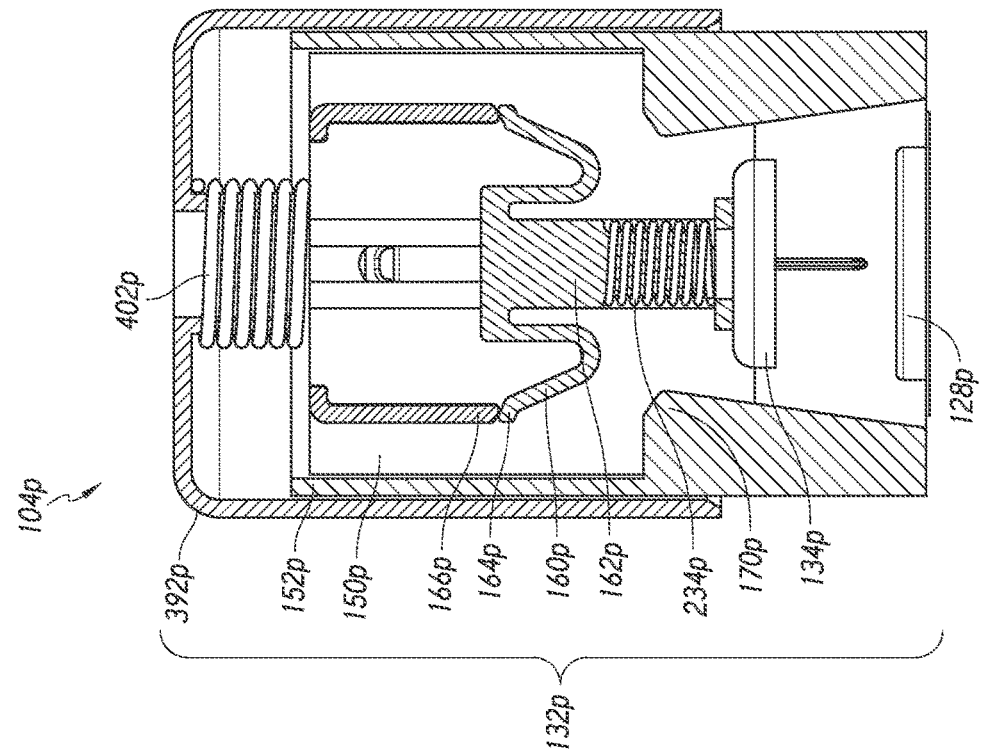
FIG. 81 illustrates a cross-sectional side view of the applicator system of FIG. 80, with the actuation member energized.

FIG. 81 illustrates a cross-sectional side view of the system 104p of FIG. 80, after the third portion 392n has been moved to a sufficiently distally position to energize the first spring 402p and optionally lock the third portion 392p to the second portion 152p. The third portion 392n and the second portion 150n can lock together in any suitable fashion, for example by cooperating locking features (e.g., the locking features described in FIGS. 76-79, or similar features) coupled to or forming part of the third portion 392p and the second portion 152p. At or about the same time as the third portion 392p locks to the second portion 152p (e.g. simultaneously or subsequently), the unlocking features 404p and 406p (see FIGS. 84 and 85) cooperate to release the lock between the first portion 150p and the second portion 152p.

Figure 82:
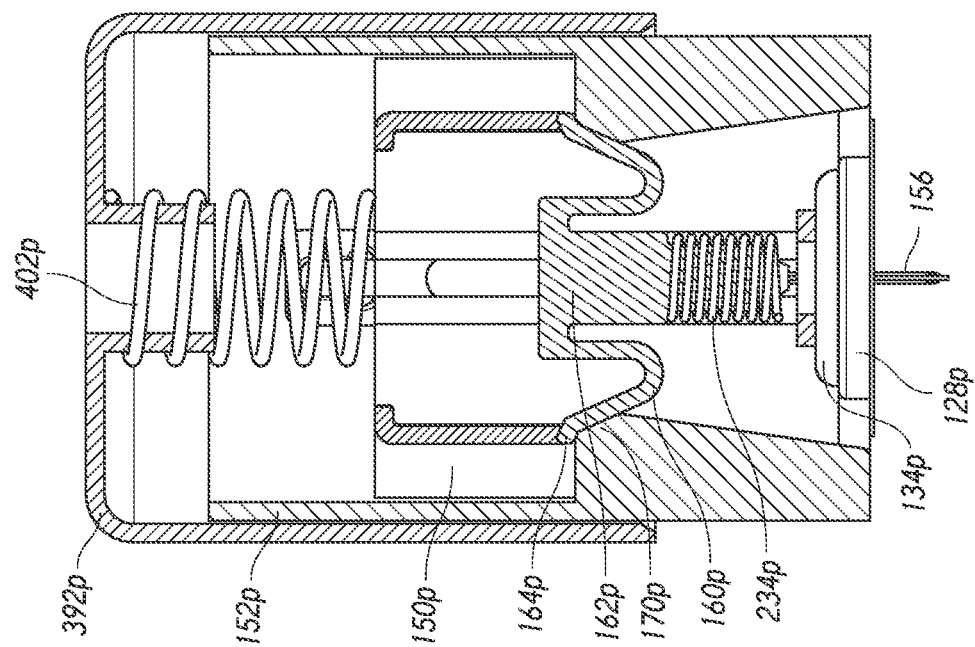
FIG. 82 illustrates a cross-sectional side view of the applicator system of FIG. 80, with the actuation member activated and with the needle assembly deployed in an insertion position.

FIG. 82 illustrates a cross-sectional side view of the system 104p, with the first spring 402p activated to drive the first portion 150p in a distal direction. The movement of the first portion 150p also urges the needle hub 162p (as well as the on-skin component 134p which is coupled to the needle hub 162p) in a distal direction, coupling the on-skin component 134p to the base 128p, and also driving the needle 156 in a distal direction, past a distal end of the system 104p. At or about the time the needle hub 162p reaches the distal insertion position illustrated in FIG. 82 (e.g., immediately before, simultaneously, or subsequently), the ends of the release feature 160p contact ramps 170p of the second portion 152p, causing the release feature 160p to compress inward (towards the central axis of the system 104p), unlocking the needle hub 162p from the first portion 150p and releasing or activating the second spring 234p. In some embodiments, ramps 170p are proximally facing ramps. In other embodiments, ramps 170p are distally facing ramps (not shown). Activation of the second spring 234p urges the needle hub 162p in a proximal direction.

Figure 83:
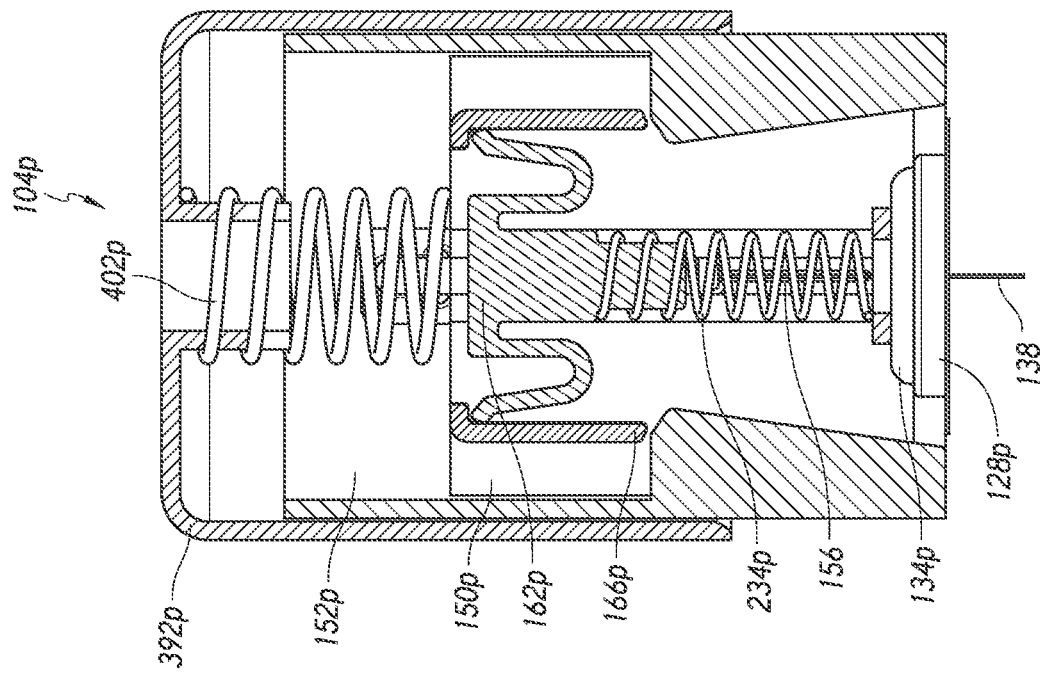
FIG. 83 illustrates a cross-sectional side view of the applicator system of FIG. 80, with the on-skin component in a deployed position and the needle assembly retracted.

FIG. 83 illustrates a cross-sectional side view of the system 104p, with the needle hub 162p unlocked from the first portion 150p and retracted to a proximal position. As the needle hub 162p retracts to a proximal position, the on-skin component 134p decouples from the needle hub 162p to remain in a deployed position, coupled to the base 128p.

Figure 85:
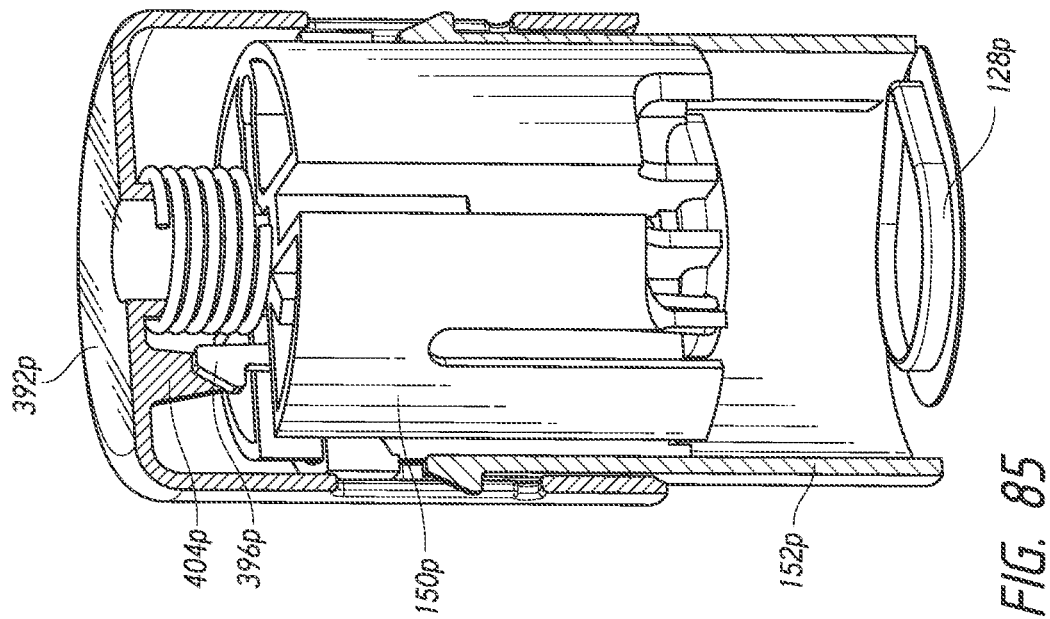
FIG. 85 illustrates a perspective view of the applicator system of FIG. 80, with the first and third portions shown in cross section to better illustrate certain portions of the system, and with the actuation member energized.
Figure 84:
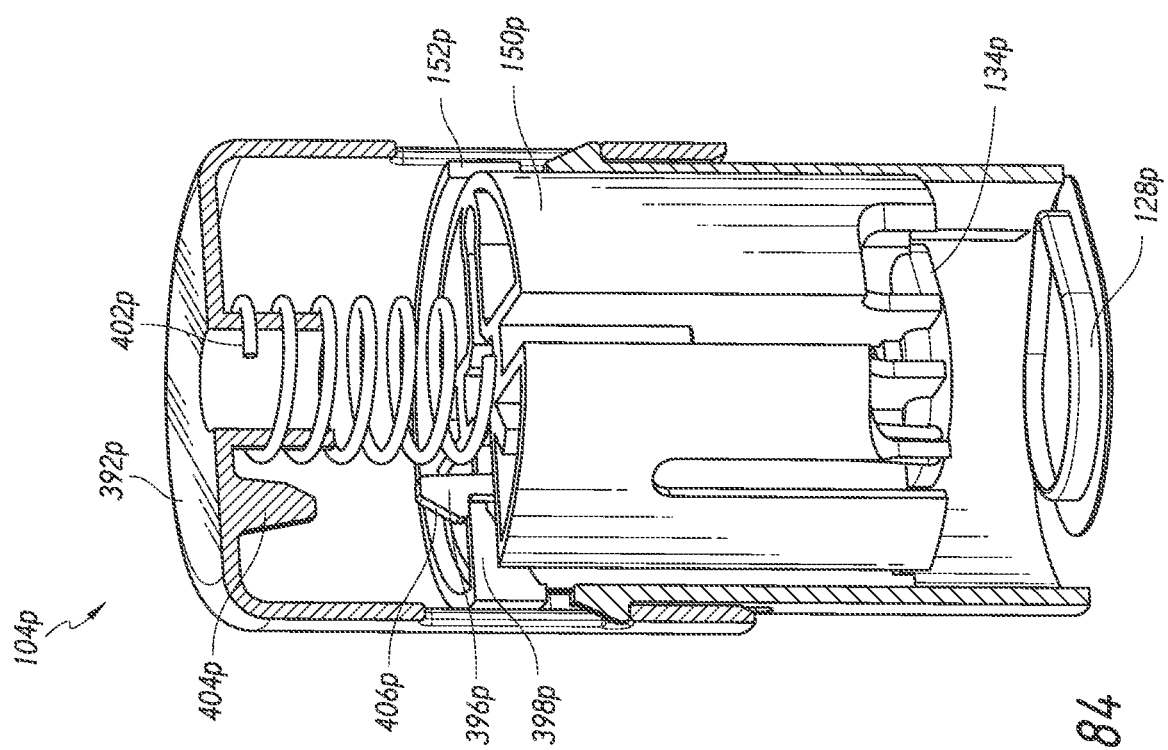
FIG. 84 illustrates a perspective view of the applicator system of FIG. 80, with the first and third portions shown in cross section to better illustrate certain portions of the system, and in a resting state.

FIG. 84 illustrates a perspective view of the system 104p in a resting state, with the first portion 150p and the third portion 392p shown in cross section to better illustrate certain portions of the system 104p, such as the locking features 396p, 398p and the unlocking features 404p, 406p. FIG. 85 illustrates another perspective view of the system 104p, also with the first portion 150p and the third portion 392p shown in cross section, with the first spring 402p energized but not yet activated.

FIGS. 86-88 illustrate another embodiment of a system 104q for applying an on-skin sensor assembly to skin of a host, wherein the insertion spring is pre-compressed and the retraction spring is substantially uncompressed. Such a system may allow a user to activate the insertion and retraction of a needle with fewer steps. It is contemplated that advantages may include a relatively smaller applicator size and more predictable spring displacement of the first spring because the first spring is already compressed, thereby aiding in ensuring proper needle insertion into the skin of a user. In some embodiments, a system incorporating a pre-energized insertion spring can provide effective and reliable insertion and retraction while requiring a lesser amount of user-supplied force than, for example, a system in which both the insertion and retraction springs are substantially unenergized prior to deployment, making such a configuration more convenient for at least some users. The system 104q includes many items that are similar to those of the embodiment illustrated in FIGS. 76-79 (e.g., a telescoping assembly 132q including a first portion 150q, a second portion 152q, and a third portion 392q; a needle hub 162q; a first spring 402q; a second spring 234q; an on-skin component 134q, and a base 128q). In the system 104q, the first spring 402q is formed separately from and operatively coupled to the third portion 392q. The second spring 234q is formed separately from and operatively coupled to the needle hub 162q. The first spring and/or the second spring can comprise metal. Alternatively, in some embodiments, one or both of the first spring and the second spring can be integrally formed with a portion of the applicator assembly.

FIG. 86 illustrates a cross-sectional side view of the system 104q in a resting state, in which the first spring 402q is already energized but in which the second spring 234q is substantially unenergized (e.g. mostly uncompressed or unstressed; can be partially energized). In the resting state illustrated in FIG. 86, the first portion 150q is locked to the second portion 152q so as to prevent proximal or distal movement of the first portion 150q with respect to the second portion 152q. The first portion 150q and the second portion 152q can be locked together in any suitable fashion, for example by cooperating releasable locking features (e.g., the locking features described in FIGS. 76-79 or other suitable locking features) coupled to or forming part of the first portion 150q and the second portion 152q. The needle hub 162q is also releasably locked to the first portion 150q. The needle hub 162q can be locked to the first portion 150q in any suitable fashion, for example by features of the first portion 150q configured to engage or compress release feature 160q of the needle hub 162q. The third portion 392q and the second portion 152q are also locked together, so as to prevent relative movement of the third portion 392p and the second portion 152q in the axial direction. The third portion 392q and the second portion 152q can be locked together in any suitable fashion, for example by cooperating locking features (not shown in FIGS. 86-89), which may be coupled to or form part of the third portion 392q and the second portion 152q. In the resting state illustrated in FIG. 80, the on-skin component 134q is disposed at a proximal starting position, such that the distal end of the needle 156 is disposed between the proximal and distal ends of the system 104q.

To trigger deployment of the system 104q, the locking features coupling the first portion 150q to the second portion 152q can be unlocked, decoupling these two portions and thereby releasing or activating the first spring 402q. The locking features can be unlocked by a user-activated trigger mechanism, such as, for example, a button disposed on or in a top or side surface of the system 104q, or a twist-release feature configured to disengage the locking features when the third portion 392q is rotated about the axis of the system, relative to the first portion 150q and/or the second portion 152q. Some examples of triggering mechanisms are described in connection with FIGS. 92-104.

FIG. 87 illustrates a cross-sectional side view of the system 104q, after the first portion 150q and the second portion 152q have been unlocked. As can be seen in FIG. 87, the first spring 402q drives the first portion 150q in a distal direction as the first spring 402q expands. The movement of the first portion 150q also urges the needle hub 162q (as well as the on-skin component 134q which is coupled to the needle hub 162q) in a distal direction, coupling the on-skin component 134q to the base 128q, compressing the second spring 234q, and driving the needle 156 in a distal direction past a distal end of the system 104q. At or about the time the needle hub 162q reaches the distal insertion position illustrated in FIG. 87 (e.g., immediately before, simultaneously, or subsequently), the ends of the release feature 160q contact interference features 170q of the second portion 152q, causing the release feature 160q to compress inward (towards the central axis of the system 104q), unlocking the needle hub 162q from the first portion 150q and activating the now-energized second spring 234q. In some embodiments, interference features 170q are proximally facing interference features. In other embodiments, interference features 170q are distally facing interference features (not shown).

Activation of the second spring 234q by the user or mechanisms urges the needle hub 162q in a proximal direction, while the on-skin component 134q, having been coupled to the base 128q, remains in a deployed distal position. FIG. 88 illustrates a cross-sectional side view of the system 104q, with the on-skin component 134q in a deployed position and the needle hub 162q retracted to a proximal position.

FIGS. 89-91 illustrate another embodiment of a system 104r for applying an on-skin sensor assembly to skin of a host. It is contemplated that the system 104r as illustrated with reference to FIGS. 89-91 provides for predictable spring displacement of the first spring 402r because it is compressed, thereby aiding in proper needle insertion into the skin of the user. Moreover, it is contemplated that the compressed second spring 234r provides predictable spring displacement and aids in properly ensuring that the needle is properly retracted from the skin of the user. In some embodiments, a system incorporating pre-energized insertion and retraction springs can provide effective and reliable insertion and retraction while requiring a lesser amount of user-supplied force than, for example, a system in which one or both of the insertion and retraction springs are substantially unenergized prior to deployment, making such a configuration more convenient for at least some users. The system 104r includes many items that are similar to those of the embodiment illustrated in FIGS. 76-79 (e.g., a telescoping assembly 132r including a first portion 150r, a second portion 152r, and a third portion 392r; a needle hub 162r; a first spring 402r; a second spring 234r; an on-skin component 134r, and a base 128r). As illustrated in FIGS. 89-91, both the first spring 402r and the second spring 234r are pre-compressed. In the system 104r, the first spring 402r is formed separately from and operatively coupled to the third portion 392r. The second spring 234r is formed separately from and operatively coupled to the needle hub 162r. The first spring and/or the second spring can comprise metal. Alternatively, in some embodiments, one or both of the first spring and the second spring can be integrally formed with a portion of the applicator assembly.

FIG. 89 illustrates a cross-sectional side view of the system 104r in a resting state, in which both the first spring 402r and the second spring 234r are pre-energized (e.g., compressed sufficiently to drive the needle insertion and retraction processes). In the resting state illustrated in FIG. 89, the first portion 150r is locked to the second portion 152r so as to prevent proximal or distal movement of the first portion 150r with respect to the second portion 152r. The first portion 150r and the second portion 152r can be locked together in any suitable fashion, for example by cooperating releasable locking features (e.g., the locking features described in connection with FIGS. 80-83, or other suitable locking features) coupled to or forming part of the first portion 150r and the second portion 152r. The needle hub 162r is also releasably locked to the first portion 150r. The needle hub 162r can be locked to the first portion 150r in any suitable fashion, for example by features of the first portion 150r configured to engage or compress release feature 160r of the needle hub 162r. The third portion 392r and the second portion 152r are also locked together, so as to prevent relative movement of the third portion 392p and the second portion 152r in at least the axial direction. The third portion 392r and the second portion 152r can be locked together in any suitable fashion, for example by cooperating locking features (not shown in FIGS. 89-91), which may be coupled to or form part of the third portion 392r and the second portion 152r. In the resting state illustrated in FIG. 89, the on-skin component 134r is disposed at a proximal starting position, such that the distal end of the needle 156 is disposed between the proximal and distal ends of the system 104r.

To trigger deployment of the system 104r, the locking features coupling the first portion 150r to the second portion 152r can be unlocked, decoupling these two portions and thereby releasing or activating the first spring 402r. FIG. 90 illustrates a cross-sectional side view of the system 104r, after the first portion 150r and the second portion 152r have been unlocked. As can be seen in FIG. 90, the first spring 402r drives the first portion 150r in a distal direction as the first spring 402r expands or decompresses. The movement of the first portion 150r also urges the needle hub 162r (as well as the on-skin component 134r which is coupled to the needle hub 162r) in a distal direction until the on-skin component 134r is coupled to the base 128r, and until the needle 156 reaches a distal insertion position beyond a distal end of the system 104r. At or about the time the needle hub 162r reaches the distal insertion position illustrated in FIG. 87 (e.g., immediately before, simultaneously, or subsequently), the ends of the release feature 160r contact corresponding interference features 170r of the second portion 152r, causing the release feature 160r to compress inward (towards the central axis of the system 104r), unlocking the needle hub 162r from the first portion 150r and releasing or activating the second spring 234r.

Activation of the second spring 234r drives the needle hub 162r in a proximal direction, while the on-skin component 134r, having been coupled to the base 128r, remains in a deployed distal position. FIG. 91 illustrates a cross-sectional side view of the system 104r, with the on-skin component 134r in a deployed position and the needle hub 162r retracted to a proximal position. From this configuration, the system 104r can be removed and separated from the deployed on-skin component 134r and the base 128r.

FIGS. 92-100 illustrate yet another embodiment of a system 104s for applying an on-skin sensor assembly to skin of a host comprising a safety feature to prevent accidental firing of the sensor insertion device. The system 104s includes many items that are similar to those of the embodiment illustrated in FIGS. 76-79 (e.g., a telescoping assembly 132s including a first portion 150s, a second portion 152s, and a third portion 392s; a needle hub 162s; a first spring 402s; a second spring 234s; an on-skin component 134s, and a base 128s). In the system 104s, the first spring 402s may be formed separately from and operatively coupled to the third portion 392s. The second spring 234s may be formed separately from and operatively coupled to the needle hub 162s. The first spring and/or the second spring can comprise metal. Alternatively, in some embodiments, either or both of the first spring and the second spring can be integrally formed with a portion of the applicator assembly.

Figure 93:
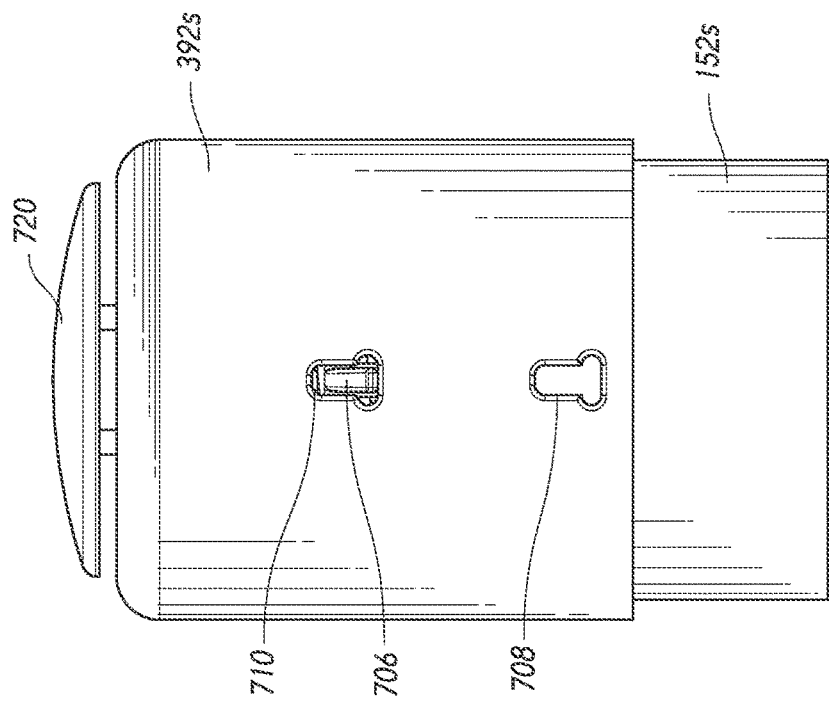
FIG. 93 illustrates a side view of the applicator system of FIG. 92, after being cocked but before being triggered.
Figure 92:
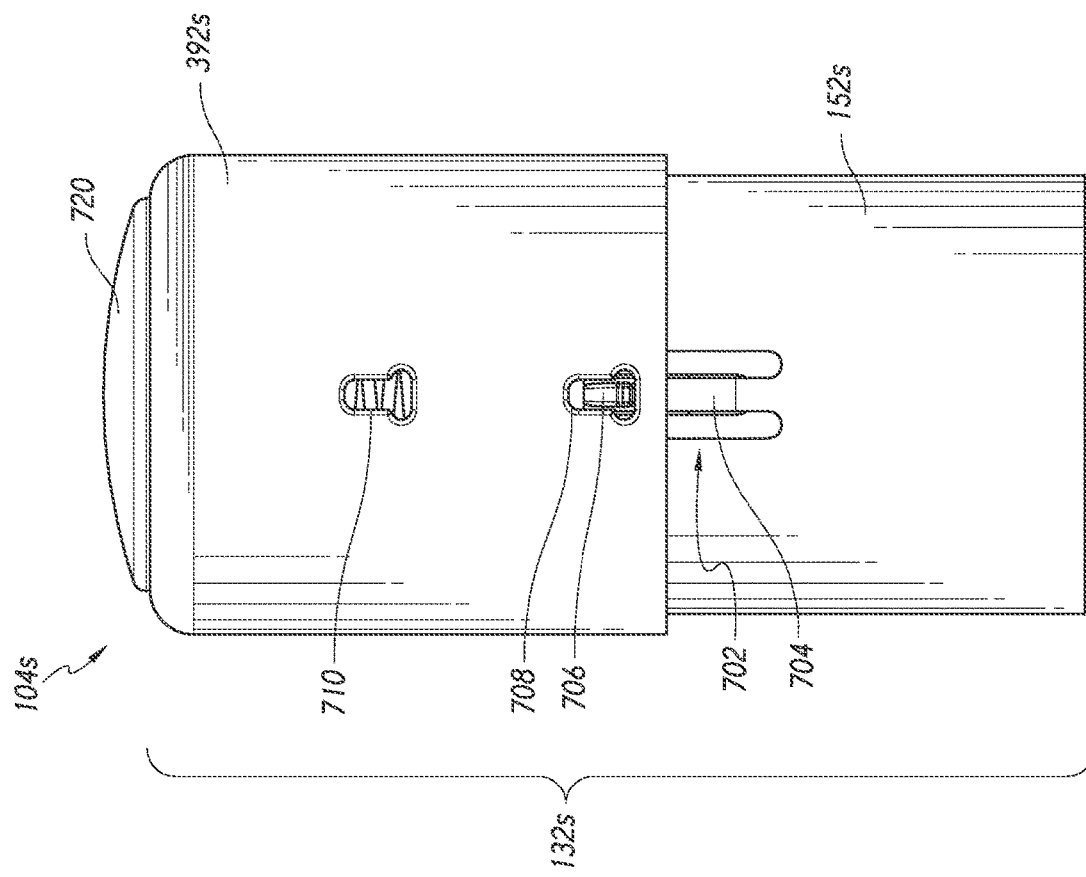
FIG. 92 illustrates a side view of another applicator system, according to some embodiments, with a top trigger member, in a resting state.

FIG. 92 illustrates a side view of the system 104s in a resting state, in which the first spring 402s is unstressed and unenergized, but in which the second spring 234s is already energized (e.g., compressed). The system 104s includes a cocking mechanism 702 by which the first spring 402s can be energized (e.g. compressed) without automatically triggering deployment of the first portion 150s or activation of the first spring 402s. The system 104s also includes a trigger button 720 configured to activate the first spring 402s after the system is cocked. FIG. 93 illustrates a side view of the applicator system 104s, after being cocked but before being triggered.

Figure 95:
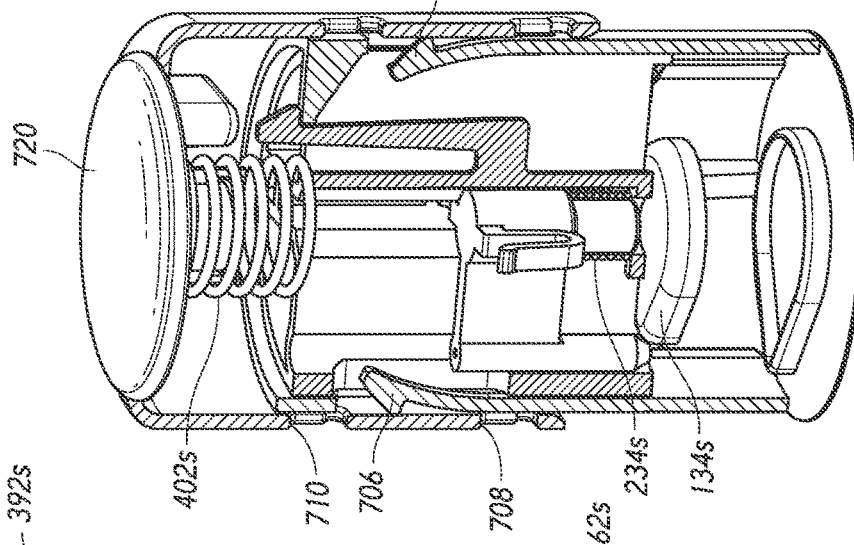
FIG. 95 illustrates a cross-sectional perspective view of the applicator system of FIG. 92 while being cocked.
Figure 94:
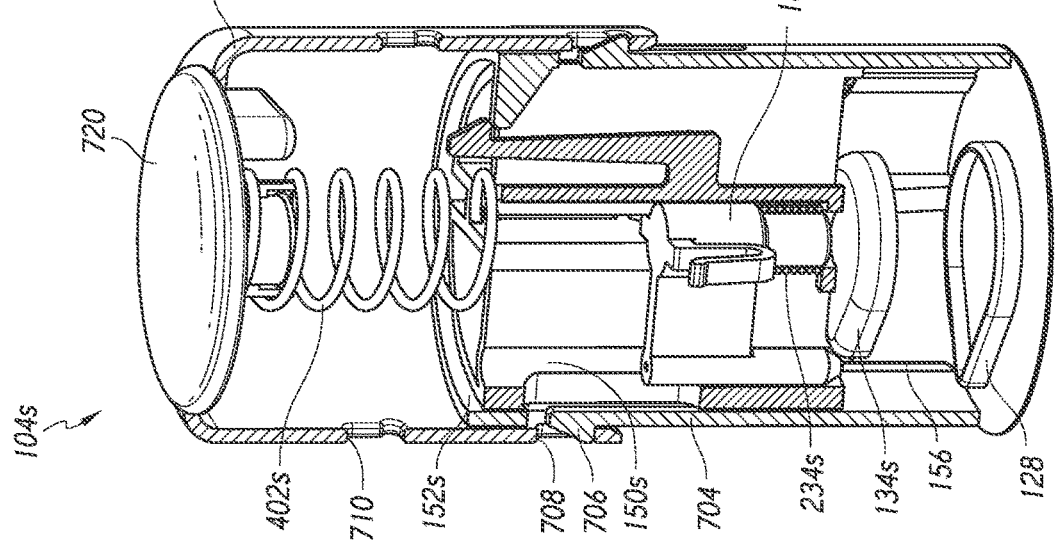
FIG. 94 illustrates a cross-sectional perspective view of the applicator system of FIG. 92, in a resting state.

FIG. 94 illustrates a cross-sectional perspective view of the system 104s in a resting state, showing the first spring 402s substantially uncompressed. The cocking mechanism 702 includes a pair of proximally-extending lever arms 704, each with a radially-extending angled tab 706. In some embodiments, the lever arms 704 can be integrally formed with the second portion 152s, as shown in FIG. 94, while in other embodiments, the lever arms 704 can be separate from and operatively coupled to the second portion 152s. In the resting state illustrated in FIG. 94, the angled tabs 706 extend through distal apertures 708 in the third portion 392s so as to prevent proximal movement of the third portion 392s with respect to the second portion 152s. The angled tabs 706 are also configured to inhibit distal movement of the third portion 392s with respect to the second portion 152s, unless and until a sufficient amount of force is applied to the third portion 392s to deflect the angled tabs 706 and the lever arms 704 inward, as illustrated in FIG. 95.

Figure 96:
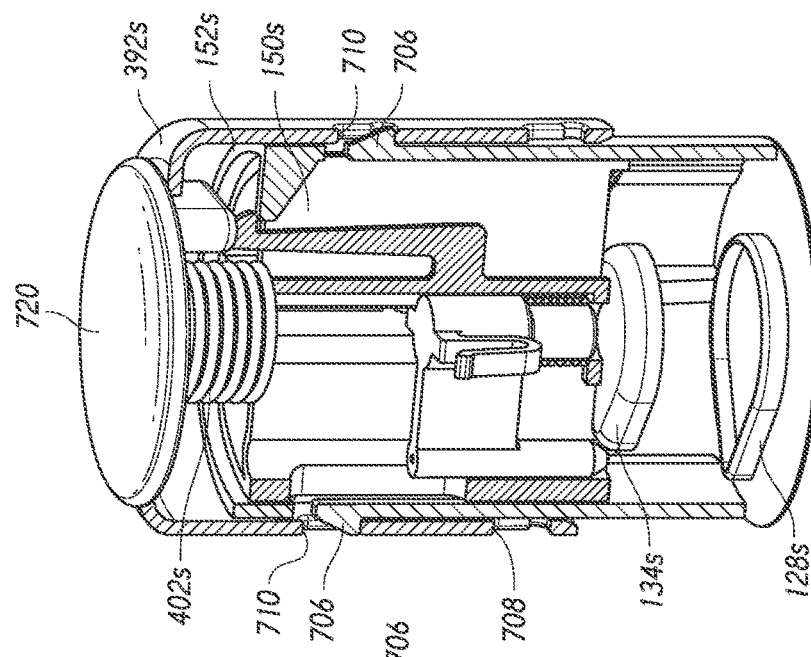
FIG. 96 illustrates a cross-sectional perspective view of the applicator system of FIG. 92, after being cocked but before being triggered.

As sufficient force is applied to the third portion 392s in a distal direction (e.g. by the hand or thumb of a user), the angled tabs 706 deflect inward and release from engagement with the distal apertures 708, allowing the third portion 392s to move distally with respect to the second portion 152s. This may allow the user to compress and energize the first spring 402s. When the third portion 392s has reached a sufficiently distal position to compress the first spring 402s enough to drive the sensor into the skin of a host, the angled tabs 706 engage with proximal apertures 710 of the third portion 392s to lock the position of the third portion 392s with respect to the second portion 152s, as illustrated in FIG. 96. The angled tabs 706 may be configured to generate a "click" sound when engaged to proximal apertures 710 so as to prevent proximal movement of the third portion 392s with respect to the second portion 152s, so that a user can feel and/or hear when these parts are engaged. In the configuration illustrated in FIG. 96, the system 104s is energized in which the third portion 392 is in a cocked position. The system 104s is ready to deploy the sensor, but does not deploy until further action is taken by the user.

FIG. 97 illustrates a cross-sectional side view of the system 104s, in a cocked but untriggered state. In this state, the first portion 150s is locked to the second portion 152s so as to prevent proximal or distal movement of the first portion 150s with respect to the second portion 152s. The first portion 150s and the second portion 152s can be locked together in any suitable fashion, for example by cooperating releasable locking features 396s and 398s operatively coupled to or forming part of the first portion 150s and the second portion 152s. The trigger button 720 includes a distally-extending protrusion 722 which, once depressed to a sufficiently distal position by a user, is configured to cooperate with an unlocking feature 406s of the locking feature 396s to decouple the first portion 150s from the second portion 152s. The trigger button 720 can be operatively coupled to the third portion 392s, as illustrated in FIGS. 92-100, or can be integrally formed with the third portion, for example as a lever arm formed within a proximal or side surface of the third portion. In some embodiments, the trigger button can be disposed at the top of the system (such that the application of force in the distal direction triggers the system to activate), or at a side of the system (such that the application of force in a radially inward direction, normal to the direction of needle deployment, triggers system to activate).

Figure 99:
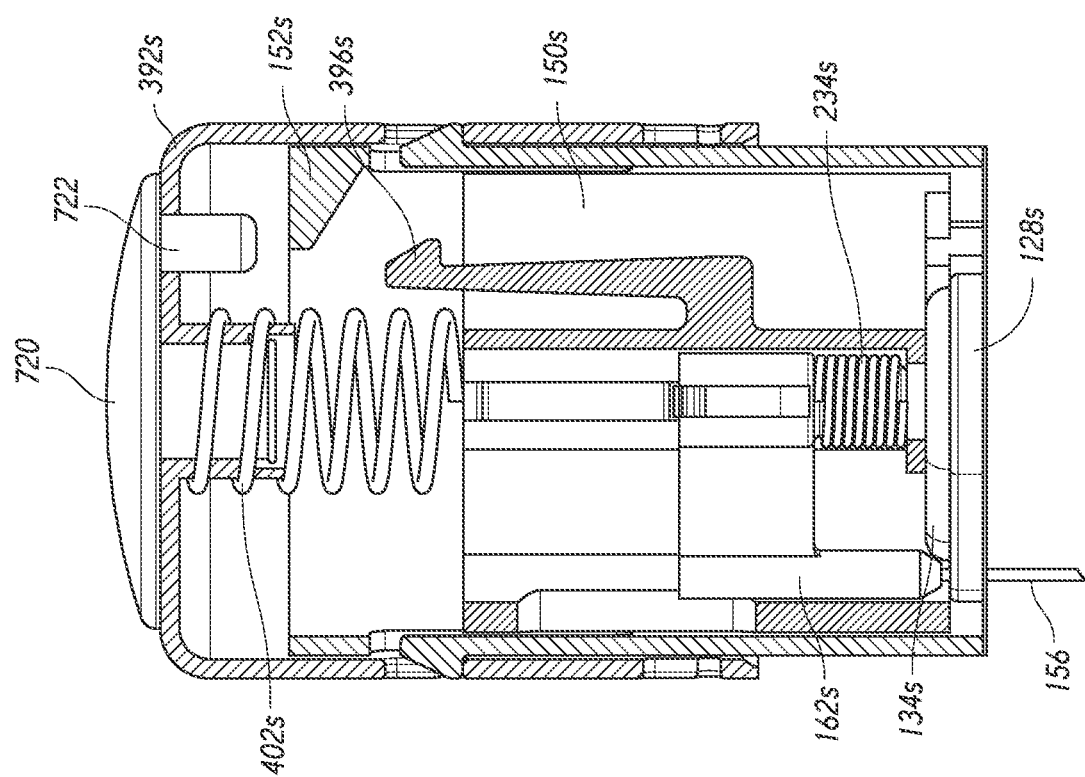
FIG. 99 illustrates a cross-sectional side view of the applicator system of FIG. 92, after being triggered and with the needle assembly deployed in an insertion position.

FIG. 98 illustrates a cross-sectional side view of the energized system 104s as the trigger button 720 has been depressed sufficiently to cause the protrusion 722 to flex the locking feature 396s radially inward, disengaging it from the opening 398s and unlocking the first portion 150s from the second portion 152s. Depressing the trigger button 720 thus activates the first spring 402, pushing the first portion 150s and the needle hub 162s, along with the on-skin component 134s which is coupled thereto, in a distal direction until the on-skin component is coupled to the base 128s, as illustrated in FIG. 99. At or about the time the needle hub 162s reaches the distal insertion position illustrated in FIG. 99 (e.g., immediately before, simultaneously, or subsequently), corresponding release features of the needle hub 162s and the first portion 150s can engage (via, for example, the release features described in any of FIGS. 76-91, or any other suitable release features), releasing the needle hub 162s from the first portion 150s and releasing or activating the second spring 234s. Activation of the second spring 234s urges the needle hub 162s in a proximal direction.

Figure 100:
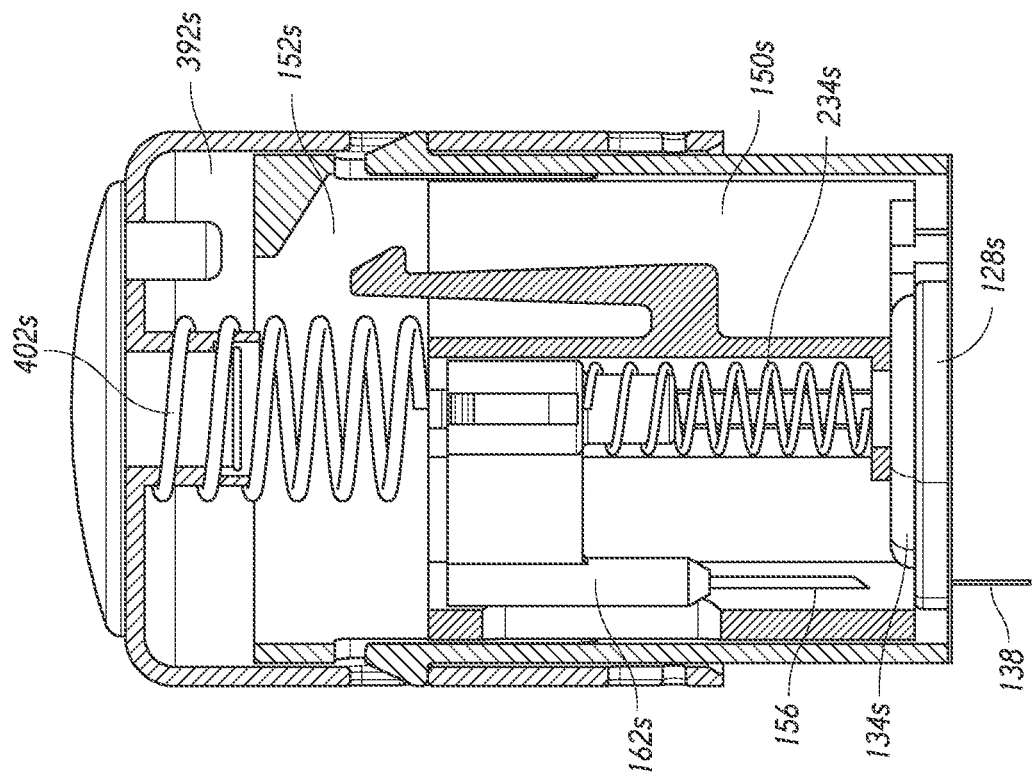
FIG. 100 illustrates a cross-sectional side view of the applicator system of FIG. 92, with the on-skin component in a deployed position and the needle assembly retracted.

FIG. 100 illustrates a cross-sectional side view of the applicator system of FIG. 92, with the on-skin component 134s in a deployed position and the needle hub 162s retracted to a proximal position. As the needle hub 162s retracts to a proximal position, the on-skin component 134s decouples from the needle hub 162s to remain in a deployed position, coupled to the base 128s. From this configuration, the remainder of the system 104s can be removed and separated from the deployed on-skin component 134s and the base 128s.

Any of the features described in the context of any of FIGS. 61-99 can be applicable to all aspects and embodiments identified herein. For example, the embodiments described in the context of FIGS. 61-64 can be combined with the embodiments described in the context of FIGS. 1-60 and 65-70. As another example, any of the embodiments described in the context of FIGS. 92-109 can be combined with any of the embodiments described in the context of FIGS. 1-60 and 65-91 and 110-143. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Trigger Mechanisms and Safety Locks

In some embodiments, the application of enough force to sufficiently energize the first spring to drive insertion of the sensor can also serve to activate the first spring. In other embodiments, the energizing of the first spring can be decoupled from the activation of the first spring, requiring separate actions on the part of the user to energize (e.g. compress) the first spring and to trigger deployment of the system.

For example, the embodiment illustrated in FIGS. 92-100 includes a trigger mechanism in the context of a user-energized actuator. In such an embodiment, the user first cocks the system 104s to energize the first spring 402s, and then, in a separate action, triggers the activation of the first spring 402s using the trigger button 720. The locking feature is easy to release by the user and when combined with a trigger mechanism, allows for single handed use.

In some embodiments, the actuator or insertion spring is already energized when the system is in a resting state. In these embodiments, a trigger mechanism, such as the trigger mechanism described in the context of FIGS. 92-100, can be used to activate the already-energized insertion spring without any action by the user to energize the spring.

Figure 101:
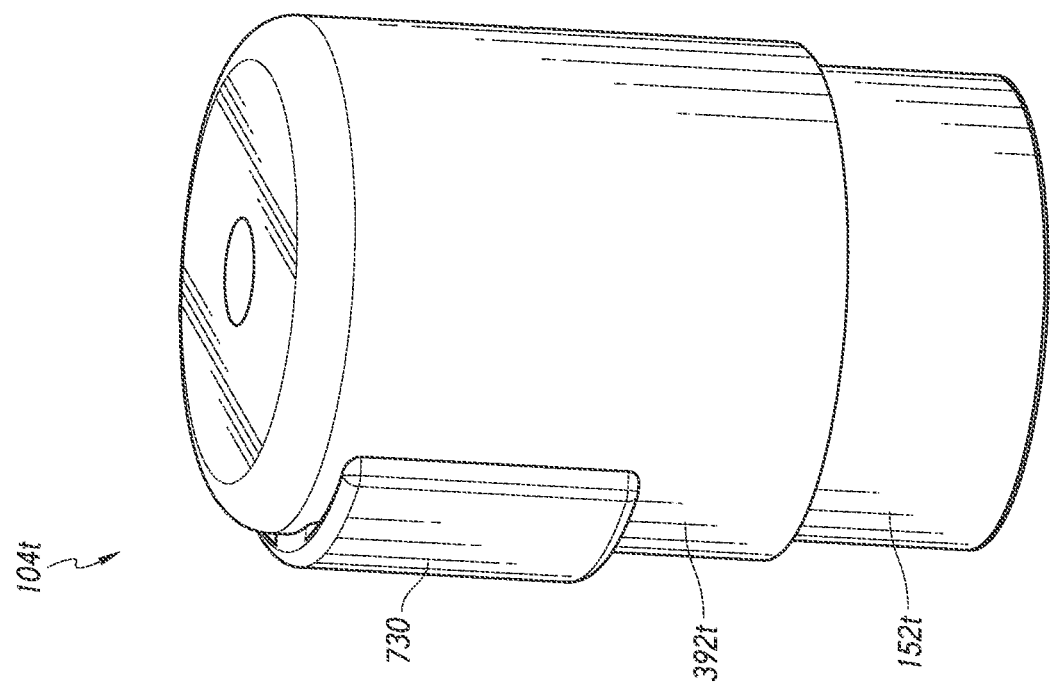
FIG. 101 illustrates a side view of another applicator system, according to some embodiments, with a side trigger member.

FIG. 101 illustrates a side view of one such applicator system 104t, with a side trigger button 730. The system 104t can be configured substantially similar to the system 104q or the system 104r illustrated within the context of FIGS. 86-88 and 89-91, respectively, with like reference numerals indicating like parts. As can be seen in FIG. 101, the trigger button 730 is operatively coupled to the third member 392t.

Figure 102:
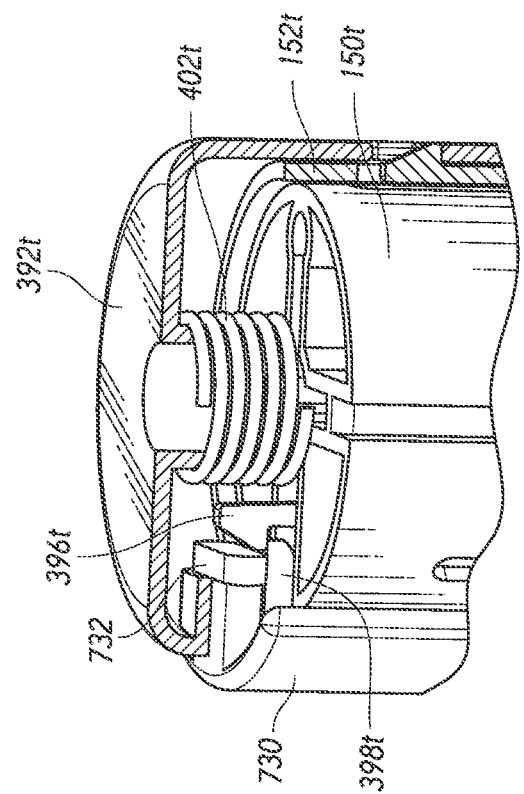
FIG. 102 illustrates another side view of the applicator system of FIG. 101, with the first and third portions shown in cross-section to illustrate the trigger mechanism.

FIG. 102 illustrates another side view of the system 104t, with the first portion 150t and the third portion 392t shown in cross-section to illustrate the trigger mechanism. As can be seen in FIG. 102, the trigger button 730 includes a protrusion 732 that extends radially inward, toward a central axis of the system 104t. The protrusion 732 is radially aligned with the locking feature 396t of the first portion 150t. When a user exerts a sideways (e.g., radially inward) force on the trigger button 730, the protrusion 732 urges the locking feature 396t radially inward, releasing it from engagement with the ledge feature 398t (which may be configured similarly to, for example, the ledge locking feature 398p illustrated in FIGS. 84 and 85) in the second portion 152t and activating the first spring 402t. In other embodiments, the locking features 396, 398 can comprise cooperating structure of a key/keyway mechanism which is configured to release when the features 396, 398 are brought into a certain orientation with respect to one another (e.g., using a radially applied force, an axially applied force, a twisting movement or rotational force, or other type of activation).

Figure 104:
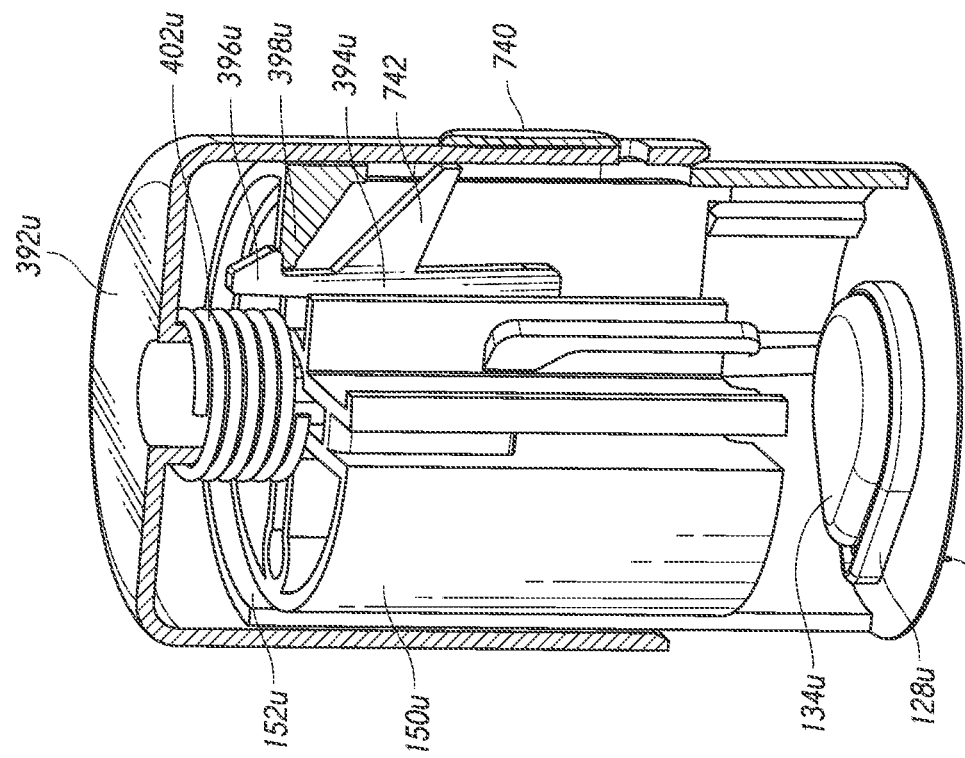
FIG. 104 illustrates another side view of the applicator system of FIG. 103, with the first and third portions shown in cross-section and with a portion of the second portion removed to illustrate the trigger mechanism.
Figure 103:
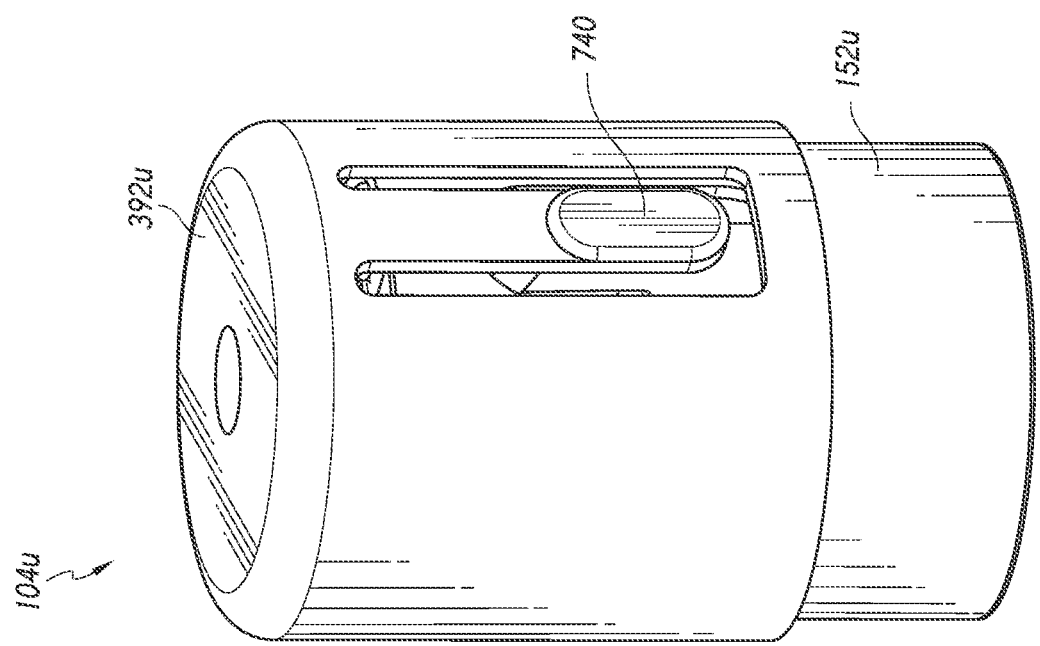
FIG. 103 illustrates a side view of another applicator system, according to some embodiments, with an integrated side trigger.

FIG. 103 illustrates a side view of another applicator system 104u, with an integrated side trigger button 730. The system 104u can be configured substantially similar to the system 104q or the system 104r illustrated within the context of FIGS. 86-88 and 89-91, respectively, with like reference numerals indicating like parts. As can be seen in FIG. 103, the trigger button 740 is a distally-extending lever arm integrally formed in the third member 392u. FIG. 104 illustrates another side view of the system 104u, with the first portion 150u and the third portion 392u shown in cross-section to better illustrate the trigger mechanism. As can be seen in FIG. 104, the trigger button 740 is radially aligned with a radially-extending tab 742 of the first portion 150u. The tab 742 is connected to the locking feature 396u via an elongated member 394u, which acts as a lever arm. In some embodiments, tab 742 locking feature 396u, and elongated member 394u are integrally formed together. When a user exerts a sideways (e.g., radially inward) force on the trigger button 740, the button 740 pushes the tab 742 radially inward, releasing the locking feature 396u from engagement with the locking feature 398u in the second portion 152u and activating the first spring 402u.

Trigger mechanisms such as those described in the context of any of FIGS. 92-104 can be used in embodiments comprising pre-energized actuators or insertion springs, as well as in embodiments comprising user-energized actuators or insertion springs.

Figure 105:
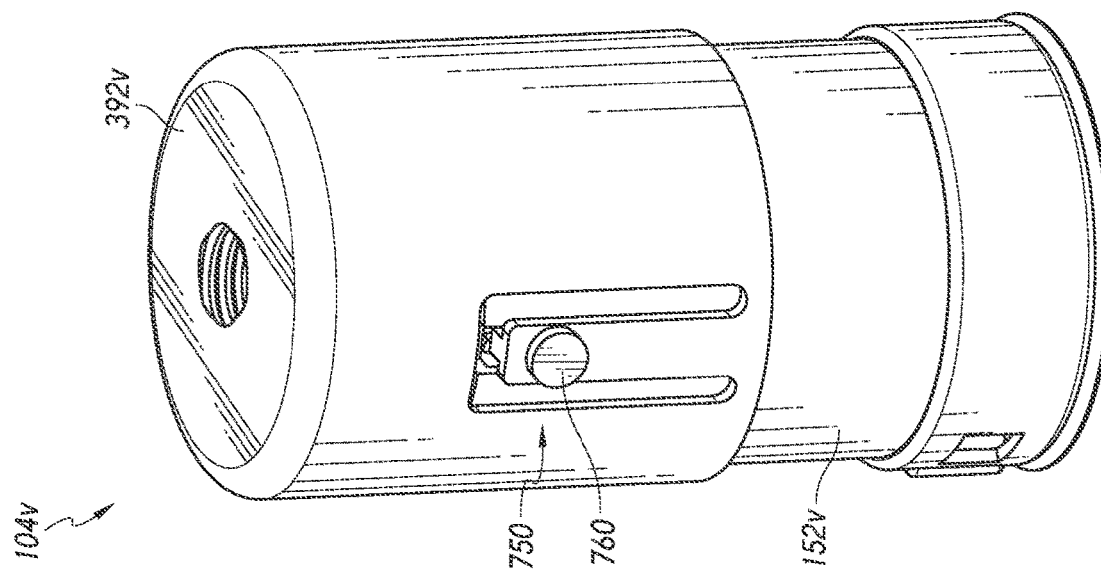
FIG. 105 illustrates a perspective view of another applicator system, according to some embodiments, with a safety feature.

In several embodiments, a sensor inserter system can include a safety mechanism configured to prevent premature energizing and/or actuation of the insertion spring. FIGS. 105-109 illustrate one such system 104v, which incorporates a safety lock mechanism 750. FIG. 105 illustrates a perspective view of the system 104v. The system 104v can be configured substantially similar to any of the systems 104m, 104n, 104p illustrated within the context of FIGS. 71-87, with like reference numerals indicating like parts. The safety lock mechanism 750 includes a release button 760, which can be integrally formed with the third portion 392v as shown in FIG. 105 (similar to the trigger button 740 described in connection with FIGS. 103-104), or which can be operatively coupled to the third portion 392v. In the system 104v, the release button 760 comprises a lever arm which is integrally formed in a side of the third portion 392v, although other configurations (e.g. a top button) are also contemplated. The release button can be configured to protrude radially from a side or a top of the third portion, or can be configured with an outer surface which is flush with the surrounding surface of the third portion 392v.

Figure 106:
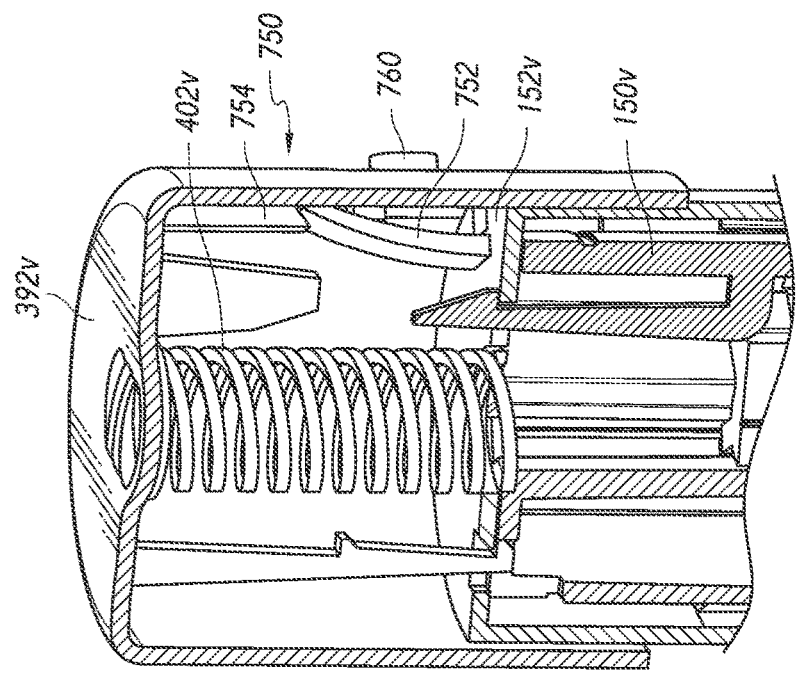
FIG. 106 illustrates a cross-sectional perspective view of a portion of the applicator system of FIG. 105, with the safety feature in a locked configuration.
Figure 109:
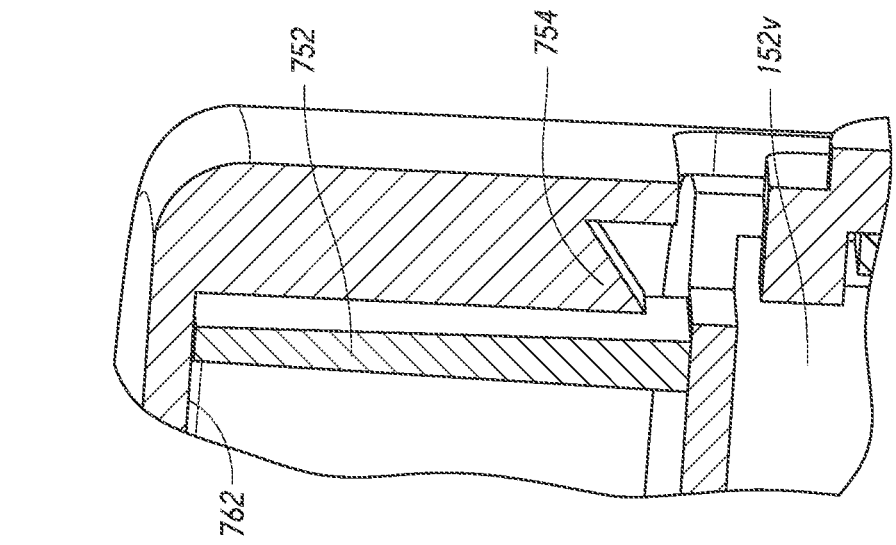
FIG. 109 illustrates a cross-sectional perspective view of a portion of the applicator system of FIG. 105, with the safety feature in a released configuration and with the third portion moved distally relative to the first portion.
Figure 108:
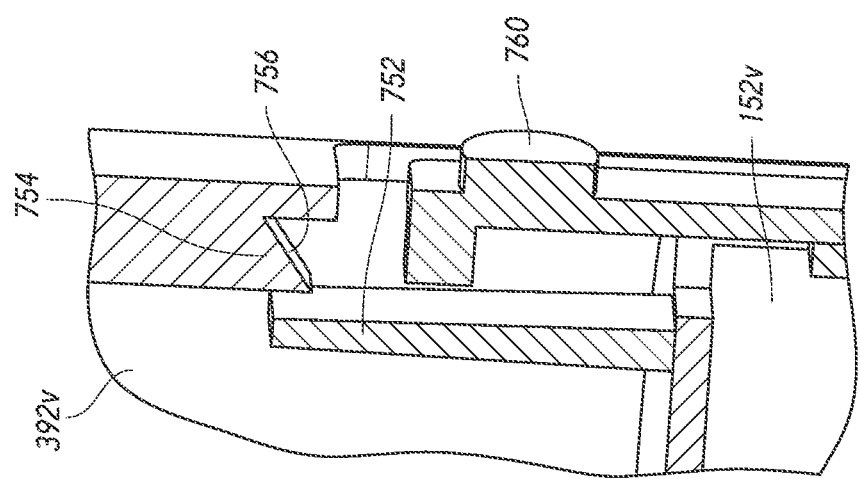
FIG. 108 illustrates a cross-sectional perspective view of a portion of the applicator system of FIG. 105, with the safety feature in a released configuration.
Figure 107:
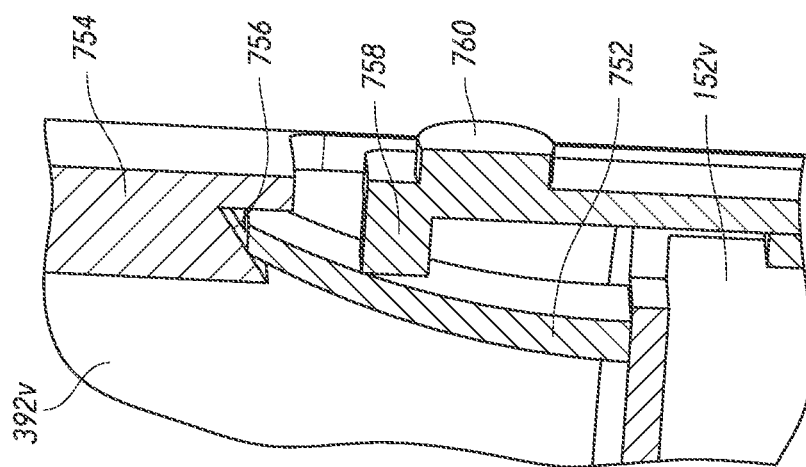
FIG. 107 illustrates an enlarged view of the portion of the applicator system of FIG. 106, with the safety feature in a locked configuration.
Figure 111:
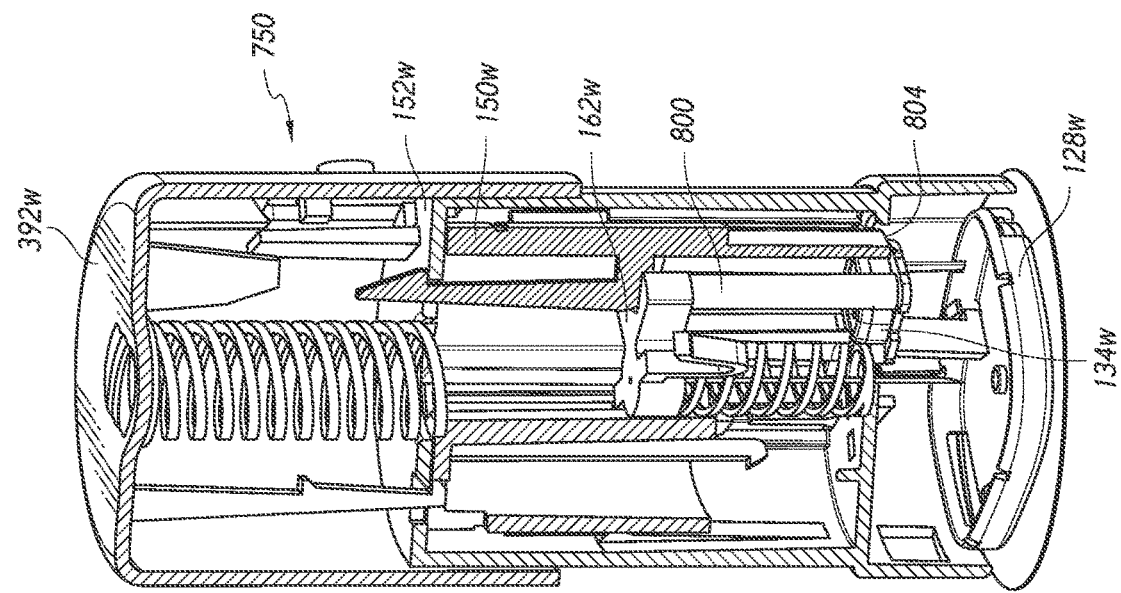
FIG. 111 illustrates a cross-sectional perspective view of the applicator system of FIG. 110, with the safety feature unlocked.

FIG. 106 illustrates a cross-sectional perspective view of a portion of the system 104v, with the safety mechanism 750 in a locked configuration and the first spring 402v unenergized. The safety mechanism 750 includes a proximally-extending locking tab 752 of the second portion and an inwardly-extending overhang (or undercut) 754 of the third portion 392v. In the locked configuration illustrated in FIG. 106, the tab 752 is flexed radially outward and its proximal end is constrained by the overhang 754, preventing distal movement of the third portion 392v with respect to the second portion 152v and thus preventing energization of the spring 392v. The release button 760 includes a protrusion 758 which extends inwardly, in radial alignment with a portion of the tab 752. A lateral (e.g. radially inward) force applied to the release button 760 pushes the tab 752 radially inward, sliding the proximal end of the tab 752 against an angled surface 756 of the overhang 754 and out of engagement with the overhang 754, so that the tab 752 can release to an unstressed configuration as shown in FIG. 108. Once the tab 752 is released, the third portion 392v can be moved distally with respect to the second portion 152v, for example to energize the first spring 402v. In some embodiments, as illustrated in FIG. 109, the tab 752 can be configured to prevent further distal movement of the third portion 392v beyond a desired threshold, for example by abutting a distally-facing surface 762 of the third portion 392v.

Although the safety lock mechanism 750 is illustrated in the context of a system configured to be energized by a user, in some embodiments, a pre-energized system can also employ a safety lock mechanism, for example to prevent premature triggering or activation of an already energized spring.

In some embodiments, the locking and unlocking (and/or coupling and decoupling) of the components of a sensor inserter assembly can follow this order: The sensor inserter assembly begins in a resting state in which the third portion 392 is locked with respect to the first portion 150, the first portion 150 is locked with respect to the second portion 152, and the sensor module 134 is coupled to the first portion 150 (optionally via the needle hub 162). Before energizing or triggering of the insertion spring 402, the third portion 392 is unlocked with respect to the first portion 150 and/or the second portion 150. The insertion spring 402, if not already energized, is then energized by distal movement of the third portion 392. Then, the third portion 392 is locked with respect to the second portion 152. The first portion 150 is then released from the second portion 152 to activate the insertion spring 402. As the insertion spring 402 deploys, the sensor module 134 couples to the base 128. Then the first portion 150 (and/or the needle hub 162) releases the sensor module 134, and the second portion 152 releases the base 128. In several embodiments, the locations of the various locking and unlocking (and/or coupling and decoupling) structures along the axis of the assembly are optimized to ensure this order is the only order that is possible. (Some embodiments use different locking and unlocking orders of operation.)

Systems such as those illustrated in FIGS. 92-109 provide reliable trigger mechanisms to release an insertion spring when the insertion spring is in a loaded condition. It is contemplated such systems provide several advantages to the user including ease in firing, single handed firing (by allowing the user to hold onto the sides of the insertion device and fire the insertion device using the same hand). It is contemplated that a system comprising a top trigger can provide a smaller width profile than a system having a side button while requiring less user dexterity.

Release after Deployment

In several embodiments, a sensor inserter system is configured to move an on-skin component (such as, for example, a sensor module 134, a sensor assembly (for example comprising a sensor, electrical contacts, and optionally a sealing structure), a combination sensor module and base, an integrated sensor module and transmitter, an integrated sensor module and transmitter and base, or any other component or combination of components which is desirably attached to the skin of a host) from a proximal starting position within the sensor inserter system to a distal deployed position in which it can attach to the skin of a host, while at the same time inserting a sensor (which may form part of the on-skin component) into the skin of the host. In some embodiments, the sensor is coupled to electrical contacts of the on-skin component during the deployment and/or insertion process. In other embodiments, the on-skin component is pre-connected, that is to say, the sensor is coupled to electrical contacts of the on-skin component before the deployment and/or insertion processes begin. The sensor assembly can be pre-connected, for example, during manufacture or assembly of the system.

Thus, in several embodiments, a sensor inserter system can be configured to releasably secure the on-skin component in its proximal starting position, at least before or until deployment of the inserter system, and can also be configured to release the on-skin component in a distal position after the inserter system is deployed. In some embodiments, the system can be configured to couple the on-skin component to a base and/or to an adhesive patch during the deployment process, either as the on-skin component is moved from the proximal starting position to the distal deployed position or once it reaches the distal deployed position. In some embodiments, the system can be configured to separate from (or become separable from) the on-skin component, base, and/or adhesive patch after the on-skin component is deployed in the distal position and the needle hub (if any) is retracted.

In embodiments, various mechanical interlocks (e.g., snap fits, friction fits, interference features, elastomeric grips) and/or adhesives can be used to couple the on-skin component to the sensor inserter system and releasably secure it in a proximal starting position, and/or to couple the on-skin component (and base, if any) to the adhesive patch once the on-skin component is deployed. In addition, various mechanical features (e.g. snap fits, friction fits, interference features, elastomeric grips, pushers, stripper plates, frangible members) and/or adhesives can be used to decouple the on-skin component from the sensor inserter system once it reaches the distal deployed position. Further, various mechanical features, (e.g. snap fits, friction fits, interference features, elastomeric grips, pushers, stripper plates, frangible members) and/or adhesives can be used to separate, unlock, or otherwise render separable the on-skin component, base, and/or adhesive patch from the remainder of the system after the on-skin component is deployed in the distal position and the needle hub (if any) is retracted.

With reference now to FIGS. 110-119, a sensor inserter system 104w according to some embodiments is illustrated. The system 104w can be configured substantially similar to the system 104v illustrated within the context of FIGS. 105-109 and system 104m illustrated within the context of FIGS. 71-75, with like reference numerals indicating like parts. The system 104w includes, for example, a telescoping assembly 132w including a first portion 150w, a second portion 152w, and a third portion 392w; a safety mechanism 750, a needle hub 162w; a first spring 402w; a second spring 234w; an on-skin component 134w, and a base 128w.

Figure 110:
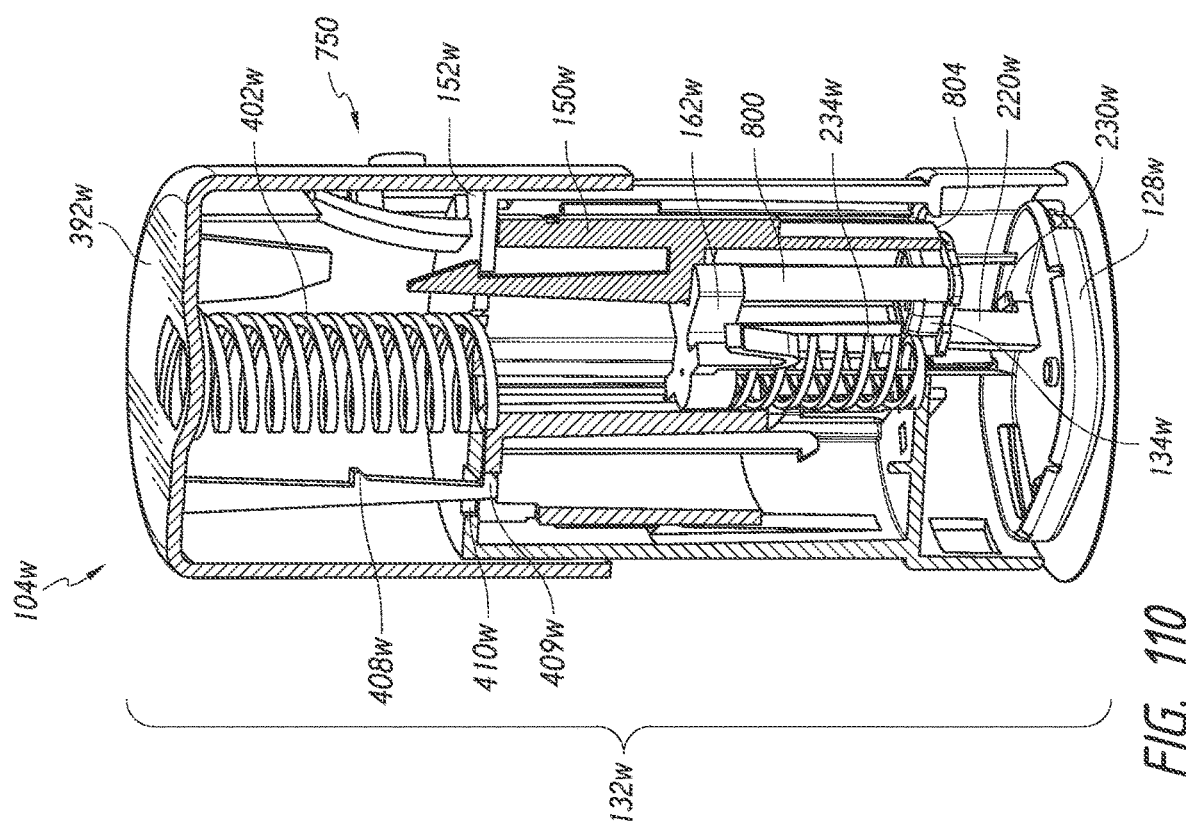
FIG. 110 illustrates a cross-sectional perspective view of an applicator system, according to some embodiments, in a resting and locked state, with the on-skin component secured in a proximal position.

FIG. 110 illustrates a cross-sectional perspective view of the system 104w in a resting and locked state, with the on-skin component 134w secured in a proximal starting position. In this state, as well as in the unlocked state illustrated in FIG. 111 and the energized state illustrated in FIG. 112, the on-skin component 134w is secured in the proximal starting position by a securement member 800. As can be seen in FIG. 110, the system 104w includes a secondary locking feature 409w, configured as a ledge extending from the distal end of the locking protrusion 408w, which is configured to cooperate with an opening 410w to prevent the third portion 392 from moving in a proximal direction with respect to the second portion 152w prior to deployment. In the embodiment illustrated in FIGS. 110-119, the securement member 800 is integrally formed with the needle hub 162w. In other embodiments, the securement member can be integrally formed with the first portion 150w. In still other embodiments, the securement member can be separately formed from and operatively coupled to the needle hub 162w and/or to the first portion 150w. The securement member 800 extends substantially parallel to the needle 158. In the embodiment illustrated in FIGS. 110-119, the securement member 800 comprises a pair of distally-extending legs 802 (see FIGS. 115 and 116). Some embodiments can, however, include only one distally-extending leg 802, while others can include three, four, or more legs 802. In embodiments comprising only one leg 802, the leg can be configured to adhere or otherwise couple to a center region or a perimeter of the on-skin component. In embodiments comprising more than one leg 802, the legs can be configured to adhere or otherwise couple to the on-skin component symmetrically or asymmetrically about a center of the on-skin component. The legs 802 can have an ovoid cross section, or can have any other suitable cross section, including circular, square, triangular, curvilinear, L-shaped, O-shaped, U-shaped, V-shaped, X-shaped, or any other regular or irregular shape or combination of shapes. In embodiments, the securement member 800 can comprise legs, columns, protrusions, and/or elongate members, or can have any other suitable configuration for holding the on-skin component in the proximal starting position.

FIG. 113 illustrates a cross-sectional perspective view of the system 104w, in an activated state, with the insertion spring 402w activated, the retraction spring 234w energized, and the needle hub 162w and the securement member 800 moved to a distal deployed position. The on-skin component 134w, being coupled to the securement member 800 until this stage, has also been moved to a distal deployed position. When the on-skin component 134w reaches the distal deployed position, it is coupled to the base 128w.

FIG. 114 illustrates a cross-sectional perspective view of the system 104w after the on-skin component has been coupled to the base 128w and the needle hub 162w (along with the securement member 800) has been retracted to a proximal position. After the on-skin component 134w is coupled to the base 128w, a resistance member 804 facilitates decoupling of the on-skin component 134w from the securement member 800 by resisting unwanted proximal movement of the on-skin component 134w away from the base 128w. Generally, the resistance member 804 can be a backstop or backing structure configured to inhibit or prevent, or otherwise resist any tendency of the on-skin component 134w to move in a proximal direction as the securement member 800, which is releasably coupled to the on-skin component 134w, moves in a proximal direction. Because the first portion 150w is fixed to the second portion 152w at this stage, and the needle hub 162w is released from the first portion 150w, the needle hub 162w can retract in a proximal direction while the first portion 150w (and the resistance member 804) remains planted in a distal position, inhibiting proximal movement of the on-skin component 134w. The energy stored in the retraction spring 234w is sufficient to overcome a retention force and decouple the on-skin component 134w from the securement member 800 and urge the needle hub 162 in a proximal direction. The potential energy stored can be between 0.25 pounds to 4 pounds. In preferred embodiments, the potential energy stored is between about 1 to 2 pounds.

In some embodiments, a sensor inserter system can be configured such that the on-skin component couples with the base at approximately the same time the retraction mechanism is activated. In some embodiments, a sensor inserter system can be configured such that the on-skin component couples with the base before the retraction mechanism is activated, before the second spring is activated, or otherwise before the second spring begins retracting the needle hub in a proximal direction away from the deployed position. In some embodiments, a sensor inserter system can be configured such that the second spring is activated at least 0.05 seconds, at least 0.1 seconds, at least 0.2 seconds, at least 0.3 seconds, at least 0.4 seconds, at least 0.5 seconds, at least 0.6 seconds, at least 0.7 seconds, at least 0.8 seconds, at least 0.8 seconds, at least 1 second, or longer than 1 second after the on-skin component couples with the base. In other embodiments, a sensor inserter system can be configured such that the second spring is activated at most 0.05 seconds, at most 0.1 seconds, at most 0.2 seconds, at most 0.3 seconds, at most 0.4 seconds, at most 0.5 seconds, at most 0.6 seconds, at most 0.7 seconds, at most 0.8 seconds, at most 0.8 seconds, or at most 1 second after the on-skin component couples with the base.

The on-skin component 134w is now coupled with the base 128w. The base 128w (and adhesive patch) is initially coupled to the second portion 152w by a latch or flex arm 220w coupled to an undercut or locking feature 230w (similarly shown in FIGS. 18-19). When the first portion 150w reaches its most distal position during insertion of the sensor 138, a delatching feature of the first portion 150w pushes the latch of the second portion 152w out of the undercut. This decouples the base 128w from the second portion 152w, and thus allows the user to take the remainder of the system 104w off the skin, leaving only the adhesive patch, the base 128w, and the on-skin component 134w on the skin.

In the embodiment illustrated in FIGS. 110-119, the resistance member 804 is integrally formed with the first portion 150w. In other embodiments, the resistance member can be integrally formed with the second portion 152w. In still other embodiments, the resistance member can be separately formed from and operatively coupled to the first portion 150w and/or to the second portion 152w. In the embodiment illustrated in FIGS. 110-119, the resistance member 804 comprises a distally-facing surface of the first portion 150w.

The system 104w can be configured to couple the on-skin component 134w to the base 128w via an adhesive 806. FIG. 115 illustrates a perspective view of the needle hub 162w, shown securing the on-skin component 134w during deployment, with the base 128w removed to illustrate the adhesive 806 disposed on a distally-facing surface of the on-skin component 134w. The adhesive 806 can be configured to couple the on-skin component 134w to the base 128w on contact. Alternatively or in addition to the adhesive 806, some embodiments can include an adhesive disposed on a proximally-facing surface of the base, so as to couple the on-skin component to the base upon contact. In some embodiments, the adhesive can be a pressure-sensitive adhesive. In some embodiments, the securement member can be configured to couple the on-skin component to the needle hub only along a plane extending normal to the axial direction of the system. In addition or in the alternative, the securement can be configured to couple the on-skin component in a lateral or radial direction.

FIG. 116 illustrates another perspective view of the needle hub 162w, shown decoupled from the on-skin component 134w, with the base 128w removed to illustrate the adhesive 808 disposed on the distally-facing surfaces of the securement member 800. The adhesive 808 can be configured to couple the on-skin component 134w to the securement member 800 while in the proximal starting position and during movement of the on-skin component 134w in the proximal direction, and to allow the release of the on-skin component 134w from the securement member 800 after the on-skin component 134w is coupled to the base 128w. Alternatively or in addition to the adhesive 808, some embodiments can include an adhesive disposed on a proximally-facing surface of the on-skin component 134w. In some embodiments, the adhesive can be a pressure-sensitive adhesive. In some embodiments, the adhesive 808 can have a smaller surface area and/or a lower adhesion strength than the adhesive 806, such that the adhesion strength of the adhesive 806 which couples the on-skin component to the base outweighs the adhesion strength of the adhesive 808 which couples the on-skin component to the securement member. In other embodiments, the adhesion strength of the adhesive 808 can be the same or greater than the adhesion strength of the adhesive 806. In these embodiments, a resistance member can be employed to facilitate the decoupling of the on-skin component 134w from the securement member 800 after deployment.

Figure 117:
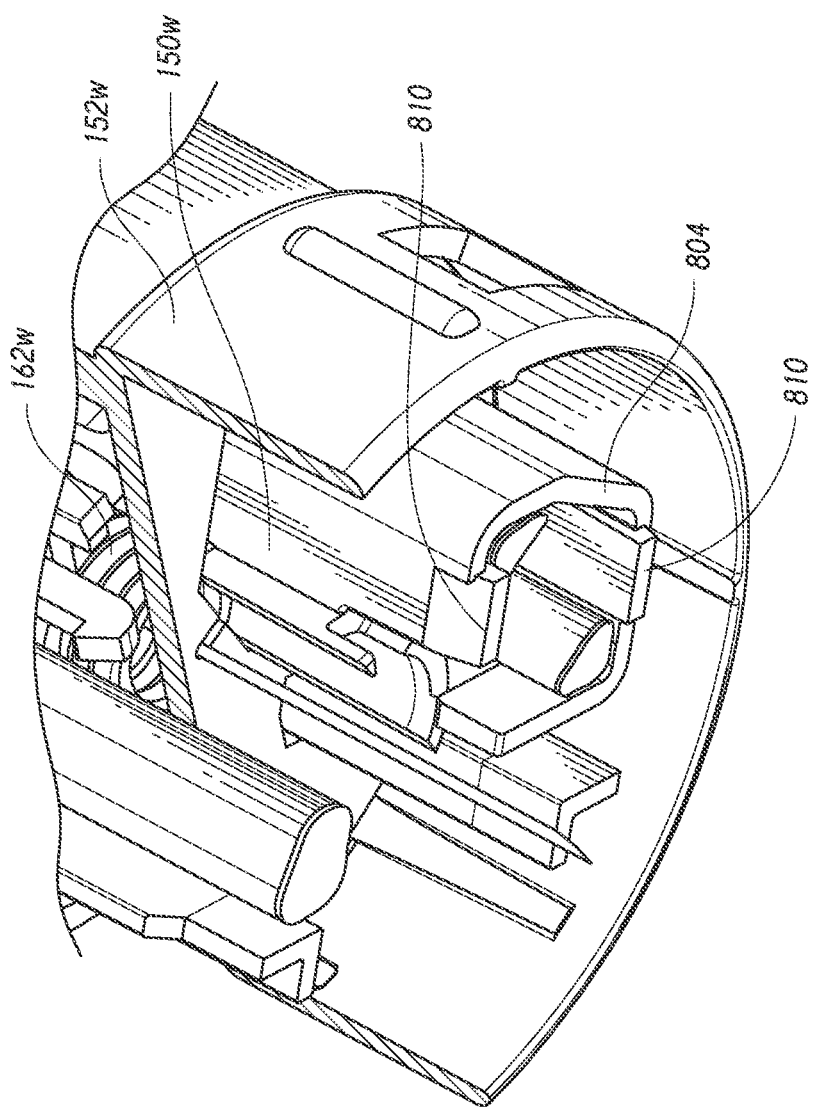
FIG. 117 illustrates a perspective view of a portion of the system of FIG. 100.

FIG. 117 illustrates a perspective view of a portion of the system 104w, illustrating the resistance member 804. The resistance member 804 is configured to rest above and/or contact a proximally-facing surface of the on-skin component 134w, at least when the on-skin component 134w is in a distal deployed position. The resistance member 804 can serve to inhibit proximal movement of the on-skin component 134w as the needle hub 162w and securement member 800 retract in a proximal direction. The resistance member 804 can function in a manner similar to a stripper plate in punch and die manufacturing or injection molding processes.

In embodiments, the resistance member can have any configuration suitable for resisting decoupling of the on-skin component from the base. In the embodiment illustrated in FIGS. 110-119, the resistance member 804 has a curvilinear cross section, and extends through an arc of roughly 300 degrees about the perimeter of the on-skin component 134w. In some embodiments, the resistance member 804 can extend through an arc of roughly 30 degrees, 60 degrees, 90 degrees, 120 degrees, 150 degrees, 180 degrees, 210 degrees, 240 degrees, 270 degrees, 300 degrees, or 330 degrees about the perimeter of the on-skin component 134w, or through an arc greater than, less than, or within a range defined by any of these numbers. In some embodiments, the resistance member 804 can extend continuously or discontinuously about the perimeter of the on-skin component. In some embodiments, the resistance member 804 can extend about the entire perimeter of the on-skin component. In some embodiments, the resistance member 804 can comprise one or more contact points or surfaces that hold the on-skin component 134w in the distal position as the securement feature 800 moves in an opposite (e.g., proximal) direction.

In other embodiments, the resistance member 804 can comprise multiple discrete members (e.g., legs) configured to contact multiple locations about the perimeter of the on-skin component 134w. For example, in some embodiments, the resistance member 804 can include at least two legs disposed apart from one another about a center point of the on-skin component. In some embodiments, the resistance member 804 can include two legs disposed roughly 180 degrees about a center point of the on-skin component. In some embodiments, the resistance member 804 can include three legs disposed roughly 120 degrees about a center point of the on-skin component. In such an embodiment, the legs can be arranged symmetrically about the on-skin component (e.g. with radial symmetry, or reflectional/bilateral symmetry).

FIG. 117 also illustrates locator features 810 which can be formed in, or integrally coupled to, the first portion 150w and/or the resistance member 804. The locator features 810 can comprise distally-extending tabs of the first portion 150w and/or of the resistance member 804. The locator features 810 can be configured to align with corresponding indentations 812 in the on-skin component (see FIG. 119) so as to ensure proper positioning of the sensor module 134w with respect to the first portion 150w and/or the resistance member 804 during assembly.

FIG. 118 illustrates a perspective view of the sensor module 134w, before being coupled to the base 128w by contacting the adhesive 806. The base 128w itself is coupled (for example by an adhesive) to a proximal surface of an adhesive patch 900. FIG. 119 illustrates a perspective view of the sensor module 134w after being coupled to the base 128w on the adhesive patch 900.

In embodiments, providing a resistance member can facilitate a reliable transfer of the on-skin component to the base, by creating a counterforce against the securement member as the needle hub retracts in the proximal direction. The counterforce allows the securement member to separate from the on-skin component while inhibiting or preventing the disengagement of the on-skin component from the base (if any) and/or from the adhesive patch. In embodiments, the retraction spring can be configured to store and provide sufficient energy to both retract the needle and decouple the on-skin component from the needle hub. The combination of the resistance member and securement member can also be configured to provide positional control of the on-skin component from a secured configuration (e.g., in the proximal starting position and during movement of the on-skin component toward the distal deployed position) to a released configuration (when the on-skin component reaches the distal deployed position and/or couples to the base and/or adhesive patch).

It is contemplated that providing a base which begins in the distal deployed position when the system is in a resting or stored state can serve to protect the needle (and the user) before the system is deployed. For example, a base which is coupled to a distal end of the system in a resting or pre-deployment state can prevent a user from reaching into the distal end of the system and pricking him or herself. This configuration can thus potentially reduce needle stick hazards. In addition, a base which is coupled to a distal end of the system in a resting or pre-deployment state facilitate the setting of the adhesive patch on the skin before deployment. For example, with such a configuration, the user can use the body of the sensor inserter system to assist in applying a force in a distal direction to adhere the adhesive patch to the skin. In addition, the base can provide structural support to guide the needle into the skin during deployment.

Figure 121:
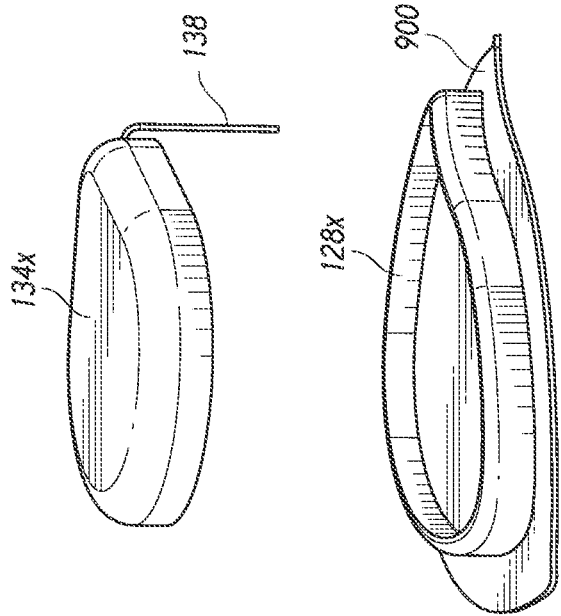
FIG. 121 illustrates a perspective view of the on-skin component and base of FIG. 120, prior to coupling of the on-skin component to the base.
Figure 122:
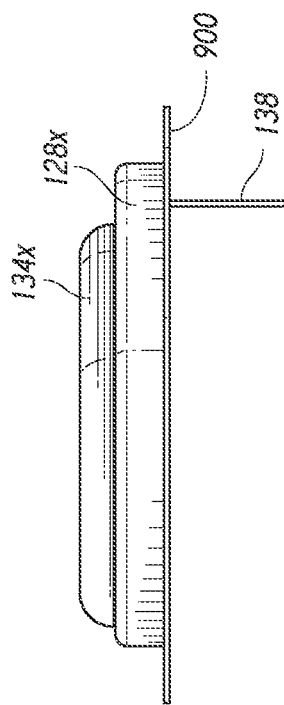
FIG. 122 illustrates a side view of the on-skin component and base of FIG. 120, after coupling of the on-skin component to the base.
Figure 120:
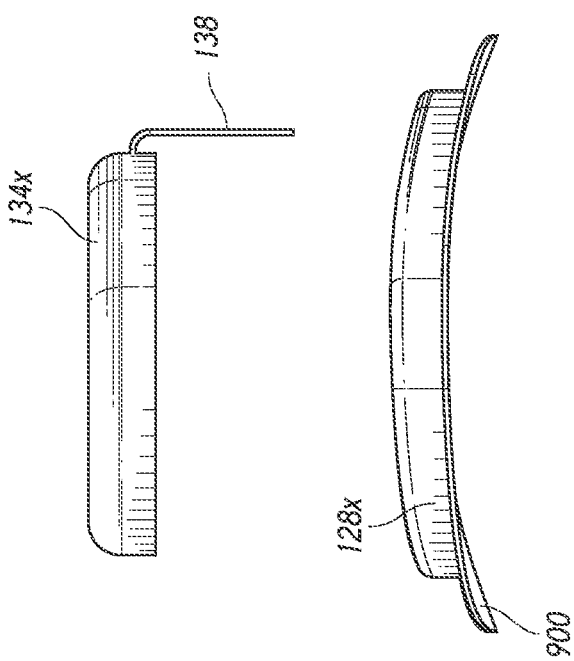
FIG. 120 illustrates a side view of an on-skin component and base, according to some embodiments, prior to coupling of the on-skin component to the base.

FIGS. 120-122 illustrate another configuration for coupling an on-skin component to a base, in accordance with several embodiments. FIG. 120 shows a side view of an on-skin component 134x and a base 128x, prior to coupling of the on-skin component 134x to the base 128x. The on-skin component 134x includes a distally-extending sensor 138, and the base 128x is coupled to an adhesive patch 900. FIG. 121 illustrates a perspective view of these same components. The base 128x comprises a flexible elastomeric member with a proximally-extending ridge 814 extending about a proximally-facing surface 816. The base 128x can have a shape configured to correspond to a shape of the on-skin component 134x. In a relaxed state, as illustrated in FIGS. 120 and 121, and before making contact with the on-skin component 134x, the base 128x has a deformed, somewhat convex curvature. The base 128x and the adhesive patch 900 can be coupled to the other components of a sensor inserter assembly in this configuration. During deployment, as the on-skin component 134x begins to contact the base 128x, the proximally-facing surface 816 flexes up to meet the distal surface of the on-skin component 134x, causing the ridge 814 to grip securely about the perimeter of the on-skin component 134x, as illustrated in FIG. 122.

Figure 123:
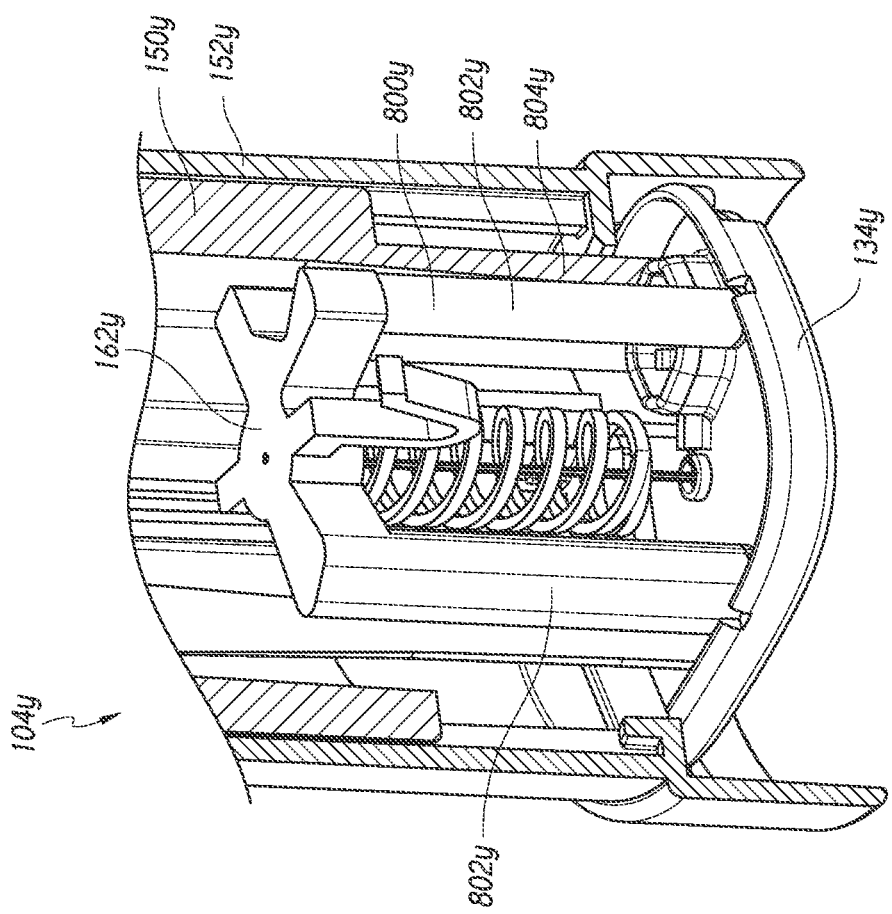
FIG. 123 illustrates a perspective view of a portion of another applicator system, according to some embodiments, with an on-skin component coupled to a needle assembly in a proximal position.

FIG. 123 illustrates a perspective view of a portion of another inserter system 104y, according to some embodiments. The system 104y can be configured substantially similar to any of the systems 104 illustrated herein, with like reference numerals indicating like parts. The inserter system 104y includes an on-skin component 134y which includes a combination sensor module and base. In embodiments, the combination sensor module and base can be integrally formed with one another, as illustrated in FIG. 123, or operatively coupled to one another. The system 104y also includes a securement member 800y which is configured to releasably secure the on-skin component 134y in a proximal starting position, at least until the system 104y is activated. The securement member 800y is integrally formed with the needle hub 162y, and includes three proximally-extending legs 802y configured to releasably couple to (e.g. via adhesive 808) various locations on the proximal surface of the on-skin component 134y. It is contemplated that the addition of a third (or further) leg 802y can help to balance the sensor module and prevent it from canting to one side or another during deployment and/or retraction. The system 104y also includes a resistance member 804. The resistance member 804 may be integrally molded with first portion 150y.

Figure 124:
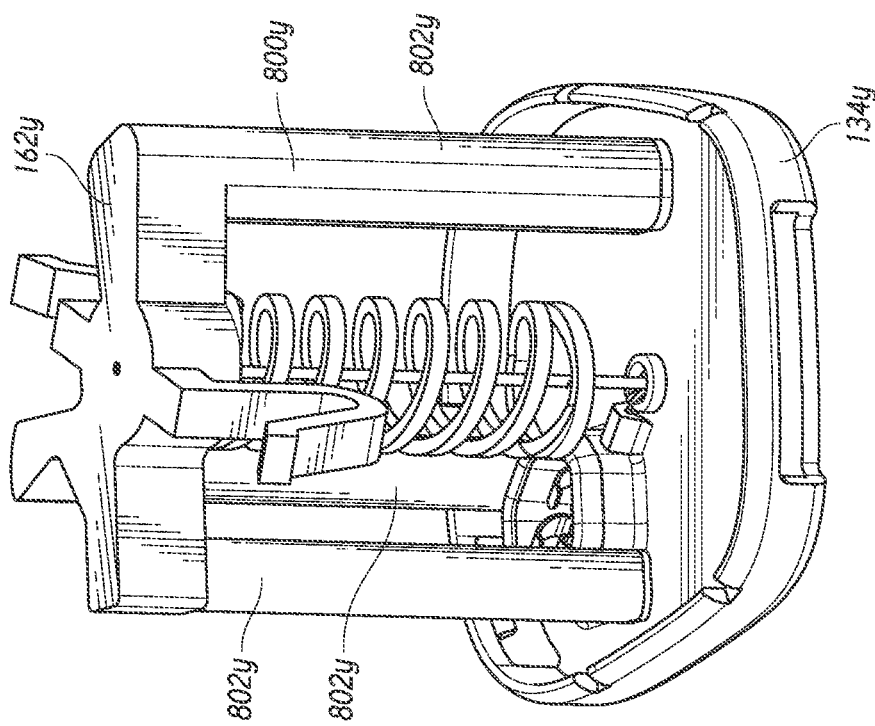
FIG. 124 illustrates a perspective view of the on-skin component and the needle assembly of FIG. 123.
Figure 125:
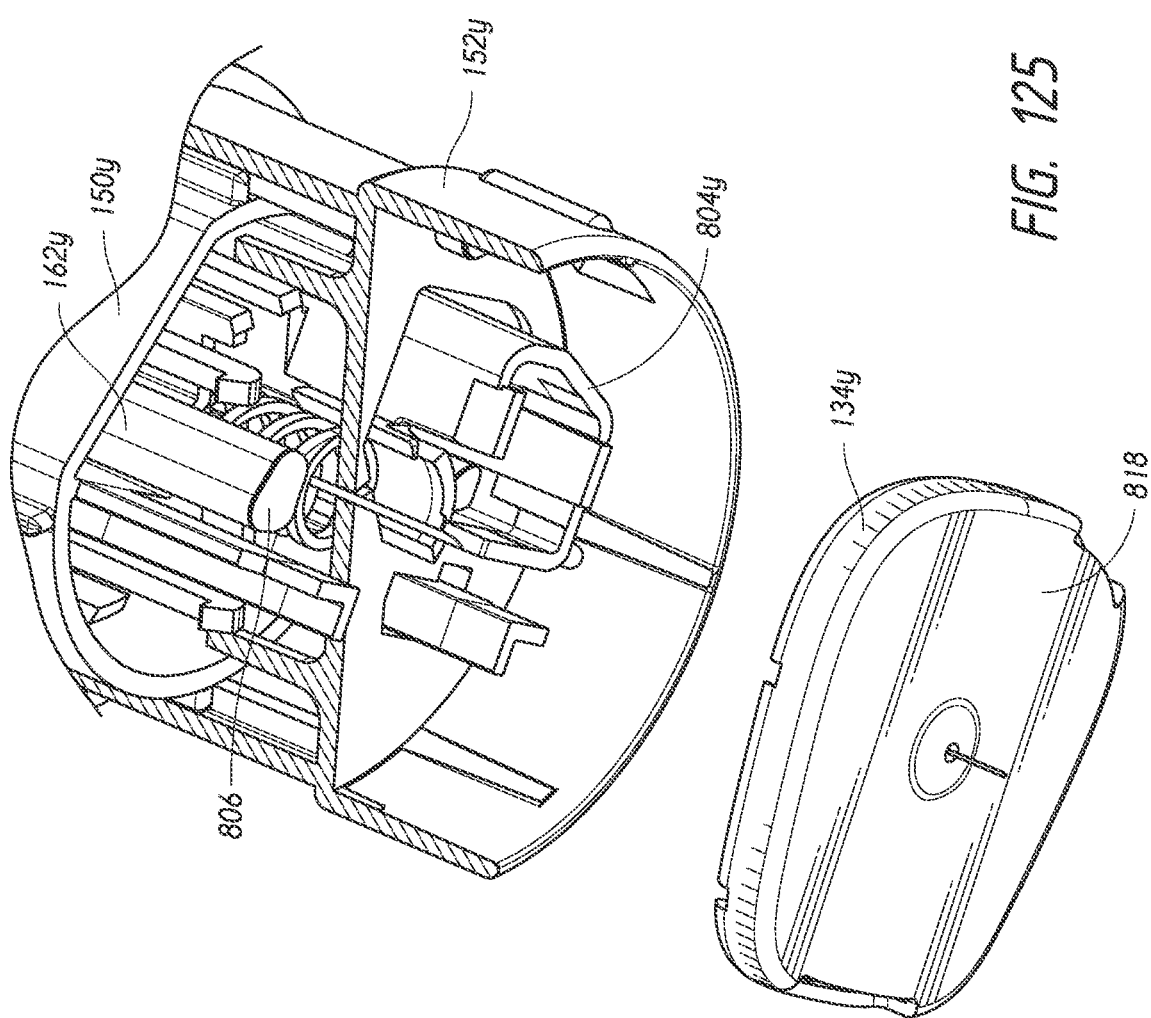
FIG. 125 illustrates a perspective view of a portion of the applicator system shown in FIG. 123, with the on-skin component separated from the needle assembly.

FIG. 124 illustrates another perspective view of the on-skin component 134y and the needle hub 162y, with the remainder of the system 104y removed to illustrate the configuration of the securement member 800y. FIG. 125 illustrates a perspective view of a portion of the applicator system shown in FIG. 123, with the on-skin component 134y in a released configuration and separated from the needle hub 162y and with two of the legs 802y removed for purposes of illustration. The resistance member 804y can be configured to encompass or at least partially encompass the sensor module portion of the on-skin component 134y. The resistance member 804y can comprise one or more elongate members, columns, legs, and/or protrusions, or can have any other suitable configuration for facilitating the release of the on-skin component from the needle hub 162y. The resistance member 804y (or any portion thereof) can have a curvilinear cross section, as illustrated in FIG. 125, or can have any other suitable cross section, including circular, square, triangular, ovoid, L-shaped, O-shaped, U-shaped, V-shaped, X-shaped, or any other regular or irregular shape or combination of shapes.

As shown in FIG. 125, the system 104y can include an adhesive patch 818 disposed on the distally-facing surface of the on-skin component 134y. The adhesive patch 818 can be configured to couple the on-skin component 134y to the skin on contact. In some embodiments, the adhesive patch can be a pressure-sensitive adhesive. In some embodiments, the adhesive patch 818 is a double sided adhesive, in which an adhesive is disposed on both the proximally facing surface of the adhesive patch 818 and the distally facing surface of the adhesive patch 818. The proximally facing adhesive can be configured to couple with the distal end of the on-skin component 134y, and the distally facing adhesive can be configured to couple with the skin. In other embodiments, the proximally facing surface of the adhesive patch 818 is configured to couple with the distally facing surface of the on-skin component by a coupling process such as, but not limited to, heat staking, fastening, welding, or bonding. In some embodiments, the adhesive patch 818 can be covered by a removable liner prior to deployment. In other embodiments, the adhesive patch 818 can be exposed (e.g., uncovered) within the system prior to deployment.

Alternatively, in some embodiments the adhesive patch 818 can be releasably secured to the distal end of the system before deployment, with an adhesive disposed on a proximally-facing surface of the adhesive patch 818, so as to couple the on-skin component to the adhesive patch 818 upon contact as part of the sensor insertion process. In addition, in such an embodiment, the adhesive patch 818 can include an adhesive disposed on a distally-facing surface of the adhesive patch 818 to couple the on-skin component to the skin.

Such a configuration can include fewer components to be coupled and decoupled during the deployment and insertion process, which can increase reliability of systems configured in accordance with embodiments. For example, systems configured in accordance with embodiments can reduce the chance of improper transfer of system components to the skin. In addition, it is contemplated that embodiments comprising an adhesive patch disposed within the system in a resting state (as opposed to an adhesive patch disposed at a distal end of the system in the resting state) can allow for the system to be more easily re-positioned on the skin as many times as desired before being adhered to the skin.

Figure 127:
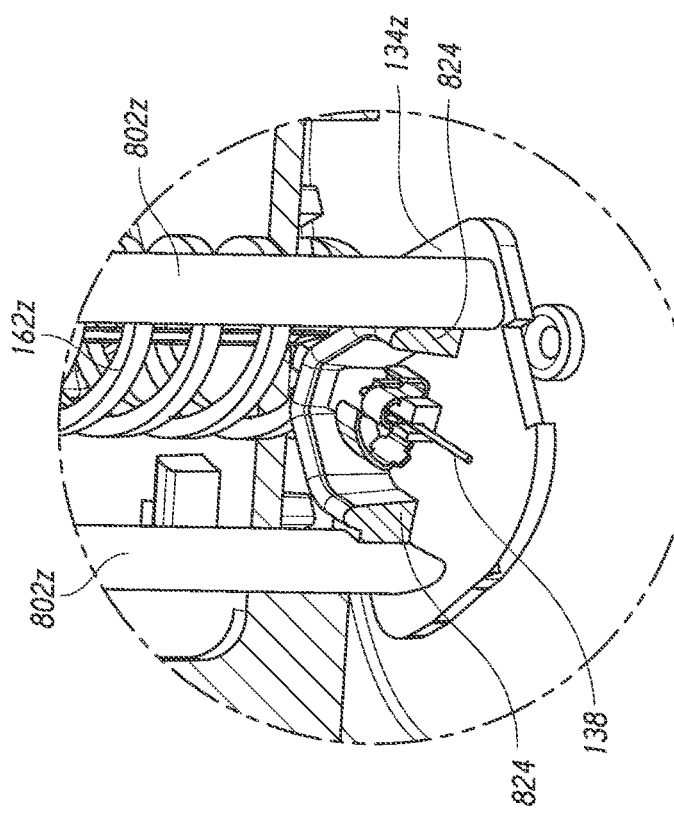
FIG. 127 illustrates a perspective view of a portion of the securing member of FIG. 126, with the sensor module of the on-skin component shown in cross section, and illustrated with a decoupling feature of an applicator assembly, according to some embodiments.
Figure 126:
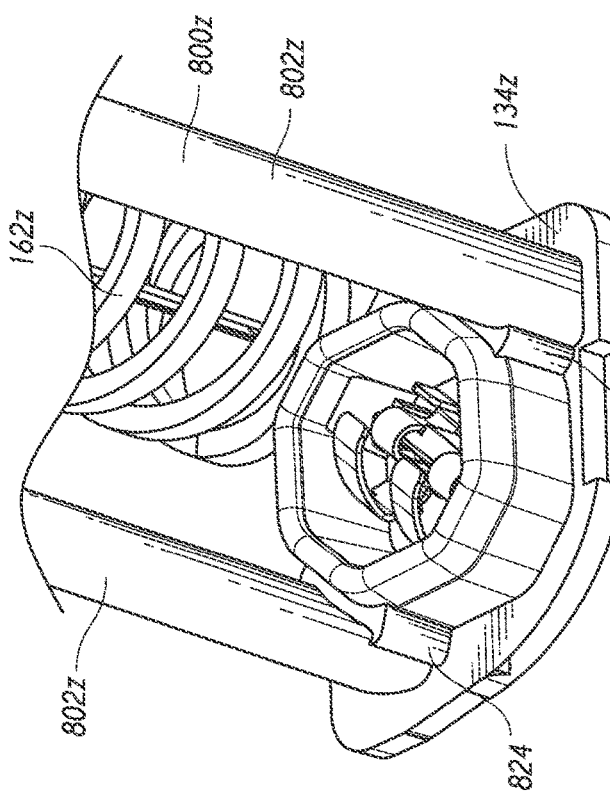
FIG. 126 illustrates a perspective view of a portion of a securing member, shown securing an on-skin component.
Figure 128:
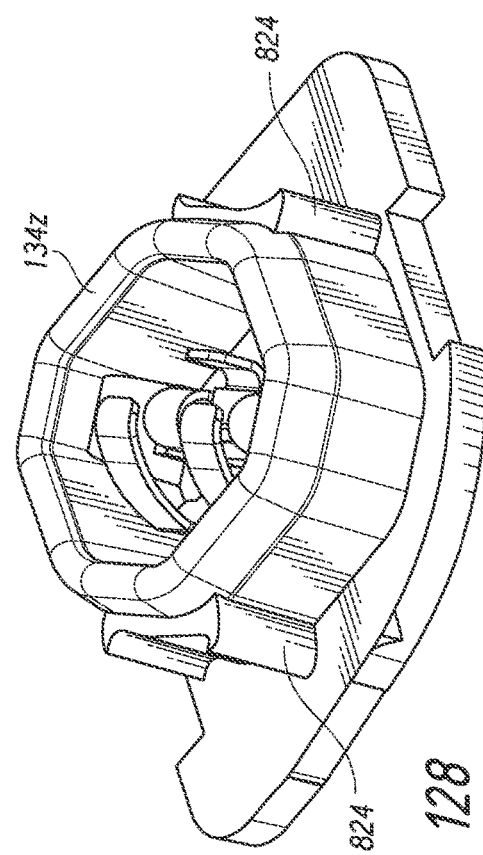
FIG. 128 illustrates a perspective view of the on-skin component of FIG. 126, after decoupling of the on-skin component from the securing member.

FIGS. 126-128 illustrate another configuration for releasably securing an on-skin component in a proximal position, in accordance with several embodiments. FIG. 126 illustrates a perspective view of a portion of a securement member 800z shown secured to an on-skin component 134z comprising a sensor module. The securement member 800z can include at least one leg 802z. As shown in the figure, the securement member 800z includes two proximally-extending legs 802z. The on-skin component 134z includes two elastomeric grips 824 extending laterally from the sensor module. The grips 824 are sized and shaped to cooperate with laterally-facing surfaces of the legs 802z to releasably secure the on-skin component 134z in a proximal position. In the embodiment illustrated in FIGS. 126-128, the grips 824 are integrally formed with the sensor module, and have a bracket-shaped cross section, as viewed in a plane extending normal to the axial direction. In embodiments, the securement member 800z and the grips 824 can have any suitable cooperating configuration to allow the on-skin component 134z to releasably couple the securement member 800z to the grips 824, for example via a friction fit, interference fit, or corresponding undercut engagement features. Some embodiments can additionally employ an adhesive disposed between the securement member 800z and the on-skin component 134z, to provide additional securement of the on-skin component 134z.

FIG. 127 illustrates a perspective view of a portion of the securement member 800z, with the sensor module of the on-skin component 134z shown in cross section to illustrate the configuration of the grips 824. FIG. 127 also shows a decoupling feature 804z configured to resist proximal movement of the on-skin component 134z after deployment of the on-skin component 134z to the distal deployed position, for example during retraction of the needle hub 162z. The decoupling feature 804z can be fixed with respect to the remainder of the sensor inserter system as the needle hub 162z retracts in a proximal direction, providing enough resistance to overcome the friction fit (and adhesive, if any) between the securement member 800z and the grips 824 to release the securement member 800z from the grips 824. FIG. 128 illustrates a perspective view of the on-skin component 134z, after decoupling of the on-skin component 134z from the securing member 800z.

Figure 129:
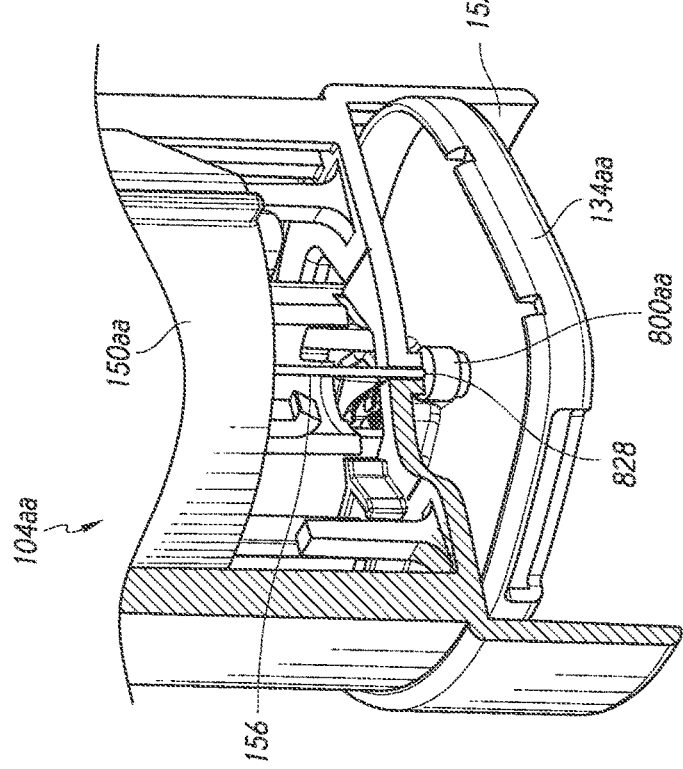
FIG. 129 illustrates a perspective view of a portion of an applicator assembly, according to some embodiments, with the second portion shown in cross section, and with a securing member shown securing an on-skin component in a proximal position.
Figure 130:
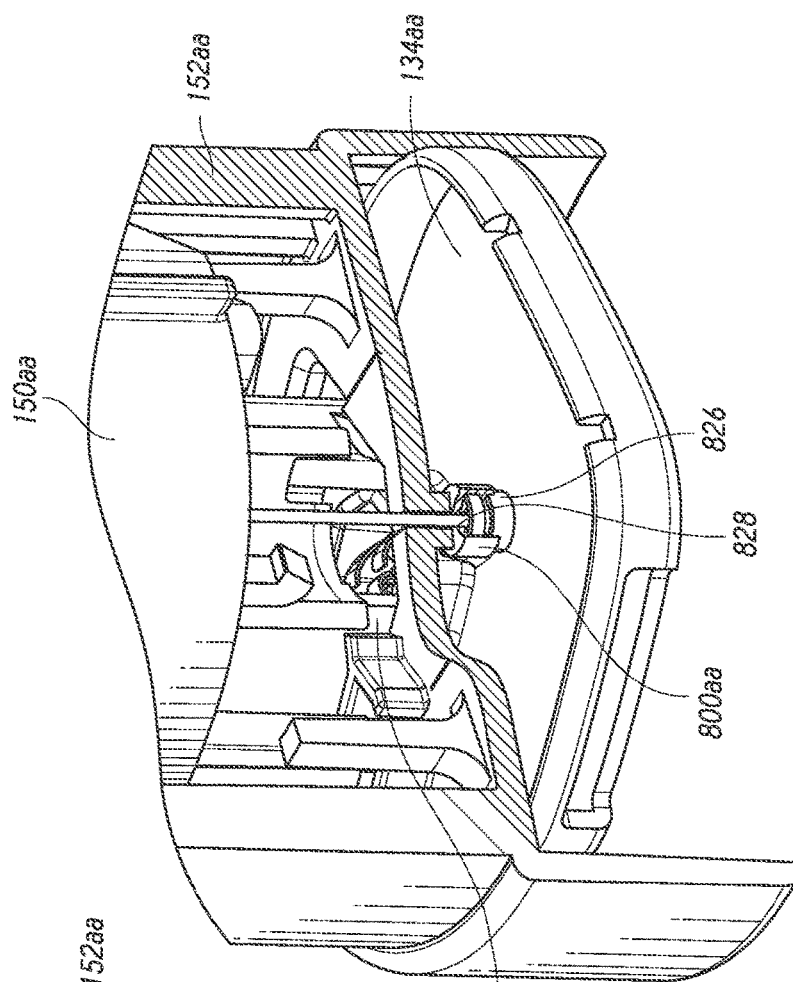
FIG. 130 illustrates a perspective view of a portion of the applicator assembly of FIG. 129, shown with a portion of the securing member cut away to better illustrate the configuration of the securing member.
Figure 131:
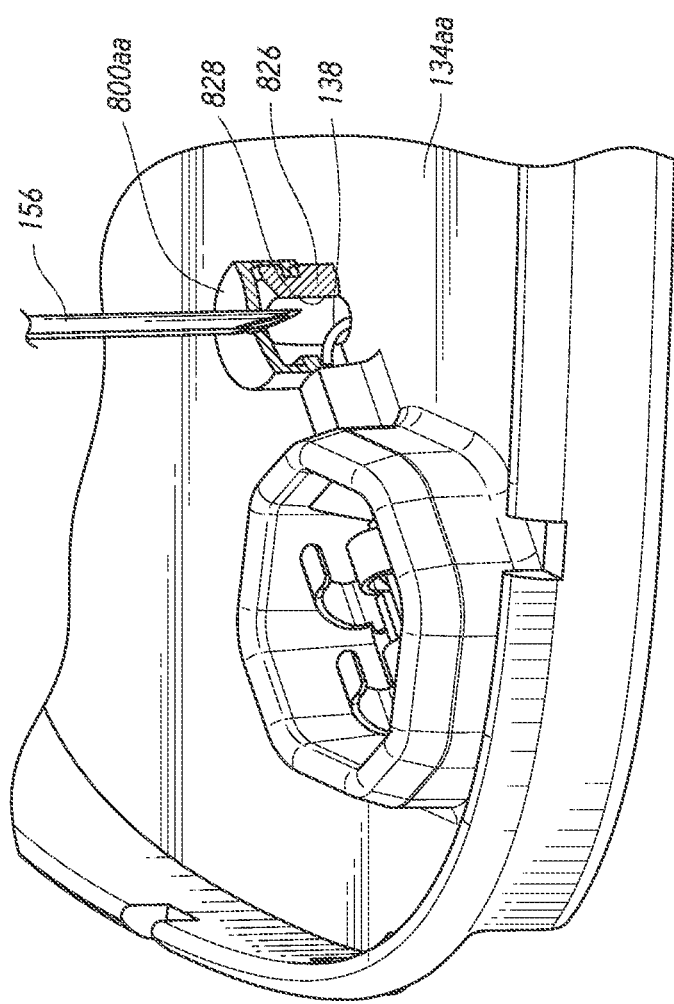
FIG. 131 illustrates a perspective view of a portion of the applicator assembly of FIG. 129, after decoupling of the on-skin component from the needle assembly, shown with portions of the on-skin component and the securing member cut away.

FIGS. 129-131 illustrate still another configuration for releasably securing an on-skin component, in accordance with several embodiments. FIG. 129 illustrates a perspective view of a portion of a sensor inserter assembly 104aa with the second portion 150aa shown in cross section, and with a securing member 800aa shown securing an on-skin component 134aa in a proximal position. The on-skin component 134aa may comprise an integrally formed sensor module/base assembly. As shown in the figure, the securement member 800aa comprises an elastomeric cap which is coupled to a portion of the on-skin component 134aa. As shown, the securement member 800aa can be coupled to a protrusion (or neck) 826 formed in the on-skin component 134aa. FIG. 130 illustrates a perspective view of a portion of the assembly 104aa of FIG. 129, shown with a portion of the securing member 800aa cut away to better illustrate the configuration of the securing member 800aa and the protrusion 826. The protrusion 826 can be configured to encircle, or at least partially encircle, the needle 158 when it extends in a proximal direction through the on-skin component 134*aa*. The protrusion 826 can also be configured to secure the securement member 800*aa* to the on-skin component 134*aa*. The securement member 800*aa* has an opening 828 which is sized and shaped to create a friction fit between the opening 828 and the needle 158. In the configuration illustrated in FIGS. 129 and 130, with the needle 158 extending distally through the securement member 800*aa* and the protrusion 826, the friction fit between the securement member 800*aa* and the needle 158 serves to resist at least distal movement of the on-skin component 134*aa* with respect to the needle 158.

The embodiment illustrated in FIGS. 129-131 may also include a resistance member 804*aa*. The resistance member may be substantially similar to any resistance member described in FIGS. 110-128. The resistance member 804*aa* can include a distally-facing surface of the first portion 150*aa*, and can have a similar configuration to the resistance member 804 described in the context of FIG. 117. The resistance member 804*aa* can provide enough resistance in a distal direction to allow the second spring and needle hub (not shown) to overcome the friction fit between the securement member 800*aa* and the needle 158. It is contemplated that this would allow the needle 158 to retract away from the skin and at the same time allow the needle to decouple from the securement member 800*aa*. FIG. 131 illustrates a perspective view of a portion of the assembly 104*aa*, after decoupling of the on-skin component 134*aa* from the needle 158, shown with the protrusion 826 of the on-skin component 134*aa* and the securing member 800*aa* cut away for purposes of illustration.

Figure 133:
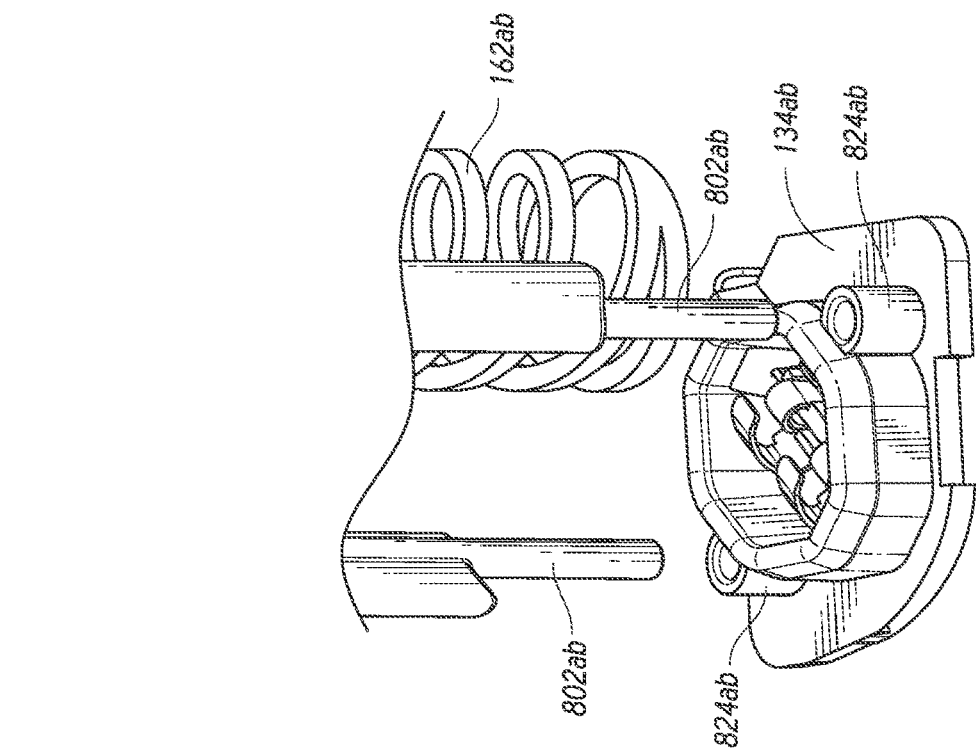
Figure 132:
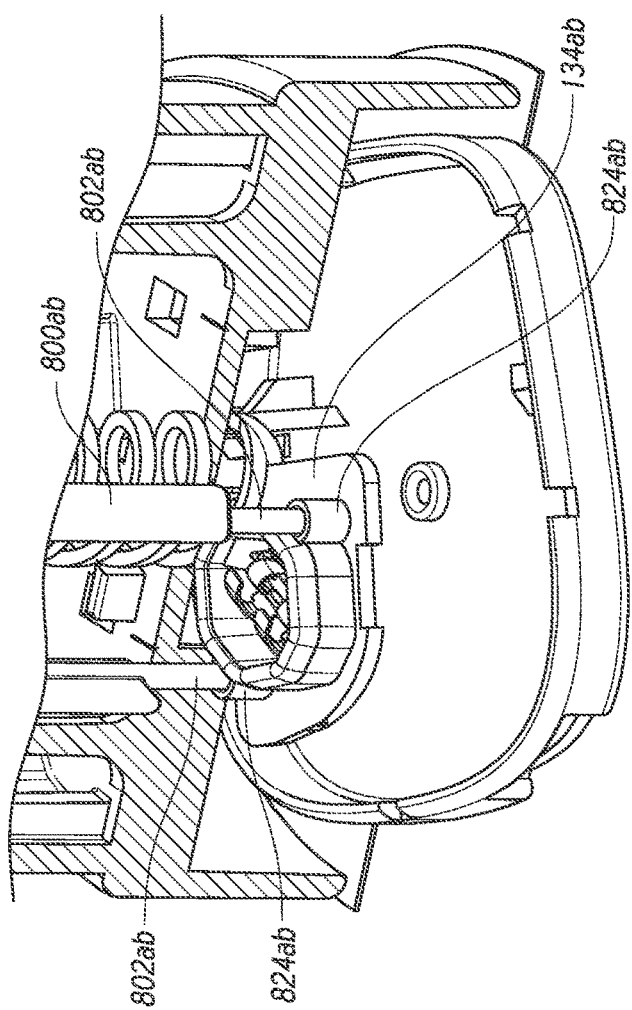
FIG. 132 illustrates a perspective view of a portion of an applicator assembly, according to some embodiments, with the second portion shown in cross section, and with a securing member shown securing an on-skin component in a proximal position.

FIGS. 132-133 illustrate another configuration for releasably securing an on-skin component in a proximal position, in accordance with several embodiments. FIG. 132 illustrates a perspective view of a portion of a securement member 800*ab* shown secured to an on-skin component 134*ab* comprising a sensor module, with the second portion 150*ab* shown in cross section. The securement member 800*ab* may include at least one engagement feature. As shown in the figure, the at least one engagement feature can be two proximally-extending legs 802*ab*. The on-skin component 134*ab* may include at least one receiving feature. As shown, the at least one receiving feature can be two elastomeric grips 824*ab* extending laterally from the on-skin component 134*ab*. The grips 824*ab* are deformable and sized and shaped to receive the legs 802*ab* via friction or interference fit and thereby releasably secure the on-skin component 134*ab* in a proximal position. In the embodiment illustrated in FIGS. 132-133, the legs 802*ab* of the securement member 800*ab* have a circular cross-section. The grips 824*ab* are integrally formed with the sensor module, and have an annular-shaped cross section, as viewed in a plane extending normal to the axial direction. The grips 824*ab* may each include an opening which can be configured to receive the legs 802*ab* via frictional engagement. In embodiments, the securement member 800*ab* and the grips 824*ab* can have any suitable cooperating configuration to releasably couple the securement member 800*ab* to the grips 824*ab*. Some embodiments can additionally employ an adhesive disposed axially between the securement member 800*ab* and the on-skin component 134*ab*, to provide additional securement of the on-skin component 134*ab* in the proximal starting position. FIG. 133 illustrates a perspective view of the needle hub 162*ab* and the on-skin component 134*ab*, after decoupling of the on-skin component 134*ab* from the needle hub 162*ab*.

Figure 136:
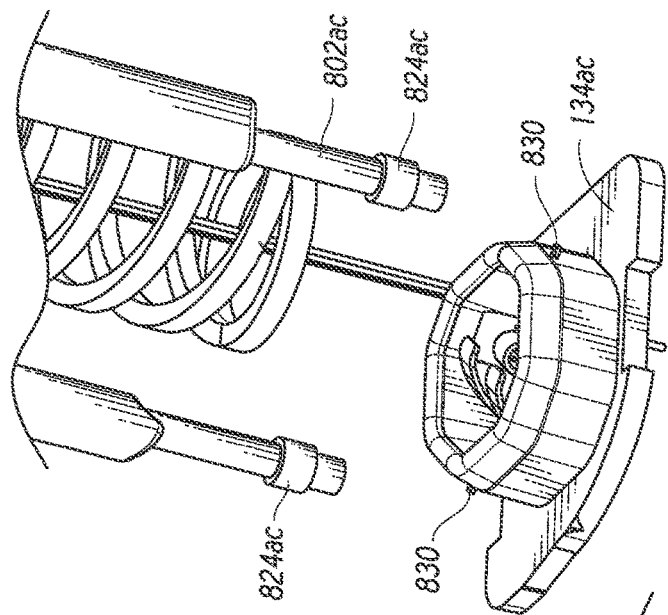
Figure 135:
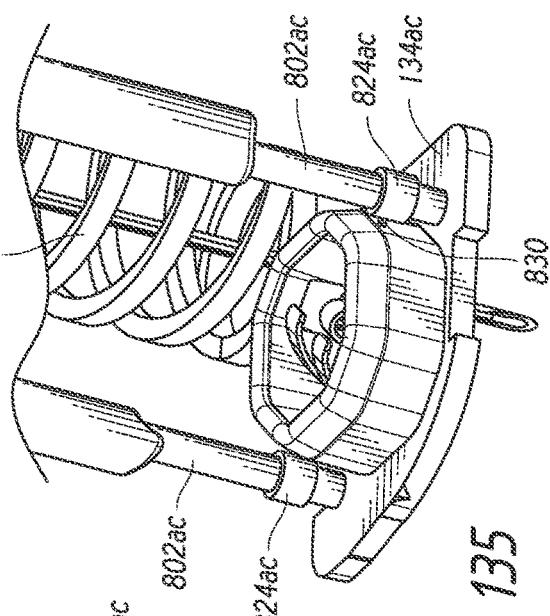
Figure 134:
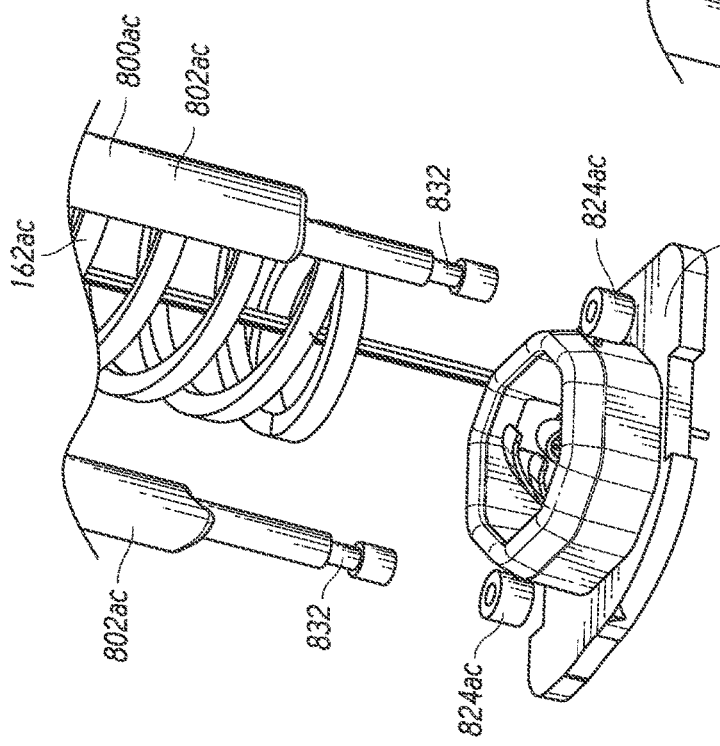

FIGS. 134-136 illustrate yet another configuration for releasably securing an on-skin component in a proximal position. FIG. 134 illustrates an exploded perspective view of a portion of an assembly 134*ac*, with a securement member 800*ac* configured to releasably couple an on-skin component 134*ac* to a needle hub 162*ac*. The securement member 800*ac* may include at least one engagement feature. As shown in the figure, the securement member 800*ac* can include two proximally-extending legs 802*ac*. The on-skin component 134*ac* includes two elastomeric grips 824*ac* extending laterally from the sensor module. The grips 824*ac* are sized and shaped to receive the legs 802*ac* in a snap fit to securely hold the on-skin component 134*ac* in a proximal position. In the embodiment illustrated in FIGS. 134-136, the legs 802*ac* of the securement member 800*ac* have a circular cross-section, with a recessed section 832 configured to receive the grips 824*ac*. The grips 824*ac* can be integrally formed with the sensor module, each grip having a frangible link 830 coupling the grips 824*ac* to the sensor module. The grips 824*ac* have an annular-shaped cross section, as viewed in a plane extending normal to the axial direction, the grips being configured to receive the recessed sections 832 of the legs in a secure interlocking engagement. In embodiments, the securement member 800*ab* and the grips 824*ab* can have any suitable cooperating configuration to securely couple the securement member 800*ac* to the grips 824*ac* and prevent slippage of the grips along the legs 802*ac* as the needle hub 162*ac* deploys and as it retracts after deployment. Some embodiments can additionally employ an adhesive disposed axially between the securement member 800*ac* and the on-skin component 134*ab*, to provide additional securement of the on-skin component 134*ac* in the proximal starting position and during deployment.

FIG. 135 illustrates a perspective view of a portion of the system 104*ac*, with the securement member 800*ac* securely coupled to the on-skin component 134*ac*. Some embodiments can additionally employ an adhesive disposed axially between the securement member 800*ac* and the on-skin component 134*ac*, to provide additional securement of the on-skin component 134*ac* in the proximal starting position. The frangible links 830 are configured to shear or otherwise detach upon application of a minimum threshold of force, as the needle hub 162 retracts in a proximal direction after deployment, separating the grips 824*ac* from the remainder of the on-skin component 134*ac* and leaving the on-skin component 824*ac* in the deployed distal position. FIG. 136 illustrates a perspective view of a portion of the system 104*ac*, with the frangible links 830 broken and the securement member 800*ac* decoupled from the on-skin component 134*ac*. In some embodiments, a resistance member can also be employed to prevent proximal movement of the on-skin component 134*ac* as the needle hub 162*ac* retracts, facilitating the breakage of the frangible links 830.

Figure 140:
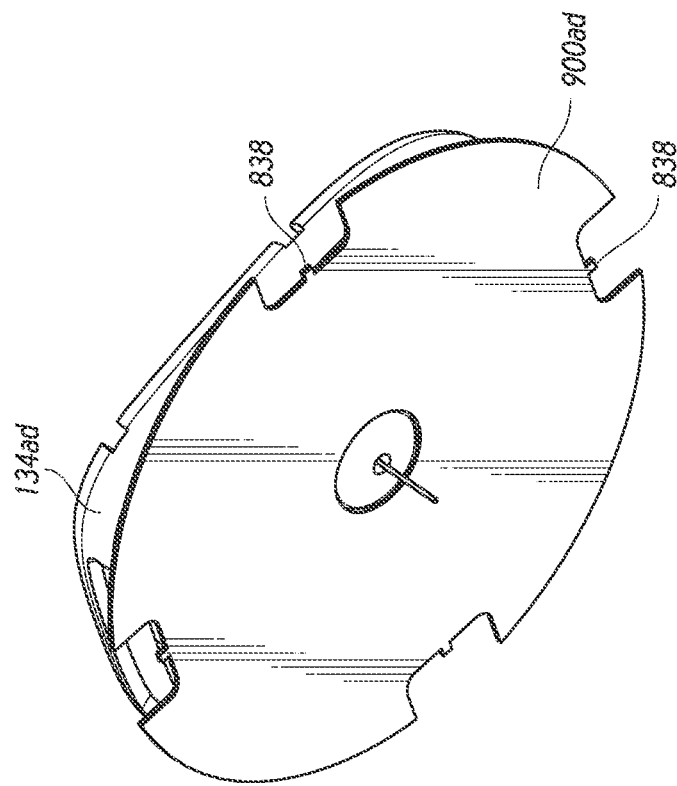
Figure 139:
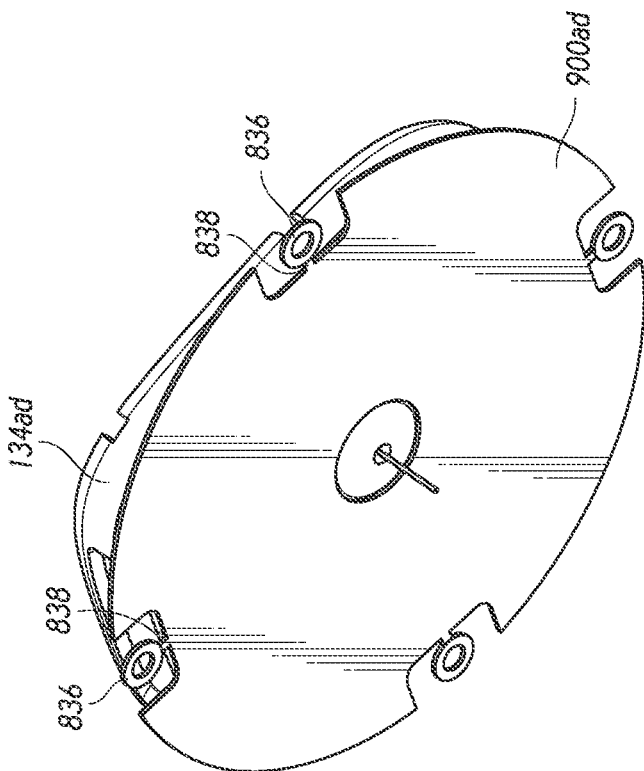

Frangible couplings can also be employed between an on-skin component and the second portion of a sensor inserter system to releasably secure the on-skin component in a proximal starting position prior to deployment. For example, FIGS. 137-140 illustrate various perspective views of a sensor inserter system 104*ad* with an on-skin component 134*ad* releasably secured in a proximal position within the system 104*ad*. The on-skin component 134*ad* can include a combination sensor module and base disposed on an adhesive patch 900*ad*. To facilitate in releasably securing the on-skin component 134*ad* to the second portion 152*ad*, the second portion 152*ad* can include at least one distally-extending protrusion 834. As shown in the figure, the second portion 152*ad* includes four distally-extending protrusions 834 configured to securely couple with corresponding sockets 836 formed in or otherwise extending from the adhesive patch 900*ad*. The sockets 836 are connected to the adhesive patch 900*ad* via frangible links 838, which can also be integrally formed in the adhesive patch 900*ad*. In the resting state illustrated in FIG. 137, the adhesive patch 900*ad* is secured in a proximal position by the coupling of the sockets 836 to the posts 838. As the system 104*ad* is deployed and a force is applied to the on-skin component 134*ad* in a distal direction, the frangible links 838 detach, allowing the adhesive patch 900*ad* (and the on-skin component 134*ad* which is already coupled thereto) to move to the distal deployed position. FIG. 138 illustrates a perspective view of the sensor inserter system 104*ad*, with the frangible links 838 detached and the adhesive patch 900*ad* released from securement. FIGS. 139 and 140 illustrate perspective views of the adhesive patch 900*ad* and the on-skin component 134*ad*, with the frangible links 838 in intact and detached configurations, respectively. Once the frangible links 838 are detached and the on-skin component 134*ad* (along with the patch 900*ad*) is deployed in the distal position, the remainder of the system 104*ad* can easily be lifted off the skin of the host and removed.

Figure 141:
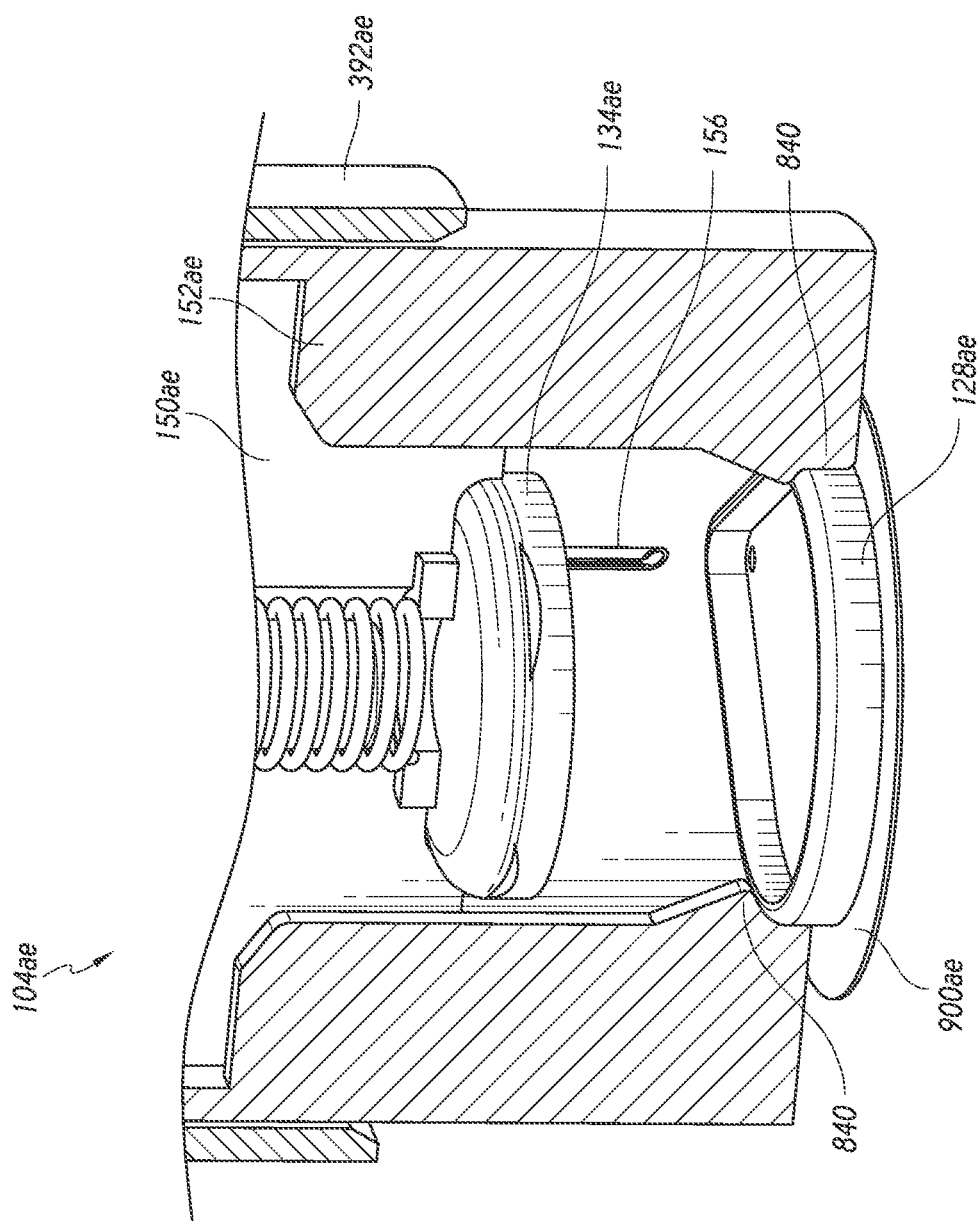

FIG. 141 illustrates another configuration for releasably securing a base and adhesive patch to a sensor inserter assembly. FIG. 141 illustrates a cross-sectional perspective view of a portion of a system 104*ae*, with the first portion 150*ae*, the second portion 152*ae*, and the third portion 392*ae* shown in cross section. The system 104*ae* includes an on-skin component 134*ae* which is releasably secured in a proximal starting position. The system 104*ae* also includes a base 128*ae* coupled to an adhesive patch 900*ae*. The base 128*ae* and the adhesive patch 900*ae* are disposed in a distal position, at a distal end of the system 104*ae*. The base 128*ae* is coupled to the system 104*ae* via a plurality of ribs 840 extending radially inward from the second portion 152*ae*. The ribs 840 can be sized and shaped to grip the edges of the base 128*ae* with a friction/interference fit. The friction/interference fit between the ribs 840 and the base 128*ae* can be configured to be strong enough to securely couple the base 128*ae* to the system 104*ae* during storage and prior to deployment, but weak enough that the adhesive coupling between the adhesive patch 900*ae* and the skin of the host overcomes the strength of the friction fit. Thus, once the adhesive patch 900*ae* is adhered to the skin of the host, the second portion 152*ae* can be lifted off the base 128*ae* and the sensor system 104*ae* can be removed without pulling the base 128 in a proximal direction. In some embodiments, the base 128*ae* may comprise an elastomeric material. Further, in some embodiments, the base 128*ae* may have a hardness value less than a hardness value of the on-skin component 134*ae*. In other embodiments, the base 128*ae* may have a hardness value more than a hardness value of the on-skin component 134*ae*.

FIGS. 142 and 143 illustrate yet another configuration for releasably securing an adhesive patch, optionally including a base, to a sensor inserter system. FIG. 142 shows a sensor inserter system 104*af* with an adhesive patch 900*af* coupled to the second portion 152*af* of the system 104*af*. FIG. 143 shows the system 104*af* with the patch 900*af* separated from the second portion 152*af*. As shown in FIG. 143, the second portion 152*af* includes a plurality of adhesive dots 842 disposed on a distally-facing surface or edge of the second portion 152*af*. The adhesive dots 842 can be configured to be strong enough to securely couple the adhesive patch 900*af* (and base, if any) to the system 104*af* during storage and prior to deployment, but weak enough that the adhesive coupling between the adhesive patch 900*af* and the skin of the host overcomes the strength of the adhesive dots 842. Thus, once the adhesive patch 900*af* is adhered to the skin of the host, the second portion 152*af* can be lifted off the applicator patch 900*af* (and base, if any) and the sensor system 104*af* can be removed without pulling the adhesive patch 900*af* (or base, if any) in a proximal direction. Alternatively or in addition to the adhesive dots 842, some embodiments can include an adhesive disposed on a proximally-facing surface of the adhesive patch 900*af*. In some embodiments, the adhesive can be a pressure-sensitive adhesive.

Interpretation

For ease of explanation and illustration, in some instances the detailed description describes exemplary systems and methods in terms of a continuous glucose monitoring environment; however it should be understood that the scope of the invention is not limited to that particular environment, and that one skilled in the art will appreciate that the systems and methods described herein can be embodied in various forms. Accordingly any structural and/or functional details disclosed herein are not to be interpreted as limiting the systems and methods, but rather are provided as attributes of a representative embodiment and/or arrangement for teaching one skilled in the art one or more ways to implement the systems and methods, which may be advantageous in other contexts.

For example, and without limitation, described monitoring systems and methods may include sensors that measure the concentration of one or more analytes (for instance glucose, lactate, potassium, pH, cholesterol, isoprene, and/or hemoglobin) and/or other blood or bodily fluid constituents of or relevant to a host and/or another party.

By way of example, and without limitation, monitoring system and method embodiments described herein may include finger-stick blood sampling, blood analyte test strips, non-invasive sensors, wearable monitors (e.g. smart bracelets, smart watches, smart rings, smart necklaces or pendants, workout monitors, fitness monitors, health and/or medical monitors, clip-on monitors, and the like), adhesive sensors, smart textiles and/or clothing incorporating sensors, shoe inserts and/or insoles that include sensors, transdermal (i.e. transcutaneous) sensors, and/or swallowed, inhaled or implantable sensors.

In some embodiments, and without limitation, monitoring systems and methods may comprise other sensors instead of or in additional to the sensors described herein, such as inertial measurement units including accelerometers, gyroscopes, magnetometers and/or barometers; motion, altitude, position, and/or location sensors; biometric sensors; optical sensors including for instance optical heart rate monitors, photoplethysmogram (PPG)/pulse oximeters, fluorescence monitors, and cameras; wearable electrodes; electrocardiogram (EKG or ECG), electroencephalography (EEG), and/or electromyography (EMG) sensors; chemical sensors; flexible sensors for instance for measuring stretch, displacement, pressure, weight, or impact; galvanometric sensors, capacitive sensors, electric field sensors, temperature/thermal sensors, microphones, vibration sensors, ultrasound sensors, piezoelectric/piezoresistive sensors, and/or transducers for measuring information of or relevant to a host and/or another party.

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

Some of the devices, systems, embodiments, and processes use computers. Each of the routines, processes, methods, and algorithms described in the preceding sections may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as, for example, volatile or non-volatile storage.

Any of the features of each embodiment is applicable to all aspects and embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

What is claimed is:

1. A sensor applicator system configured for delivery to a host, the sensor applicator system configured to apply an on-skin sensor assembly provided as part of the sensor applicator system to a skin of the host, the applicator system comprising:
   a shell;
   an on-skin sensor assembly disposed in the applicator system, the on-skin sensor assembly comprising:
      at least one electrical interconnect;
      a transcutaneous analyte sensor comprising an in-vivo portion and an ex-vivo portion;
      sensor electronics configured to process a signal received from the transcutaneous analyte sensor;
      an electrical connection established between the transcutaneous analyte sensor and the sensor electronics;
      a first mechanical connection established between the transcutaneous analyte sensor and the at least one electrical interconnect;
      a second mechanical connection established between the sensor electronics and the at least one electrical interconnect;
      wherein the first mechanical connection and the second mechanical connection are configured to establish the electrical connection between the transcutaneous analyte sensor and the sensor electronics;
      a base comprising a hole and an adhesive to adhere the on-skin sensor assembly to a skin of a host; and
      wherein the transcutaneous analyte sensor is configured to extend during use from the electrical interconnect, through the hole in the base, to under the skin of the host; and
   a needle configured to guide the sensor under the skin of the host; and
   a user removable cap removably coupled to the shell and covering the on-skin sensor assembly and the needle.

2. The applicator system of claim 1, wherein the user removable cap seals the on-skin sensor assembly and the needle from contaminants prior to application of the on-skin sensor assembly to the skin of the host.

3. The applicator system of claim 2, wherein the shell comprises a first material, wherein the cap comprises a second material, and wherein the second material is softer than the first material.

4. The applicator system of claim 1, wherein the system is configured to retain the needle in the shell after the on-skin sensor assembly is applied to the host.

5. The applicator system of claim 1, wherein the needle comprises a channel, and wherein the transcutaneous analyte sensor extends from the first mechanical connection into the channel of the needle.

6. The applicator system of claim 5, comprising a compressed spring configured for pushing the needle and the in-vivo portion of the transcutaneous analyte sensor under the skin of the host.

7. The applicator system of claim 1, wherein the electrical connection is sealed to prevent fluid ingress after application of the on-skin sensor assembly to the skin of the host.

8. The applicator system of claim 1, wherein the electrical interconnect comprises a spring.

9. The applicator system of claim 8, wherein the spring comprises a leaf spring.

10. The applicator system of claim 1, wherein the electrical interconnect is compressed between the first mechanical connection and the second mechanical connection.

11. The applicator system of claim 1, wherein the electrical interconnect comprises a plated portion.

12. The applicator system of claim 10, wherein the plated portion is gold plated.

13. The applicator system of claim 1, wherein the needle is sterilized.

14. The applicator system of claim 13, wherein the sensor electronics is not sterilized.

15. A sensor applicator system configured for delivery to a host, the sensor applicator system configured to apply an on-skin sensor assembly provided as part of the sensor applicator system to a skin of the host, the applicator system comprising:
   a shell;
   an on-skin sensor assembly disposed in the applicator system, the on-skin sensor assembly comprising:
      a sensor module comprising a sensor module housing and an electrical interconnect, wherein the electrical interconnect is mounted to the sensor module housing;
      a transcutaneous analyte sensor comprising an in-vivo portion and an ex-vivo portion;
      sensor electronics configured to process a signal received from the transcutaneous analyte sensor;
      an electrical connection established between the transcutaneous analyte sensor and the sensor electronics;
      a first mechanical connection established between the transcutaneous analyte sensor and the electrical interconnect, wherein the ex-vivo portion of the transcutaneous analyte sensor is pressed against a portion of the electrical interconnect;
      a second mechanical connection established between the sensor electronics and the electrical interconnect;
      wherein the electrical connection is established by conductive material of the electrical interconnect that extends from the first mechanical connection to the second mechanical connection;
      a base comprising a hole and an adhesive to adhere the on-skin sensor assembly to a skin of a host; and
      wherein the transcutaneous analyte sensor is configured to extend during use from the electrical interconnect, through the hole in the base, to under the skin of the host;
   a needle configured to guide the sensor under the skin of the host; and
   a user removable cap removably coupled to the shell and covering the on-skin sensor assembly and the needle.

16. The applicator system of claim 15, wherein the ex-vivo portion of the transcutaneous analyte sensor is pressed between the portion of the electrical interconnect and the sensor module housing.

17. The applicator system of claim 15, wherein the sensor module housing comprises a groove, and wherein the electrical interconnect comprises a tab positioned in the groove to inhibit rotation of the electrical interconnect.

18. The applicator system of claim 15, wherein the user removable cap seals the on-skin sensor assembly and the needle from contaminants prior to application of the on-skin sensor assembly to the skin of the host.

19. The applicator system of claim 18, wherein the shell comprises a first material, wherein the cap comprises a second material, and wherein the second material is softer than the first material.

20. The applicator system of claim 15, wherein the system is configured to retain the needle in the shell after the on-skin sensor assembly is applied to the host.

21. The applicator system of claim 15, wherein the needle comprises a channel, and wherein the transcutaneous analyte sensor extends from the first mechanical connection into the channel of the needle.

22. The applicator system of claim 21, comprising a compressed spring configured for pushing the needle and the in-vivo portion of the transcutaneous analyte sensor under the skin of the host.

23. The applicator system of claim 15, wherein the electrical connection is sealed to prevent fluid ingress after application of the on-skin sensor assembly to the skin of the host.

24. The applicator system of claim 15, wherein the electrical interconnect comprises a spring.

25. The applicator system of claim 24, wherein the spring comprises a leaf spring.

26. The applicator system of claim 24, wherein the electrical interconnect is compressed between the first mechanical connection and the second mechanical connection.

27. The applicator system of claim 15, wherein the electrical interconnect comprises a plated portion.

28. The applicator system of claim 27, wherein the plated portion is gold plated.

29. The applicator system of claim 15, wherein the needle is sterilized.

30. The applicator system of claim 29, wherein the sensor electronics is not sterilized.

\* \* \* \* \*